US008734718B2

(12) United States Patent
Dacey, Jr. et al.

(10) Patent No.: US 8,734,718 B2
(45) Date of Patent: May 27, 2014

(54) SYSTEMS, DEVICES, AND METHODS INCLUDING CATHETERS HAVING AN ACTIVELY CONTROLLABLE THERAPEUTIC AGENT DELIVERY COMPONENT

(75) Inventors: Ralph G. Dacey, Jr., St. Louis, MO (US); Roderick A. Hyde, Redmond, WA (US); Muriel Y. Ishikawa, Livermore, CA (US); Jordin T. Kare, Seattle, WA (US); Eric C. Leuthardt, St. Louis, MO (US); Nathan P. Myhrvold, Bellevue, WA (US); Dennis J. Rivet, Chesapcake, VA (US); Michael A. Smith, Phoenix, AZ (US); Elizabeth A. Sweeney, Seattle, WA (US); Clarence T. Tegreene, Bellevue, WA (US); Lowell L. Wood, Jr., Bellevue, WA (US); Victoria Y. H. Wood, Livermore, CA (US)

(73) Assignee: The Invention Science Fund I, LLC

( * ) Notice: Subject to any disclaimer, the term of this patent is extended or adjusted under 35 U.S.C. 154(b) by 390 days.

(21) Appl. No.: 12/927,288

(22) Filed: Nov. 10, 2010

(65) Prior Publication Data
US 2011/0144566 A1 Jun. 16, 2011

Related U.S. Application Data

(63) Continuation-in-part of application No. 12/315,880, filed on Dec. 4, 2008, now Pat. No. 8,162,924, and a continuation-in-part of application No. 12/315,881, filed on Dec. 4, 2008, and a continuation-in-part of application No. 12/315,882, filed on Dec. 4, 2008, now abandoned, and a continuation-in-part of application No. 12/315,883, filed on Dec. 4, 2008, and a (Continued)

(51) Int. Cl.
| | | |
|---|---|---|
| A61L 2/00 | (2006.01) | |
| A61L 2/18 | (2006.01) | |
| A61L 9/00 | (2006.01) | |
| A61L 2/04 | (2006.01) | |
| A61L 11/00 | (2006.01) | |
| C23F 11/00 | (2006.01) | |

(52) U.S. Cl.
USPC .................. 422/22; 422/23; 422/24; 422/28; 422/1

(58) Field of Classification Search
USPC ...................................... 422/22, 23, 24, 28, 1
See application file for complete search history.

(56) References Cited

U.S. PATENT DOCUMENTS 3,274,406 A 9/1966 Sommers, Jr.
3,825,016 A 7/1974 Lale et al.

(Continued)

FOREIGN PATENT DOCUMENTS

EP 1 614 442 A2 1/2006
WO WO 91/06855 A2 5/1991

(Continued)

OTHER PUBLICATIONS

PCT International Search Report; International App. No. PCT/US2010/003088; Apr. 1, 2011; pp. 1-4.

(Continued)

*Primary Examiner* — Regina M Yoo

(57) ABSTRACT

Systems, devices, methods, and compositions are described for providing an actively-controllable disinfecting implantable device configured to, for example, treat or prevent an infection in a biological subject.

11 Claims, 25 Drawing Sheets

Related U.S. Application Data continuation-in-part of application No. 12/315,884, filed on Dec. 4, 2008, and a continuation-in-part of application No. 12/315,885, filed on Dec. 4, 2008, now abandoned, and a continuation-in-part of application No. 12/380,553, filed on Feb. 27, 2009, and acontinuation-in-part of application No. 12/592,976, filed on Dec. 3, 2009, and a continuation-in-part of application No. 12/660,156, filed on Feb. 19, 2010, now Pat. No. 8,366,652, and a continuation-in-part of application No. 12/800,766, filed on May 21, 2010, now Pat. No. 8,216,173, and a continuation-in-part of application No. 12/800,774, filed on May 21, 2010, and a continuation-in-part of application No. 12/800,778, filed on May 21, 2010, now abandoned, and a continuation-in-part of application No. 12/800,779, filed on May 21, 2010, and a continuation-in-part of application No. 12/800,780, filed on May 21, 2010, and a continuation-in-part of application No. 12/800,781, filed on May 21, 2010, now abandoned, and a continuation-in-part of application No. 12/800,786, filed on May 21, 2010, now abandoned, and a continuation-in-part of application No. 12/800,790, filed on May 21, 2010, now Pat. No. 8,343,086, and a continuation-in-part of application No. 12/800,791, filed on May 21, 2010, now Pat. No. 8,282,593, and a continuation-in-part of application No. 12/800,792, filed on May 21, 2010, and a continuation-in-part of application No. 12/800,793, filed on May 21, 2010, now Pat. No. 8,414,517, and a continuation-in-part of application No. 12/800,798, filed on May 21, 2010.

(56) References Cited

U.S. PATENT DOCUMENTS

| | | |
|---|---|---|
| 4,081,764 A | 3/1978 | Christmann et al. |
| 4,598,579 A | 7/1986 | Cummings et al. |
| 4,698,058 A | 10/1987 | Greenfeld et al. |
| 4,718,417 A | 1/1988 | Kittrell et al. |
| 4,788,975 A | 12/1988 | Shturman et al. |
| 4,863,849 A | 9/1989 | Melamede |
| 4,900,553 A | 2/1990 | Silver et al. |
| 5,000,731 A | 3/1991 | Wong et al. |
| 5,127,735 A | 7/1992 | Pitt |
| 5,155,707 A | 10/1992 | Fisher |
| 5,156,839 A | 10/1992 | Pennell et al. |
| 5,240,675 A | 8/1993 | Wilk et al. |
| 5,260,020 A | 11/1993 | Wilk et al. |
| 5,281,199 A | 1/1994 | Ensminger et al. |
| 5,302,345 A | 4/1994 | Oksman et al. |
| 5,324,275 A | 6/1994 | Raad et al. |
| 5,326,567 A | 7/1994 | Capelli |
| 5,431,694 A | 7/1995 | Snaper et al. |
| 5,445,608 A | 8/1995 | Chen et al. |
| 5,594,544 A | 1/1997 | Horiuchi et al. |
| 5,607,683 A | 3/1997 | Capelli |
| 5,622,848 A | 4/1997 | Morrow |
| 5,681,260 A | 10/1997 | Ueda et al. |
| 5,704,352 A | 1/1998 | Tremblay et al. |
| 5,733,270 A | 3/1998 | Ling et al. |
| 5,735,276 A | 4/1998 | Lemelson |
| 5,750,093 A | 5/1998 | Menon et al. |
| 5,797,898 A | 8/1998 | Santini, Jr. et al. |
| 5,810,015 A | 9/1998 | Flaherty |
| 5,855,203 A | 1/1999 | Matter |
| 5,865,744 A | 2/1999 | Lemelson |
| 5,961,923 A | 10/1999 | Nova et al. |
| 5,978,713 A | 11/1999 | Prutchi et al. |
| 5,993,378 A | 11/1999 | Lemelson |
| 5,993,382 A | 11/1999 | Pruitt, Sr. |
| 6,008,896 A | 12/1999 | Sabsabi et al. |
| 6,057,561 A | 5/2000 | Kawasaki et al. |
| 6,086,851 A | 7/2000 | Boni et al. |
| 6,135,990 A | 10/2000 | Heller et al. |
| 6,143,035 A | 11/2000 | McDowell |
| 6,162,242 A | 12/2000 | Peyman |
| 6,222,953 B1 | 4/2001 | Hoekstra et al. |
| 6,266,551 B1 | 7/2001 | Osadchy et al. |
| 6,280,604 B1 | 8/2001 | Allen et al. |
| 6,282,444 B1 | 8/2001 | Kroll et al. |
| 6,304,786 B1 | 10/2001 | Heil, Jr. et al. |
| 6,312,770 B1 | 11/2001 | Sage et al. |
| 6,348,042 B1 | 2/2002 | Warren, Jr. |
| 6,350,263 B1 | 2/2002 | Wetzig et al. |
| 6,418,342 B1 | 7/2002 | Owen et al. |
| 6,426,066 B1 | 7/2002 | Najafi et al. |
| 6,428,491 B1 | 8/2002 | Weiss |
| 6,440,097 B1 | 8/2002 | Kupiecki |
| 6,443,147 B1 | 9/2002 | Matter |
| 6,451,003 B1 | 9/2002 | Prosl et al. |
| 6,461,569 B1 | 10/2002 | Boudreaux |
| 6,470,888 B1 | 10/2002 | Matter |
| 6,478,778 B1 | 11/2002 | Jacobsen et al. |
| 6,488,704 B1 | 12/2002 | Connelly et al. |
| 6,491,666 B1 | 12/2002 | Santini, Jr. et al. |
| 6,506,416 B1 | 1/2003 | Okauchi et al. |
| 6,533,733 B1 | 3/2003 | Ericson et al. |
| 6,542,767 B1 | 4/2003 | McNichols et al. |
| 6,551,346 B2 * | 4/2003 | Crossley .................. 607/88 |
| 6,562,295 B1 | 5/2003 | Neuberger |
| 6,585,677 B2 | 7/2003 | Cowan, Jr. et al. |
| 6,667,807 B2 | 12/2003 | Lieberman |
| 6,730,113 B2 | 5/2004 | Eckhardt et al. |
| 6,743,190 B2 | 6/2004 | Connelly et al. |
| 6,750,055 B1 | 6/2004 | Connelly et al. |
| 6,764,501 B2 | 7/2004 | Ganz |
| 6,789,183 B1 | 9/2004 | Smith et al. |
| 6,793,642 B2 | 9/2004 | Connelly et al. |
| 6,802,811 B1 | 10/2004 | Slepian |
| 6,831,748 B2 | 12/2004 | Tittel et al. |
| 6,849,463 B2 | 2/2005 | Santini, Jr. et al. |
| 6,853,765 B1 | 2/2005 | Cochran |
| 6,887,202 B2 | 5/2005 | Currie et al. |
| 6,908,460 B2 | 6/2005 | DiStefano |
| 6,913,589 B2 | 7/2005 | Dextradeur et al. |
| 6,914,279 B2 | 7/2005 | Lu et al. |
| 6,918,869 B2 * | 7/2005 | Shaw et al. .................. 600/3 |
| 6,932,787 B2 | 8/2005 | Cowan et al. |
| 6,939,290 B2 | 9/2005 | Iddan |
| 6,960,201 B2 | 11/2005 | Cumbie |
| 6,969,382 B2 * | 11/2005 | Richter .................. 604/890.1 |
| 6,980,716 B1 | 12/2005 | Diaz et al. |
| 7,020,355 B2 | 3/2006 | Lahann et al. |
| 7,030,989 B2 | 4/2006 | Yager et al. |
| 7,041,130 B2 | 5/2006 | Santini, Jr. et al. |
| 7,052,488 B2 | 5/2006 | Uhland |
| 7,070,590 B1 | 7/2006 | Santini, Jr. et al. |
| 7,070,592 B2 | 7/2006 | Santini, Jr. et al. |
| 7,078,903 B2 | 7/2006 | Paliwal et al. |
| 7,116,857 B2 | 10/2006 | Faris |
| 7,117,807 B2 | 10/2006 | Bohn, Jr. et al. |
| 7,118,548 B2 | 10/2006 | Børgesen |
| 7,130,459 B2 | 10/2006 | Anderson et al. |
| 7,134,999 B2 | 11/2006 | Brauker et al. |
| 7,143,709 B2 | 12/2006 | Brennan et al. |
| 7,151,139 B2 | 12/2006 | Tiller et al. |
| 7,159,590 B2 | 1/2007 | Rife |
| 7,160,931 B2 | 1/2007 | Cheng et al. |
| 7,167,734 B2 | 1/2007 | Khalil et al. |
| 7,167,755 B2 | 1/2007 | Seeberger et al. |
| 7,183,048 B2 | 2/2007 | Felkner et al. |
| 7,195,608 B2 | 3/2007 | Burnett |
| 7,217,425 B2 | 5/2007 | Serhan et al. |
| 7,221,456 B2 | 5/2007 | Kanai et al. |
| 7,226,441 B2 | 6/2007 | Kulessa |
| 7,232,429 B2 | 6/2007 | Moreci |
| 7,236,821 B2 | 6/2007 | Cates et al. |
| 7,238,363 B2 | 7/2007 | Mansouri et al. |

(56) References Cited

U.S. PATENT DOCUMENTS

| | | |
|---|---|---|
| 7,244,232 B2 | 7/2007 | Connelly et al. |
| 7,250,615 B1 | 7/2007 | Soong et al. |
| 7,253,152 B2 | 8/2007 | Panero et al. |
| 7,276,255 B2 | 10/2007 | Selkon |
| 7,288,232 B2 | 10/2007 | Morrow et al. |
| 7,306,620 B2 | 12/2007 | Cumbie |
| 7,309,330 B2 | 12/2007 | Bertrand et al. |
| 7,310,459 B1 | 12/2007 | Rahman |
| 7,322,965 B2 | 1/2008 | Gibson et al. |
| 7,334,594 B2 | 2/2008 | Ludin |
| 7,345,372 B2 | 3/2008 | Roberts et al. |
| 7,348,021 B2 | 3/2008 | Klein |
| 7,354,575 B2 | 4/2008 | Shachar et al. |
| 7,365,859 B2 | 4/2008 | Yun et al. |
| 7,367,342 B2 | 5/2008 | Butler |
| 7,390,310 B2 | 6/2008 | McCusker et al. |
| 7,396,676 B2 | 7/2008 | Robotti et al. |
| 7,442,372 B2 | 10/2008 | Kakkis |
| 7,455,667 B2 | 11/2008 | Uhland et al. |
| 7,524,298 B2 | 4/2009 | Gharib et al. |
| 7,535,692 B2 | 5/2009 | Krupenkin et al. |
| 7,621,905 B2 | 11/2009 | Penner et al. |
| 7,650,848 B2 | 1/2010 | Brennan et al. |
| 7,691,684 B2 | 4/2010 | Breitwisch et al. |
| 7,691,894 B2 | 4/2010 | Ono et al. |
| 7,706,178 B2 | 4/2010 | Parkinson |
| 7,714,326 B2 | 5/2010 | Kim et al. |
| 7,744,555 B2 | 6/2010 | DiMauro et al. |
| 7,837,719 B2 | 11/2010 | Brogan et al. |
| 8,197,452 B2 | 6/2012 | Harding et al. |
| 8,496,610 B2 | 7/2013 | Levenson et al. |
| 2002/0030196 A1 | 3/2002 | Iwata et al. |
| 2002/0090388 A1 | 7/2002 | Humes et al. |
| 2002/0123787 A1 | 9/2002 | Weiss |
| 2002/0182262 A1 | 12/2002 | Selkon |
| 2002/0188323 A1 | 12/2002 | Penner et al. |
| 2002/0192366 A1 | 12/2002 | Cramer et al. |
| 2002/0192680 A1 | 12/2002 | Chan et al. |
| 2003/0014091 A1 | 1/2003 | Rastegar et al. |
| 2003/0017073 A1 | 1/2003 | Eckhardt et al. |
| 2003/0092996 A1 | 5/2003 | Lowe et al. |
| 2003/0109907 A1 | 6/2003 | Shadduck |
| 2003/0165702 A1 | 9/2003 | Disse et al. |
| 2003/0195415 A1 | 10/2003 | Iddan |
| 2003/0199806 A1 | 10/2003 | Kieval |
| 2003/0204163 A1 | 10/2003 | Marchitto et al. |
| 2003/0214579 A1 | 11/2003 | Iddan |
| 2003/0225331 A1 | 12/2003 | Diederich et al. |
| 2004/0022669 A1 | 2/2004 | Ruan et al. |
| 2004/0073278 A1 | 4/2004 | Pachys |
| 2004/0098005 A1 | 5/2004 | Mirza et al. |
| 2004/0098055 A1 | 5/2004 | Kroll et al. |
| 2004/0149582 A1 | 8/2004 | Kovacs |
| 2004/0186546 A1 | 9/2004 | Mandrusov et al. |
| 2004/0208940 A1 | 10/2004 | Selkon |
| 2004/0253138 A1 | 12/2004 | Malak |
| 2004/0260249 A1 | 12/2004 | Kulessa |
| 2005/0008285 A1 | 1/2005 | Kim et al. |
| 2005/0045183 A1 | 3/2005 | Callister et al. |
| 2005/0063647 A1 | 3/2005 | Thornton et al. |
| 2005/0089890 A1 | 4/2005 | Cubicciotti |
| 2005/0095351 A1 | 5/2005 | Zumeris et al. |
| 2005/0100937 A1 | 5/2005 | Holmes |
| 2005/0105077 A1 | 5/2005 | Padmanabhan et al. |
| 2005/0142157 A1 | 6/2005 | Alimi |
| 2005/0164169 A1 | 7/2005 | Malak |
| 2005/0171434 A1 | 8/2005 | Madden et al. |
| 2005/0171437 A1 | 8/2005 | Carberry |
| 2005/0175658 A1 | 8/2005 | DiMauro et al. |
| 2005/0180678 A1 | 8/2005 | Panepucci et al. |
| 2005/0192478 A1 | 9/2005 | Williams et al. |
| 2005/0196421 A1 | 9/2005 | Hunter et al. |
| 2005/0203495 A1 | 9/2005 | Malak |
| 2005/0203582 A1 | 9/2005 | Healy et al. |
| 2005/0209665 A1 | 9/2005 | Hunter et al. |
| 2005/0245557 A1 | 11/2005 | Schoenhard et al. |
| 2005/0256554 A1 | 11/2005 | Malak |
| 2005/0263386 A9 | 12/2005 | Pitts, Jr. et al. |
| 2005/0266582 A1 | 12/2005 | Modlin et al. |
| 2005/0268921 A1 | 12/2005 | Zumeris et al. |
| 2005/0272974 A1 | 12/2005 | Iddan |
| 2005/0288654 A1 | 12/2005 | Nieman et al. |
| 2006/0004317 A1 | 1/2006 | Mauge et al. |
| 2006/0004431 A1 | 1/2006 | Fuller et al. |
| 2006/0020186 A1 | 1/2006 | Brister et al. |
| 2006/0020239 A1 | 1/2006 | Geiger et al. |
| 2006/0047283 A1 | 3/2006 | Evans, III et al. |
| 2006/0047329 A1 | 3/2006 | Krespi et al. |
| 2006/0079740 A1 | 4/2006 | Silver et al. |
| 2006/0079762 A1 | 4/2006 | Norris et al. |
| 2006/0122543 A1 | 6/2006 | Mayer et al. |
| 2006/0139667 A1 | 6/2006 | Morimoto et al. |
| 2006/0140911 A1 | 6/2006 | Sharp et al. |
| 2006/0147492 A1 | 7/2006 | Hunter et al. |
| 2006/0210602 A1 | 9/2006 | Sehl et al. |
| 2006/0247525 A1 | 11/2006 | Huo et al. |
| 2006/0253259 A1 | 11/2006 | Fernandez |
| 2006/0271112 A1 | 11/2006 | Martinson et al. |
| 2006/0276713 A1 | 12/2006 | Maier |
| 2006/0287660 A1 | 12/2006 | Syed et al. |
| 2006/0289761 A1 | 12/2006 | Nabet et al. |
| 2007/0016163 A1 | 1/2007 | Santini, Jr. et al. |
| 2007/0031777 A1 | 2/2007 | Wang et al. |
| 2007/0073135 A1 | 3/2007 | Lee et al. |
| 2007/0087445 A1 | 4/2007 | Tearney et al. |
| 2007/0111201 A1 | 5/2007 | Doranz |
| 2007/0142874 A1 | 6/2007 | John |
| 2007/0156039 A1 | 7/2007 | Casciani et al. |
| 2007/0173755 A1 | 7/2007 | Alimi et al. |
| 2007/0176117 A1 | 8/2007 | Redmond et al. |
| 2007/0187626 A1 | 8/2007 | Gaska et al. |
| 2007/0196357 A1 | 8/2007 | Alimi et al. |
| 2007/0197890 A1 | 8/2007 | Boock et al. |
| 2007/0205382 A1 | 9/2007 | Gaska et al. |
| 2007/0208245 A1 | 9/2007 | Brauker et al. |
| 2007/0225634 A1 | 9/2007 | Ferren et al. |
| 2007/0225800 A1 | 9/2007 | Sahatjian et al. |
| 2007/0249969 A1 | 10/2007 | Shields, Jr. |
| 2007/0259017 A1 | 11/2007 | Francis |
| 2007/0274909 A1 | 11/2007 | Justel et al. |
| 2007/0275068 A1 | 11/2007 | Martens et al. |
| 2007/0299384 A1 | 12/2007 | Faul et al. |
| 2008/0007885 A1 | 1/2008 | Mehrl et al. |
| 2008/0014632 A1 | 1/2008 | Cunningham et al. |
| 2008/0033519 A1 | 2/2008 | Burwell et al. |
| 2008/0039678 A1 | 2/2008 | Montpetit et al. |
| 2008/0039768 A1 | 2/2008 | Francis |
| 2008/0051691 A1 | 2/2008 | Dragoon et al. |
| 2008/0051736 A1 | 2/2008 | Rioux et al. |
| 2008/0058798 A1 | 3/2008 | Wallace et al. |
| 2008/0064980 A1 | 3/2008 | Lee et al. |
| 2008/0095977 A1 | 4/2008 | Aizenberg et al. |
| 2008/0118546 A1 | 5/2008 | Thatcher et al. |
| 2008/0119421 A1 | 5/2008 | Tuszynski et al. |
| 2008/0125838 A1 | 5/2008 | Francis |
| 2008/0195170 A1 | 8/2008 | Asgari |
| 2008/0223717 A1 | 9/2008 | Isaksson et al. |
| 2008/0234786 A1 | 9/2008 | Cumbie |
| 2008/0243231 A1 | 10/2008 | Flanagan et al. |
| 2008/0248993 A1 | 10/2008 | Hannappel et al. |
| 2008/0253712 A1 | 10/2008 | Allen et al. |
| 2008/0257355 A1 | 10/2008 | Rao et al. |
| 2008/0265179 A1 | 10/2008 | Havens et al. |
| 2009/0012626 A1 | 1/2009 | Thompson et al. |
| 2009/0015841 A1 | 1/2009 | Downey |
| 2009/0018424 A1 | 1/2009 | Kamath et al. |
| 2009/0048542 A1 | 2/2009 | Varadan et al. |
| 2009/0048648 A1 | 2/2009 | Dacey, Jr. et al. |
| 2009/0054824 A1 | 2/2009 | Melsheimer et al. |
| 2009/0054827 A1 | 2/2009 | Eide |
| 2009/0066195 A1 | 3/2009 | Wang et al. |
| 2009/0110711 A1 | 4/2009 | Trollsas et al. |
| 2009/0118661 A1 | 5/2009 | Moehle et al. |
| 2009/0156460 A1 | 6/2009 | Jiang et al. |

(56) References Cited

U.S. PATENT DOCUMENTS

| | | |
|---|---|---|
| 2009/0177254 A1 | 7/2009 | Boyden et al. |
| 2009/0185988 A1 | 7/2009 | Maleski et al. |
| 2009/0195120 A1 | 8/2009 | Knospe |
| 2009/0209904 A1 | 8/2009 | Peeters |
| 2009/0281412 A1 | 11/2009 | Boyden et al. |
| 2009/0316195 A1 | 12/2009 | Tseng et al. |
| 2010/0063404 A1 | 3/2010 | Kaplan et al. |
| 2010/0145286 A1 | 6/2010 | Zhang et al. |
| 2010/0174346 A1 | 7/2010 | Boyden et al. |
| 2010/0204802 A1 | 8/2010 | Wilson et al. |
| 2010/0234792 A1 | 9/2010 | Dacey, Jr. et al. |
| 2010/0249692 A1 | 9/2010 | Dacey, Jr. et al. |
| 2010/0256607 A1 | 10/2010 | Burnett |
| 2011/0160643 A1 | 6/2011 | Dacey, Jr. et al. |

FOREIGN PATENT DOCUMENTS

| | | |
|---|---|---|
| WO | WO/92/01222 | 1/1992 |
| WO | WO/97/00586 | 1/1997 |
| WO | WO/00/09733 | 2/2000 |
| WO | WO/00/29613 | 5/2000 |
| WO | WO/00/56185 | 9/2000 |
| WO | WO/01/13926 A2 | 3/2001 |
| WO | WO/01/54704 | 8/2001 |
| WO | WO 02/068049 A1 | 9/2002 |
| WO | WO/02/102421 A2 | 12/2002 |
| WO | WO/2004/027116 A2 | 4/2004 |
| WO | WO/2004/031077 A2 | 4/2004 |
| WO | WO/2005/100100 | 10/2005 |
| WO | WO/2005/117914 A2 | 12/2005 |
| WO | WO 2006/000764 A1 | 1/2006 |
| WO | WO/2006/044324 | 4/2006 |
| WO | WO/2007/070801 A3 | 6/2007 |
| WO | WO/2007/085021 | 7/2007 |
| WO | WO 2007/140544 A1 | 12/2007 |
| WO | WO/2008/020770 A1 | 2/2008 |
| WO | WO/2008/073774 A1 | 6/2008 |
| WO | WO/2008/083390 A2 | 10/2008 |

OTHER PUBLICATIONS

European Search Report; European App. No. EP 08 83 4851; Dec. 2, 2010 (received by our Agent on Dec. 14, 2010); pp. 1-6.

European Patent Office; Extended Supplementary European Search Report; Application No. EP 09 83 0731; Dec. 18, 2012; (Received by our associate Dec. 19, 2012) ; pp. 1-3.

Apple et al.; "Review: Future Biomarkers for Detection of Ischemia and Risk Stratification in Acute Coronary Syndrome"; Clinical Chemistry; bearing a date of 2005; pp. 810-824; vol. 51, No. 5; American Association for Clinical Chemistry.

Barnes et al.; "Novel Biomarkers Associated with Deep Venous Thrombosis: A Comprehensive Review"; Biomarker Insights; bearing a date of 2008; pp. 93-100; vol. 3; Creative Commons Attribution.

Beebe et al.; "Nanosecond, High-Intensity Pulsed Electric Fields Induce Apoptosis in Human Cells"; The FASEB Journal; bearing a date of Jun. 17, 2003; pp. 1-23.

Cheng et al.; "Electrically Switchable and Optically Rewritable Reflective Fresnel Zone Plate in Dye-Doped Cholesteric Liquid Crystals"; Optics Express; bearing a date of Oct. 17, 2007; pp. 14078-14085; vol. 15, No. 21; OSA.

Coppola et al.; "Visualization of Optical Deflection and Switching Operations by a Domain-Engineered-Based $LinbO_3$ Electro-Optic Device"; Optics Express; bearing a date of May 19, 2003; vol. 11, No. 10; OSA.

Davis et al.; "A New Electro-Optic Waveguide Architecture and the Unprecedented Devices it Enables"; Proc. of SPIE; bearing a date of 2008; pp. 697503-1-697503-12; vol. 6975.

Frasca et al.; "Review: Prevention of Central Venous Catheter-Related Infection in the Intensive Care Unit"; Critical Care; bearing a date of 2010; pp. 1-8; vol. 14, No. 212; Springer-Verlag Berlin Heidelberg.

Feng et al.; "Plasmonic Effects in Dynamic Tunable Metal-Dielectric Composites"; PIERS Online; bearing a date of 2008; pp. 625-630; vol. 4, No. 6.

Giannitsis et al.; "Risk Stratification in Pulmonary Embolism Based on Biomarkers and Echocardiography"; Circulation: Journal of the American Heart Association; bearing a date of 2005; pp. 1520-1521; American Heart Association; located at: http://circ.ahajournals.org/cgi/content/full/112/11/1520.

Hall et al.; "Nanosecond Pulsed Electric Fields Induce Apoptosis in p53-wildtype and p53-null HCT116 Colon Carcinoma Cells"; Apoptosis; bearing a date of May 23, 2007; pp. 1721-1731; vol. 12; Springer Science+Business Media, LLC.

Horng et al.; "Tunable Optical Switch Using Magnetic Fluids"; Applied Physics Letters; bearing a date of Dec. 6, 2004; pp. 5592-5594; vol. 85, No. 23; American Institute of Physics.

Jaffer et al.; "In Vivo Imaging of Thrombin Activity in Experimental Thrombi with Thrombin-Sensitive Near-Infrared Molecular Probe"; Arteriosclerosis, Thrombosis, and Vascular Biology: Journal of the American Heart Association; bearing a date of Aug. 8, 2002; pp. 1929-1935; American Heart Association, Inc.; located at: http://atvb.ahajournals.org/cgi/content/full/22/11/1929.

Jaiswal et al.; "Long-Term Multiple Color Imaging of Live Cells Using Quantum Dot Bioconjugates"; Nature Biotechnology; bearing a date of Jan. 2003; pp. 47-51; vol. 21; Nature Publishing Group.

Kamphuisen et al.; "Can Anticoagulant Treatment be Tailored with Biomarkers in Patients with Venous Thromboembolism?"; Journal of Thrombosis and Haemostasis; bearing a date of 2006; pp. 1206-1207; vol. 4; International Society on Thrombosis and Haemostasis.

Krupenkin et al.; "Electrically Tunable Superhydrophobic Nanostructured Surfaces"; Bell Labs Technical Journal; bearing a date of 2005; pp. 161-170; vol. 10, No. 3; Lucent Technologies Inc.

Li et al.; "Feasibility of Interstitial Doppler Optical Coherence Tomography for In Vivo Detection of Microvascular Changes During Photodynamic Therapy"; Lasers in Surgery and Medicine; bearing a date of Jul. 2, 2006; pp. 754-761; vol. 38; Wiley-Liss Inc.

Liou et al.; "An ASIC Control Circuit for Thermal Actuated Large Optical Packet Switch Array"; Proceedings of the World Congress of Engineering; bearing a date of Jul. 2-4, 2008; pp. 1-6; vol. I; WCE.

Olcum et al.; "Tunable Surface Plasmon Resonance on an Elastomeric Substrate"; Optics Express; bearing a date of May 11, 2009; pp. 8542-8547; vol. 17, No. 10; OSA.

Piccolo et al.; "Antifuse Injectors for SOI LEDs"; printed in 2009; pp. 573-575.

Reynolds et al.; "Early Biomarkers of Stroke"; Clinical Chemistry: Oak Ridge Conference; bearing a date of Apr. 7, 2003; pp. 1733-1739; vol. 49, No. 10; American Association for Clinical Chemistry.

Rosalki et al.; "Cardiac Biomarkers for Detection of Myocardial Infarction: Perspectives from Past to Present"; Clinical Chemistry; bearing a date of Aug. 17, 2004; pp. 2205-2213; vol. 50, No. 11; American Association for Clinical Chemistry.

Shackleford et al.; "Integrated Plasmonic Iens Photodetector"; Applied Physics Letters; bearing a date of Nov. 24, 2008; pp. 1-3; vol. 94, No. 083501; American Institute of Physics.

Smith et al.; "Evanescent Wave Imaging in Optical Lithography"; printed on Dec. 10, 2010; pp. 1-9.

Spori et al.; "Cassie-State Wetting Investigated by Means of a Hole-to-Pillar Density Gradient"; Langmuir Article; bearing a date Dec. 15, 2009; pp. 9465-9473; vol. 26, No. 12; American Chemical Society.

Thai et al.; "Development of a Fully-Integrated Ultrasensitive Wireless Sensor Utilizing Carbon Nanotubes and Surface Plasmon Theory"; Electronic Components and Technology Conference; bearing a date of 2008; pp. 436-439; IEEE.

Timko et al.; "Remotely Triggerable Drug Delivery Systems"; Advanced Materials; bearing a date of Jun. 4, 2010; pp. 4925-4943; vol. 22; Wiley-VCH Verlag GmbH&Co.

Tsutsui et al.; "Research: The use of Microbubbles to Target Drug Delivery"; BioMed Central-Open Access; bearing a date of Aug. 17, 2004; pp. 1-7; vol. 2, No. 23; BioMed Central Ltd.

Vàzquez et al.; "Optical Router for Optical Fiber Sensor Networks Based on a Liquid Crystal Cell"; IEEE Sensors Journal; bearing a date of Aug. 2003; pp. 513-518; vol. 3, No. 4; IEEE.

(56) References Cited

OTHER PUBLICATIONS

Wang et al.; "Effective in Plane Launching and Focusing Surface Plasmons by a Plasmonic Lens"; OSA; bearing a date of 2009; pp. 1-2; IEEE.

Yang et al.; "Polyimide-Waveguide-Based Thermal Optical Switch Using Total-Internal-Reflection Effect"; Applied Physics Letters; bearing a date of Oct. 14, 2002; pp. 2947-2949; vol. 81, No. 16; American Institute of Physics.

European Patent Office; Extended European Search Report; App. No. EP 10 74 6554; Apr. 5, 2013 (received by our agent on Apr. 8, 2013); 8 pages (1 cover page, 1 supplementary European search report, 6 European search opinion pages).

McCarthy et al.; "Steroid Modulation of Astrocytes in the Neonatal Brain: Implications for Adult Reproductive Function"; Biology of Reproduction; bearing a date of Apr. 5, 2002; pp. 691-698; vol. 67; Society for the Study of Reproduction, Inc.

Dienel et al.; Astrocyte activation in vivo during graded photic stimulation ; Journal of Neurochemistry; bearing a date of 2007; pp. 1506-1522; vol. 103; International Society for Neurochemistry.

PCT International Search Report; International App. No. PCT/US11/01883; May 3, 2012; pp. 1-5.

Elmore, Susan; "Apoptosis: A Review of Programmed Cell Death"; Toxicol Pathology; Dec. 6, 2007; pp. 495-516 (pp. 1-40 as provided); vol. 35, No. 4; National Institute of Health.

U.S. Appl. No. 12/218,214, Hyde et al.
U.S. Appl. No. 12/231,676, Hyde et al.
U.S. Appl. No. 11/973,010, Hyde et al.
U.S. Appl. No. 11/973,367, Hyde et al.
U.S. Appl. No. 11/973,357, Hyde et al.

Albert, Richard K. and Condie, Frances; "Medical Intelligence: Hand-Washing Patterns in Medical Intensive-Care Units"; New England Journal of Medicine; Jun. 1981; pp. 1465-1466; vol. 304, No. 24.

Aarabi, Shahram et al.; "Research in Translation: Hypertrophic Scar Formation Following Burns and Trauma: New Approaches to Treatment"; PLoS Medicine; Sep. 2007; pp. 1464-1470; vol. 4, Issue 9, No. e234; located at: www.plosmedicine.org.

Abdollahi, Amir; "Apoptosis Signals in Lymphoblasts Induced by Focused Ultrasound"; The FASEB Journal-FJ Express; Sep. 2004; pp. 1413-1414; vol. 18; FASEB.

"Arglaes® Controlled-Release Silver Technology"; Medline; 2003; 6 pages; Medline Industries, Inc.; located at: www.medline.com.

Ashush, Hagit et al.; "Apoptosis Induction of Human Myeloid Leukemic Cells by Ultrasound Exposure"; Cancer Research; bearing a date of Feb. 15, 2000; pp. 1014-1020; vol. 60.

Bozhevolnyi, Sergey I. et al.; "Photonic bandgap structures for long-range surface plasmon polaritons"; Optics Communications; bearing a date of 2005; pp. 328-333; vol. 250; Elsevier B.V.

Brogden, Kim A.; "Antimicrobial Peptides: Pore Formers or Metabolic Inhibitors in Bacteria?"; Nature Reviews , Microbiology; Mar. 2005; pp. 238-250; vol. 3.

Carcillo, Joseph A. et al.; "Early Markers of Infection and Sepsis in Newborns and Children"; Leading Article, Advances in Sepsis; 2006; pp. 118-125; vol. 5, No. 4.

Caricchio, Roberto et al.; "Ultraviolet B Radiation-Induced Cell Death: Critical Role of Ultraviolet Dose in Inflammation and Lupus Autoantigen Redistribution"; The Journal of Immunology; 2003; pp. 5778-5786; vol. 171; The American Association of Immunologists, Inc.

Chen, Ting-Hsuan et al.; "A Wettability Switchable Surface Driven by Electrostatic Induced Surface Morphology Change Without Energy Interference on Reagents in Droplets"; MEMS; Jan. 2006; pp. 178-181; IEEE.

Cheng, Gang et al.; "Switchable Polymer Surfaces: A Switchable Biocompatible Polymer Surface with Self-Sterilizing and Nonfouling Capabilities"; Angewandte Chemie; 2008; pp. 8831-8834; vol. 47; Wiley-VCH Verlag GmbH & Co.

De Fabo, Edward C.; "Advances in Brief: Ultraviolet B but not Ultraviolet A Radiation Initiates Melanoma"; Cancer Research; bearing a date of Sep. 15, 2004; pp. 6372-6376; vol. 64; American Association for Cancer Research.

Donlan, R. M. et al.; "Model Systems for Growing and Quantifying *Streptococcus pneumoniae* Biofilms In Situ and in Real Time"; Applied and Environmental Microbiology; Aug. 2004; pp. 4980-4988; vol. 70, No. 8; American Society for Microbiology.

Dubinsky et al.; "High-Intensity Focused Ultrasound: Current Potential and Oncologic Applications"; Ultrasound Imaging-Review, AJR; bearing a date of Jan. 2008; pp. 191-199; vol. 190; American Roentgen Ray Society.

ESR European Search Report; European App. No. EP 08 25 1153; Dec. 15, 2008; p. 1.

European Search Report; European App. No. EP 08 25 1153; Jul. 10, 2009; pp. 1-2.

"Fact Sheet: Cerebrospinal Fluid Shunt Systems for the Management of Hydrocephalus"; Hydrocephalus Association; 2000; 7 pages; Hydrocephalus Association; located at: www.hydroassoc.org.

Feng, Xinjian et al.; "Reversible Super-Hydrophobicity to Super-Hydrophilicity Transition of Aligned ZnO Nanorod Films"; JACS Communications; 2004; pp. 62-63; vol. 126; American Chemical Society.

Feng, Yi et al.; "Gastric Cancer: Low Intensity Ultrasound-Induced Apoptosis in Human Gastric Carcinoma Cells"; World Journal of Gastroenterology; bearing a date of Aug. 21, 2008; pp. 4873-4879; vol. 14, No. 31; The WJG Press; located at: www.wjgnet.com.

Fogh-Andersen, Niels et al.; "Composition of Interstitial Fluid"; General Clinical Chemistry; 1995; pp. 1522-1525; vol. 41, No. 10.

Forbes, Peter; "Scientific American: Self-Cleaning Materials: Lotus Leaf-Inspired Nanotechnology"; Scientific American Magazine; bearing a date of Jul. 30, 2008; pp. 1-5; printed on Nov. 21, 2008.

Goclawski, Jaroslaw et al.; "The Measurement of Wetting Angle by Applying and ADSA Model of Sessile Drop on Selected Textile Surfaces"; Fibres and Textiles in Eastern Europe; Apr./Jun. 2008; pp. 84-88; vol. 16, No. 2(67).

Gavrieli et al.; "Identification of Programmed Cell Death in situ via Specific Labeling of Nuclear DNA Fragmentation"; The Journal of Cell Biology; bearing a date of Nov. 1992; pp. 493-501; vol. 119, No. 3; The Rockefeller University Press; located at: http://jcb.rupress.org/.

Grunfeld, Carl; "Lipids, Lipoproteins, Triglyceride Clearance, and Cytokines in Human Immunodeficiency Virus Infection and the Acquired Immunodeficiency Syndrome"; Journal of Clinical Endocrinology and Metabolism; 1992; pp. 1045-1052; vol. 74, No. 5; The Endocrine Society.

Harmon et al.; "Cell Death Induced in a Murine Mastocytoma by 42-47° C. Heating in vitro: Evidence that the Form of Death Changes From Apoptosis to Necrosis Above a Critical Heat Load"; Int. J. Radiat. Biol., Rights Links; 1990; pp. 845-858; vol. 58, No. 5; Taylor & Francis Ltd.

Imam, S.K. et al.; "Radiotracers for Imaging of Infection and Inflammation—A Review"; World Journal Nuclear Medicine.; Jan. 2006; pp. 40-55; vol. 5, No. 1.

"Introduction to ORP as the Standard of Postharvest Water Disinfection Monitoring"; UC Davis, Vegetable Research and Information Center; pp. 1-4; 2005.

Khan et al.; "The Effect of Hyperthermia on the Induction of Cell Death in Brain, Testis, and Thymus of the Adult and Developing Rat"; Cell Stress & Chaperones; 2002; pp. 73-90; vol. 7, No. 1; Cell Stress Society International.

Killer, H. E. et al.; "The Optic Nerve: A New Window into Cerebrospinal Fluid Composition?"; Brain; 2006; pp. 1027-1030; vol. 129.

Lahann, Joerg; "A Reversibly Switching Surface"; Reports, Science; bearing a date of Jan. 17, 2003; pp. 371-374 (plus Erratum); vol. 299; located at: www.sciencemag.org.

Lepock, James R.; "Cellular Effects of Hyperthermia: Relevance to the Minimum Dose for Thermal Damage"; International Journal of Hyperthermia, Taylor & Francis healthsciences; May-Jun. 2003; pp. 252-266; vol. 19, No. 3; Taylor & Francis Ltd.

(56) References Cited

OTHER PUBLICATIONS

Lin, Yi-Hsin; "Electrically Tunable Wettability of Liquid Crystal/Polymer Composite Films"; Optics Express; bearing a date of Oct. 27, 2008; pp. 17591-17598; vol. 16, No. 22; OSA.

Masteikova, Ruta et al.; "Stimuli-Sensitive Hydrogels in Controlled and Sustained Drug Delivery"; Medicina; 2003; pp. 19-24; vol. 39, No. 2.

McDannold et al.; "Microbubble Contrast Agent with Focused Ultrasound to Create Brain Lesions at Low Power Levels: MR Imaging and Histologic Study in Rabbits[1]"; Original Research, Experimental Studies, Radiology; bearing a date of Oct. 2006; pp. 95-106; vol. 241, No. 1; RSNA.

McKenna, Susan M. et al.; "The Inhibition of Bacterial Growth by Hypochlorous Acid"; Biochemistry; 1988; pp. 685-692; vol. 254.

Nejat, Farideh et al.; "Original Article: A Randomized Trial of Ceftriaxone Versus Trimethoprimsulfamethoxazole to Prevent Ventriculoperitoneal Shunt Infection"; Journal of Microbiology, Immunology and Infection; 2008; pp. 112-117; vol. 41; Journal of Microbiology, Immunology and Infection.

NG, P C; "Review: Diagnostic Markers of Infection in Neonates"; Arch Dis Child Fetal Neonatal Ed; 2004; pp. F229-F235; vol. 89; located at: www.archdischild.com.

Okada, Ayako et al.; "Inhibition of Biofilm Formation Using Newly Developed Coating Materials with Self-Cleaning Properties"; Dental Materials Journal; 2008; pp. 565-572; vol. 27, No. 4.

PCT International Search Report; International App. No. PCT/US10/00579; May 3, 2010; pp. 1-2.

PCT International Search Report; International App. No. PCT/US09/06393; May 13, 2010; pp. 1-4.

Piper, Kerryl E. et al.; "MIST Ultrasound Therapy Device Removal of In Vitro Bacterial Biofilms"; Mayo Clinic; 2005.

Rathmell, James P. et al.; "Infectious Risks of Chronic Pain Treatments: Injection Therapy, Surgical Implants, and Intradiscal Techniques"; Regional Anesthesia and Pain Medicine; 2006; pp. 346-352; vol. 31, No. 4.

Rediske, Andrea M. et al.; "Pulsed Ultrasound Enhances the Killing of *Escherichia coli* Biofilms by Aminoglycoside Antibiotics In Vivo"; Antimicrobial Agents and Chemotherapy; Mar. 2000; pp. 771-772; vol. 44, No. 3; American Society for Microbiology; downloaded on Aug. 24, 2009.

Reid, Marvin et al.; "The Acute-Phase Protein Response to Infection in Edematous and Nonedematous Protein-Energy Malnutrition"; The American Journal of Clinical Nutrition; 2002; pp. 1409-1415; vol. 76; American Society for Clinical Nutrition.

Roti Roti, Joseph L.; "Review: Cellular Responses to Hyperthermia (40-46° C.): Cell Killing and Molecular Events"; Informa healthcare; Feb. 2008; pp. 3-15; vol. 24, No. 1; Informa UK Ltd.

Seehusen, Dean A. et al.; "Cerebrospinal Fluid Analysis"; American Family Physician; bearing a date of Sep. 15, 2003; pp. 1103-1108; vol. 68, No. 6; located at: www.aafg.org/afp.

Setroikromo, R.; "Heat Shock Proteins and Bcl-2 Expression and Function in Relation to the Differential Hyperthermic Sensitivity between Leukemic and Normal Hematopoietic Cells"; Cell Stress & Chaperones; 2007; pp. 320-330; vol. 12, No. 4; Cell Stress Society International.

Shellman et al.; "Hyperthermia Induces Endoplasmic Reticulum-Mediated Apoptosis in Melanoma and Non-Melanoma Skin Cancer Cells" Original Article, Journal of Investigative Dermatology; 2008; pp. 949-956; vol. 128; The Society of Investigative Dermatology; located at: www.jidonline.org.

"SilvaSorb® Targeted Antimicrobial Protection"; Medline; 2005; 16 pages; Medline Industries Inc.; located at www.medline.com.

Sodja, Caroline; "Splenic T Lymphocytes Die Preferentially During Heat-Induced Apoptosis: NuMA Reorganization as a Marker"; Journal of Cell Science; 1998; pp. 2305-2313; vol. 111; The Company of Biologists Limited.

Somwaru et al.; "Heat Induced Apoptosis of Mouse Meiotic Cells is Suppressed by Ectopic Expression of Testis-Specific Calpastatin"; Journal of Andrology; bearing a date of Jul./Aug. 2004; pp. 506-513; vol. 25, No. 4; American Society of Andrology.

Stankiewicz, Adam R.; "Hsp70 Inhibits Heat-Induced Apoptosis Upstream of Mitochondria by Preventing Bax Translocation"; The Journal of Biological Chemistry; Bearing a date of Nov. 18, 2005; pp. 38729-38739; vol. 280, No. 46; The American Society for Biochemistry and Molecular Biology, Inc.

"Study E: Comparison of the Moisture Uptake and Retention Properties of Biopatch® and SilvaSorb Site®"; 2 pages; 2005.

Tuteja, Anish et al.; "Robust Omniphobic Surfaces"; PNAS; bearing a date of Nov. 25, 2008; pp. 18200-18205; vol. 105, No. 47; The National Academy of Sciences of the USA.

Vykhodtseva et al.; "Induction of Apoptosis in vivo in the Rabbit Brain with Focused Ultrasound and Optison®"; Original Contribution, Ultrasound in Med. & Biol.; 2006; pp. 1923-1929; vol. 32, No. 12; World Federation for Ultrasound in Medicine & Biology.

Wang, Shutao; "Review: Photoresponsive Surfaces with Controllable Wettability"; Journal of Photochemistry and Photobiology C: Photochemistry Review, Science Direct; 2007; pp. 18-29; vol. 8; Elsevier B.V.

Wang, Zhe et al.; "APD: The Antimicrobial Peptide Database"; Nucleic Acids Research; 2004; pp. D590-D592; vol. 32; Oxford University Press.

Watson, Mark A.; "Review: Clinical Utility of Biochemical Analysis of Cerebrospinal Fluid"; Clinical Chemistry; 1995; pp. 343-360; vol. 41, No. 3.

Wentworth, Jr., Paul et al.; "Reports: Evidence for Antibody-Catalyzed Ozone Formation in Bacterial Killing and Inflammation"; Science AAAS; 2002; pp. 2195-2199; vol. 298; downloaded on Jul. 14, 2009; located at: www.sciencemag.org.

Zhong, Yinghui et al.; "Review: Biomaterials for the Central Nervous System"; Journal of the Royal Society Interface; 2008; pp. 957-975; vol. 5; The Royal Society.

Hashimoto et al.; "$TiO_2$ Photocatalysis: A Historical Overview and Future Prospects"; Japanese Journal of Applied Physics; bearing a date of 2005 published Dec. 8, 2005; pp. 8269-8285; vol. 44, No. 12; The Japan Society of Applied Physics.

Gal'China et al., "Electroluminescence Spectra of Ultraviolet Light-Emitting Diodes Based on *p-n*-Heterostructures Coated with Phosphors"; Semiconductors; bearing a date of 2007; pp. 1126-11311; vol. 41, No. 9; Pleiades Publishing Ltd.; ISSN 1063-7826.

Kim et al.; "Realization of p-type ZnO thin films via phosphorus doping and thermal activation of the dopant"; Applied Physics Letters; bearing a date of Jul. 7, 2003; pp. 63-65; vol. 83, No. 1; American Institute of Physics.

Könenkamp et al.; "Ultraviolet Electrolumiscence from ZnO/Polymer Heterojunction Light-Emitting Diodes"; Nano Letters; bearing a date of 2005; pp. 2005-2008; vol. 5, No. 10; American Chemical Society.

Li et al.; "Ultraviolet nanophosphors"; Journal of Luminescence; bearing a date of 2007; pp. 345-347; vol. 122-123; Elsevier B.V.

Lim et al.; "UV Electroluminescence Emission from ZnO Light-Emitting Diodes Grown by High-Temperatures Radiofrequencey Sputtering"; Advanced Materials; bearing a date of 2006; pp. 2720-2724; vol. 18; Wiley-VCH Verlag GmbH & Co.

Sun et al.; "Realization of ultraviolet electroluminescence from ZnO homojunction with n-ZnO/p-ZnO:As/GaAs structure"; Applied Physics Letters; bearing a date of 2007; pp. 121128-1-121128-3; vol. 90; American Institute of Physics.

Tang et al.; "Cerium Phosphate Nanotubes: Synthesis, Valence State, and Optical Properties"; Angew. Chem. Int. Ed.; bearing a date of 2005; pp. 576-579; vol. 44; Wiley-VCH Verlag GmbH.

Zhang et al.; "Milliwatt power deep ultraviolet light-emitting diodes over sapphire with emission at 278 nm"; Applied Physics Letters; bearing a date of Dec. 23, 2002; pp. 4910-4912; vol. 81, No. 26; American Institute of Physics.

\* cited by examiner

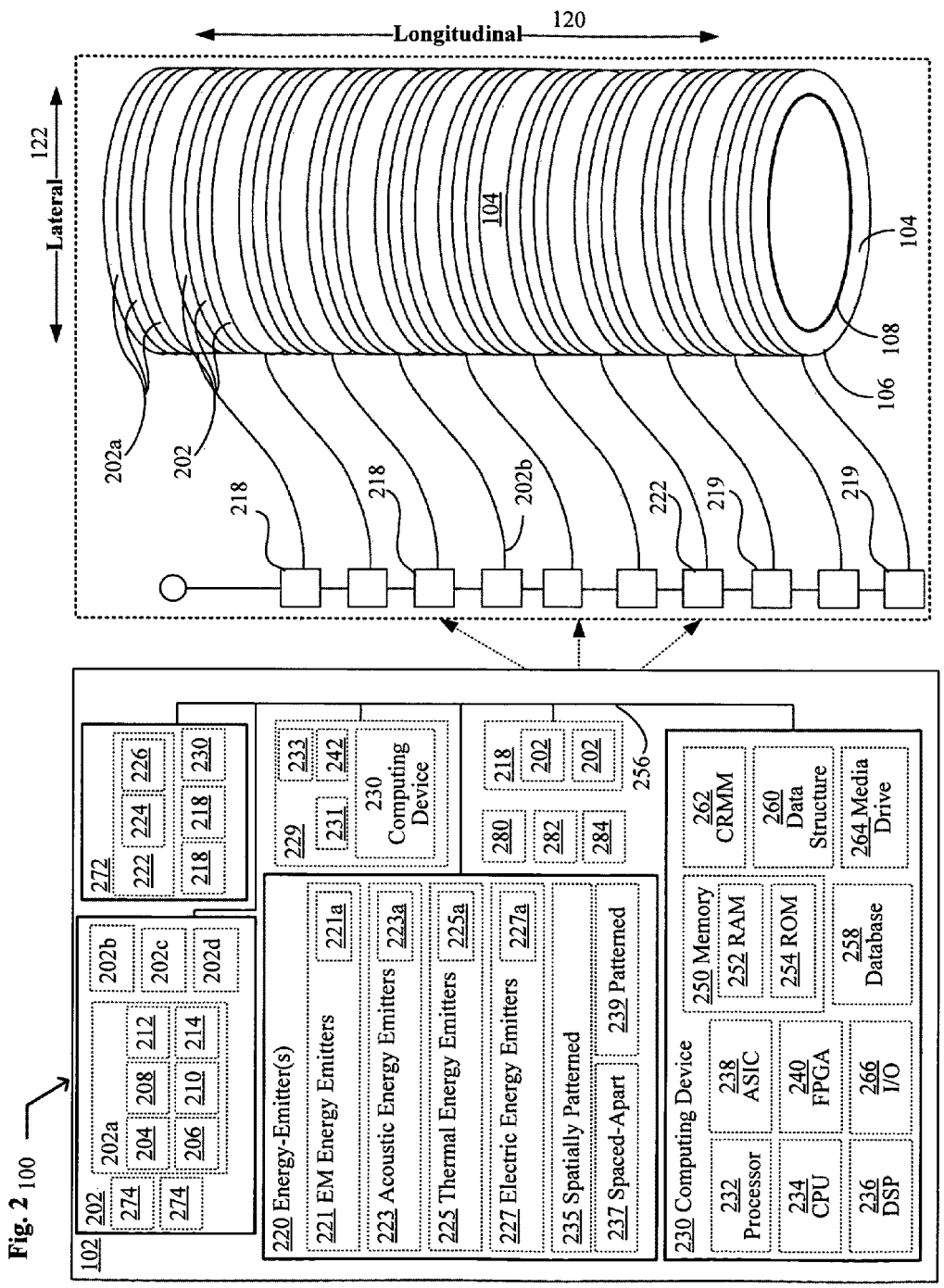

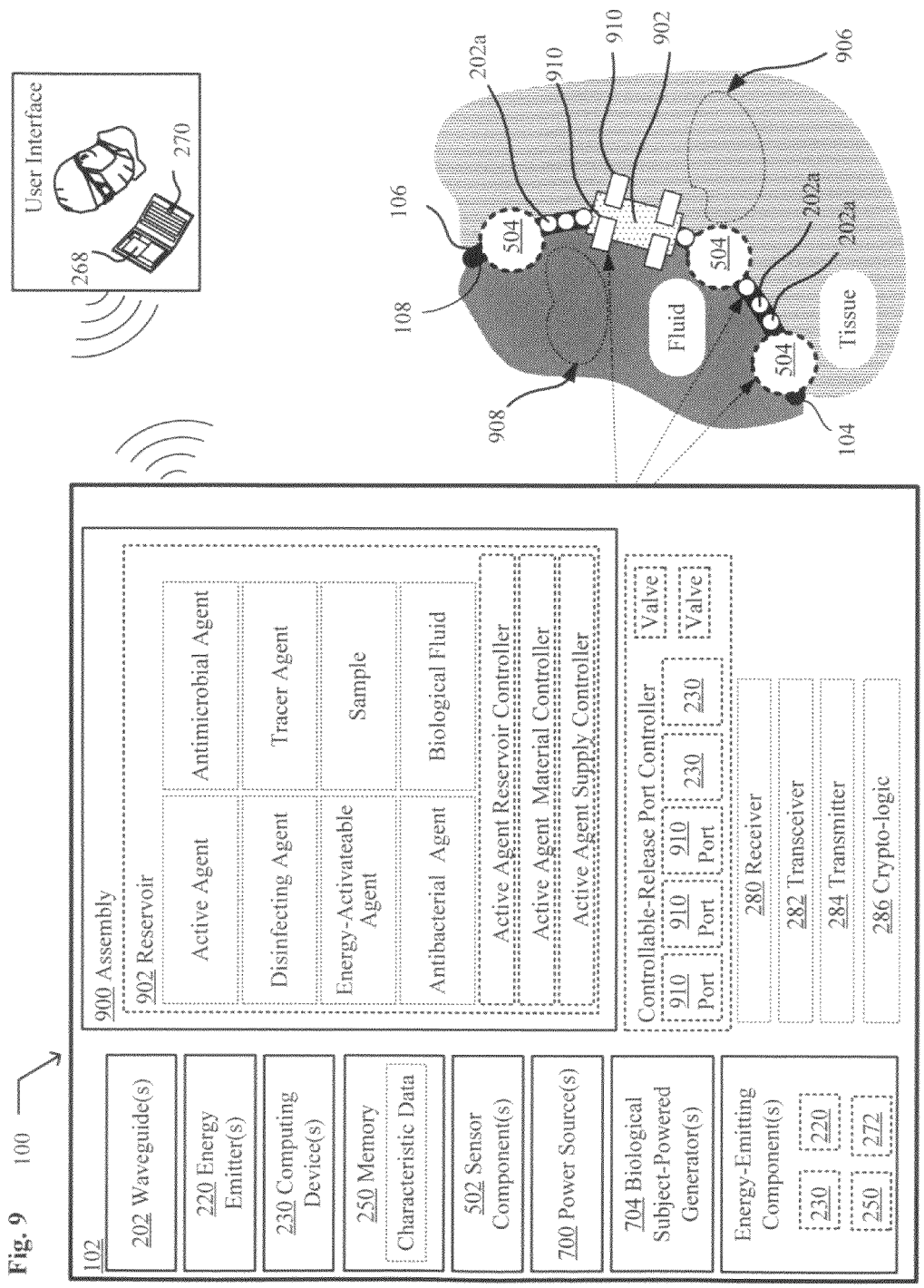

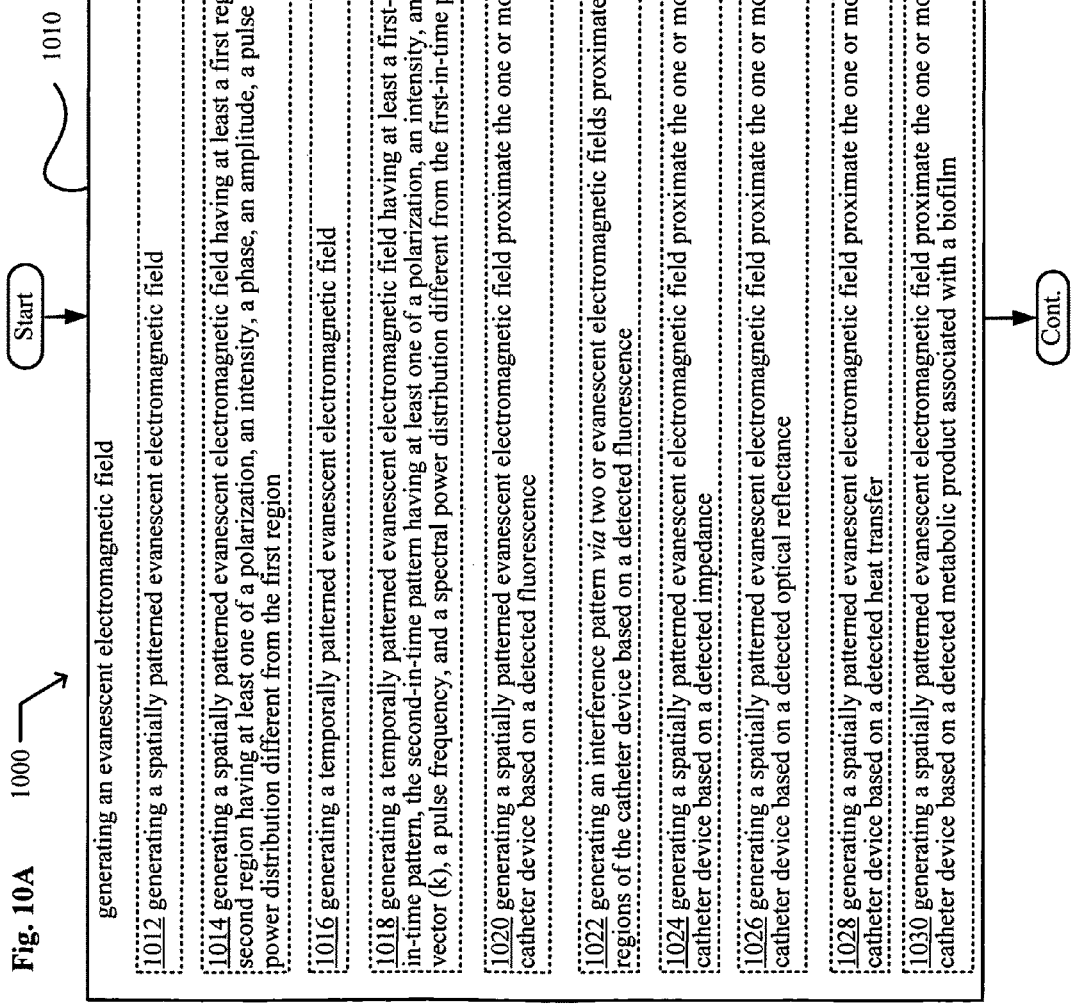

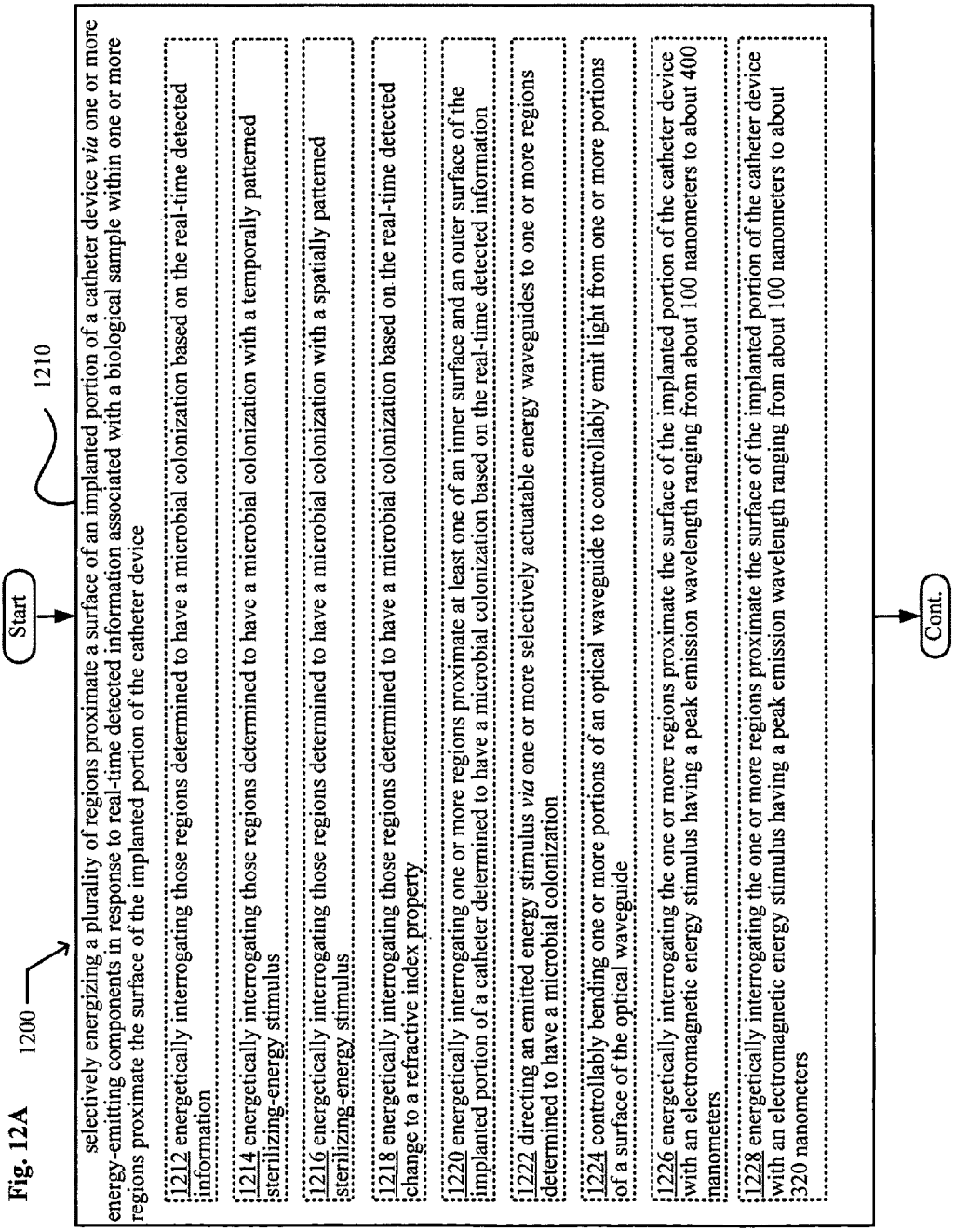

Fig. 12A 1200

1210 selectively energizing a plurality of regions proximate a surface of an implanted portion of a catheter device *via* one or more energy-emitting components in response to real-time detected information associated with a biological sample within one or more regions proximate the surface of the implanted portion of the catheter device 1212 energetically interrogating those regions determined to have a microbial colonization based on the real-time detected information 1214 energetically interrogating those regions determined to have a microbial colonization with a temporally patterned sterilizing-energy stimulus 1216 energetically interrogating those regions determined to have a microbial colonization with a spatially patterned sterilizing-energy stimulus 1218 energetically interrogating those regions determined to have a microbial colonization based on the real-time detected change to a refractive index property 1220 energetically interrogating one or more regions proximate at least one of an inner surface and an outer surface of the implanted portion of a catheter determined to have a microbial colonization based on the real-time detected information 1222 directing an emitted energy stimulus *via* one or more selectively actuatable energy waveguides to one or more regions determined to have a microbial colonization 1224 controllably bending one or more portions of an optical waveguide to controllably emit light from one or more portions of a surface of the optical waveguide 1226 energetically interrogating the one or more regions proximate the surface of the implanted portion of the catheter device with an electromagnetic energy stimulus having a peak emission wavelength ranging from about 100 nanometers to about 400 nanometers 1228 energetically interrogating the one or more regions proximate the surface of the implanted portion of the catheter device with an electromagnetic energy stimulus having a peak emission wavelength ranging from about 100 nanometers to about 320 nanometers Cont.

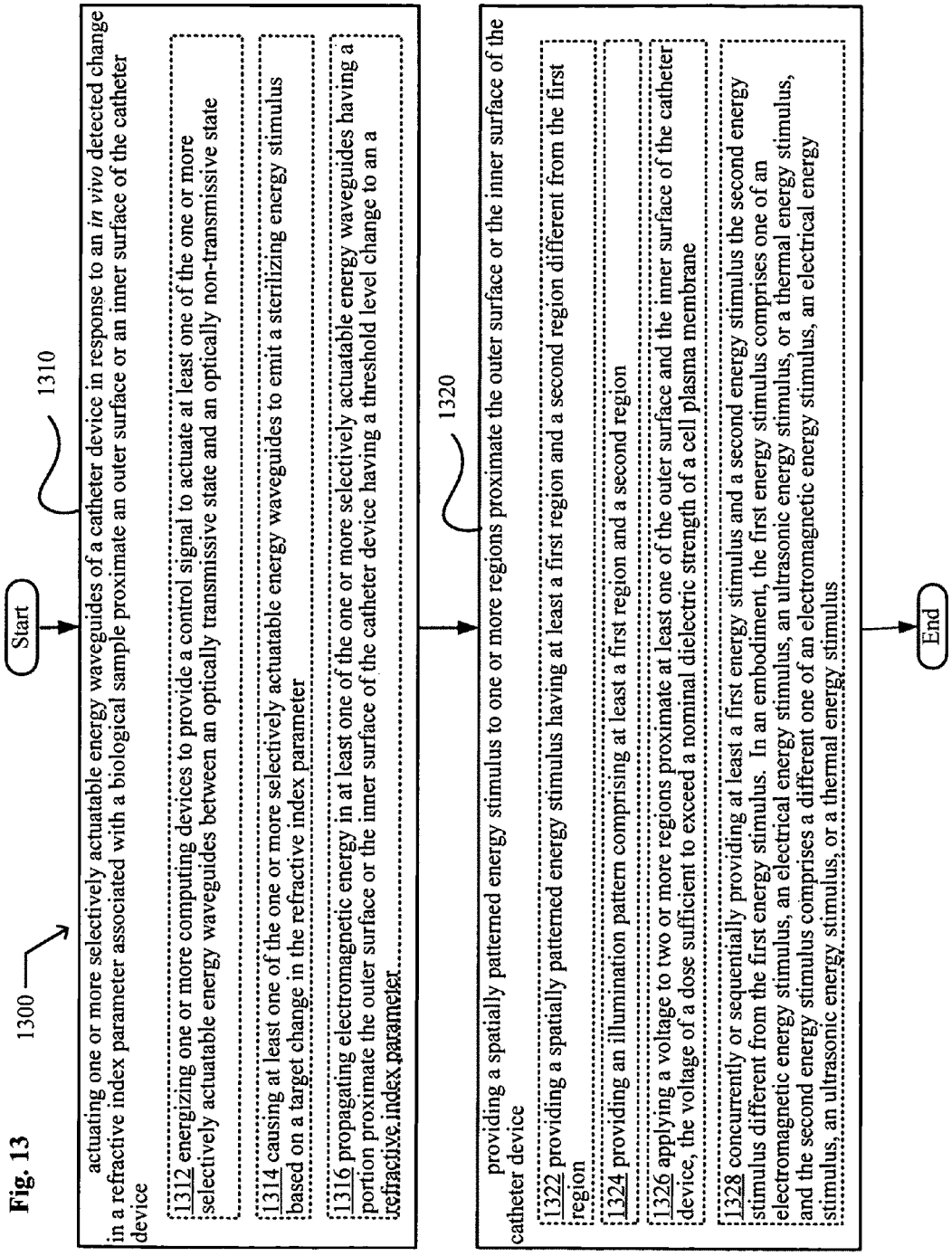

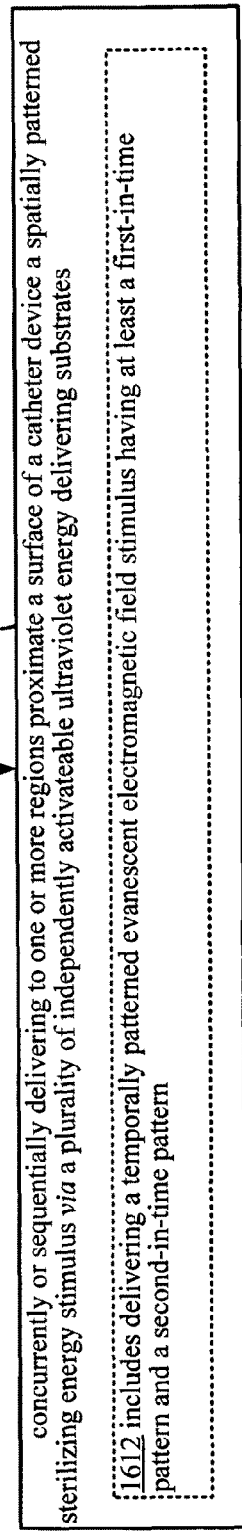

Fig. 16 1600

1610: concurrently or sequentially delivering to one or more regions proximate a surface of a catheter device a spatially patterned sterilizing energy stimulus via a plurality of independently activateable ultraviolet energy delivering substrates 1612 includes delivering a temporally patterned evanescent electromagnetic field stimulus having at least a first-in-time pattern and a second-in-time pattern

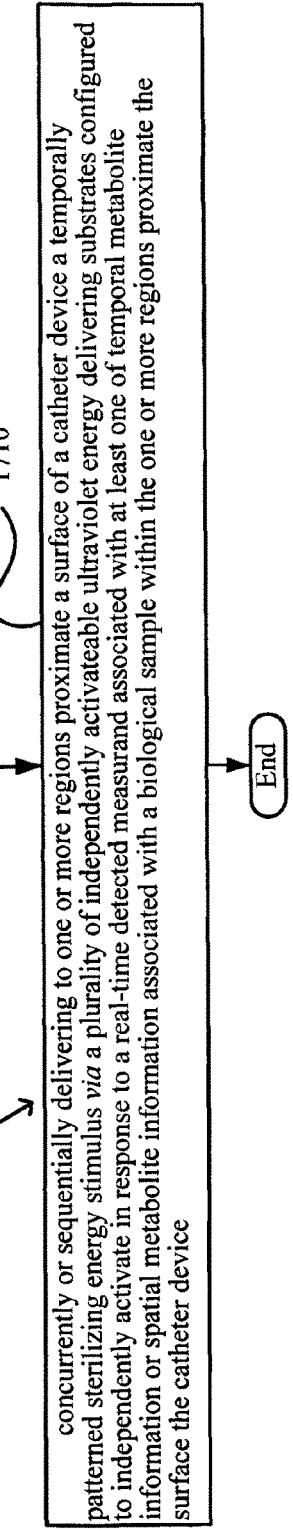

Fig. 17 1700

1710: concurrently or sequentially delivering to one or more regions proximate a surface of a catheter device a temporally patterned sterilizing energy stimulus via a plurality of independently activateable ultraviolet energy delivering substrates configured to independently activate in response to a real-time detected measurand associated with at least one of temporal metabolite information or spatial metabolite information associated with a biological sample within the one or more regions proximate the surface the catheter device

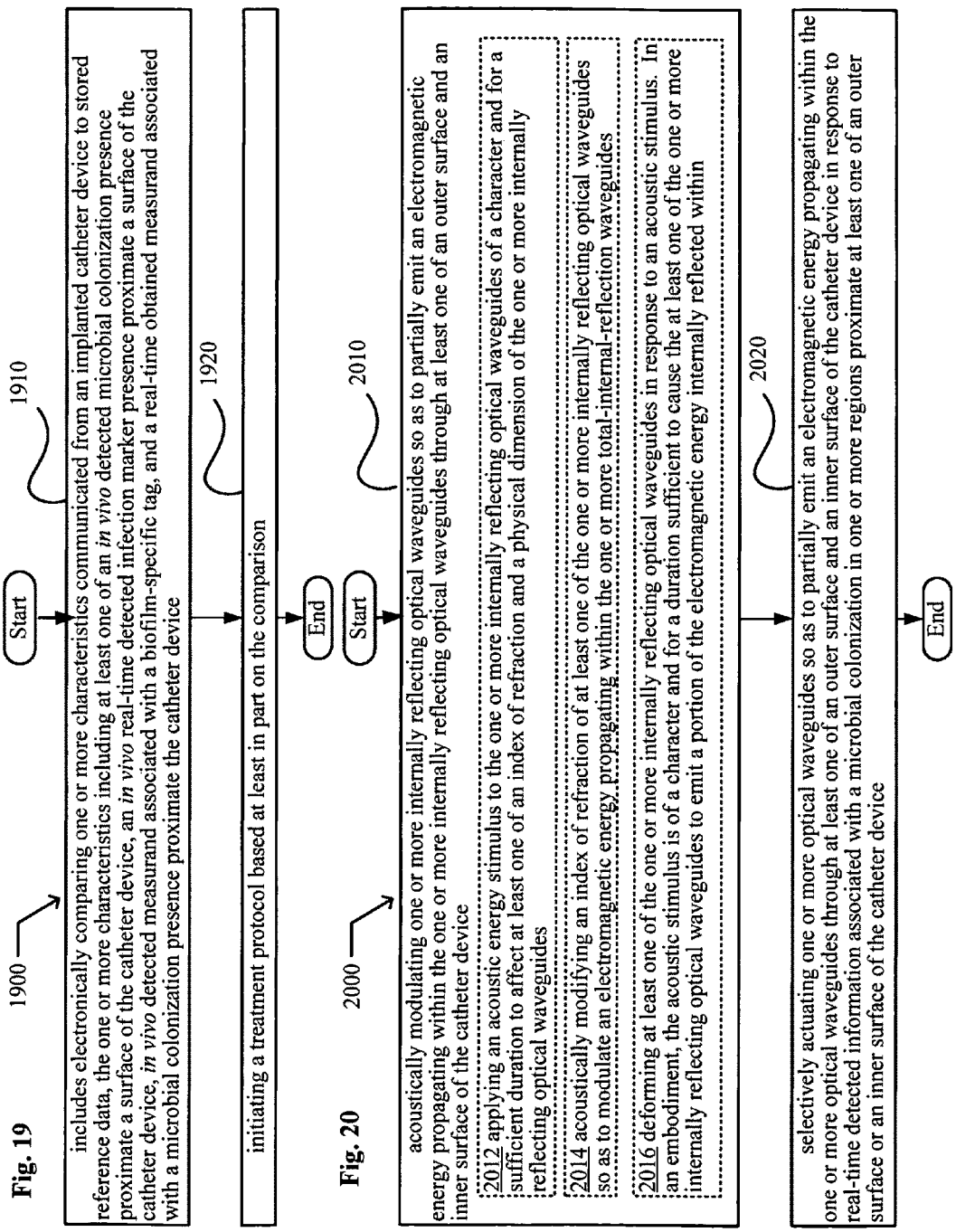

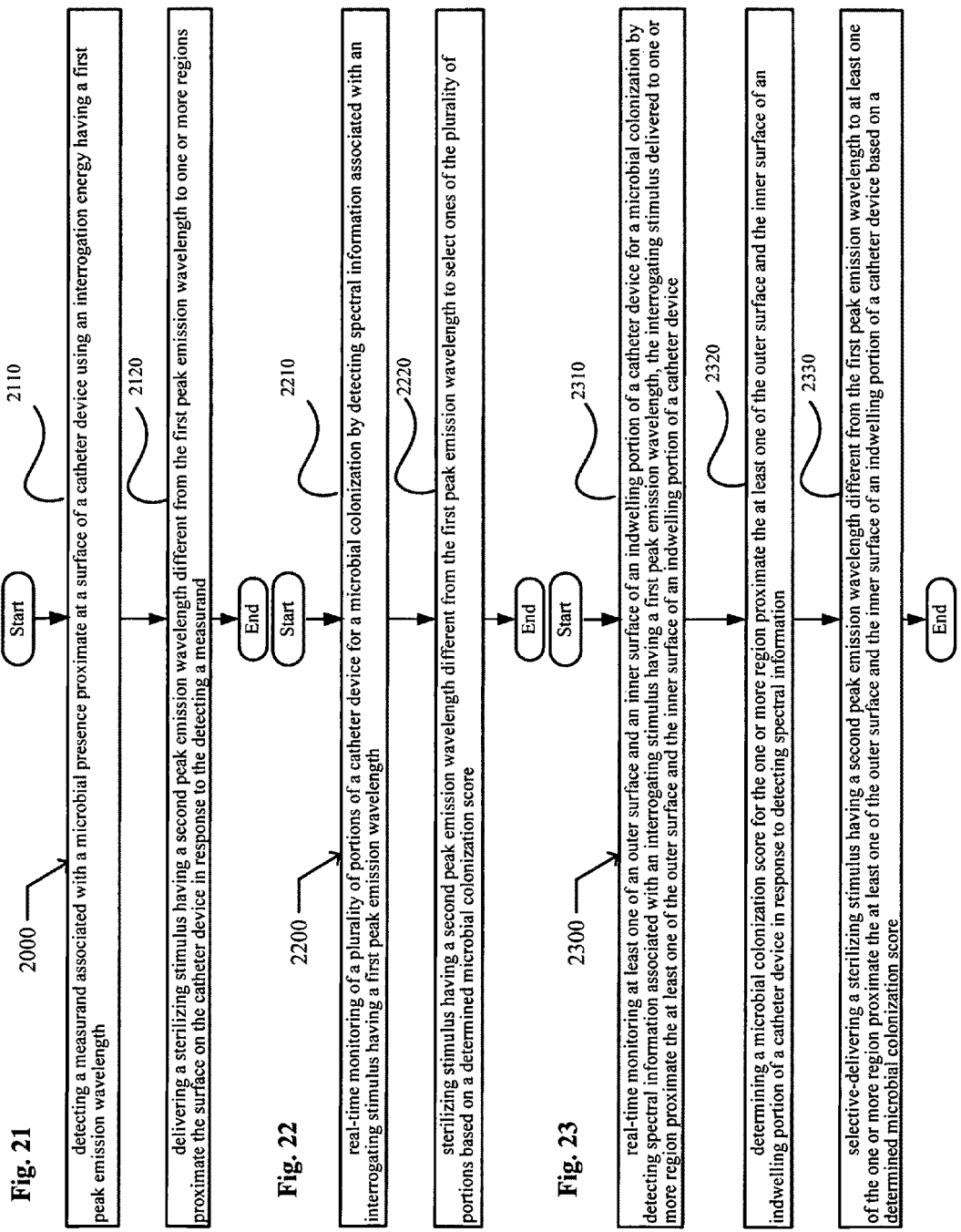

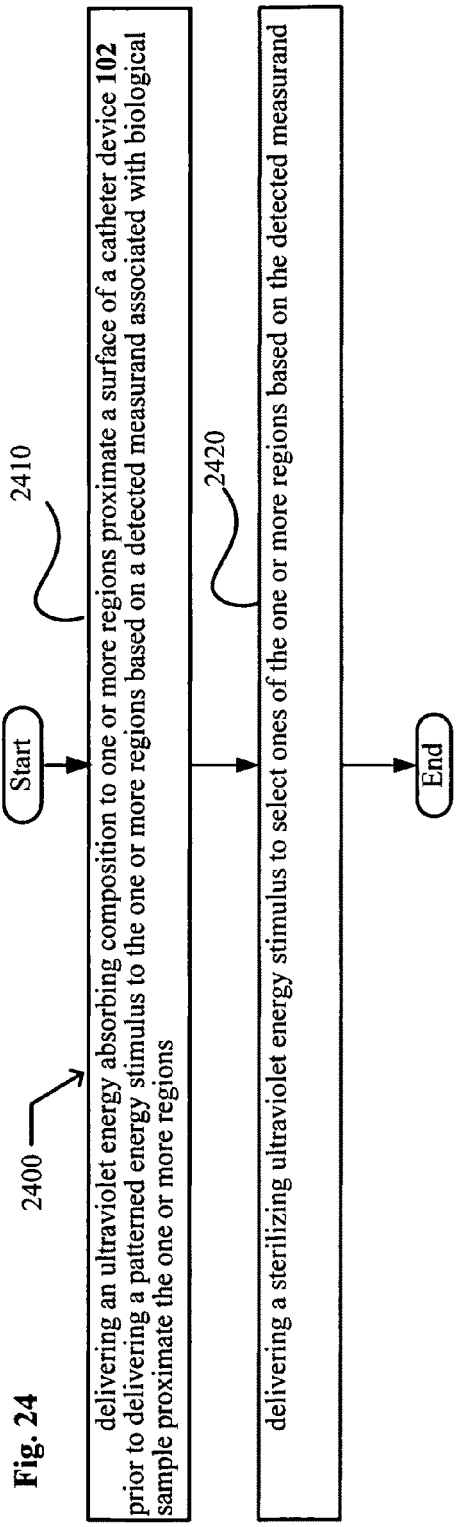
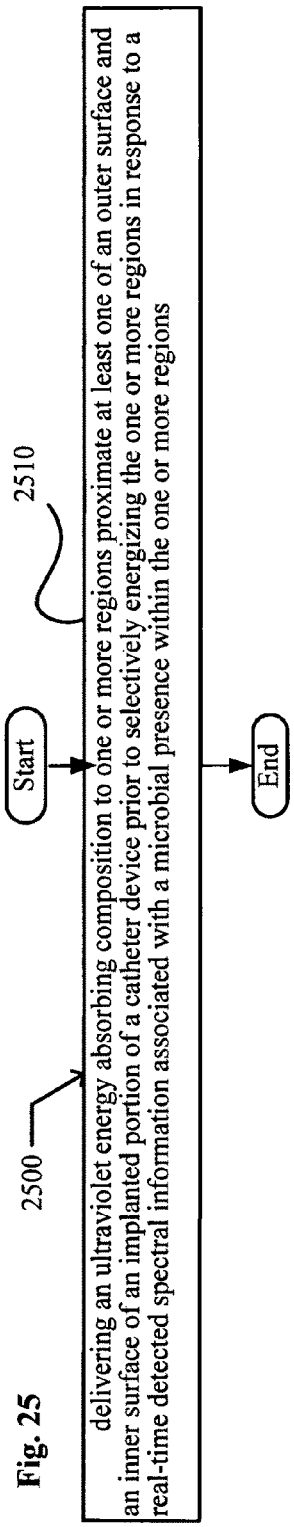

Fig. 24

2400 — delivering an ultraviolet energy absorbing composition to one or more regions proximate a surface of a catheter device 102 prior to delivering a patterned energy stimulus to the one or more regions based on a detected measurand associated with biological sample proximate the one or more regions — 2410 delivering a sterilizing ultraviolet energy stimulus to select ones of the one or more regions based on the detected measurand — 2420

Fig. 25

2500 — delivering an ultraviolet energy absorbing composition to one or more regions proximate at least one of an outer surface and an inner surface of an implanted portion of a catheter device prior to selectively energizing the one or more regions in response to a real-time detected spectral information associated with a microbial presence within the one or more regions — 2510

SYSTEMS, DEVICES, AND METHODS INCLUDING CATHETERS HAVING AN ACTIVELY CONTROLLABLE THERAPEUTIC AGENT DELIVERY COMPONENT

CROSS-REFERENCE TO RELATED APPLICATIONS

The present application is related to and claims the benefit of the earliest available effective filing dates from the following listed applications (the "Related applications") (e.g., claims earliest available priority dates for other than provisional patent applications or claims benefits under 35 U.S.C. §116(e) for provisional patent applications, for any and all parent, grandparent, great-grandparent, etc. applications of the Related applications). All subject matter of the Related applications and of any and all parent, grandparent, great-grandparent, etc. applications of the Related applications is incorporated herein by reference to the extent such subject matter is not inconsistent herewith.

RELATED APPLICATIONS

For purposes of the United States Patent and Trademark Office (USPTO) extra-statutory requirements, the present application constitutes a continuation-in-part of U.S. patent application Ser. No. 12/315,880, titled SYSTEM, DEVICES, AND METHODS INCLUDING ACTIVELY-CONTROLLABLE SUPEROXIDE WATER GENERATING SYSTEMS, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood, Jr.; and Victoria Y. H. Wood as inventors, filed 4 Dec. 2008, now U.S. Pat. No. 8,162,924 or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/315,881, titled SYSTEM, DEVICES, AND METHODS INCLUDING STERILIZING EXCITATION DELIVERY IMPLANTS WITH CRYPTOGRAPHIC LOGIC COMPONENTS, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood, Jr.; and Victoria Y. H. Wood as inventors, filed 4 Dec. 2008, which is currently co-pending or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/315,882, titled SYSTEM, DEVICES, AND METHODS INCLUDING STERILIZING EXCITATION DELIVERY IMPLANTS WITH GENERAL CONTROLLERS AND ONBOARD POWER, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood, Jr.; and Victoria Y. H. Wood as inventors, filed 4 Dec. 2008, now abandoned or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/315,883, titled SYSTEM, DEVICES, AND METHODS INCLUDING ACTIVELY-CONTROLLABLE ELECTROMAGNETIC ENERGY-EMITTING DELIVERY SYSTEMS AND ENERGY-ACTIVATABLE DISINFECTING AGENTS, naming Ralph G. Dacey, Jr., Roderick A. Hyde, Muriel Y. Ishikawa, Jordin T. Kare, Eric C. Leuthardt, Nathan P. Myhrvold, Dennis J. Rivet, Michael A. Smith, Elizabeth A. Sweeney, Clarence T. Tegreene, and Lowell L. Wood, Jr., Victoria Y. H. Wood as inventors, filed 4 Dec. 2008, which is currently co-pending or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/315,884, titled SYSTEM, DEVICES, AND METHODS INCLUDING ACTIVELY-CONTROLLABLE STERILIZING EXCITATION DELIVERY IMPLANTS, naming Edward S. Boyden, Ralph G. Dacey, Jr., Gregory J. Della Rocca, Joshua L. Dowling, Roderick A. Hyde, Muriel Y. Ishikawa, Jordin T. Kare, Eric C. Leuthardt, Nathan P. Myhrvold, Dennis J. Rivet, Paul Santiago, Michael A. Smith, Todd J. Stewart, Elizabeth A. Sweeney, Clarence T. Tegreene, Lowell L. Wood, Jr., Victoria Y. H. Wood as inventors, filed 4 Dec. 2008, which is currently co-pending or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/315,885, titled SYSTEM, DEVICES, AND METHODS INCLUDING ACTIVELY-CONTROLLABLE ELECTROSTATIC AND ELECTROMAGNETIC STERILIZING EXCITATION DELIVERY SYSTEM, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood, Jr.; and Victoria Y. H. Wood as inventors, filed 4 Dec. 2008, now abandoned or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/380,553, titled SYSTEM, DEVICES, AND METHODS INCLUDING ACTIVELY-CONTROLLABLE STERILIZING EXCITATION DELIVERY IMPLANTS, naming Edward S. Boyden; Ralph G. Dacey, Jr.; Gregory J. Della Rocca; Joshua L. Dowling; Roderick A. Hyde; Muriel Y. Ishikawa; Jordin T. Kare; Eric C. Leuthardt; Nathan P. Myhrvold; Dennis J. Rivet; Paul Santiago; Michael A. Smith; Todd J. Stewart; Elizabeth A. Sweeney; Clarence T. Tegreene; Lowell L. Wood; and Jr.; and Victoria Y. H. Wood as inventors, filed 27 Feb. 2009, which is currently co-pending or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/592,976, titled SYSTEM, DEVICES, AND METHODS INCLUDING ACTIVELY-CONTROLLABLE STERILIZING EXCITATION DELIVERY IMPLANTS, naming Edward S. Boyden, Ralph G. Dacey, Jr., Gregory J. Della Rocca, Joshua L. Dowling, Roderick A. Hyde, Muriel Y. Ishikawa, Jordin T. Kare, Eric C. Leuthardt, Nathan P. Myhrvold, Dennis J. Rivet, Paul Santiago, Michael A. Smith, Todd J. Stewart, Elizabeth A. Sweeney, Clarence T. Tegreene, Lowell L. Wood, Jr., and Victoria Y. H. Wood. as inventors, filed 3 Dec. 2009, which is currently co-pending or is an application of which a currently copending application is entitled to the benefit of the filing date.

For purposes of the United States Patent and Trademark Office (USPTO) extra-statutory requirements, the present application constitutes a continuation-in-part of U.S. patent application Ser. No. 12/660,156, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 19, Feb., 2010, now U.S. Pat. No. 8,366,652 or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/800,766, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21, May, 2010, now U.S. Pat. No. 8,216,173 or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/800,774, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21, May, 2010, which is currently co-pending or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/800,778, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21, May, 2010, now abandoned or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/800,779, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21, May, 2010, which is currently co-pending or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/800,780, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21, May, 2010, which is currently co-pending or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/800,781, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21, May, 2010, now abandoned or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/800,786, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21, May, 2010, now abandoned or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/800,790, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21, May, 2010, now U.S. Pat. No. 8,343,086 or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/800,791, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21, May, 2010, now U.S. Pat. No. 8,282,593 or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/800,792, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21, May, 2010, which is currently co-pending or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/800,793, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21, May, 2010, now U.S. Pat. No. 8,414,517 or is an application of which a currently co-pending application is entitled to the benefit of the filing date.

For purposes of the United States Patent and Trademark Office (USPTO) extra-statutory requirements, the present application constitutes a continuation-in-part of U.S. patent application Ser. No. 12/800,798, titled SYSTEMS, DEVICES, AND METHODS INCLUDING INFECTION-FIGHTING AND MONITORING SHUNTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 21, May, 2010, which is currently co-pending or is an application of which a currently co-pending application is entitled to the benefit of the filing date.

For purposes of the USPTO extra-statutory requirements, the present application is related to U.S. patent application Ser. No. 12/927,290, titled SYSTEMS, DEVICES, AND METHODS INCLUDING CATHETERS CONFIGURED TO MONITOR AND INHIBIT BIOFILM FORMATION, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10, Nov., 2010.

For purposes of the USPTO extra-statutory requirements, the present application is related to U.S. patent application Ser. No. 12/927,297, titled SYSTEMS, DEVICES, AND METHODS INCLUDING CATHETERS HAVING COMPONENTS THAT ARE ACTIVELY CONTROLLABLE BETWEEN TRANSMISSIVE AND REFLECTIVE STATES, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10, Nov., 2010.

For purposes of the USPTO extra-statutory requirements, the present application is related to U.S. patent application Ser. No. 12/927,284, titled SYSTEMS, DEVICES, AND METHODS INCLUDING CATHETERS HAVING COMPONENTS THAT ARE ACTIVELY CONTROLLABLE BETWEEN TWO OR MORE WETTABILITY STATES, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10, Nov., 2010.

For purposes of the USPTO extra-statutory requirements, the present application is related to U.S. patent application Ser. No. 12/927,296, titled SYSTEMS, DEVICES, AND METHODS INCLUDING CATHETERS HAVING UV-ENERGY EMITTING COATINGS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10, Nov., 2010.

For purposes of the USPTO extra-statutory requirements, the present application is related to U.S. patent application Ser. No. 12/927,287, titled SYSTEMS, DEVICES, AND METHODS INCLUDING CATHETERS HAVING SELF-CLEANING SURFACES, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10, Nov., 2010.

For purposes of the USPTO extra-statutory requirements, the present application is related to U.S. patent application Ser. No. 12/927,294, titled SYSTEMS, DEVICES, AND METHODS INCLUDING CATHETERS CONFIGURED TO MONITOR BIOFILM FORMATION HAVING BIOFILM SPECTRAL INFORMATION CONFIGURED AS A DATA STRUCTURE, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10, Nov., 2010.

For purposes of the USPTO extra-statutory requirements, the present application is related to U.S. patent application Ser. No. 12/927,285, titled SYSTEMS, DEVICES, AND METHODS INCLUDING CATHETERS HAVING ACOUSTICALLY ACTUATABLE WAVEGUIDE COMPONENTS FOR DELIVERING A STERILIZING STIMULUS TO A REGION PROXIMATE A SURFACE OF THE CATHETER, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10, Nov., 2010.

For purposes of the USPTO extra-statutory requirements, the present application is related to U.S. patent application Ser. No. 12/927,291, titled SYSTEMS, DEVICES, AND METHODS INCLUDING CATHETERS HAVING LIGHT REMOVABLE COATINGS BASED ON A SENSED CONDITION, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10, Nov., 2010.

For purposes of the USPTO extra-statutory requirements, the present application is related to U.S. patent application Ser. No. 12/927,295, titled SYSTEMS, DEVICES, AND METHODS INCLUDING CATHETERS CONFIGURED TO RELEASE ULTRAVIOLET ENERGY ABSORBING AGENTS, naming RALPH G. DACEY, JR., RODERICK A. HYDE, MURIEL Y. ISHIKAWA, JORDIN T. KARE, ERIC C. LEUTHARDT, NATHAN P. MYHRVOLD, DENNIS J. RIVET, MICHAEL A. SMITH, ELIZABETH A. SWEENEY, CLARENCE T. TEGREENE, LOWELL L. WOOD, JR., VICTORIA Y. H. WOOD as inventors, filed 10, Nov., 2010.

The USPTO has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related applications and of any and all parent, grandparent, great-grandparent, etc. applications of the Related applications is incorporated herein by reference to the extent such subject matter is not inconsistent herewith.

SUMMARY

In an aspect, the present disclosure is directed to, among other things, a catheter device. In an embodiment, the catheter device includes a body structure having an outer surface and an inner surface defining one or more fluid-flow passageways. In an embodiment, the catheter device includes a plurality of selectively actuatable energy waveguides operably coupled to one or more energy emitters and configured to direct electromagnetic energy to one or more regions near or on the catheter device. For example, in an embodiment, selected ones of the plurality of selectively actuatable energy waveguides are actuated to direct a patterned electromagnetic energy stimulus to one or more regions proximate (e.g., on, near, or the like) at least one of the outer surface or the inner surface of the body structure.

In an embodiment, the plurality of selectively actuatable energy waveguides are operably coupled to one or more energy emitters via at least one optical router. In an embodiment, the optical router is configured to create a translucent optical connection from the one or more energy emitters to selective ones of the plurality of selectively actuatable energy waveguides. Such a connection allows electromagnetic energy to flow from the one or more energy emitters to selected ones of the plurality of selectively actuatable energy waveguides. In an embodiment, the optical router is actuated via one or more mechanical-optic components, electro-optic components, or acousto-optic components. In an embodiment, the catheter device includes an overmoded electromagnetic energy waveguide photonically coupled to one or more of the plurality of selectively actuatable energy waveguides. In an embodiment, the overmoded electromagnetic energy waveguide is configured to actuate one or more of the plurality of selectively actuatable energy waveguides.

In an embodiment, the catheter device includes at least one reflective surface forming part of at least a portion of the body structure that is reflective at a first wavelength and transmissive at a second wavelength different from the first wavelength. In an embodiment, the catheter device includes at least one reflective surface forming part of at least a portion of the body structure that is reflective at a first polarization and transmissive at a second polarization. In an embodiment, the catheter device includes at least one reflective surface forming part of at least a portion of the body structure that is reflective at a first power level and transmissive at a second power level.

In an embodiment, the catheter device includes one or more internally reflective components forming part of at least a portion of the body structure. For example, in an embodiment, the catheter device includes at least one of an outer internally reflective coating and an inner internally reflective coating configured to internally reflect at least a portion of an emitted energy stimulus within an interior of at least one of the one or more fluid-flow passageways.

In an embodiment, the internally reflective components are configured to manage a delivery of interrogation energy to a sample and configured to manage a collection of emitted interrogation energy or remitted interrogation energy from the sample. For example, in an embodiment, the internally reflective components are configured to direct electromagnetic energy to a sample within at least one of the one or more fluid-flow passageways and further configured to manage a collection of a spectral response to the interrogation energy from the sample.

In an embodiment, the catheter device includes one or more optical materials forming part of at least a portion of the body structure. In an embodiment, the one or more optical materials are configured to limit an amount of the energy stimulus that can traverse within the one or more fluid-flow passageways and through the outer surface of the body structure. In an embodiment, the catheter device includes one or more optical materials on at least a portion of the body structure that reflect an emitted energy stimulus within an interior of at least one of the one or more fluid-flow passageways. In an embodiment, the catheter device includes an optical component that directs at least a portion of an emitted energy stimulus from the one or more energy emitters to one or more of the plurality of selectively actuatable energy waveguides. In an embodiment, the catheter device includes one or more proximal catheters, distal catheters, or flow-regulating devices having one or more fluid-flow passageways extending through an interior of the one or more proximal catheters, distal catheters, or flow-regulating devices.

In an embodiment, the catheter device includes a power source having at least one of a thermoelectric generator, a piezoelectric generator, an electromechanical generator, or a biomechanical-energy harvesting generator. In an embodiment, the catheter device includes one or more sensors for detecting a microbial presence in one or more regions proximate at least one of the outer surface of the body structure, the inner surface of the body structure, or within at least one of the one or more fluid flow passageways. In an embodiment, the catheter device includes a computing device operably coupled to at least one of the plurality of selectively actuatable energy waveguides, the one or more sensors, the power source, as well as other components of the catheter device. In an embodiment, the computing device actuates one or more of the plurality of selectively actuatable energy waveguides in response to detected information from the one or more sensors. In an embodiment, the computing device actuates one or more of the plurality of selectively actuatable energy waveguides in response to a scheduled program, an external command, a history of a previous microbial presence, or a history of a previous actuation.

In an aspect, the present disclosure is directed to, among other things, a catheter device including an energy emitter component that delivers optical energy to one or more regions proximate the catheter device. In an embodiment, the catheter device includes a sensor component and one or more computer-readable memory media having biofilm marker information configured as a data structure. In an embodiment, the data structure includes a characteristic information section having characteristic microbial colonization spectral information representative of the presence of a microbial colonization proximate the catheter device. In an embodiment, the sensor component is operable to detect at least one of an electromagnetic energy, a thermal energy, or an acoustic energy from one or more regions proximate the catheter device and to generate a first response based on the detected energy. In an embodiment, the generated first response includes comparing detect at least one of the electromagnetic energy, the thermal energy, or the acoustic energy to the biofilm marker information and initiating a treatment protocol based on the comparison. In an embodiment, the catheter device includes at least one transmitter for sending information based at least in part on detecting at least one of the electromagnetic energy, the thermal energy, or the acoustic energy. In an embodiment, the catheter device includes at least one transmitter configured to send a request for transmission of at least one of data, a command, an authorization, an update, or a code. In an embodiment, the catheter device includes circuitry configured to obtain information and circuitry configured to store the obtained information. In an embodiment, the catheter device includes a cryptographic logic component.

In an aspect, the present disclosure is directed to, among other things, a system including a catheter device having a plurality of independently addressable energy emitting components disposed along a longitudinal axis of the catheter device. In an embodiment, the plurality of independently addressable energy emitting components are configured to direct an emitted energy stimulus to one or more regions proximate at least one of the outer surface or the inner surface of the body structure. In an embodiment, the system further includes circuitry configured to determine a microorganism colonization event in one or more regions proximate at least one of the outer surface or the inner surface of the body structure. In an embodiment, the system further includes actuating means for concurrently or sequentially actuating two or more of the plurality of independently addressable energy emitting components in one or more regions determined to have a microorganism colonization event.

In an aspect, the present disclosure is directed to, among other things, a catheter device. In an embodiment, the catheter device includes one or more selectively actuatable energy waveguides extending over a portion of a surface of a body structure. In an embodiment, the one or more selectively actuatable energy waveguides are configured to direct an emitted energy stimulus from one or more energy emitters to one or more regions proximate the surface of the body structure. In an embodiment, the catheter device includes one or more sensors and one or more switches associated with one or more of the selectively actuatable energy waveguides. In an embodiment, the one or more sensors are configured to detect a spectral property associated with the presence of a microbial colonization in one or more regions proximate the surface of the body structure. For example, in an embodiment, at least one sensor is configured to detect a change to a refractive index associated with the presence of a microbial colonization. In an embodiment, the switches are configured to establish or interrupt a connection between the selectively actuatable energy waveguides and respective ones of the one or more energy emitters based on the detected spectral property.

In an aspect, the present disclosure is directed to, among other things, a method of inhibiting a microbial colonization of a partially or completely implanted catheter device. In an embodiment, the method includes generating an evanescent electromagnetic field proximate one or more regions of at least one of an outer surface or an inner surface of a body structure of the partially or completely implanted catheter device based on an automatically detected spectral parameter indicative of the presence of an infectious agent.

In an aspect, the present disclosure is directed to, among other things, a method of modulating microbial activity proximate a surface of an at least partially implanted catheter device. In an embodiment, the method includes generating a spatially patterned evanescent electromagnetic field proximate one or more surface regions of the at least partially implanted catheter device based on a detected change to a refractive index property associated with the one or more surface regions of the at least partially implanted catheter device.

In an aspect, a method includes, among other things, selectively energizing a plurality of regions proximate a surface of an implanted portion of a catheter device via one or more energy-emitting components in response to real-time detected information associated with a biological sample within one or more regions proximate the surface of the implanted portion of the catheter device. In an embodiment, the method further includes determining a microbial colonization score in response to real-time detected information. In an embodiment, the method further includes energetically interrogating the one or more regions proximate the surface of the implanted portion of the catheter device based on the determined microbial colonization score.

In an aspect, the present disclosure is directed to, among other things, a method of inhibiting biofilm formation in a catheter device. In an embodiment, the method includes actuating one or more selectively actuatable energy waveguides of an at least partially implanted catheter device in response to an in vivo detected change in a refractive index parameter associated with a biological sample proximate an outer surface or an inner surface of the catheter device.

In an aspect, the present disclosure is directed to, among other things, an at least partially implantable catheter device including a body structure having a plurality of actuatable regions that are independently actuatable between at least a first transmissive state and a second transmissive state. In an embodiment, the at least partially implantable catheter device includes one or more sensors for detecting at least one characteristic associated with a biological sample proximate at least one of an outer surface or an inner surface of the body structure. In an embodiment, the at least partially implantable catheter device includes one or more energy emitters configured to emit an energy stimulus based at least in part on at least one detected characteristic associated with the biological sample.

In an embodiment, the at least partially implantable catheter device includes one or more actively controllable reflective or transmissive components for outwardly transmitting or internally reflecting an energy stimulus propagated therethrough. In an embodiment, the at least partially implantable catheter device includes one or more optical materials on a portion of a body structure to internally reflect at least a portion of an emitted energy stimulus from the one or more energy emitters into an interior of at least one fluid-flow passageway.

In an embodiment, the at least partially implantable catheter device includes a computing device operably coupled to at least one of the plurality of actuatable regions, the actively controllable reflective or transmissive components, or the energy emitters. In an embodiment, the computing device causes a change between the first and the second transmissive states based on detected information from the one or more sensors. For example, in an embodiment, the computing device causes a change between a transmissive state and a reflective state based on detected information from the one or more sensors. In an embodiment, the computing device actuates one or more of the plurality of actuatable regions between the at least first transmissive state and the second transmissive state based on a comparison of a detected characteristic associated with the biological sample proximate the body structure.

In an aspect, the present disclosure is directed to, among other things, a catheter device including a body structure having one or more surface regions that are configured to controllably actuate between at least a first wettability state and a second wettability state. In an embodiment, the catheter device includes a computing device operably coupled to the surface regions and configured to controllably actuate the surface regions between at least a first wettability state and a second wettability state. For example, in an embodiment, the computing device is configured to cause a change between a first wettability state and a second wettability state based on detected information indicating a presence of an infectious agent near or on the catheter device.

In an embodiment, the catheter device includes an actively controllable excitation component configured to deliver, in vivo, an energy stimulus to one or more regions proximate at least one of the outer surface or the inner surface of the body structure. In an embodiment, the actively controllable excitation component is configured to deliver, concurrently or sequentially, at least a first energy stimulus or a second energy stimulus. In an embodiment, the first energy stimulus comprises an electromagnetic energy stimulus, an electrical energy stimulus, an acoustic energy stimulus, or a thermal energy stimulus, and the second energy stimulus comprises a different one of an electromagnetic energy stimulus, an electrical energy stimulus, an acoustic energy stimulus, or a thermal energy stimulus.

In an aspect, the present disclosure is directed to, among other things, a method of inhibiting biofilm formation. In an embodiment, the method includes actuating one or more surface regions of a catheter device between at least a first wettability state and a second wettability state in response to a detected event associate with a microbial colonization proximate one or more surface regions of a catheter device.

In an aspect, the present disclosure is directed to, among other things, a catheter device including a body structure having an outer surface and an inner surface defining one or more fluid-flow passageway and one or more actuatable energy waveguides. In an embodiment, the one or more actuatable energy waveguides are configured to direct an emitted energy stimulus to one or more regions proximate at least one of the outer surface or the inner surface of the body structure, and to deliver a patterned energy stimulus to the one or more regions proximate at least one of the outer surface or the inner surface of the body structure. In an embodiment, the catheter device includes an active agent assembly including at least one reservoir. In an embodiment, the active agent assembly is configured to deliver one or more active agents from the at least one reservoir to one or more regions proximate at least one of the outer surface or the inner surface of the body structure.

In an embodiment, the catheter device includes control circuitry operably coupled to the one or more actuatable energy waveguides and configured to control at least one of a spaced-apart configuration parameter, an electromagnetic energy spatial distribution parameter, or an electromagnetic energy temporal distribution parameter associated with the delivery of the patterned energy stimulus. In an embodiment, the catheter device includes a computing device operably coupled to the one or more actuatable energy waveguides and configured to control at least one of a delivery regiment, a spatial distribution, or a temporal distribution associated with the delivery of the patterned energy stimulus.

In an embodiment, the catheter device includes one or more sensors configured to detect at least one characteristic associated one or more regions proximate at least one of the outer surface or the inner surface of the body structure. In an embodiment, the catheter device includes a plurality of spaced-apart-release-ports operably coupled to at least one computing device. In an embodiment, the computing device is configured to actuate one or more of the plurality of spaced-apart-release-ports between an active agent discharge state and an active agent retention state based on a comparison of a detected characteristic to stored reference data. In an embodiment, the catheter device includes at least one receiver configured to acquire information based at least in part on whether a detect optical energy from one or more regions proximate at least one of the outer surface or the inner surface of the body structure satisfies a target condition.

In an aspect, the present disclosure is directed to, among other things, a method of inhibiting a microbial colonization of a surface on an implanted portion of a catheter device. In an embodiment, the method includes selectively energizing one or more regions proximate at least one of an outer surface or an inner surface of the implanted portion of the catheter device via one or more energy-emitting components. In an embodiment, the method includes delivering an active agent composition to the one or more regions proximate one or more surfaces of the implanted portion of the catheter device, via one or more active agent assemblies, in response to an automatically detected measurand associated with biological sample proximate the one or more surfaces of the implanted portion.

In an aspect, the present disclosure is directed to, among other things, an at least partially implantable fluid management system. In an embodiment, the at least partially implantable fluid management system includes a catheter device having a body structure having at least an outer surface and an inner surface defining one or more fluid-flow passageways. In an embodiment, the at least partially implantable fluid management system includes a plurality of independently activatable ultraviolet energy delivering substrates configured to deliver a sterilizing energy stimulus to one or more regions proximate at least one of the outer surface or the inner surface of the body structure. In an embodiment, the plurality of independently activatable ultraviolet energy delivering substrates define at least a portion of at least one of the outer surface or the inner surface of the body structure.

In an embodiment, the at least partially implantable fluid management system includes a sensor component including one or more sensors configured to detect a microbial presences proximate at least one of the outer surface or the inner surface of the body structure. In an embodiment, the at least partially implantable fluid management system includes a computing device operably coupled to the plurality of independently activatable ultraviolet energy delivering substrates, and configured to activate one or more of the plurality of independently activatable ultraviolet energy delivering substrates in response to detected microbial presence information from the sensor component.

In an aspect, a method includes, but is not limited to, concurrently or sequentially delivering to one or more regions proximate a surface of a catheter device a spatially patterned sterilizing energy stimulus via a plurality of independently activatable ultraviolet energy delivering substrates. In an embodiment, the plurality of independently activatable ultraviolet energy delivering substrates are configured to independently activate in response to a real-time detected measurand associated with a biological sample within the one or more regions proximate the surface of the catheter device.

In an aspect, a method includes, but is not limited to, concurrently or sequentially delivering to one or more regions proximate a surface of a catheter device a temporally patterned sterilizing energy stimulus via a plurality of independently activatable ultraviolet energy delivering substrates. In an embodiment, the plurality of independently activatable ultraviolet energy delivering substrates are configured to independently activate in response to a real-time detected measurand associated with at least one of temporal metabolite information or spatial metabolite information associated with a biological sample within the one or more regions proximate the surface of the catheter device.

In an aspect, the present disclosure is directed to, among other things, a catheter device having a body structure defining one or more catheters. In an embodiment, at least a portion of the body structure includes one or more self-cleaning surface regions. For example, in an embodiment, the catheter device includes one or more self-cleaning surface regions having structural components or coatings that modulate (e.g., inhibit, etc.) the adherence of biofilms. In an embodiment, the catheter device includes one or more self-cleaning surface regions including a self-cleaning coating composition.

In an embodiment, the catheter device further includes one or more selectively actuatable energy waveguides configured to direct an emitted energy stimulus to one or more regions proximate at least one of an outer surface or an inner surface of the one or more catheters. In an embodiment, the catheter device includes one or more energy emitters operatively coupled to the one or more selectively actuatable energy waveguides and configured to emit an energy stimulus.

In an aspect, a method includes, but is not limited to, automatically comparing one or more characteristics communicated from a catheter device to stored reference data. In an embodiment, the one or more characteristics include at least one of information associated with a microbial colonization proximate the catheter device, information associated with an infection marker detected proximate the catheter device, or information associated with a sample received within one or more fluid-flow passageways of the catheter device. In an embodiment, the method includes initiating a treatment protocol based at least in part on the comparison.

In an embodiment, the method includes selectively energizing one or more regions proximate the surface on an implanted portion of the catheter device via one or more energy-emitting components based at least in part on the comparison. In an embodiment, the method includes selectively energizing one or more regions proximate the surface on an implanted portion of the catheter device via one or more selectively actuatable energy waveguides configured to direct an emitted energy stimulus to one or more regions proximate at least one of the outer surface or the inner surface of the body structure. In an embodiment, the method includes selectively energizing one or more regions proximate the surface on an implanted portion of the catheter device determined to have a microbial colonization based at least in part on the comparison.

In an aspect, a method includes, but is not limited to, electronically comparing one or more characteristics communicated from an implanted catheter device to stored reference data, the one or more characteristics including at least one of an in vivo detected microbial colonization presence proximate a surface of the implanted catheter device, an in vivo real-time detected infection marker presence proximate a surface of the implanted catheter device, and in vivo detected measurand associated with a biofilm-specific tag. In an embodiment, the method includes initiating a treatment protocol based at least in part on the comparison.

In an aspect, the present disclosure is directed to, among other things, a catheter device. In an embodiment, the catheter device includes a body structure and one or more acoustically actuatable electromagnetic energy waveguides configured to direct an emitted energy stimulus to one or more regions proximate the body structure. In an embodiment, the catheter device includes one or more energy emitters operatively coupled to the one or more acoustically actuatable electromagnetic energy waveguides.

In an aspect, the present disclosure is directed to, among other things, a method of inhibiting biofilm formation in catheter device. In an embodiment, the method includes acoustically modulating one or more internally reflecting optical waveguides so as to partially emit an electromagnetic energy propagating within the one or more internally reflecting optical waveguides through at least one of an outer surface or an inner surface of the catheter device. In an embodiment, the method includes applying an acoustic energy stimulus to the one or more internally reflecting optical waveguides of a character and for a sufficient duration to affect at least one of an index of refraction or a physical dimension of the one or more internally reflecting optical waveguides.

In an aspect, the present disclosure is directed to, among other things, a method of inhibiting biofilm formation in a catheter device. In an embodiment, the method includes selectively actuating one or more optical waveguides so as to partially emit an electromagnetic energy propagating within the one or more optical waveguides through at least one of an outer surface or an inner surface of the catheter device. In an embodiment, the method includes selectively actuating the one or more optical waveguides in response to real-time detected information associated with a microbial colonization in one or more regions proximate at least one of an outer surface or an inner surface of the catheter device.

In an aspect, a method includes, but is not limited to, detecting a measurand associated with a microbial presence proximate at a surface of a catheter device using an interrogation energy having a first peak emission wavelength. In an embodiment, the method includes delivering a sterilizing stimulus having a second peak emission wavelength different from the first peak emission wavelength to one or more regions proximate the surface on the catheter device in response to the detecting a measurand.

In an aspect, a method includes, but is not limited to, real-time monitoring of a plurality of portions of a catheter device for a microbial colonization by detecting spectral information associated with an interrogating stimulus having a first peak emission wavelength. In an embodiment, the method includes delivering a sterilizing stimulus having a second peak emission wavelength different from the first peak emission wavelength to select ones of the plurality of portions of the catheter device based on a determined microbial colonization score.

In an aspect, a method includes, but is not limited to, real-time monitoring at least one of an outer surface or an inner surface of an indwelling portion of a catheter device for a microbial colonization by detecting spectral information associated with an interrogating stimulus having a first peak emission wavelength. In an embodiment, the method includes delivering an interrogating stimulus to one or more region proximate the at least one of the outer surface or the inner surface of an indwelling portion of a catheter device.

In an embodiment, the method includes determining a microbial colonization score for the one or more region proximate one or more surfaces of an indwelling portion of a catheter device in response to detecting spectral information. In an embodiment, the method includes selective-delivering a sterilizing stimulus having a second peak emission wavelength different from the first peak emission wavelength to at least one of the one or more region proximate one or more surfaces of an indwelling portion of a catheter device based on a determined microbial colonization score.

In an aspect, the present disclosure is directed to, among other things, an implantable catheter device including a plurality of regions having one or more in vivo selectively removable protective coatings defining at least a portion of at least one of the outer surface or the inner surface of the body structure. In an embodiment, the body structure includes an outer surface or an inner surface defining one or more fluid-flow passageways and is configured to transmit at least a portion of an emitted energy stimulus propagated within the body structure though one or more of a the plurality of regions having had an in vivo selectively removable protective coat-ing removed. In an embodiment, the implantable catheter device includes circuitry configured to determine a microorganism colonization event in one or more of the plurality of regions having the one or more in vivo selectively removable protective coatings.

In an aspect, the present disclosure is directed to, among other things, a catheter device including a body structure a plurality of selectively actuatable waveguides elements defining at least a portion of a surface of the body structure. In an embodiment, the selectively actuatable waveguides elements are configured to guide an emitted ultraviolet energy stimulus to one or more regions proximate the surface of the body structure. In an embodiment, the catheter device includes an active agent assembly including at least one reservoir, the active agent assembly configured to deliver an ultraviolet energy absorbing agent from the at least one ultraviolet energy absorbing reservoir to one or more regions proximate the surface of the body structure. In an embodiment, one or more of the plurality of selectively actuatable waveguides elements are configured to guide one or more of an electromagnetic energy stimulus, an acoustic energy stimulus, an acoustic energy stimulus, and a thermal energy stimulus.

In an aspect, a method includes, but is not limited to, delivering an ultraviolet energy absorbing composition to one or more regions proximate a surface of a catheter device prior to delivering a patterned energy stimulus to the one or more regions based on a detected measurand associated with biological sample proximate the one or more regions.

In an aspect, a method includes, but is not limited to, delivering an ultraviolet energy absorbing composition to one or more regions proximate an implanted portion of a catheter device prior to selectively energizing the one or more regions in response to a real-time detected spectral information associated with a microbial presence within the one or more regions. In an embodiment, the method includes delivering a sterilizing stimulus to select ones of the one or more regions in response to the real-time detected spectral information associated with the microbial presence within the one or more regions.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 1B is a perspective view of a portion of catheter device including a fluid-flow passageway according to one embodiment.

FIG. 2 is a perspective view of a system including a catheter device according to one embodiment.

FIG. 9 is a schematic diagram of a system including a catheter device according to one embodiment.

FIG. 10A is a flow diagram of a method according to one embodiment.

FIGS. 12A, 12B, and 12C are flow diagrams of a method according to one embodiment.

FIG. 13 is a flow diagram of a method according to one embodiment.

FIG. 16 is a flow diagram of a method according to one embodiment.

FIG. 17 is a flow diagram of a method according to one embodiment.

FIG. 19 is a flow diagram of a method according to one embodiment.

FIG. 20 is a flow diagram of a method according to one embodiment.

FIG. 21 is a flow diagram of a method according to one embodiment.

FIG. 22 is a flow diagram of a method according to one embodiment.

FIG. 23 is a flow diagram of a method according to one embodiment.

FIG. 24 is a flow diagram of a method according to one embodiment.

FIG. 25 is a flow diagram of a method according to one embodiment.

DETAILED DESCRIPTION

Figure 1A:
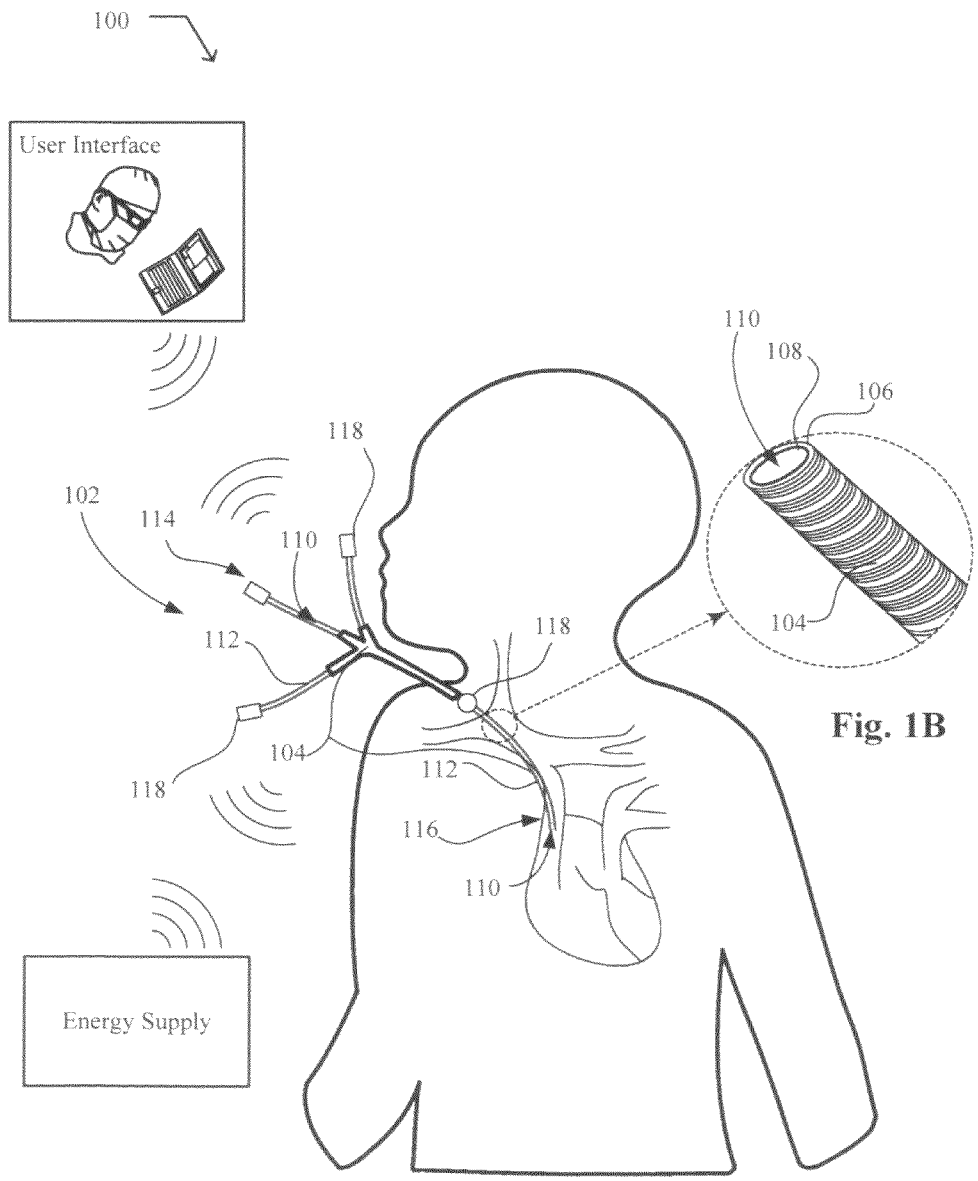
FIG. 1A is a perspective view of a system including a catheter device according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments can be utilized, and other changes can be made, without departing from the spirit or scope of the subject matter presented here.

Catheters (e.g., central venous catheters, multi-lumen catheters, peripherally inserted central catheters, Quinton catheters, Swan-Ganz catheters, tunneled catheters, intravenous lines, or the like), shunts (e.g., cardiac shunts, cerebral shunts, portacaval shunts, portosystemic shunts, pulmonary shunts, or the like), medical ports (e.g., arterial ports, low profile ports, multi-lumen ports, vascular ports, or the like), or the like are useful for, among other things, managing movement of fluids; directly detecting (e.g., assessing, calculating, evaluating, determining, gauging, identifying, measuring, monitoring, quantifying, resolving, sensing, or the like) mechanical, physical, or biochemical information (e.g., the presence of a biomarker, intracranial pressure, blood pressure, a disease state, or the like) associated with a biological subject; draining or collecting body fluids; providing access to surgical tools; as well as for administering therapeutics, medications, pharmaceuticals, intravenous fluids, blood products, or parenteral nutrition.

Infections, malfunctions (e.g., blocked or clogged fluid-flow passageways, etc.), and failures account for many of the complications associated with implantable medical devices (e.g., catheter devices, etc.) and pose tremendous consequences for patients. For example, during an infection, an infectious agent (e.g., fungi, microorganisms, parasites, pathogens (e.g., viral pathogens, bacterial pathogens, or the like), prions, viroids, viruses, or the like) generally interferes with the normal functioning of a biological subject, and causes, in some cases, chronic wounds, necrosis, loss of an infected tissue, loss of an infected limb, and occasionally death of the biological subject. Implant-associated infections account for a significant amount of nosocomial infections and despite sterilization and aseptic procedures, remain as a major impediment to medical implants including artificial hearts, artificial joints, artificial prosthetics, breast implants, catheters, contact lens, implantable biological sample drainage system, mechanical heart valves, stents, subcutaneous sensors, shunts, vertebral spacers, or the like. Implant-associated infections are often difficult to detect, problematic to cure, and at times expensive to manage. For example, in cases where the infection fails to subside quickly, it sometimes becomes necessary to remove the implant.

Implant-associated infections can result from bacterial adhesion and subsequent biofilm formation proximate an implantation site. For example, biofilm-forming microorganisms sometimes colonize the surface of a catheter device. Once a biofilm-induced infection takes hold, it can prove difficult to treat. In the case of catheters, for example, infectious agents can make their way from an insertion site into an outer surface of an indwelling portion of a catheter device. Likewise, contamination of an outer portion, such as a venous line of catheter device, can initiate migration of an infectious agent along an internal passageway. Adherence of infections agents to host proteins, such as fibronectin, commonly found on catheter components at times worsens the problem. See e.g., Frasca et al., *Critical Care* 14:212 1-8 (2010).

Accordingly, an aspect includes systems, devices, and methods, including a catheter device configured to, for example, detect (e.g., assess, calculate, evaluate, determine, gauge, identify, measure, monitor, quantify, resolve, sense, or the like) an infectious agent present proximate the catheter device. A non-limiting example includes systems, devices, and methods including a catheter device configured to, for example, detect an infectious agent present in, for example, a biological specimen (e.g., tissue, biological fluid, target sample, infectious agent, or the like) proximate (e.g., on, near, or the like) a surface of the catheter device.

An aspect includes systems, devices, methods, and compositions for actively detecting, treating, or preventing an infection associated with an indwelling catheter. An aspect includes systems, devices, and methods for managing movement of fluids; directly detecting and monitoring functions or conditions (e.g., mechanical, physical, physiological, or biochemical functions or conditions) associated with a biological subject; draining or collecting body fluids; providing access to an interior of a biological subject; distending at least one passageway; as well as for administering therapeutics, medications, pharmaceuticals, intravenous fluids, or parenteral nutrition. A non-limiting example includes systems, devices, and methods for actively detecting, treating, or preventing fluid-flow obstructions in catheters.

FIGS. 1A and 1B show a system 100 (e.g., a catheter system, an implantable catheter system, an implantable system, an indwelling system, a partially implantable system, a fluid management system, or the like) in which one or more methodologies or technologies can be implemented such as, for example, managing a transport of fluids, providing surgical access, as well as actively detecting, treating, or preventing an infection (e.g., an implant-associated infection, a hematogenous associated infection, an infection present in tissue or biological fluid, a biofilm formation, a microbial colonization, or the like), a biological sample abnormality (e.g., a cerebral spinal fluid abnormality, a hematological abnormality, a tissue abnormality, or the like), or the like.

In an embodiment, the system 100 is configured to, among other things, reduce an in vivo concentration of an infectious agent present in a biological fluid (e.g., bodily fluid, blood, amniotic fluid, ascites, bile, cerebrospinal fluid, interstitial fluid, pleural fluid, transcellular fluid, or the like) managed by the system 100, or a biological sample proximate one or more components of the system 100. In an embodiment, the system 100 is configured to provide antimicrobial therapy.

In an embodiment, the system 100 includes, among other things, at least one catheter device 102. In an embodiment, the catheter device 102 includes, among other things, a body structure 104 having an outer surface 106 and an inner surface 108 defining one or more fluid-flow passageways 110. In an embodiment, the system 100 is configured to reduce the concentration of an infectious agent in the immediate vicinity of a catheter device 102. For example, in an embodiment, the system 100 is configured to controllably deliver one or more energy stimuli to at least one of an interior or an exterior of one or more fluid-flow passageways 110 of a catheter device 102 at a dose sufficient to modulate the activity of the infectious agent in the immediate vicinity of a catheter device.

In an embodiment, the catheter device 102 includes, among other things, one or more catheters 112. In an embodiment, the catheter device 102 is positioned to facilitate the administration of therapeutics, medications, pharmaceuticals, intravenous fluids, blood products, parenteral nutrition, or the like. In an embodiment, the catheter device 102 is positioned to provide access for surgical instruments. In an embodiment, the catheter device 102 is positioned to provide vascular access. In an embodiment, the catheter device 102 is positioned to facilitate drainage.

Among catheters 112, examples include, but are not limited to, arterial catheters, dialysis catheters, drainage catheters, indwelling catheters, long term non-tunneled central venous catheters, long term tunneled central venous catheters, mechanical catheters, peripheral venous catheters, peripherally insertable central venous catheters, peritoneal catheters, pulmonary artery Swan-Ganz catheters, short-term central venous catheters, urinary catheters, ventricular catheters, or the like. In an embodiment, the body structure 104 includes one or more catheters 112 each having a proximal portion 114, a distal portion 116, and at least one inner fluid-flow passageway 110 extending therethrough. In an embodiment, one or more of the catheters 112 are configured for insertion into a body cavity, a duct, a vessel, or the like of a subject in need thereof.

In an embodiment, the catheter device 102 includes one or more catheters 112 configured for directly detecting and monitoring mechanical, physical, or biochemical functions associated with a biological subject; draining or collecting body fluids; providing access to an interior of a biological subject; or distending at least one passageway 110; as well as for administering therapeutics, medications, pharmaceuticals, intravenous fluids, or nutrition. In an embodiment, the catheter device 102 includes one or more at least partially implantable catheters 112. In an embodiment, the catheter device 102 includes one or more ports 118 configured to provide access to, or from, an interior environment of at least one of the one or more fluid-flow passageways 110. In an embodiment, the catheter device 102 includes one or more biocompatible materials, polymeric materials, thermoplastics, silicone materials (e.g., polydimethysiloxanes), polyvinyl chloride materials, latex rubber materials, or the like.

Further non-limiting examples of catheters 112, shunts, or components thereof, may be found in, for example the following documents (each of which is incorporated herein by reference): U.S. Pat. No. 7,524,298 (issued Apr. 28, 2009), U.S. Pat. No. 7,390,310 (issued Jun. 24, 2008), U.S. Pat. No. 7,334,594 (issued Feb. 26, 2008), U.S. Pat. No. 7,309,330 (issued Dec. 18, 2007), U.S. Pat. No. 7,226,441 (issued Jun. 5, 2007), U.S. Pat. No. 7,118,548 (issued Oct. 10, 2006), U.S. Pat. No. 6,932,787 (issued Aug. 23, 2005), U.S. Pat. No. 6,913,589 (issued Jul. 5, 2005), U.S. Pat. No. 6,743,190 (issued Jun. 1, 2004), U.S. Pat. No. 6,585,677 (issued Jul. 1, 2003); and U.S. Patent Publication Nos. 2009/0118661 (published May 7, 2009), 2009/0054824 (published Feb. 26, 2009), 2009/0054827 (published Feb. 26, 2009), 2008/0039768 (published Feb. 14, 2008), and 2006/0004317 (published Jan. 5, 2006); each of which is incorporated herein by reference).

FIG. 2 shows various configurations of a system 100 in which one or more methodologies or technologies can be implemented. In an embodiment, the system 100 includes, among other things, at least one catheter device 102 including one or more energy waveguides 202. The energy waveguides 202 can take a variety of shapes, configurations, and geometries including, but not limited to, cylindrical, conical, planar, parabolic, regular or irregular forms. In an embodiment, multiple energy waveguides 202 are formed from a single substrate or structure. Non-limiting examples of energy waveguides 202 include electromagnetic waveguides 204, acoustic energy waveguides 206 (e.g., ultrasonic energy waveguides), thermal energy waveguides 208, optical energy waveguides 210 (e.g., optical fibers, photonic-crystal fibers, or the like), ultrasound energy waveguides 212, multi-energy waveguides 214, or the like. Further non-limiting examples of energy waveguides 202 include lens structures, light-diffusing structures, mirror structures, mirrored surfaces, reflective coatings, reflective materials, reflective surfaces, or combinations thereof. Further non-limiting examples of energy waveguides 202 include etchings, facets, grooves, thin-films, optical micro-prisms, lenses (e.g., micro-lenses, or the like), diffusing elements, diffractive elements (e.g., gratings, cross-gratings, or the like), texturing, or the like. In an embodiment, the energy waveguides 202 include structures suitable for directing energy waves.

In an embodiment, one or more of the energy waveguides 202 include at least one of a transparent, translucent, or light-transmitting material, and combinations or composites thereof. Among transparent, translucent, or light-transmitting materials, examples include those materials that offer a low optical attenuation rate to the transmission or propagation of light waves. Non-limiting examples of transparent, translucent, or light-transmitting materials include crystals, epoxies, glasses, borosilicate glasses, optically clear materials, semi-clear materials, plastics, thermo plastics, polymers, resins, thermal resins, or the like, or combinations or composites thereof.

In an embodiment, the system 100 includes, among other things, a plurality of selectively actuatable energy waveguides 202a. For example, in an embodiment, the catheter device 102 includes a plurality of selectively actuatable energy waveguides 202a that define one or more portions of the body structure 104. In an embodiment, at least a portion of the outer surface of the body structure 104 includes one or more of the plurality of selectively actuatable energy waveguides 202a. In an embodiment, at least a portion of the inner surface of the body structure 104 includes one or more of the plurality of selectively actuatable energy waveguides 202a.

Figure 3:
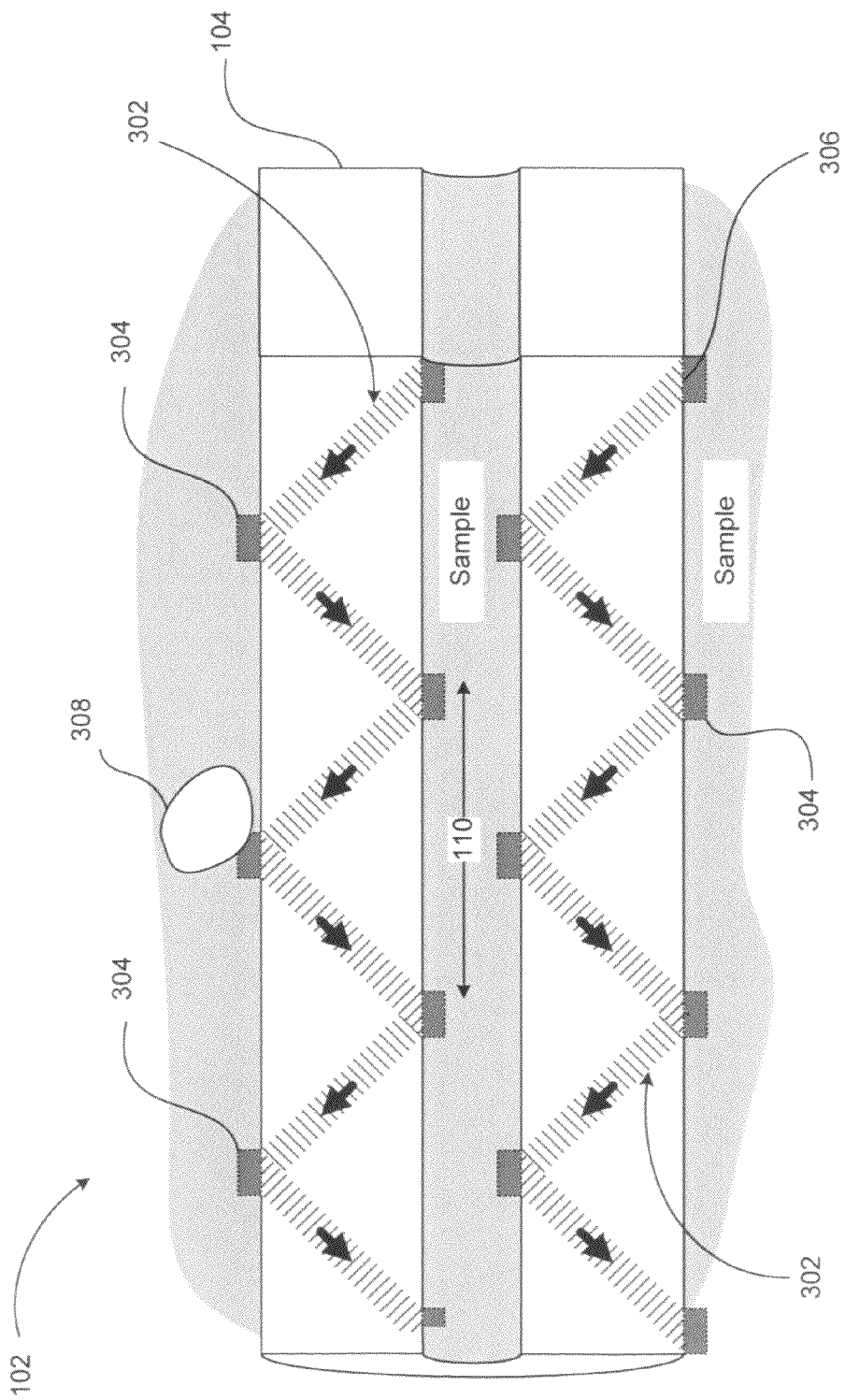
FIG. 3 is a schematic diagram of a system including a catheter device according to one embodiment.

Referring to FIG. 3, in an embodiment, the system 100 includes, among other things, a catheter device 102 having body structure 104 configured to sufficiently internally reflect at least a portion of an emitted energy stimulus 302 and to generate an evanescent field 304 across one or more regions of the body structure 104. In an embodiment, at least a portion of the body structure 104 includes one or more energy waveguides 202 configured to sufficiently internally reflect at least a portion of an emitted energy stimulus 302 and to generate an evanescent field 304.

Evanescent fields 304 can be generated, for example, via diffraction from a grating or a collection of apertures; scattering from an aperture; or total internal reflection at the interface between two media See e.g., Smith et. al, *Evanescent Wave Imaging in Optical Lithography*, Proc. SPIE 6154, (2006). For example, electromagnetic energy 302 crossing a boundary 306 between materials with different refractive indices ($n_i$), partially refracts at the boundary surface, and partially reflects. (See, e.g., FIG. 3). When the incident angle ($\theta_i$), exceeds the critical angle of incidence, define as:

$$\theta_{critical} = \sin^{-1}\left(\frac{n_{low}}{n_{high}}\right),$$

the electromagnetic energy traveling from a medium of higher refractive index ($n_{high}$) to that of a lower one ($n_{low}$) undergoes total internal reflection (see e.g., FIG. 3), and generates an evanescent field 304 near the boundary 306 (the intensity of which decays exponentially with increasing distance from the surface). In an embodiment, at least a portion of the body structure 104 is configured to sufficiently internally reflect at least a portion of an emitted energy stimulus 302 to cause an evanescent electromagnetic field 304 to emanate from at least a portion of the body structure 104. In an embodiment, at least a portion of the body structure 104 is configured to internally reflect at least a portion of an emitted energy stimulus 302 within an interior of at least one of the one or more fluid-flow passageways 110. In an embodiment, at least a portion of the body structure 104 is configured to totally internally reflect at least a portion of an emitted energy stimulus 302 propagated within an interior of at least one of the one or more fluid-flow passageways.

In an embodiment, infectious agents 308 cause changes in the local index of refraction, resulting in changes in the resonance conditions of the evanescent electromagnetic field 304. In an embodiment, detected index of refraction changes are correlated to the presence of an infectious agent.

With continued reference to FIG. 2, in an embodiment, one or more of the energy waveguides 202 include at least one of an optically transparent, optically translucent, or light-transmitting component. In an embodiment, one or more of the energy waveguides 202 include at least one optically transparent, translucent, or light-transmitting material. Non-limiting examples of optically transparent, translucent, or light-transmitting material include one or more of acetal copolymers, acrylic, glass, AgBr, AgCl, $Al_2O_3$, GeAsSe glass, $BaF_2$, $CaF_2$, CdTe, AsSeTe glass, CsI, diamond, GaAs, Ge, ITRAN materials, KBr, thallium bromide-Iodide, LiF, $MgF_2$, NaCl, polyethylene, Pyrex, Si, $SiO_2$, ZnS, ZnSe, thermoplastic polymers, or thermoset polymers, and composites thereof. Further non-limiting examples of optically transparent, translucent, or light-transmitting material include one or more of acrylonitrile butadaine styrene polymers, cellulosic, epoxy, ethylene butyl acrylate, ethylene tetrafluoroethylene, ethylene vinyl alcohol, fluorinated ethylene propylene, furan, nylon, phenolic, poly[2,2,4-trifluoro-5-trifluoromethoxy-1,3-dioxole-co-tetrafluoroethylene], poly[2,2-bistrifluoromethyl-4,5-difluoro-1,3-dioxole-co-tetrafluoroethylene], poly[2,3-(perfluoroalkenyl)perfluorotetrahydrofuran], polyacrylonitrile butadiene styrene, polybenzimidazole, polycarbonate, polyester, polyetheretherketone, polyetherimide, polyethersulfone, polyethylene, polyimide, polymethyl methacrylate, polynorbornene, polyperfluoroalkoxyethylene, polystyrene, polysulfone, polyurethane, polyvinyl chloride, polyvinylidene fluoride, diallyl phthalate, thermoplastic elastomer, transparent polymers, an vinyl ester, and composites thereof.

In an embodiment, a plurality of energy waveguides 202 are coupled (e.g., optically coupled, operably coupled, physically coupled, or the like) to form, for example, an array of energy waveguides 202. In an embodiment, one or more of the plurality of energy waveguides 202 comprise a laminate including one or more optically active coatings, materials, or the like. In an embodiment, one or more of the plurality of energy waveguides 202 direct an emitted energy stimulus to one or more regions proximate at least one of the outer surface 106 or the inner surface 108 of the body structure 104. In an embodiment, the plurality of energy waveguides 202 are arranged to form a part of patterned energy emitting component 216.

In an embodiment, the system 100 includes, among other things, a plurality of selectively actuatable energy waveguides 202a. In an embodiment, the catheter device 102 includes a plurality of selectively actuatable energy waveguides 202a. In an embodiment, the plurality selectively actuatable energy waveguides 202a direct an emitted energy stimulus to one or more regions proximate at least one of the outer surface 106 or the inner surface 108 of the body structure 104.

In an embodiment, the system 100 is configured to, among other things, treat a condition associated with an infection. For example, in an embodiment, upon an indication of a presence or severity of an infection, selected ones of the plurality selectively actuatable energy waveguides 202a are actuated to deliver an emitted energy stimulus to modulate microbial activity within those regions having an indication of a presence or severity of an infection. In an embodiment, the system 100 is configured to, among other things, reduce the risk of infection. In an embodiment, the system 100 is configured to, among other things, modulate a microbial colonization.

In an embodiment, the plurality of selectively actuatable energy waveguides 202a include one or more acoustic energy waveguides 206 (e.g., one or more ultrasound-guiding waveguides, or the like). In an embodiment, the plurality of selectively actuatable energy waveguides 202a include one or more thermal energy waveguides 208. In an embodiment, the plurality of selectively actuatable energy waveguides 202a include one or more electrical energy waveguides.

In an embodiment, the plurality of selectively actuatable energy waveguides 202a include a light-transmitting material. In an embodiment, at least one of the plurality of selectively actuatable energy waveguides 202a includes an electromagnetic energy transmitting material and a reflective boundary. In an embodiment, at least one of the plurality of selectively actuatable energy waveguides 202a includes an electrical conducting portion and an electrical insulating portion. In an embodiment, at least one of the plurality of selectively actuatable energy waveguides 202a includes a thermal conducting portion and a thermal insulating portion.

In an embodiment, the plurality of selectively actuatable energy waveguides 202a include one or more optical waveguides. In an embodiment, the selectively actuatable energy waveguides 202a include one or more optical waveguides having one or more ports configured to allow electromagnetic energy to escape. In an embodiment, the plurality of selectively actuatable energy waveguides 202a include one or more optical waveguides having distributed light escape along a portion of a length of the one or more optical waveguides. In an embodiment, the plurality of selectively actuatable energy waveguides 202a include one or more optical fibers. In an embodiment, one or more of the plurality of selectively actuatable energy waveguides 202a comprise an optically transparent material and an optically opaque material.

In an embodiment, one or more of the plurality of selectively actuatable energy waveguides 202a are disposed along the outer surface of the body structure, the inner surface 108 of the body structure 104, or both. For example, in an embodiment, one or more of the plurality of selectively actuatable energy waveguides 202a form part of the outer surface 106, to form part of the inner surface 108, or both.

In an embodiment, the system 100 includes, among other things, at least one catheter device 102 including one or more acoustically actuatable electromagnetic energy waveguides. In an embodiment, the one or more acoustically actuatable electromagnetic energy waveguides direct an emitted energy stimulus to one or more regions proximate at least one of an outer surface 106 or an inner surface 108 of the body structure 104.

In an embodiment, the one or more acoustically actuatable electromagnetic energy waveguides include at least one of an acoustically sensitive cladding material; an acoustically sensitive material coating; or an acoustically deforming material coating. In an embodiment, the one or more acoustically actuatable electromagnetic energy waveguides are configured for selective-actuation via one or more transducers. In an embodiment, the one or more acoustically actuatable electromagnetic energy waveguides are configured to outwardly transmit a portion of an electromagnetic energy internally reflected within in the presence of an acoustic stimulus. In an embodiment, the one or more acoustically actuatable electromagnetic energy waveguides are configured to deform in the presence of an acoustic stimulus. In an embodiment, the one or more acoustically actuatable electromagnetic energy waveguides are configured to exhibit a change to a refractive index in the presence of an acoustic stimulus. In an embodiment, the one or more acoustically actuatable electromagnetic energy waveguides are configured to generate an evanescent electromagnetic field across one or more regions of the body structure in the presence of an acoustic stimulus. In an embodiment, the one or more acoustically actuatable electromagnetic energy waveguides are operably coupled to one or more acoustic energy emitters.

Figure 4:
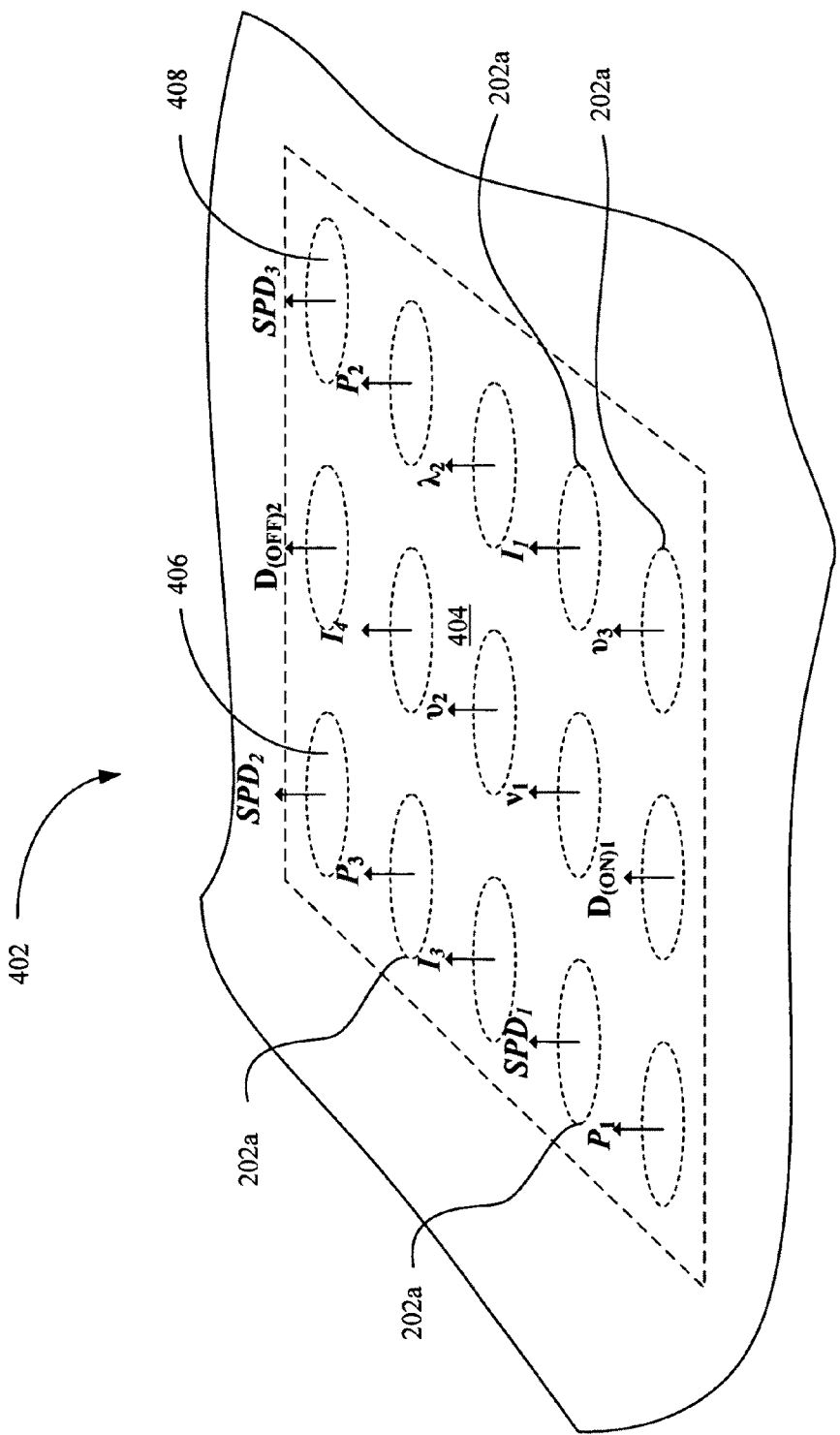
FIG. 4 is a top plan view of a portion of a catheter device including plurality of selectively actuatable energy waveguides configured to provide a patterned energy stimulus, according to one embodiment.

Referring to FIG. 4, in an embodiment, the plurality of selectively actuatable energy waveguides 202a provide a spatially patterned energy stimulus 402. In an embodiment, the plurality of selectively actuatable energy waveguides 202a deliver an energy stimulus of a dose sufficient (e.g., of character and for a duration sufficient, of sufficient strength or duration, etc.) to provide a spatially patterned energy stimulus to one or more regions proximate at least a first surface 404 of the body structure 104.

In an embodiment, the plurality of selectively actuatable energy waveguides 202a provide a spatially patterned energy stimulus having at least a first region 406 and a second region 408 different from the first region 406. For example, in an embodiment, the second region 408 includes at least one of a spectral power distribution ($SPD_n$), an irradiance ($I_n$), or a peak power ($P_n$) different from the first region 406. In an embodiment, the second region 408 includes at least one of an illumination intensity, a peak emission wavelength, or a pulse frequency different from the first region 406. In an embodiment, the second region 408 includes at least one of an intensity, a phase, or a polarization different from the first region 406. In an embodiment, the second region 408 includes at least one of a frequency, a repetition rate, or a bandwidth different from the first region 406. In an embodiment, the second region 408 includes at least one of an energy-emitting pattern, an ON-pulse duration, or an OFF-pulse duration different from the first region 406. In an embodiment, the second region 408 includes at least one of an emission intensity, an emission phase, an emission polarization, or an emission wavelength different from the first region 406.

In an embodiment, the plurality of selectively actuatable energy waveguides 202a include at least a first waveguide and a second waveguide, the second waveguide configured to transport electromagnetic energy of a wavelength different from that of the first waveguide. For example, in an embodiment, the first waveguide provides an electromagnetic energy stimulus, an electrical energy stimulus, an acoustic energy stimulus, or a thermal energy stimulus, and the second waveguide provides a different one of an electromagnetic energy stimulus, an electrical energy stimulus, an acoustic energy stimulus, or a thermal energy stimulus. In an embodiment, the plurality of selectively actuatable energy waveguides 202a are configured to deliver at least one of a spatially collimated energy stimulus; spatially focused energy stimulus; a temporally patterned energy stimulus; or a spaced-apart patterned energy stimulus.

In an embodiment, the plurality of selectively actuatable energy waveguides 202a provide an illumination pattern comprising at least a first actuated selectively actuatable energy waveguide and a second actuated selectively actuatable energy waveguide. In an embodiment, the plurality of selectively actuatable energy waveguides 202a provide an illumination pattern comprising selectively actuatable energy waveguides 202a configured to be concurrently actuated.

In an embodiment, one or more energy emitter 220 are operably coupled to a plurality of selectively actuatable energy waveguides 202a and are configured to deliver a multiplex energy stimulus having, for example, two or more peak emission wavelengths. In an embodiment, a multiplex energy stimulus can be routed to two or more of the selectively actuatable energy waveguides 202a based on a wavelength, an intensity, a spectral power distribution, a waveguide-specific address, or the like. Once routed, the a plurality of selectively actuatable energy waveguides 202a can deliver a spatially patterned energy stimulus having at least a first region and a second region 408 different from the first region 406 where the difference depends on the selection rule (e.g., spectral power distribution, irradiance, peak power, intensity, phase, polarization, frequency, repetition rate, bandwidth, waveguide-specific address, or the like) used to route the energy stimulus.

Referring to FIG. 2, in an embodiment, the plurality of selectively actuatable energy waveguides 202a are configured to internally direct at least a portion of an emitted energy stimulus propagated within an interior of at least one of the one or more fluid-flow passageways 110. In an embodiment, the plurality of selectively actuatable energy waveguides 202a are configured to direct at least a portion of an emitted energy stimulus within an interior of at least one of the one or more fluid-flow passageways 110 based on at least one of a polarization, an intensity, or a wavelength. For example, in an embodiment, the plurality of selectively actuatable energy waveguides 202a include one or more polarization-, intensity-, or wavelength-selective elements, coatings, materials, etchings, facets, grooves, thin-films, optical micro-prisms, lenses (e.g., micro-lenses, or the like), diffusing elements, diffractive elements (e.g., gratings, cross-gratings, or the like), texturing, or the like configured to direct at least a portion of an emitted energy stimulus.

In an embodiment, the plurality of selectively actuatable energy waveguides 202a are configured to direct at least a portion of an emitted energy stimulus within an interior of at least one of the one or more fluid-flow passageways 110 based on a power level of the emitted energy stimulus. In an embodiment, one or more of the plurality of selectively actuatable energy waveguides 202a extend over a portion of a surface of the body structure 104.

In an embodiment, the catheter device 102 includes at least one selectively actuatable energy waveguide 202a that forms part of a surface along a longitudinal direction 120 of a fluid-flow passageway 110. In an embodiment, the catheter device 102 includes at least one selectively actuatable energy waveguide 202a that forms part of a surface along a lateral direction 122 of a fluid-flow passageway 110. In an embodiment, the plurality of selectively actuatable energy waveguides 202a are configured to laterally internally direct or longitudinally internally direct at least a portion of an emitted energy stimulus within an interior of at least one of the one or more fluid-flow passageways 110. For example, in an embodiment, a catheter device 102 includes one or more selectively actuatable energy waveguides 202a that extend along a longitudinal direction of a fluid-flow passageway 110. Accordingly, when actuated, the one or more selectively actuatable energy waveguides 202a direct at least a portion of an emitted energy stimulus within an interior of at least one of the one or more fluid-flow passageways 110 along a longitudinal direction.

In an embodiment, one or more of the plurality of selectively actuatable energy waveguides 202a extend substantially longitudinally along at least one of the one or more fluid-flow passageways 110. In an embodiment, one or more of the plurality of selectively actuatable energy waveguides 202a extend substantially laterally within at least one of the one or more fluid-flow passageways 110. In an embodiment, at least one of the plurality of selectively actuatable energy waveguides 202a extends substantially laterally along a first portion of the body structure 104 and a different one of the plurality of selectively actuatable energy waveguides 202a extends substantially laterally along a second portion of the body structure 104. In an embodiment, one or more of the plurality of selectively actuatable energy waveguides 202a extend substantially helically within at least one of the one or more fluid-flow passageways 110. In an embodiment, at least one of the plurality of selectively actuatable energy waveguides 202a extends substantially helically along a first portion of the body structure 104 and a different one of the plurality of selectively actuatable energy waveguides 202a extends substantially helically along a second portion of the body structure 104.

In an embodiment, the plurality of selectively actuatable energy waveguides 202a are configured to direct a first portion of an emitted energy stimulus along a substantially lateral direction in one or more regions of at least one of the one or more fluid-flow passageways 110 and configured to direct a second portion of the emitted energy stimulus along a substantially longitudinal direction in one or more regions of at least one of the one or more fluid-flow passageways 110. In an embodiment, the plurality of selectively actuatable energy waveguides 202a are configured to direct at least a portion of an emitted energy stimulus along a substantially lateral direction in a first region of at least one of the one or more fluid-flow passageways 110 and configured to direct at least a portion of the emitted energy stimulus along a substantially lateral direction in a second region of the one or more fluid-flow passageways 110, the second region different from the first region. In an embodiment, the plurality of selectively actuatable energy waveguides 202a are configured to direct at least a portion of an emitted energy stimulus along a substantially longitudinal direction in a first region of at least one of the one or more fluid-flow passageways 110 and configured to direct at least a portion of the emitted energy stimulus along a substantially longitudinal direction in a second region of the one or more fluid-flow passageways 110, the second region different from the first region. In an embodiment, the plurality of selectively actuatable energy waveguides 202a are configured to externally direct at least a portion of an emitted energy stimulus propagated within. In an embodiment, the plurality of selectively actuatable energy waveguides 202a are configured to externally direct at least a portion of an emitted energy stimulus propagated within one or more regions proximate at least one surface of the body structure 104.

In an embodiment, the catheter device 102 includes a plurality of selectively actuatable energy waveguides 202a configured to selectively actuate via one or more switches 218. In an embodiment, the plurality of selectively actuatable energy waveguides 202a are selectively actuatable via one or more opto-mechanical switches; electro-optic switches; acousto-optic switches; thermo-optic switches, or the like. In an embodiment, the plurality of selectively actuatable energy waveguides 202a can be actuated via one or more thermally actuated devices (e.g., thermally activatable switches, or the like), electromagnetically actuated devices (e.g., electromagnetic activatable switches, optically activatable switches, or the like), acoustically actuated devices, electrically actuated devices, or the like.

Non-limiting examples of switches 218, or components thereof, may be found in, for example the following documents: U.S. Patent Publication No. 2009/0316195 (published Dec. 24, 2009); U.S. Pat. No. 7,706,178 (issued Apr. 27, 2010), U.S. Pat. No. 7,130,459 (issued Dec. 18, 2007), U.S. Pat. No. 6,853,765 (issued Feb. 8, 2005), and U.S. Pat. No. 6,222,953 (issued Apr. 24, 2001); Coppola, G. et al., *Visualization of Optical Deflection and Switching Operations by a Domain-Engineered Based LiNbO$_3$ Electro-Optic Device*, Optics Express, 11 (10), 1212-1222, (May 2003); Liou, J. C. et al., *An ASIC Control Circuit for Thermal Actuated Large Optical Packet Switch Array*, Proceedings of the World Congress on Engineering 2008, Vol. I, WCE 2008, pp 386-391 (2008); and Yang, J., et al., *Polyimide-Waveguide-Based Thermal Optical Switch Using Total-Internal-Reflection Effect*, Applied Physics Letters, 81 (16): 2947-2949 (2002); each of which is incorporated herein by reference.

In an embodiment, the catheter device 102 includes, among other things, a plurality of selectively actuatable energy waveguides 202a configured to selectively actuate via one or more antifuses 219. In an embodiment, the one or more antifuses 219 are operably coupled to at least one of the plurality of selectively actuatable energy waveguides 202a and are configured to establish an electromagnetic energy path when an electromagnetic energy transmitted therethrough exceeds a threshold value.

In an embodiment, the plurality of selectively actuatable energy waveguides 202a are selectively actuatable via one or more optical antifuses 219. In an embodiment, the plurality of selectively actuatable energy waveguides 202a are selectively actuatable via one or more antifuses 219 that are configured to actuate from a first transmissive state to a second transmissive state when a power level of an electromagnetic energy exceeds a exceeds a threshold value. For example, during operation when the input power level is lower than a designated threshold level, the optical antifuse 219 remains opaque. When the input power level exceeds the designated threshold level, the optical antifuse 219 becomes transparent. In an embodiment, the antifuse 219 is configured to transition from a non-transmissive state to a transmissive state by, for example, insulation breakdown.

Non-limiting examples of antifuses 219, or components thereof, may be found in, for example the following documents: U.S. Patent Publication No. 2008/0007885 (published Jan. 10, 2008); U.S. Pat. No. 7,714,326 (issued May 11, 2010), U.S. Pat. No. 7,691,894 (issued Apr. 6, 2010), and U.S. Pat. No. 7,116,857 (issued Oct. 3, 2006); Davis et al., *A New Electro-Optic Waveguide Architecture and the Unprecedented Devices it Enables*, Proc. of SPIE Vol. 6975, pp. 697503-1-12 (2008); Piccolo et al., *Antifuse Injectors for SOI LEDs*, Proceedings of the 11th Annual Workshop on Semiconductor Advances for Future Electronics and Sensors (SAFE 2008), pp. 573-575 (2008); and Vázquez et al., *Optical Router for Optical Fiber Sensor Networks Based on a Liquid Crystal Cell*, IEEE Sensors Journal, Vol. 3:(4), pp. 513-518 (2003); each of which is incorporated herein by reference.

In an embodiment, the catheter device 102 includes, among other things, a plurality of selectively actuatable energy waveguides 202a configured to selectively actuate via one or more light movable liquid crystals. For example, in an embodiment, during operation, a position of one or more light movable liquid crystals is altered by impinging a sufficient electromagnetic energy to cause physical movement of the light movable liquid crystals. Accordingly, one or more of the light movable liquid crystals are actuated between transmissive and reflective states by interrogation with electromagnetic energy. Non-limiting examples of light movable crystals, or components thereof, may be found in, for example U.S. Pat. No. 7,116,857 (issued Oct. 3, 2006) and U.S. Pat. No. 7,197,204 (issued Mar. 27, 2004); each of which is incorporated herein by reference). In an embodiment, the plurality of selectively actuatable energy waveguides 202a are selectively actuatable via one or more light movable liquid crystals positionable between at least a transmissive position and a reflective position. In an embodiment, the plurality of selectively actuatable energy waveguides 202a are selectively actuatable via one or more light movable liquid crystals positionable between at least an activated position and an inactivated position. In an embodiment, the plurality of selectively actuatable energy waveguides 202a are selectively actuatable via one or more prisms. In an embodiment, the plurality of selectively actuatable energy waveguides 202a are selectively actuatable via one or more diffractive beam directing elements. In an embodiment, the plurality of selectively actuatable energy waveguides 202a are selectively actuatable via one or more reflective mirrors. In an embodiment, the plurality of selectively actuatable energy waveguides 202a include one or more electromagnetic energy waveguides.

In an embodiment, the system 100 includes, among other things, at least one router 222 (e.g., energy router, signal router, data packets router, information router, or the like) operably coupled to one or more of the plurality of selectively actuatable energy waveguides 202a. In an embodiment, the catheter device 102 includes at least one router 222 operably coupled to one or more of the plurality of selectively actuatable energy waveguides 202a. In an embodiment, the router 222 is configured to actuate via one or more mechanical-optic components, electro-optic components, or acousto-optic components. In an embodiment, the catheter device 102 includes, among other things, at least one router 222 operably coupled to one or more energy emitters 220. In an embodiment, at least one router 222 is configured to guide an energy stimulus based on one or more selection rules. For example, in an embodiment, the system 100 includes a router 224 operably coupled to at least one of the one or more energy emitters 220, and configured to guide an energy stimulus based on one or more selection rules. Non-limiting examples of selection rules include routing schemes, energy characteristics, waveguide-specific destination information, delivery protocols, routing metrics, address protocols, waveguide-specific addresses, or the like.

In an embodiment, two or more of the plurality of selectively actuatable energy waveguides 202a are operably coupled to at least one optical router 224. In an embodiment, the optical router 224 includes at least one switch 218 (e.g., an optical switch, an opto-mechanical switch, an electro-optic switch, an acousto-optic switch, a thermo-optic switch, or the like). In an embodiment, the optical router 224 includes at least one of an electro-mechanical switch, an opto-mechanical switch, an electro-optic switch, an acousto-optic switch, or a thermo-optic switch.

In an embodiment, the system 100 includes, among other things, at least one optical router 224 operably coupled to at least one of the one or more energy emitters via one or more switches 218. In an embodiment, the optical router 224 is activatable via one or more acousto-optic components, electro-mechanical components, electro-optic components, or mechanical-optic components.

In an embodiment, two or more of the plurality of selectively actuatable energy waveguides 202a are operably coupled to at least one passive optical router 226. In an embodiment, the at least one passive optical router 226 is configured to guide electromagnetic energy based on at least one of waveguide-specific address, wavelength, polarization, intensity, or frequency. In an embodiment, the at least one passive optical router 226 is configured to guide electromagnetic energy based on a polarization. In an embodiment, the router 222 includes one or more switches 218.

In an embodiment, the system 100 includes, among other things, an overmoded electromagnetic energy waveguide 202b photonically coupled to one or more of the plurality of selectively actuatable energy waveguides 202a. In an embodiment, the catheter device 102 includes an overmoded electromagnetic energy waveguide 202b photonically coupled to one or more of the plurality of selectively actuatable energy waveguides 202a. In an embodiment, the overmoded electromagnetic energy waveguide 202b is configured to selectively actuate one or more of the plurality of selectively actuatable energy waveguides 202a. In an embodiment, two or more of the plurality of selectively actuatable energy waveguides 202a are selectively actuatable via one or more overmoded electromagnetic energy waveguides 202b. In an embodiment, the overmoded electromagnetic energy waveguide 202b is configured to propagate electromagnetic energy in at least a first mode and a second mode different from the first mode. In an embodiment, the first mode is configured to actuate one or more of the plurality of selectively actuatable energy waveguides 202a, and the second mode is configured to actuate a different ones of the one or more the plurality of selectively actuatable energy waveguides 202a. In an embodiment, the plurality of selectively actuatable energy waveguides 202a include one or more single-mode electromagnetic energy waveguides 202c coupled to an overmoded electromagnetic energy waveguide 202b. In an embodiment, the plurality of selectively actuatable energy waveguides 202a include one or more single-mode electromagnetic energy waveguides 202c coupled to a multimode electromagnetic energy waveguide 202d.

Referring to FIG. 2, in an embodiment, the system 100 includes, among other things, one or more energy emitters 220. In an embodiment, the catheter device 102 includes one or more energy emitters 220. In an embodiment, the one or more energy emitters 220 are configured to emit at least one of an electromagnetic stimulus, an electrical stimulus, an acoustic stimulus (e.g., ultrasonic stimulus, or the like), and a thermal stimulus. In an embodiment, the one or more energy emitters 220 are configured to generate a sterilizing energy stimulus. In an embodiment, the one or more energy emitters 220 are configured to deliver an energy stimulus to a biological sample received within the one or more fluid-flow passageways 110. In an embodiment, the one or more energy emitters 220 are configured to deliver an emitted energy stimulus to a biological sample proximate a surface of catheter device 102.

In an embodiment, the one or more energy emitters 220 are configured to deliver an energy stimulus along a substantially longitudinal direction, along a substantially lateral direction, or both of at least one of the one or more fluid-flow passageways 110. In an embodiment, the one or more energy emitters 220 are configured to deliver a first portion of an emitted energy stimulus along a substantially lateral direction in one or more regions of at least one of the one or more fluid-flow passageways 110 and deliver a second portion of the emitted energy stimulus along a substantially longitudinal direction in one or more regions of at least one of the one or more fluid-flow passageways 110. In an embodiment, the one or more energy emitters 220 are configured to deliver at least a portion of an emitted energy stimulus along a substantially lateral direction in a first region of at least one of the one or more fluid-flow passageways 110 and deliver at least a portion of the emitted energy stimulus along a substantially lateral direction in a second region of the one or more fluid-flow passageways 110, the second region different from the first region. In an embodiment, the one or more energy emitters 220 are configured to deliver at least a portion of an emitted energy stimulus along a substantially longitudinal direction in a first region of at least one of the one or more fluid-flow passageways 110 and deliver at least a portion of the emitted energy stimulus along a substantially longitudinal direction in a second region of the one or more fluid-flow passageways 110, the second region different from the first region. In an embodiment, the one or more energy emitters 220 are configured to deliver at least a portion of an emitted energy stimulus along a substantially lateral direction in a first region of at least one of the one or more fluid-flow passageways 110 and at least a portion of the emitted energy stimulus along a substantially lateral direction in a second region of the one or more fluid-flow passageways 110, the second region different from the first region.

In an embodiment, the one or more energy emitters 220 are configured to emit one or more energy stimuli (e.g., one or more electromagnetic stimuli, electrical stimuli, acoustic stimuli, and thermal stimuli, or the like) at a dose sufficient to modulate microbial activity proximate a surface of the catheter device 102. For example, in an embodiment, the one or more energy emitters 220 are configured to emit one or more energy stimuli of a dose sufficient to inhibit a DNA replication process of an infectious agent proximate a surface of the catheter device 102.

In an embodiment, the one or more energy emitters 220 are configured to deliver an in vivo stimulus waveform to a biological subject. For example, in an embodiment, the one or more energy emitters 220 are configured to generate one or more continuous or pulsed energy waves, or combinations thereof. In an embodiment, the one or more energy emitters 220 are configured to deliver a sterilizing energy stimulus to a region proximate the catheter device 102. In an embodiment, the one or more energy emitters 220 are configured to deliver an emitted energy to a biological specimen (e.g., tissue, biological fluid, target sample, infectious agent, or the like) proximate at least one of an outer surface 106 or an inner surface 108 of the catheter device 102.

In an embodiment, the one or more energy emitters 220 are energetically coupled to the exterior or interior surfaces 108, 110 of a body structure 104 via one or more waveguides 202 (e.g., via one or more selectively actuatable energy waveguides 202a). In an embodiment, one or more of the waveguides 202 are operably coupled to respective energy emitters 220 and are configured to direct an emitted energy stimulus from the respective energy emitters 220 to one or more regions proximate the body structure 104 based on a determined microorganism colonization event. In an embodiment, at least one of the one or more energy emitters 220 is operably coupled to two or more of the plurality of selectively actuatable energy waveguides 202a. In an embodiment, at least one of the one or more energy emitters 220 is operably coupled to three or more of the plurality of selectively actuatable energy waveguides 202a.

Energy emitters 220 forming part of the catheter device 102 can take a variety of forms, configurations, and geometrical patterns including for example, but not limited to, a one-, two-, or three-dimensional arrays, a pattern comprising concentric geometrical shapes, a pattern comprising rectangles, squares, circles, triangles, polygons, any regular or irregular shapes, or the like, or any combination thereof. One or more of the energy emitters 220 can have a peak emission wavelength in the x-ray, ultraviolet, visible, infrared, near infrared, terahertz, microwave, or radio frequency spectrum. In an embodiment, at least one of the one or more energy emitters 220 is configured to deliver one or more charged particles.

Non-limiting examples of energy emitters 220 include electromagnetic energy emitters 221, acoustic energy emitters 223, thermal energy emitters 225, or electrical energy emitters 227. Further non-limiting examples of energy emitters 220 include optical energy emitters and ultrasound energy emitters. Further non-limiting examples of energy emitters 220 include, electric circuits, electrical conductors, electrodes (e.g., nano- and micro-electrodes, patterned-electrodes, electrode arrays (e.g., multi-electrode arrays, microfabricated multi-electrode arrays, patterned-electrode arrays, or the like), electrocautery electrodes 225a, or the like), cavity resonators, conducting traces 227a, ceramic patterned electrodes, electro-mechanical components, lasers, quantum dots, laser diodes, light-emitting diodes 221a (e.g., organic light-emitting diodes, polymer light-emitting diodes, polymer phosphorescent light-emitting diodes, microcavity light-emitting diodes, high-efficiency UV light-emitting diodes, or the like), arc flashlamps, incandescent emitters, transducers 223a, heat sources, continuous wave bulbs, ultrasound emitting elements, ultrasonic transducers, thermal energy emitting elements, or the like. In an embodiment, the one or more energy emitters 220 include at least one two-photon excitation component. In an embodiment, the one or more energy emitters 220 include at least one of an exciplex laser, a diode-pumped solid state laser, or a semiconductor laser.

Further non-limiting examples of energy emitters 220 include radiation emitters, ion emitters, photon emitters, electron emitters, gamma emitters, or the like. In an embodiment, the one or more energy emitters 220 include one or more incandescent emitters, transducers, heat sources, or continuous wave bulbs. In an embodiment, the one or more energy emitters 220 include one or more laser, light-emitting diodes, laser diodes, fiber lasers, lasers, or ultra-fast lasers, quantum dots, organic light-emitting diodes, microcavity light-emitting diodes, or polymer light-emitting diodes.

Further non-limiting examples of energy emitters 220 include electromagnetic energy emitters 221. In an embodiment, the catheter device 102 includes one or more electromagnetic energy emitters 221. In an embodiment, the one or more electromagnetic energy emitters 221 provide a voltage across at least a portion of cells proximate an outer surface 106 of the catheter device 102. In an embodiment, the one or more electromagnetic energy emitters 221 include one or more electrodes. In an embodiment, the one or more electromagnetic energy emitters 221 include one or more light-emitting diodes 221a. In an embodiment, the one or more electromagnetic energy emitters 221 include at least one electron emitting material.

In an embodiment, the one or more electromagnetic energy emitters 221 provide a voltage across at least a portion of tissue proximate the catheter device 102, and to induce pore formation in a plasma membrane of at least a portion of infectious agents within a region proximate the catheter device 102. In an embodiment, the voltage is of a dose sufficient to exceed a nominal dielectric strength of at least one cell plasma membrane. In an embodiment, the one or more electromagnetic energy emitters 221 provide a voltage across at least a portion of cells within a biological fluid received within at least one of the one or more fluid-flow passageways 110. In an embodiment, the voltage is of sufficient strength and duration to exceed a nominal dielectric strength of at least one cell plasma membrane. In an embodiment, the voltage is of sufficient strength and duration to exceed a nominal dielectric strength of a cell plasma membrane without substantially interfering with a normal operation of the implantable shunt system.

Further non-limiting examples of energy emitters 220 include thermal energy emitters 225. Non-limiting examples of thermal energy emitters 225 include transducers 223a, metallic heat-radiating elements, high power light-emitting diodes, thermal energy emitting elements, thermal energy conducting elements, thermal energy dissipating elements, electrodes, or the like. In an embodiment, the one or more thermal energy emitters 225 are configured to emit a sufficient amount of an energy stimulus to inactivate an infectious agent. In an embodiment, the catheter device 102 includes one or more thermal energy emitters 225 configured to thermally shock an infectious agent.

Further non-limiting examples of energy emitters 220 include electrical energy emitters 227. In an embodiment, the one or more electrical energy emitters 227 include at least one electrode 227a. In an embodiment, a plurality of electrodes 227a are configured to energize a region proximate the catheter device 102 in the presence of an applied potential. In an embodiment, the applied potential is sufficient to produce superoxidized water from an aqueous salt composition proximate the plurality of electrodes 227a. In an embodiment, the applied potential is sufficient to produce at least one of a triplet excited-state specie, a reactive oxygen specie, a reactive nitrogen specie, a free radical, a peroxide, or any other inorganic or organic ion or molecules that include oxygen ions. Further non-limiting examples of energy emitters 220 can be found in, for example, U.S. Pat. No. 6,488,704 (issued Dec. 3, 2002), which is incorporated herein by reference.

In an embodiment, a plurality of electrodes 227a provide an electrical energy stimulus. Electrodes 227a can take a variety of forms, configurations, and geometrical patterns including for example, but not limited to, a one-, two-, or three-dimensional arrays, a pattern comprising concentric geometrical shapes, a pattern comprising rectangles, squares, circles, triangles, polygons, any regular or irregular shapes, or the like, and any combination thereof. Techniques suitable for making patterned electrodes include, but are not limited to, electro-deposition, electro-deposition onto laser-drilled polymer molds, laser cutting and electro-polishing, laser micro-machining, surface micro-machining, soft lithography, x-ray lithography, LIGA techniques (e.g., X-ray lithography, electroplating, and molding), conductive paint silk screen techniques, conventional patterning techniques, injection molding, conventional silicon-based fabrication methods (e.g., inductively coupled plasma etching, wet etching, isotropic and anisotropic etching, isotropic silicon etching, anisotropic silicon etching, anisotropic GaAs etching, deep reactive ion etching, silicon isotropic etching, silicon bulk micromachining, or the like), complementary-symmetry/metal-oxide semiconductor (CMOS) technology, deep x-ray exposure techniques, or the like.

In an embodiment, the one or more energy emitters 220 include at least one light-emitting diode 221a. In an embodiment, the catheter device 102 includes one or more light-emitting diodes 221a. Light-emitting diodes 221a come in a variety of forms and types including, for example, standard, high intensity, super bright, low current types, or the like. Typically, the light-emitting diode's color is determined by the peak wavelength of the light emitted. For example, red light-emitting diodes have a peak emission ranging from about 610 nm to about 660 nm. Non-limiting examples of light-emitting diode colors include amber, blue, red, green, white, yellow, orange-red, ultraviolet, or the like. Further non-limiting examples of light-emitting diodes include bi-color, tri-color, or the like. Light-emitting diode's emission wavelength may depend on a variety of factors including, for example, the current delivered to the light-emitting diode. The color or peak emission wavelength spectrum of the emitted light may also generally depend on the composition or condition of the semi-conducting material used, and can include, among other things, peak emission wavelengths in the infrared, visible, near-ultraviolet, or ultraviolet spectrum, or combinations thereof.

Light-emitting diodes 221a can be mounted on, for example, but not limited to a surface, a substrate, a portion, or a component of the catheter device 102 using a variety of methodologies and technologies including, for example, wire bonding, flip chip, controlled collapse chip connection, integrated circuit chip mounting arrangement, or the like. In an embodiment, the light-emitting diodes 221a are mounted on a surface, substrate, portion, or component of the catheter device 102 using, for example, but not limited to a flip-chip arrangement. A flip-chip is one type of integrated circuit chip mounting arrangement that generally does not require wire bonding between chips. In an embodiment, instead of wire bonding, solder beads or other elements are positioned or deposited on chip pads such that when the chip is mounted, electrical connections are established between conductive traces carried by circuitry within the system 100. In an embodiment, the one or more energy emitters 220 include one or more light-emitting diode arrays. In an embodiment, the one or more energy emitters 220 include at least one of a one-dimensional light-emitting diode array, a two-dimensional light-emitting diode array, or a three-dimensional light-emitting diode array.

In an embodiment, the one or more energy emitters 220 include at least one acoustic energy emitter 223. In an embodiment, the catheter device 102 includes one or more acoustic energy emitters 223. In an embodiment, the one or more energy emitters 220 include one or more transducers 223a (e.g., acoustic transducers, electroacoustic transducers, electrochemical transducers, electromagnetic transducers, electromechanical transducers, electrostatic transducers, photoelectric transducers, radioacoustic transducers, thermoelectric transducers, ultrasonic transducers, or the like). In an embodiment, the one or more transducers 223a are configured to deliver an acoustic energy stimulus (e.g., an acoustic non-thermal stimulus, an acoustic thermal stimulus, a low or high intensity acoustic stimulus, a pulsed acoustic stimulus, a focused acoustic stimulus, or the like) to a region within the biological subject. In an embodiment, the one or more transducers 223a are configured to generate an ultrasonic stimulus. In an embodiment, the one or more transducers 223a are configured to detect an acoustic signal. In an embodiment, the one or more transducers 223a are configured to transmit and receive acoustic waves. In an embodiment, the one or more transducers 223a are configured to deliver an ultrasonic stimulus to a region proximate the catheter device 102. In an embodiment, the one or more transducers 223a are configured to deliver an in vivo ultrasonic interrogation waveform to a biological subject. In an embodiment, the one or more transducers 223a are configured to generate one or more continuous or a pulsed ultrasonic waves, or combinations thereof.

Non-limiting examples of transducers 223a include, among others, acoustic transducers, composite piezoelectric transducers, conformal transducers, flexible transducers, flexible ultrasonic multi-element transducer arrays, flexible ultrasound transducers, immersible ultrasonic transducers, integrated ultrasonic transducers, micro-fabricated ultrasound transducers, piezoelectric materials (e.g., lead-zirconate-titanate, bismuth titanate, lithium niobate, piezoelectric ceramic films or laminates, sol-gel sprayed piezoelectric ceramic composite films or laminates, piezoelectric crystals, or the like), piezoelectric ring transducers, piezoelectric transducers, ultrasonic sensors, ultrasonic transducers, or the like. In an embodiment, the one or more energy emitters 220 include one or more one-dimensional transducer arrays, two-dimensional transducer arrays, or three-dimensional transducer arrays. The one or more transducers 223a can include, but are not limited to, a single design where a single piezoelectric component outputs one single waveform at a time, or can be compound where two or more piezoelectric components are utilized in a single transducer 223a or in multiple transducers 223a thereby allowing multiple waveforms to be output sequentially or concurrently.

The effects of therapeutic ultrasound on living tissues vary. For example, ultrasound typically has a greater affect on highly organized, structurally rigid tissues such as bone, tendons, ligaments, cartilage, and muscle. Due to their different depths within the body, however, the different tissue types require different ultrasonic frequencies for effective treatment. See, e.g., U.S. Publication No. 2007/0249969 (published Oct. 25, 2007) (which is incorporated herein by reference). Ultrasound can cause increases in tissue relaxation, local blood flow, and scar tissue breakdown. In an embodiment, the effect of the increase in local blood flow are used to, for example, aid in reducing local swelling and chronic inflammation, as well as promote bone fracture healing. In an embodiment, applying a sufficient ultrasonic energy to tissue infected with, for example, pathogenic bacteria, can lead to a reduction of the pathogenic bacteria in at least a portion of the infected tissue. In an embodiment, applying a sufficient ultrasonic energy to tissue infected with, for example, pathogenic bacteria, in the presence of one or more disinfecting agents can lead to a reduction of the pathogenic bacteria in at least a portion of the infected tissue. In an embodiment, applying a sufficient ultrasonic energy to tissue infected with, for example, pathogenic bacteria, in the presence of one or more disinfecting agents can reduce biofilm viability, as well as actively-impeding biofilm formation on an implant.

In an embodiment, the system 100 includes electro-mechanical components for generating, transmitting, or receiving waves (e.g., ultrasonic waves, electromagnetic waves, or the like). For example, in an embodiment, the system 100 includes one or more waveform generators 229, as well as any associated hardware, software, or the like. In an embodiment, the system 100 includes one or more computing devices 230 configured to concurrently or sequentially operate multiple transducers 223a. In an embodiment, the system 100 includes multiple drive circuits (e.g., one drive circuit for each transducer 223a) and is configured to generate varying waveforms from each coupled transducer 223a (e.g., multiple waveform generators, or the like). In an embodiment, the system 100 includes, among other things, an electronic timing controller coupled to an ultrasonic waveform generator. In an embodiment, one or more computing devices 230 are configured to automatically control one or more of a frequency, a duration, a pulse rate, a duty cycle, an amount of energy, or the like associated with the ultrasonic energy generated by the one or more transducers 223a.

In an embodiment, the one or more transducers 223a are communicatively coupled to one or more waveform generators 229. In an embodiment, a waveform generator 229 can include, among other things, an oscillator 231 and a pulse generator 233 configured to generate one or more drive signals for causing one or more transducer 223a to ultrasonically vibrate and generate ultrasonic energy.

In an embodiment, the catheter device 102 employs high intensity focused ultrasound (HIFU) to induce localized heating. For example, in an embodiment, the catheter device 102 includes one or more acoustic energy emitters 223 configured to deliver a high intensity focused ultrasound stimulus. High acoustic intensities associated with HIFU can cause rapid heat generation in cells and tissue due to absorption of the acoustic energy. Delivering a HIFU stimulus can cause the temperature in a region including cells (e.g., subject cells, intracellularly infected cells, microbial cells, bacterial cell, yeast cells, fungal cells, or the like) and or tissue to rise very rapidly, inducing thermal stressing of at least one of the targeted cells or tissue which in turn can lead to programmed cell death. The degree of thermal stressing of cells may be a function of the character or duration of the energy stimulus delivered to induce a temperature change. For example, rapid heating of cells using HIFU may be advantageous for rapidly attenuating an infectious activity by inducing cell death as opposed to slow increases in temperature to which the cells may become adapted. See, e.g., Somwaru, et al., *J. Androl.* 25:506-513, 2004; Stankiewicz, et al., *J. Biol. Chem.* 280: 38729-38739, 2005; Sodja, et al., *J. Cell Sci.* 111:2305-2313, (1998); Setroikromo, et al., *Cell Stress Chaperones* 12:320-330, 2007; Dubinsky, et al., *AJR* 190:191-199, 2008; Lepock. *Int. J. Hyperthermia,* 19:252-266, 2003; Roti *Int. J. Hyper-*

*thermia* 24:3-15, 2008; Fuchs, et al., "The Laser's Position in Medicine" pp 187-198 in *Applied Laser Medicine*. Ed. Hans-Peter Berlien, Gerhard J. Muller, Springer-Verlag New York, LLC, 2003; each of which is incorporated herein by reference.

In an embodiment, one or more energy emitters 220 are configured to emit a sterilizing energy stimulus having one or more peak emission wavelengths in the infrared, visible, or ultraviolet spectrum, or combinations thereof. For example, in an embodiment, at least one of the one or more energy emitters 220 comprises a peak emission wavelength ranging from about 100 nanometers to about 400 nanometers. In an embodiment, at least one of the one or more energy emitters 220 comprises a peak emission wavelength ranging from about 100 nanometers to about 320 nanometers. In an embodiment, at least one of the one or more energy emitters 220 comprises an electromagnetic energy peak emission wavelength ranging from about 100 nanometers to about 280 nanometers. In an embodiment, at least one of the one or more energy emitters 220 comprises an electromagnetic energy peak emission wavelength ranging from about 200 nanometers to about 290 nanometers. In an embodiment, at least one of the one or more energy emitters 220 comprises a peak emission wavelength ranging from about 280 nanometers to about 320 nanometers. In an embodiment, at least one of the one or more energy emitters 220 comprises a peak emission wavelength ranging from about 260 nanometers to about 265 nanometers. In an embodiment, at least one of the one or more energy emitters 220 comprises a peak emission wavelength about 260 nanometers In an embodiment, an operational fluence of one or more energy emitters 220 is less than about 80 milli-joules per square centimeter. In an embodiment, an operational fluence of one or more energy emitters 220 is less than about 35 milli-joules per square centimeter. In an embodiment, an operational fluence of one or more energy emitters 220 is less than about 15 milli-joules per square centimeter. In an embodiment, an average energy density of one or more energy emitters 220 ranges from about less than about 15 milli-joules per square centimeter to about less than about 80 milli-joules per square centimeter.

In an embodiment, the one or more energy emitters 220 are configured to emit one or more energy stimuli of at a dose sufficient to induce programmed cell death (PCD) (e.g., apoptosis) of at least a portion of cells proximate the catheter device 102. PCD can be induced using a variety of methodologies and technologies including, for example, using acoustic energy, electricity, electromagnetic energy, thermal energy, pulsed electric fields, pulsed ultrasound, focused ultrasound, low intensity ultrasound, ultraviolet radiation, or the like. Localized heating therapy caused by the delivery of energy, for example via one or more energy emitters 220, can likewise induce PCD (e.g., apoptosis) or necrosis of cells or tissue depending upon the temperature experienced by the cells or tissue. For example, localized heating therapy between 40° C. and 60° C. can result in disordered cellular metabolism and membrane function and in many instances, cell death (e.g., PCD). In general, at temperatures below 60° C., localized heating is more likely to induce PCD in cells without substantially inducing necrosis. At temperatures greater than about 60° C., the likelihood of inducing coagulation necrosis of cells and tissue increases. Relatively small increases in temperature (e.g., a 3° C. increase) above the normal functioning temperature of a cell can cause apoptotic cell death. For example, temperatures ranging from 40° C. to 47° C. can induce cell death in a reproducible time and temperature dependent manner in cells normally functioning at 37° C.

Non-limiting examples of methodologies and technologies for inducing PCD can be found the following documents: Abdollahi et al., *Apoptosis signals in Lymphoblasts Induced by Focused Ultrasound*, FASEB Journal Express Article doi: 10.1096/fj.04-1601fje (Published online Jul. 1, 2004); Ashush et al., *Apoptosis Induction of Human Myeloid Leukemic Cells by Ultrasound Exposure*, Cancer Res. 60: 1014-1020 (2000); Beebe et al., *Nanosecond, High-intensity Pulsed Electric Fields Induce Apoptosis in Human Cells*, The FASEB Journal express article 10.1096/fj.02-0859fje (Published online Jun. 17, 2003); Caricchio et al., *Ultraviolet B Radiation-Induced Cell Death: Critical Role of Ultraviolet Dose in Inflammation and Lupus Autoantigen Redistribution*, J. Immunol., 171: 5778-5786 (2003); Fabo et al., *Ultraviolet B but not Ultraviolet A Radiation Initiates Melanoma*, Cancer Res. 64 (18): 6372-376 (2004); Fent et al., *Low intensity Ultrasound-induced Apoptosis in Human Gastric Carcinoma Cells*, World J Gastroenterol, 14 (31):4873-879 (2008); Hall et al., *Nanosecond Pulsed Electric Fields Induce Apoptosis in p53-Wildtype and p53-Null HCT116 Colon Carcinoma Cells*, Apoptosis, 12 (9):1721-31 (2007); and Rediske et al., *Pulsed Ultrasound Enhances the Killing of Escherichia coli Biofilms by Aminoglycoside Antibiotics In vivo*, Antimicrob. Agents Chemother., 44 (3): 771-72 (2000); each of which is incorporated herein by reference.

In an embodiment, the catheter device 102 is configured to emit a sufficient amount of an energy stimulus to induce PCD without substantially inducing necrosis of a portion of cells in the vicinity of the catheter device 102. For example, in an embodiment, the catheter device 102 includes one or more energy emitters 220 configured to deliver electromagnetic radiation of a dose sufficient to induce PCD without substantially inducing necrosis of a tissue proximate a surface (e.g., an outer surface, inner surface, or the like) of the catheter device 102. In an embodiment, at least one of the one or more energy emitters 220 is configured to emit a pulsed energy stimulus of a dose sufficient to induce PCD without substantially inducing necrosis of an infectious agent within a biological sample proximate the surface of the body structure 104. In an embodiment, one or more of the energy emitters 220 are configured to deliver a sufficient amount of an ultraviolet radiation to induce cell death by PCD. In an embodiment, one or more of the energy emitters 220 are configured to deliver an effective dose of optical energy at which a cell preferentially undergoes PCD compared to necrosis.

In an embodiment, one or more of the energy emitters 220 are configured to deliver a thermal sterilizing stimulus (e.g., a pulse thermal sterilizing stimulus, a spatially patterned thermal sterilizing stimulus, a temporally patterned sterilizing stimulus, or the like) of a dose sufficient to elevate a temperature of at least a portion of cells proximate a catheter device 102. Elevating the temperature of a mammalian cell, for example, to 43° C. can cause changes in cellular protein expression and increased PCD.

In an embodiment, the catheter device 102 includes one or more thermal energy emitters 225 configured to emit a thermal energy stimulus of a dose to thermally induce PCD of a portion of infected cells proximate the catheter device 102. For example, in an embodiment, one or more of the thermal energy emitters 225 are operable to emit a sufficient amount of an energy stimulus to increase the temperature of at least a portion of a biological sample received within at least one of the one or more fluid-flow passageways 110 by about 5° C. to about 20° C. In an embodiment, the one or more thermal energy emitters 225 are operable to emit a sufficient amount of an energy stimulus to increase the temperature of at least a portion of a biological sample received within at least one of the one or more fluid-flow passageways 110 by about 5° C. to about 6° C.

In an embodiment, at least one of the one or more energy emitters 220 is configured to emit an energy stimulus of a dose sufficient to induce PCD in a pathogen within a fluid received within at least one of the one or more fluid-flow passageways 110. In an embodiment, at least one of the one or more energy emitters 220 is configured to deliver an energy stimulus of a dose sufficient to induce poration (e.g., electroporation) of a plasma membrane in at least a portion of cells proximate the catheter device 102. In an embodiment, the one or more energy emitters 220 include at least one ultraviolet energy emitter. In an embodiment, the one or more energy emitters 220 are configured to deliver a sufficient amount of an optical energy to initiate ultraviolet energy induced PCD. In an embodiment, the one or more energy emitters 220 include at least one ultraviolet B energy emitter. In an embodiment, the one or more energy emitters 220 include at least one ultraviolet C energy emitter. In an embodiment, at least one of the one or more energy emitters 220 is a germicidal light emitter. In an embodiment, at least one of the one or more energy emitters 220 is an ultraviolet C light emitting diode.

In an embodiment, the catheter device 102 includes, among other things, one or more energy emitters 220 configured to emit a pulsed thermal sterilizing stimulus of a dose sufficient to induce PCD without substantially inducing necrosis of at least a portion of cells proximate the catheter device 102 in response to a detected measurand. In an embodiment, at least one of the one or more energy emitters 220 is configured to emit a pulsed thermal sterilizing stimulus of a dose sufficient to induce PCD without substantially inducing necrosis of an infectious agent within a tissue proximate the catheter device 102 in response to a detect level of an infectious agent. In an embodiment, at least one of the one or more energy emitters 220 is configured to deliver a pulsed thermal sterilizing stimulus of a dose sufficient to induce thermally enhanced poration of a plasma membrane in at least a portion of cells within a tissue proximate the catheter device 102. In an embodiment, at least of the one or more energy emitters 220 is configured to deliver a pulsed thermal sterilizing stimulus of a dose sufficient to induce poration of a plasma membrane in at least a portion of cells on a surface of the catheter device 102.

In an embodiment, the one or more energy emitters 220 are operable to emit a sufficient amount of a pulsed sterilizing stimulus to increase the temperature of at least a portion of cells proximate a surface of the catheter device 102. In an embodiment, the one or more energy emitters 220 are operable to emit a sufficient amount of a pulsed sterilizing stimulus to increase the temperature of at least a portion cells within a biological sample received within at least one of the one or more fluid-flow passageways 110. For example, in an embodiment, the one or more energy emitters 220 are operable to emit a sufficient amount of a pulsed thermal sterilizing stimulus to increase the temperature of at least a portion of cells proximate the catheter device 102 by about 3° C. to about 22° C.

In an embodiment, the one or more energy emitters 220 are operable to emit a sufficient amount of a pulsed thermal sterilizing stimulus to increase the temperature of at least a portion of cells proximate the catheter device 102 by about 3° C. to about 10° C. In an embodiment, the one or more energy emitters 220 are operable to emit a sufficient amount of a pulsed thermal sterilizing stimulus to increase the temperature of at least a portion of cells proximate the catheter device 102 by about 3° C. to about 4° C.

In an embodiment, at least one of the one or more energy emitters 220 is configured to deliver a pulsed thermal sterilizing stimulus of a dose sufficient to elevate a temperature of at least a portion of cells proximate the catheter device 102 from about 37° C. to less than about 60° C. In an embodiment, at least one of the one or more energy emitters 220 is configured to deliver a pulsed thermal sterilizing stimulus of a dose sufficient to elevate a temperature of at least a portion of cells proximate the catheter device 102 from about 37° C. to less than about 47° C. In an embodiment, at least one of the one or more energy emitters 220 is configured to deliver a pulsed thermal sterilizing stimulus 37° C. of a dose sufficient to elevate a temperature of at least a portion of cells proximate the catheter device 102 from about 37° C. to less than about 45° C. In an embodiment, at least one of the one or more energy emitters 220 is configured to deliver a pulsed thermal sterilizing stimulus of a dose sufficient to elevate a temperature of at least a portion of cells proximate the catheter device 102 from about 37° C. to less than about 42° C. In an embodiment, at least one of the one or more energy emitters 220 is configured to deliver a pulsed thermal sterilizing stimulus of a dose sufficient to elevate a temperature of at least a portion of cells proximate the catheter device 102 from about 37° C. to a temperature ranging from greater than about 41° C. to less than about 63° C.

In an embodiment, the one or more energy emitters 220 are configured to direct optical energy along the optical path for a duration sufficient to interact with a biological sample received within one or more fluid-flow passageways 110. For example, in an embodiment, the one or more energy emitters 220 are configured to generate one or more non-ionizing laser pulses in an amount and for a duration sufficient to induce the formation of sound waves associated with changes in a biological mass present along an optical path. In an embodiment, the one or more energy emitters 220 are configured to direct a pulsed optical energy waveform along an optical path of a dose sufficient to cause a biological mass, a portion of cells, a sample, or the like within a focal volume interrogated by the pulsed optical energy waveform to temporarily expand. In an embodiment, the one or more energy emitters 220 are configured to direct a pulsed optical energy stimulus along an optical path in an amount and for a duration sufficient to elicit the formation of acoustic waves associated with changes in a biological mass present along the optical path.

In an embodiment, the one or more energy emitters 220 are configured to direct a pulsed optical energy waveform along an optical path of a dose sufficient to cause at least a portion of cells within a focal volume interrogated by the pulsed optical energy waveform to temporarily expand. In an embodiment, the one or more energy emitters 220 are configured to direct a pulsed optical energy waveform along an optical path in an amount and for a duration sufficient to cause at least a portion of cells within a focal volume interrogated by the pulsed optical energy waveform to temporarily fluoresce. In an embodiment, the one or more energy emitters 220 are further configured to direct a portion of an emitted optical energy to a sensor component in optical communication along the optical path.

In an embodiment, the one or more energy emitters 220 are concurrently or sequentially deliver one or more electromagnetic stimuli, electrical stimuli, acoustic stimuli, or thermal stimuli, in vivo, to at least one of a target sample, a biological sample, an infectious agent, or the like received within at least one of the one or more fluid-flow passageways 110. In an embodiment, at least one of the one or more energy emitters 220 is photonically coupleable to at least one of an interior or an exterior of one or more of the one or more fluid-flow passageways 110 via one or more energy waveguides 202. In an embodiment, at least one of the one or more energy emitters 220 is configured to emit an energy stimulus from an interior of at least one of the one or more fluid-flow passageways to an exterior of at least one of the one or more fluid-flow passageways 110.

In an embodiment, the one or more energy emitters 220 provide a voltage across at least a portion of cells in the vicinity of the catheter device 102. In an embodiment, the voltage is of a dose sufficient to exceed a nominal dielectric strength of at least one cell plasma membrane. In an embodiment, the voltage is of a dose sufficient to exceed a nominal dielectric strength of a cell plasma membrane without substantially interfering with a normal operation of the implantable shunt system 100 or the catheter device 102.

In an embodiment, the one or more energy emitters 220 are implanted within a biological subject. In an embodiment, the one or more energy emitters 220 are configured to apply energy (e.g., electrical energy, electromagnetic energy, thermal energy, ultrasonic energy, or the like, or combinations thereof) to tissue proximate a catheter device 102 to, for example, treat or prevent an infection (e.g., an implant-associated infection, hematogenous implant-associated infection, or the like), a hematological abnormality, or the like. In an embodiment, the one or more energy emitters 220 are configured to apply energy to tissue proximate a catheter device 102 to promote at least one of a tissue healing process, a tissue growing process, a tissue scarring process, or the like. In an embodiment, the one or more energy emitters 220 are configured to apply energy of a dose sufficient to tissue proximate an implant to inhibit a tissue scarring process. In an embodiment, the one or more energy emitters 220 are configured to apply energy to tissue proximate an implant to treat, prevent, inhibit, or reduce post-operative adhesion, fibrin sheath formation, or scar tissue formation. In an embodiment, the one or more energy emitters 220 are configured to apply an energy stimulus to tissue proximate a catheter device 102 to treat, prevent, inhibit, or reduce the presence or concentration of an infectious agent within at least a portion of the tissue proximate the catheter device 102.

In an embodiment, the one or more energy emitters 220 are concurrently or sequentially deliver at least a first energy stimulus and a second energy stimulus, the second energy stimulus different from the first energy stimulus. In an embodiment, the second energy stimulus differs in at least one of a spatial energy distribution and a temporal energy distribution. In an embodiment, the first energy stimulus comprises an electromagnetic energy stimulus, an electrical energy stimulus, an ultrasonic energy stimulus, or a thermal energy stimulus, and the second energy stimulus comprises a different one of an electromagnetic energy stimulus, an electrical energy stimulus, an ultrasonic energy stimulus, or a thermal energy stimulus.

In an embodiment, at least one of the one or more energy emitters 220 is configured to provide an illumination pattern comprising at least a first region and a second region. In an embodiment, the second region includes at least one of an illumination intensity, an energy-emitting pattern, a peak emission wavelength, an ON-pulse duration, an OFF-pulse duration, or a pulse frequency different from the first region. In an embodiment, the second region includes at least one of a spatial pattern or a temporal pattern different from the first region.

In an embodiment, at least one of the one or more energy emitters 220 is operably coupled to a plurality of energy waveguides 202 (e.g., a plurality of selectively actuatable energy waveguides 202a, or the like) that are configured to deliver a spatially or temporally patterned energy stimulus. In an embodiment, at least one of the one or more energy emitters 220 is configured to emit a multiplex energy stimulus having two or more peak emission wavelengths. In an embodiment, a multiplex energy stimulus can be routed to respective waveguides 202 based on a wavelength, an intensity, a spectral power distribution, a waveguide-specific address, a polarization, or the like. In an embodiment, the catheter device 102 includes one or more polarization rotators operably coupled to at least one of the one or more energy emitters 220. In an embodiment, at least one of the one or more energy emitters 220 is operably coupled to one or more polarization rotators.

In an embodiment, the system 100 includes, among other things, one or more energy emitters 220 configured to provide a spatially patterned energy stimulus having at least a first region and a second region different from the first region. In an embodiment, the first region comprises one of a spatially patterned electromagnetic energy stimulus, a spatially patterned electrical energy stimulus, a spatially patterned ultrasonic energy stimulus, or a spatially patterned thermal energy stimulus, and the second region comprises a different one of a spatially patterned electromagnetic energy stimulus, a spatially patterned electrical energy stimulus, a spatially patterned ultrasonic energy stimulus, or a spatially patterned thermal energy stimulus. In an embodiment, the second region comprises at least one of an emission intensity, an emission phase, an emission polarization, or an emission wavelength different from the first region. In an embodiment, the second region comprises a peak irradiance different from the first region.

In an embodiment, the system 100 includes one or more spatially patterned energy emitters 235. In an embodiment, the system 100 includes, among other things, one or more spaced-apart energy emitters 237. In an embodiment, the system 100 includes, among other things, one or more patterned energy emitters 239. Patterned energy emitters 239 can be sized and shaped to provide a spatially patterned energy stimulus to, for example, a region proximate a catheter device 102. In an embodiment, a plurality of energy emitters 220 provides a spatially patterned energy stimulus. The spatially patterned energy stimulus can take a variety forms, configurations, and geometrical patterns including for example, but not limited to, lines, circles, ellipses, triangles, rectangles, polygons, any regular or irregular geometrical patterns, one-dimensional patterns, two-dimensional patterns, three-dimensional patterns, or the like, and any combination thereof. In an embodiment, a plurality of energy emitters 220 includes a patterned energy-emitting source. In an embodiment, at least one of the one or more energy emitters 220 includes at least one of a patterned electromagnetic energy-emitting source, a patterned electrical energy-emitting source, a patterned ultrasonic energy-emitting source, or a patterned thermal energy-emitting source. In an embodiment, at least one of the one or more energy emitters 220 includes a patterned electrode.

In an embodiment, the catheter device 102 includes at least a first energy emitter and a second energy emitter. In an embodiment, the second energy emitter is configured to emit an energy stimulus having an emission wavelength different from an energy stimulus emitted by the first energy emitter. In an embodiment, the second energy emitter is configured to emit an energy stimulus having a polarization different from an energy stimulus emitted by the first energy emitter.

In an embodiment, one or more of the energy emitters 220 are configured to concurrently or sequentially emit at least a first energy stimulus to an interior 108 of one or more fluid-flow passageways 104 and a second energy stimulus to an exterior 106 of one or more fluid-flow passageways. In an embodiment, the catheter device 102 includes an optical component that directs at least a portion of an emitted energy stimulus from one or more of the energy emitters 220 to one or more of the plurality of selectively actuatable energy waveguides 202a.

In an embodiment, the at least one of the one or more energy emitters 220 is operably coupled to a router 222 having an output directed to two or more of the plurality of selectively actuatable energy waveguides 202a. In an embodiment, the at least one of the one or more energy emitters 220 is operably coupled to an optical router 224 having one or more outputs directed to two or more of a plurality of selectively actuatable energy waveguides 202a.

In an embodiment, the at least one of the one or more energy emitters 220 is operably coupled to a first electromagnetic energy waveguide that is operably coupled to two or more of a selectively actuatable energy waveguides 202a. In an embodiment, the at least one of the one or more energy emitters 220 is operably coupled to a first electromagnetic energy waveguide that is operably coupled to an optical router 224 having one or more outputs directed to two or more of a plurality of selectively actuatable energy waveguides 202a. In an embodiment, at least one of the one or more energy emitters 220 is photonically coupled to one or more of the plurality of selectively actuatable energy waveguides 202a. In an embodiment, the at least one of the one or more energy emitters 220 is photonically coupled to an interior environment of the body structure 104 via at least one of the plurality of selectively actuatable energy waveguides 202a. In an embodiment, at least one of the one or more energy emitters 220 is photonically coupled to an exterior environment of the body structure 104 via at least one of the plurality of selectively actuatable energy waveguides 202a. In an embodiment, at least one of the one or more energy emitters 220 is configured to emit an energy stimulus from an interior to an exterior of at least one of the one or more fluid-flow passageways 110.

In an embodiment, one or more of the energy emitters 220 are configured to concurrently or sequentially provide one or more electromagnetic stimuli, electrical stimuli, ultrasonic stimuli, or thermal stimuli. In an embodiment, one or more of the energy emitters 220 are configured to concurrently or sequentially provide at least a first energy stimulus and a second energy stimulus.

In an embodiment, the second energy stimulus differs from the first energy stimulus. For example, in an embodiment, the second energy stimulus includes an electromagnetic energy stimulus, an electrical energy stimulus, an ultrasonic energy stimulus, or a thermal energy stimulus different from the first energy stimulus. In an embodiment, the second energy stimulus includes at least one of a peak emission wavelength, a repetition rate, or a bandwidth different from the first energy stimulus. In an embodiment, the second energy stimulus includes at least one of an irradiance, a spectral power distribution, or a peak power different from the first energy stimulus.

In an embodiment, the system 100 includes, among other things, a plurality of independently addressable energy emitting components 274 disposed along a longitudinal axis of the catheter device 102. In an embodiment, the independently addressable energy emitting components 274 include one or more waveguides 202 operably coupled to one or more energy emitters 220. In an embodiment, the plurality of independently addressable energy emitting components 274 is configured to direct an emitted energy stimulus to one or more regions proximate at least one of the outer surface and the inner surface of the body structure 104. In an embodiment, one or more of the plurality of independently addressable energy emitting components 274 are operably coupled to respective energy emitters 220 and are configured to direct an emitted energy stimulus from the respective energy emitters 220 to one or more regions proximate the body structure 104 based on a determined microorganism colonization event. In an embodiment, one or more of the plurality of independently addressable energy emitting components 274 are operably coupled to respective energy emitters 220 and are configured to direct an emitted energy stimulus from the respective energy emitters 220 to one or more regions proximate at least one of the outer surface 106 and the inner surface 108 of the body structure 104 based on a determined microorganism colonization event.

In an embodiment, the system 102 includes actuating means 272 for concurrently or sequentially actuating two or more of the plurality of independently addressable energy emitting components 274 in one or more regions determined to have a microorganism colonization event. In an embodiment, the actuating means 272 includes one or more switches 218. In an embodiment, the actuating means 272 includes one or more switches 218 operably coupled to one or more computing devices. In an embodiment, the actuating means 272 includes at least one computing device 230 configured to generate a response that causes a switching element to establish or interrupt a connection between the selectively actuatable energy waveguides and respective one or more energy emitters 220.

In an embodiment, the one or more switches 218 include at least one acoustically active material. In an embodiment, the one or more switches 218 include at least one electro-mechanical switch. In an embodiment, the one or more switches 218 include at least one electro-optic switch. In an embodiment, the one or more switches 218 include at least one acousto-optic switch. In an embodiment, the one or more switches 218 include at least one optical switch. In an embodiment, the actuating means 272 includes at least one of an electro-mechanical switch, an electro-optic switch, an acousto-optic switch, or an optical switch.

In an embodiment, the actuating means 272 includes at least one computing device 230 operably coupled to one or more switches. In an embodiment, the actuating means 272 includes at least one optical antifuse. In an embodiment, the actuating means 272 includes a movable component having an optical energy reflecting substrate. In an embodiment, the movable component is actuated by an electromagnetic energy stimulus generated by one or more energy emitters 220, and configured to guide an optical energy along at least one of the plurality of independently addressable energy emitting components 274 when actuated. In an embodiment, the actuating means 272 is configured to concurrently or sequentially actuate two or more of the plurality of independently addressable energy emitting components 274 in one or more regions based on a determined microorganism colonization event.

With continued reference to FIG. 2, in an embodiment the system 100 includes, among other things, at least one computing device 230 including one or more processors 232 (e.g., microprocessors), central processing units (CPUs) 234, digital signal processors (DSPs) 236, application-specific integrated circuits (ASICs) 238, field programmable gate arrays (FPGAs) 240, controllers, or the like, or any combinations thereof, and can include discrete digital or analog circuit elements or electronics, or combinations thereof. In an embodiment, the system 100 includes, among other things, one or more field programmable gate arrays 240 having a plurality of programmable logic components. In an embodiment, the system 100 includes, among other things, one or more application specific integrated circuits having a plurality of predefined logic components.

In an embodiment, at least one computing device 230 is operably coupled to one or more energy emitters 220 and one or more energy waveguide 202. In an embodiment, the system 100 includes one or more computing devices 230 configured to concurrently or sequentially operate multiple energy emitters 220. In an embodiment the computing device 230 comprises at least one controller. In an embodiment, at least one computing device 230 is operably coupled to one or more energy waveguide 202. In an embodiment, one or more of the energy waveguides 202 are configured for selectively actuation via one or more computing devices 230.

In an embodiment, the system 100 includes one or more catheter devices 102 including, among other things, one or more receivers 280, transceivers 282, or transmitters 284. In an embodiment, at least one of the one or more receiver 280, transceivers 282, and transmitters 284, can be, for example, wirelessly coupled to a computing device 230 that communicates with a control unit of the system 100 via wireless communication. In an embodiment, at least one of the one or more receivers 280 and transceivers 282 is configured to acquire information associated with a set of targets, markers, or the like for detection. In an embodiment, at least one of the one or more receivers 280 and transceivers 282 is configured to acquire information associated with a set of physiological characteristic for detection. In an embodiment, at least one of the one or more receivers 280 and transceivers 282 is configured to acquire information associated with one or more physiological characteristics for detection. In an embodiment, at least one of the one or more receivers 280 and transceivers 282 is configured to acquire information associated with one or more cerebrospinal fluid characteristics for detection.

In an embodiment, at least one receiver 280 is configured to acquire information associated with a delivery of an energy stimulus. In an embodiment, the at least one receiver 280 is configured to acquire data. In an embodiment, the at least one receiver 280 is configured to acquire software. In an embodiment, the at least one receiver 280 is configured to receive data from one or more distal sensors. In an embodiment, the at least one receiver 280 is configured to receive stored reference data. In an embodiment, the at least one receiver 280 is configured to acquire at least one of instructions, instructions associated with a delivery of an energy stimulus, instructions associated with a delivery of an active agent, information associated with a biological sample, instructions associated with a biological fluid, instructions associated with a disease state, or the like.

In an embodiment, the at least one receiver 280 is configured to acquire information based at least in part on a detected characteristic associated with a cerebrospinal fluid received within at least one of the one or more fluid-flow passageways 110. In an embodiment, the at least one receiver 280 is configured to acquire information based at least in part on a detected characteristic associated with a tissue proximate the one or more fluid-flow passageways 110. In an embodiment, the at least one receiver 280 is configured to acquire information based at least in part on a detected physiological characteristic associated with the biological subject. In an embodiment, the at least one receiver 280 is configured to acquire information associated with delivery of an active agent.

In an embodiment, the system 100 includes one or more receivers 280 configured to acquire spectral information (e.g., radio frequency (RF) information) emitted by an in vivo biological sample. In an embodiment, the one or more receivers 280 include one or more of analog-to-digital converters, signal amplifier, matching networks, oscillators, power amplifiers, RF receive coils, RF synthesizers, or signal filters. In an embodiment, the system 100 includes one or more transceivers 282 (e.g., RF transceivers) configured to generate RF excitation pulses that interacts with, for example, an in vivo target.

In an embodiment, the system 100 includes control circuitry operably coupled to the one or more selectively actuatable energy waveguides 202a and configured to control at least one of a spaced-apart configuration parameter, an electromagnetic energy spatial distribution parameter, or an electromagnetic energy temporal distribution parameter associated with the delivery of the patterned energy stimulus. In an embodiment, at least one computing device 230 is operably coupled to one or more selectively actuatable energy waveguides 202a and configured to control at least one of a delivery regiment, a spatial distribution, or a temporal distribution associated with the delivery of the patterned energy stimulus. In an embodiment, the one or more computing devices 230 are configured to actuate at least one of the plurality of selectively actuatable energy waveguides 202a in response to a scheduled program, an external command, a history of a previous microbial presence, or a history of a previous actuation.

In an embodiment, one or more computing devices 230 are configured to automatically control at least one waveform characteristic (e.g., intensity, frequency, peak power, spectral power distribution, pulse intensity, pulse duration, pulse ratio, pulse repetition rate, or the like) associated with the delivery of one or more energy stimuli. For example, pulsed waves can be characterized by the fraction of time the energy stimulus is present over one pulse period. This fraction is called the duty cycle and is calculated by dividing the pulse time ON by the total time of a pulse period (e.g., time ON plus time OFF). In an embodiment, a pulse generator 242 is configured to electronically generate pulsed periods and non-pulsed (or inactive) periods.

In an embodiment, the system 100 includes one or more catheter devices 102 including for example, but not limited to, circuitry for providing information. In an embodiment, the circuitry for providing information includes circuitry for providing status information regarding the implantable device. In an embodiment, the circuitry for providing information includes circuitry for providing information regarding at least one characteristic associated with a biological subject. For example, in an embodiment, the circuitry for providing information includes circuitry for providing information regarding at least one characteristic associated with a tissue or biological fluid proximate the catheter device 102. In an embodiment, the circuitry for providing information includes circuitry for providing information regarding at least one physiological characteristic associated with the biological subject. In an embodiment, the circuitry for providing information includes circuitry for providing information regarding at least one characteristic associated with a biological sample of the biological subject. In an embodiment, the circuitry for providing information includes circuitry for providing information regarding at least one characteristic associated with a tissue proximate the one or more fluid-flow passageways 110. In an embodiment, the system 100 includes one or more catheter devices 102 including for example, but not limited to, circuitry for transmitting information. In an embodiment, the at least one transmitter 284 is configured to send information based at least in part on a detected characteristic associated with a cerebrospinal fluid received within at least one of the one or more fluid-flow passageways 110. In an embodiment, the at least one transmitter 284 is configured to send a request for transmission of at least one of data, a command, an authorization, an update, or a code.

In an embodiment, the system 100 includes one or more catheter devices 102 including for example, but not limited to, one or more cryptographic logic components 286. In an embodiment, at least one of the one or more cryptographic logic components 286 are configured to implement at least one cryptographic process, or cryptographic logic, or combinations thereof. Non-limiting examples of a cryptographic process include one or more processes associated with cryptographic protocols, decryption protocols, encryption protocols, regulatory compliance protocols (e.g., FDA regulatory compliance protocols, or the like), regulatory use protocols, authentication protocols, authorization protocols, treatment regimen protocols, activation protocols, encryption protocols, decryption protocols, or the like. Non-limiting examples of a cryptographic logic include one or more crypto-algorithms signal-bearing media, crypto controllers (e.g., crypto-processors), cryptographic modules (e.g., hardware, firmware, or software, or combinations thereof for implementing cryptographic logic, or cryptographic processes), or the like.

In an embodiment, the cryptographic logic component 286 is configured to implement at least one cryptographic process or cryptographic logic. In an embodiment, the cryptographic logic component 286 is configured to implement one or more processes associated with at least one of a cryptographic protocol, a decryption protocol, an encryption protocol, a regulatory compliance protocol, a regulatory use protocol, an authentication protocol, an authorization protocol, a delivery protocol, an activation protocol, an encryption protocol, or a decryption protocol. In an embodiment, the cryptographic logic component 286 includes one or more crypto-algorithms, signal-bearing media, crypto controllers, or cryptographic modules.

In an embodiment, the cryptographic logic component 286 is configured to generate information associated with at least one of an authentication protocol, an authorization protocol, a delivery protocol (e.g., a sterilizing energy stimulus delivery protocol), an activation protocol, an encryption protocol, or a decryption protocol. In an embodiment, the cryptographic logic component 286 is configured to generate information associated with at least one of an authorization instruction, an authentication instruction, a prescription dosing instruction, a sterilizing energy stimulus administration instruction, or a prescribed regimen instruction.

In an embodiment, the cryptographic logic component 286 is configured to generate information associated with at least one of an instruction stream, an encrypted data stream, an authentication data stream, or an authorization data stream. In an embodiment, the cryptographic logic component 286 is configured to generate information associated with at least one of an activation code, an error code, a command code, or an authorization code. In an embodiment, the cryptographic logic component 286 is configured to generate information associated with at least one of a cryptographic protocol, a decryption protocol, an encryption protocol, a regulatory compliance protocol, or regulatory use protocol.

In an embodiment, the system 100 includes at least one computing device 230 communicably coupled to one or more energy emitters 220 and configured to control at least one of a duration time, an amount of energy (e.g., a fluence, peak power, average power, spectral power distribution, operational fluence, or the like), a delivery schedule, a delivery pattern, a delivery regimen, an excitation amount, an excitation type, or a delivery location associated with the delivery of an energy stimulus. In an embodiment, the system 100 includes at least one computing device 230 communicably coupled to one or more energy waveguides 202, and configured to control at least one parameter associated with selectively actuating one or more energy waveguides 202.

For example, in an embodiment, the computing device 230 is configured to control at least one parameter associated with an emission intensity, an emission phase, an emission polarization, an emission power, or an emission wavelength of an energy stimulus. In an embodiment, the computing device 230 is configured to control at least one parameter associated with an intensity, an irradiance ($I_n$), a peak power ($P_n$), a phase, a polarization, or a spectral power distribution ($SPD_n$) of an energy stimulus. In an embodiment, the computing device 230 is configured to control at least one parameter associated with a spatial illumination field modulation, a spatial illumination field intensity, or a spatial illumination delivery pattern. In an embodiment, the computing device 230 is configured to control at least one of an excitation intensity, an excitation frequency, an excitation pulse frequency, an excitation pulse ratio, an excitation pulse intensity, an excitation pulse duration time, an excitation pulse frequency, or an excitation pulse repetition rate. In an embodiment, the computing device 230 is configured to control at least one of a bandwidth, a frequency, a repetition rate, an energy-emitting pattern, an OFF-pulse duration, an OFF-rate, an ON-pulse duration, or an ON-rate.

In an embodiment, the catheter device 102 is, for example, wirelessly coupled to a computing device 230 that communicates with the catheter device 102 via wireless communication. Non-limiting examples of wireless communication include optical connections, ultraviolet connections, infrared, BLUETOOTH®, Internet connections, radio, network connections, or the like.

In an embodiment, the catheter device 102 includes at least one computing device 230 configured to control one or more parameter associated with the operation of the catheter device 102. For example, in an embodiment, the catheter device 102 includes at least one computing device 230 operably coupled to one or more of the energy emitters 220 and configured to control at least one parameter associated with the delivery of the energy stimulus. In an embodiment, the at least one computing device 230 is configured to control at least one of a duration time, an amount of energy, an excitation amount, an excitation type, a delivery location, or a spatial-pattern stimulation configuration associated with the delivery of the energy stimulus.

In an embodiment, the system 100 includes, among other things, one or more memories 250 that, for example, store instructions or data, for example, volatile memory (e.g., Random Access Memory (RAM) 252, Dynamic Random Access Memory (DRAM), or the like), non-volatile memory (e.g., Read-Only Memory (ROM) 254, Electrically Erasable Programmable Read-Only Memory (EEPROM), Compact Disc Read-Only Memory (CD-ROM), or the like), persistent memory, or the like. Further non-limiting examples of one or more memories 250 include Erasable Programmable Read-Only Memory (EPROM), flash memory, or the like. Various components of the catheter device 102 (e.g., memories 250, processors 232, or the like) can be operably coupled to each other via one or more instruction, data, or power buses 256.

In an embodiment, the system 100 includes, among other things, one or more databases 258. In an embodiment, a database 258 includes spectral information configured as a physical data structure. In an embodiment, a database 258 includes at least one of inflammation indication parameter data, infection indication parameter data, diseased tissue indication parameter data, or the like. In an embodiment, a database 258 includes at least one of absorption coefficient data, extinction coefficient data, scattering coefficient data, or the like. In an embodiment, a database 258 includes at least one of stored reference data such as infection marker data, inflammation marker data, infective stress marker data, a systemic inflammatory response syndrome data, sepsis marker data, or the like.

In an embodiment, a database 258 includes information associated with a disease state of a biological subject. In an embodiment, a database 258 includes measurement data. In an embodiment, a database 258 includes at least one of psychosis state indication information, psychosis trait indication information, or predisposition for a psychosis indication information. In an embodiment, a database 258 includes at least one of infection indication information, inflammation indication information, diseased state indication information, or diseased tissue indication information. In an embodiment, a database 258 includes at least one of cryptographic protocol information, regulatory compliance protocol information (e.g., FDA regulatory compliance protocol information, or the like), regulatory use protocol information, authentication protocol information, authorization protocol information, delivery regimen protocol information, activation protocol information, encryption protocol information, decryption protocol information, treatment protocol information, or the like. In an embodiment, a database 258 includes at least one of energy stimulus control delivery information, energy emitter 220 control information, power control information, energy waveguide 202 control information, or the like.

In an embodiment, the system 100 is configured to compare an input associated with at least one characteristic associated with a biological subject to a database 258 of stored reference values, and to generate a response based in part on the comparison. In an embodiment, the system 100 is configured to compare an input associated with at least one physiological characteristic associated with a biological subject to a database 258 of stored reference values, and to generate a response based in part on the comparison.

In an embodiment, the at least one characteristic associated with a biological subject includes real-time detected information associated with a sample (e.g., tissue, biological fluid, infections agent, biomarker, or the like) proximate a catheter device 102. In an embodiment, the at least one characteristic associated with a biological subject includes a measurand detected at a plurality of time intervals. In an embodiment, the at least one characteristic associated with a biological subject includes real-time detected information associated with a sample (e.g., a biological fluid) received within one or more fluid-flow passageways 110.

In an embodiment, the system 100 is configured to compare an input associated with at least one characteristic associated with a biological sample proximate the catheter device 102 (e.g., received within one or more fluid-flow passageways 110, on or near a surface of the body structure 104, or the like) to a database 258 of stored reference values, and to generate a response based in part on the comparison. In an embodiment, the response includes at least one of a visual representation, an audio representation (e.g., an alarm, an audio waveform representation of a tissue region, or the like), a haptic representation, and a tactile representation (e.g., a tactile diagram, a tactile display, a tactile graph, a tactile interactive depiction, a tactile model (e.g., a multidimensional model of an infected tissue region, or the like), a tactile pattern (e.g., a refreshable Braille display), a tactile-audio display, a tactile-audio graph, or the like). In an embodiment, the response includes generating at least one of a visual, an audio, a haptic, or a tactile representation of biological sample spectral information (e.g., biological fluid spectral information, tissue spectral information, fat spectral information, muscle spectral information, bone spectral information, blood component spectral information, biomarker spectral information, infectious agent spectral information, or the like). In an embodiment, the response includes generating at least one of a visual, an audio, a haptic, or a tactile representation of at least one physical or biochemical characteristic associated with a biological subject.

In an embodiment, the response includes initiating one or more treatment protocols. In an embodiment, the response includes activating one or more sterilization protocols. In an embodiment, the response includes initiating at least one treatment regimen. In an embodiment, the response includes delivering an energy stimulus. In an embodiment, the response includes delivering an active agent. In an embodiment, the response includes concurrently or sequentially delivering an energy stimulus and an active agent.

In an embodiment, the response includes at least one of a response signal, a control signal, a change to a sterilizing stimulus parameter (e.g., an electrical sterilizing stimulus, an electromagnetic sterilizing stimulus, an acoustic sterilizing stimulus, or a thermal sterilizing stimulus), or the like. In an embodiment, the response includes at least one of a change in an excitation intensity, a change in an excitation frequency, a change in an excitation pulse frequency, a change in an excitation pulse ratio, a change in an excitation pulse intensity, a change in an excitation pulse duration time, a change in an excitation pulse repetition rate, or the like.

In an embodiment, the response includes at least one of a change to a sterilizing stimulus spatial pattern parameter (e.g., an electrical sterilizing stimulus spatial pattern parameter, an electromagnetic sterilizing stimulus spatial pattern parameter, an acoustic sterilizing stimulus spatial pattern parameter, or a thermal sterilizing stimulus spatial pattern parameter), or a change in a sterilizing stimulus delivery regiment parameter (e.g., an electrical sterilizing stimulus delivery regiment parameter, an electromagnetic sterilizing stimulus delivery regiment parameter, an acoustic sterilizing stimulus delivery regiment parameter, or a thermal sterilizing stimulus delivery regiment parameter), or the like.

In an embodiment, the response includes at least one of activating an authorization protocol, activating an authentication protocol, activating a software update protocol, activating a data transfer protocol, or activating an infection sterilization diagnostic protocol. In an embodiment, the response includes sending information associated with at least one of an authentication protocol, an authorization protocol, a delivery protocol, an activation protocol, an encryption protocol, or a decryption protocol.

In an embodiment, a database 258 includes at least one of stored reference data such as characteristic biological sample (e.g., cerebrospinal fluid) component signature data, characteristic blood component signature data, characteristic tissue signature data, or the like. In an embodiment, a database 258 includes information indicative of one or more spectral events associated with transmitted optical energy or a remitted optical energy from at least one of a biological tissue or biological fluid.

In an embodiment, a database 258 includes at least one of cerebrospinal fluid spectral information, blood spectral information, tissue spectral information, fat spectral information, muscle spectral information, and bone spectral information.

In an embodiment, a database 258 includes at least one of modeled tissue (e.g., blood, bone, muscle, tendons, organs, fluid-filled cysts, ventricles, or the like) spectral information or modeled biological fluid spectral information. In an embodiment, a database 258 includes modeled biological sample spectral information.

In an embodiment, a database 258 includes at least one of inflammation indication parameter data, infection indication parameter data, diseased tissue indication parameter data, or the like. In an embodiment, a database 258 includes at least one of absorption coefficient data, extinction coefficient data, scattering coefficient data, or the like. In an embodiment, a database 258 includes stored reference data such as characteristic spectral signature data. In an embodiment, a database 258 includes stored reference data such as infection marker data, inflammation marker data, infective stress marker data, a systemic inflammatory response syndrome data, sepsis marker data, or the like. In an embodiment, a database 258 includes information associated with a disease state of a biological subject. In an embodiment, a database 258 includes user-specific measurement data.

In an embodiment, the system 100 is configured to compare an input associated with a biological subject to a database 258 of stored reference values, and to generate a response based in part on the comparison. In an embodiment, the system 100 is configured to compare an output of one or more of the plurality of logic components and to determine at least one parameter associated with a cluster centroid deviation derived from the comparison. In an embodiment, the system 100 is configured to compare a measurand associated with the biological subject to a threshold value associated with a spectral model and to generate a response based on the comparison. In an embodiment, the system 100 is configured to generate the response based on the comparison of a measurand that modulates with a detected heart beat of the biological subject to a target value associated with a spectral model.

In an embodiment, the system 100 is configured to compare the measurand associated with the biological subject to the threshold value associated with a spectral model and to generate a real-time estimation of an infection state based on the comparison. In an embodiment, the system 100 is configured to compare an input associated with at least one characteristic associated with, for example, a tissue proximate a catheter device 102 to a database 258 of stored reference values, and to generate a response based in part on the comparison.

In an embodiment, the system 100 includes, among other things, one or more data structures (e.g., physical data structures) 260. In an embodiment, a data structure 260 includes information associated with at least one parameter associated with a tissue water content, an oxy-hemoglobin concentration, a deoxyhemoglobin concentration, an oxygenated hemoglobin absorption parameter, a deoxygenated hemoglobin absorption parameter, a tissue light scattering parameter, a tissue light absorption parameter, a hematological parameter, a pH level, or the like. In an embodiment, the system 100 includes, among other things, at least one of inflammation indication parameter data, infection indication parameter data, diseased tissue indication parameter data, or the like configured as a data structure 260. In an embodiment, a data structure 260 includes information associated with least one parameter associated with a cytokine plasma concentration or an acute phase protein plasma concentration. In an embodiment, a data structure 260 includes information associated with a disease state of a biological subject. In an embodiment, a data structure 260 includes measurement data. In an embodiment, the computing device 230 includes a processor 232 configured to execute instructions, and a memory 250 that stores instructions configured to cause the processor 232 to generate a second response from information encoded in a data structure 260.

In an embodiment, the system 100 includes, among other things, one or more computer-readable memory media (CRMM) 262 having biofilm marker information configured as a data structure 260. In an embodiment, the data structure 260 includes a characteristic information section having characteristic microbial colonization spectral information representative of the presence of a microbial colonization proximate at least one of the outer surface 106 or the inner surface 108 of the body structure 104. In an embodiment, the data structure 260 includes infection marker information. In an embodiment, the data structure 260 includes biofilm marker information.

In an embodiment, the data structure 260 includes a characteristic information component including metabolite information associated with a microorganism colonization event. In an embodiment, the data structure 260 includes a characteristic information component including temporal metabolite information or spatial metabolite information associated with a microorganism colonization event. In an embodiment, the data structure 260 includes a characteristic information component including oxygen concentration gradient information associated with a microorganism colonization event. In an embodiment, the data structure 260 includes a characteristic information component including pH information associated with a microorganism colonization event. In an embodiment, the data structure 260 includes a characteristic information component including nutrient information associated with a microorganism colonization event. In an embodiment, the data structure 260 includes a characteristic information component including spectral information associate with a biofilm-specific tag.

In an embodiment, the data structure 260 includes a characteristic information component including optical density information. In an embodiment, the data structure 260 includes a characteristic information component including opacity information. In an embodiment, the data structure 260 includes a characteristic information component including refractivity information. In an embodiment, the data structure 260 includes a characteristic information component including characteristic infection marker spectral information. In an embodiment, the data structure 260 includes a characteristic information component including characteristic infective stress marker spectral information. In an embodiment, the data structure 260 includes a characteristic information component including characteristic sepsis maker spectral information.

In an embodiment, the data structure 260 includes at least one of psychosis state marker information, psychosis trait marker information, or psychosis indication information. In an embodiment, the data structure 260 includes at least one of psychosis state indication information, psychosis trait indication information, or predisposition for a psychosis indication information. In an embodiment, the data structure 260 includes at least one of infection indication information, inflammation indication information, diseased state indication information, or diseased tissue indication information.

In an embodiment, a data structure 260 includes biological sample spectral information. In an embodiment, the data structure 260 includes one or more heuristically determined parameters associated with at least one in vivo or in vitro determined metric. For example, information associated with a biological sample can be determined by one or more in vivo or in vitro technologies or methodologies including, for example, remittance (reflectance, etc.) spectroscopy, high-resolution proton magnetic resonance spectroscopy, nano-probe nuclear magnetic resonance spectroscopy, in vivo micro-dialysis, flow cytometry, or the like. Non-limiting examples of heuristics include a heuristic protocol, heuristic algorithm, threshold information, a threshold level, a target parameter, or the like. in an embodiment, the system 100 includes, among other things, a means for generating one or more heuristically determined parameters associated with at least one in vivo or in vitro determined metric including at least one computing device 230 and one or more data structures 260 having heuristic modeling information. In an embodiment, the system 100 includes, among other things, a means for generating a response based on a comparison, of a detected at least one of an emitted energy or a remitted energy to at least one heuristically determined parameter, including at least one computing device 230, one or more sensor components 502, or one or more data structures 260. In an embodiment, the system 100 includes, among other things, means for generating a response based on a comparison, of a detected at least one of an emitted energy or a remitted energy to at least one heuristically determined parameter, including one or more computing devices 230 and one or more data structures 260 configured with characteristic information.

In an embodiment, a data structure 260 includes one or more heuristics. In an embodiment, the one or more heuristics include a heuristic for determining a rate of change associated with at least one physical parameter associated with a biological sample. For example, in an embodiment, the one or more heuristics include a heuristic for determining the presence of an infectious agent. In an embodiment, the one or more heuristics include a heuristic for determining at least one dimension of an infected tissue region. In an embodiment, the one or more heuristics include a heuristic for determining a location of an infection. In an embodiment, the one or more heuristics include a heuristic for determining a rate of change associated with a biochemical marker within the one or more fluid-flow passageways 110.

In an embodiment, the one or more heuristics include a heuristic for determining a biochemical marker aggregation rate. In an embodiment, the one or more heuristics include a heuristic for determining a type of biochemical marker. In an embodiment, the one or more heuristics include a heuristic for generating at least one initial parameter. In an embodiment, the one or more heuristics include a heuristic for forming an initial parameter set from one or more initial parameters. In an embodiment, the one or more heuristics include a heuristic for generating at least one initial parameter, and for forming an initial parameter set from the at least one initial parameter. In an embodiment, the one or more heuristics include at least one pattern classification and regression protocol.

In an embodiment, a data structure 260 includes information associated with at least one parameter associated with a tissue water content, an oxy-hemoglobin concentration, a deoxyhemoglobin concentration, an oxygenated hemoglobin absorption parameter, a deoxygenated hemoglobin absorption parameter, a tissue light scattering parameter, a tissue light absorption parameter, a hematological parameter, a pH level, or the like. In an embodiment, the system 100 includes, among other things, at least one of inflammation indication parameter data, infection indication parameter data, diseased tissue indication parameter data, or the like configured as a data structure 260. In an embodiment, a data structure 260 includes information associated with least one parameter associated with a cytokine plasma concentration or an acute phase protein plasma concentration. In an embodiment, a data structure 260 includes information associated with a disease state of a biological subject. In an embodiment, a data structure 260 includes measurement data.

Figure 5:
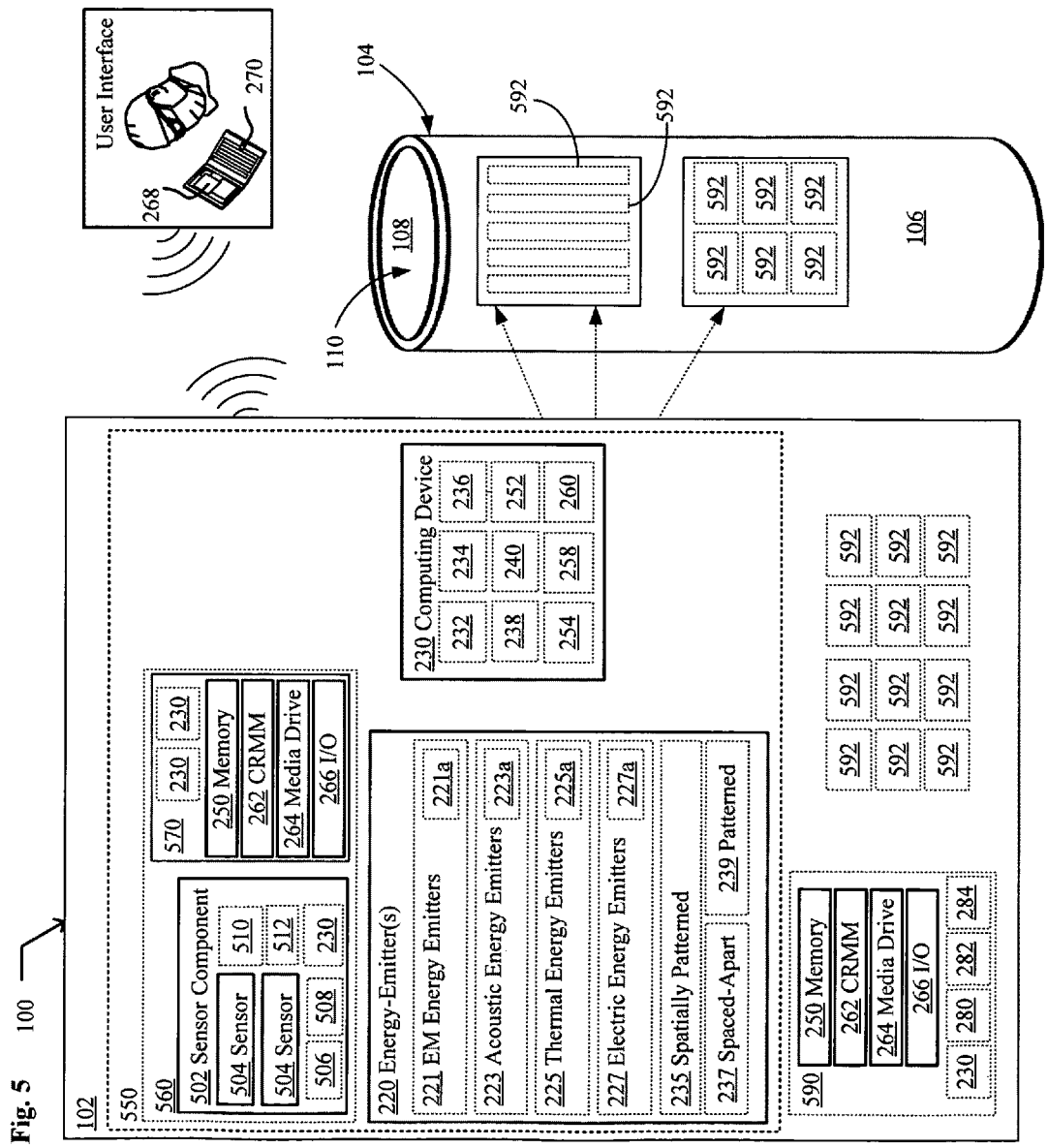
FIG. 5 is a schematic diagram of a system including a catheter device according to one embodiment.

Referring to FIG. 5, in an embodiment, the system 100 includes, among other things, one or more computer-readable media drives 264, interface sockets, Universal Serial Bus (USB) ports, memory card slots, or the like, or one or more input/output components 266 such as, for example, a graphical user interface 268, a display, a keyboard 270, a keypad, a trackball, a joystick, a touch-screen, a mouse, a switch, a dial, or the like, and any other peripheral device. In an embodiment, the system 100 includes one or more user input/output components 266 that operably couple to at least one computing device 230 to control (electrical, electromechanical, software-implemented, firmware-implemented, or other control, or combinations thereof) at least one parameter associated with the energy delivery associated with one or more of the energy emitters 220.

In an embodiment, the system 100 includes, among other things, one or more modules optionally operable for communication with one or more input/output components 266 that are configured to relay user output and/or input. In an embodiment, a module includes one or more instances of electrical, electromechanical, software-implemented, firmware-implemented, or other control devices. Such devices include one or more instances of memory 250, computing devices 230, ports, valves, fuses, antifuses, antennas, power, or other supplies; logic modules or other signaling modules; gauges or other such active or passive detection components; or piezoelectric transducers, shape memory elements, micro-electromechanical system (MEMS) elements, or other actuators.

The computer-readable media drive 264 or memory slot can be configured to accept signal-bearing medium (e.g., computer-readable memory media, computer-readable recording media, or the like). In an embodiment, a program for causing the system 100 to execute any of the disclosed methods can be stored on, for example, a computer-readable recording medium (CRMM) 262, a signal-bearing medium, or the like. Non-limiting examples of signal-bearing media include a recordable type medium such as a magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transmission logic, reception logic, etc.), etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

In an embodiment, the system 100 includes signal-bearing media in the form of one or more logic devices (e.g., programmable logic devices, complex programmable logic device, field-programmable gate arrays, application specific integrated circuits, or the like) comprising, for example, a data structure 260 including one or more look-up tables. In an embodiment, the system 100 includes, among other things, signal-bearing media having sample information (e.g., biological sample information, reference information, characteristic spectral information, or the like) configured as a data structure 260. In an embodiment, the data structure 260 includes at least one of psychosis state indication information, psychosis trait indication information, or predisposition for a psychosis indication information. In an embodiment, the data structure 260 includes at least one of infection indication information, inflammation indication information, diseased state indication information, or diseased tissue indication information.

Referring to FIG. 5, in an embodiment, the system 100 includes, among other things, at least one sensor component 502. In an embodiment, the catheter device 102 includes at least one sensor component 502. In an embodiment, the sensor component 502 is configured to detect (e.g., assess, calculate, evaluate, determine, gauge, measure, monitor, quantify, resolve, sense, or the like) at least one characteristic (e.g., a spectral characteristic, a spectral signature, a physical quantity, a relative quantity, an environmental attribute, a physiologic characteristic, or the like) associated with a biological subject. In an embodiment, the sensor component 502 is configured to perform a real-time comparison of a measurand associated with a biological sample proximate the catheter device 102 to stored reference data and to generate a response based on the comparison.

In an embodiment, the sensor component 502 is operably coupled to one or more computing device 230. In an embodiment, at least one computing device 230 is operably coupled to the sensor component 502 and configured to process an output associated with one or more sensor measurands. In an embodiment, at least one computing devices 230 is configured to concurrently or sequentially operate multiple sensor components 502. In an embodiment, the sensor component 502 includes a computing device 230 configured to process sensor measurand information and configured to cause the storing of the measurand information in a data storage medium. In an embodiment, the sensor component 502 includes a component identification code and is configured to implement instructions addressed to the sensor component 502 according to the component identification code.

In an embodiment, the sensor component 502 includes one or more surface plasmon resonance sensors. For example, in an embodiment, the sensor component 502 includes one or more localized surface plasmon resonance sensors. In an embodiment, the sensor component 502 includes a light transmissive support and a reflective metal layer. In an embodiment, the sensor component 502 includes a wavelength-tunable surface plasmon resonance sensor. In an embodiment, the sensor component 502 includes a surface plasmon resonance microarray sensor having a wavelength-tunable metal-coated grating. In an embodiment, the sensor component 502 includes a surface plasmon resonance microarray sensor having an array of micro-regions configured to capture target molecules.

In an embodiment, the sensor component 502 includes one or more electrochemical transducers, optical transducers, piezoelectric transducers, or thermal transducers. For example, in an embodiment, the sensor component 502 includes one or more transducers configured to detect acoustic waves associated with changes in a biological mass present proximate a surface of the body structure 104.

In an embodiment, the sensor component 502 includes one or more thermal detectors, photovoltaic detectors, or photomultiplier detectors. In an embodiment, the sensor component 502 includes one or more charge-coupled devices, complementary metal-oxide-semiconductor devices, photodiode image sensor devices, whispering gallery mode micro cavity devices, or scintillation detector devices. In an embodiment, the sensor component 502 includes one or more ultrasonic transducers. In an embodiment, the sensor component 502 includes at least one of a charge-coupled device, a complementary metal-oxide-semiconductor device, a photodiode image sensor device, a Whispering Gallery Mode (WGM) micro cavity device, and a scintillation detector device.

In an embodiment, the sensor component 502 includes at least one of an imaging spectrometer, a photo-acoustic imaging spectrometer, a thermo-acoustic imaging spectrometer, or a photo-acoustic/thermo-acoustic tomographic imaging spectrometer. In an embodiment, the sensor component 502 includes at least one of a thermal detector, a photovoltaic detector, or a photomultiplier detector.

In an embodiment, the sensor component 502 includes one or more density sensors. In an embodiment, the sensor component 502 includes one or more optical density sensors. In an embodiment, the sensor component 502 includes one or more refractive index sensors. In an embodiment, the sensor component 502 includes one or more fiber optic refractive index sensors.

In an embodiment, the sensor component 502 includes one or more acoustic biosensors, amperometric biosensors, calorimetric biosensors, optical biosensors, or potentiometric biosensors. In an embodiment, the sensor component 502 includes one or more fluid flow sensors. In an embodiment, the sensor component 502 includes one or more differential electrodes, biomass sensors, immunosensors, or the like. In an embodiment, the sensor component 502 includes one or more one-, two-, or three-dimensional photodiode arrays.

In an embodiment, the sensor component 502 is operably coupled to a microorganism colonization biomarker array. In an embodiment, the sensor component 502 includes one or more functionalized cantilevers. In an embodiment, the sensor component 502 includes a biological molecule capture layer. In an embodiment, the sensor component 502 includes a biological molecule capture layer having an array of different binding molecules that specifically bind one or more target molecules. In an embodiment, the sensor component 502 includes one or more computing devices 230 operably coupled to one or more sensors. For example, in an embodiment, the sensor component 502 includes a computing device 230 operably coupled to one or more surface plasmon resonance microarray sensors.

In an embodiment, the sensor component 502 is configured to detect at least one characteristic associated with a biological subject. In an embodiment, the sensor component 502 is configured to detect at least one characteristic associated with a biological specimen proximate a surface of the catheter device 102. For example, in an embodiment, the sensor component 502 is configured to detect at least one characteristic associated with a tissue proximate the catheter device 102.

In an embodiment, the at least one characteristic includes at least one of a transmittance, an energy frequency change, a frequency shift, an energy phase change, or a phase shift. In an embodiment, the at least one characteristic includes at least one of a fluorescence, an intrinsic fluorescence, a tissue fluorescence, or a naturally occurring fluorophore fluorescence. In an embodiment, the at least one characteristic includes at least one of an electrical conductivity, electrical polarizability, or an electrical permittivity. In an embodiment, the at least one characteristic includes at least one of a thermal conductivity, a thermal diffusivity, a tissue temperature, or a regional temperature.

In an embodiment, the at least one characteristic includes at least one parameter associated with a doppler optical coherence tomograph. (See, e.g., Li et al., *Feasibility of Interstitial Doppler Optical Coherence Tomography for In vivo Detection of Microvascular Changes During Photodynamic Therapy*, Lasers in surgery and medicine 38 (8):754-61.

(2006); see, also U.S. Pat. No. 7,365,859 (issued Apr. 29, 2008); each of which is incorporated herein by reference.

In an embodiment, the at least one characteristic includes spectral signature information associated with an implant device. For example, in an embodiment, the at least one characteristic includes implant device spectral signature information associated with at least one of a bio-implants, bioactive implants, breast implants, cochlear implants, dental implants, neural implants, orthopedic implants, ocular implants, prostheses, implantable electronic device, implantable medical devices, or the like. Further non-limiting examples of implant devices include replacements implants (e.g., joint replacements implants, or the like), knee, shoulder, wrists replacements implants, or the like), subcutaneous drug delivery devices (e.g., implantable pills, drug-eluting stents, or the like), shunts (e.g., cardiac shunts, lumbo-peritoneal shunts, cerebrospinal fluid shunts, cerebral shunts, pulmonary shunts, portosystemic shunts, portacaval shunts, or the like), stents (e.g., coronary stents, peripheral vascular stents, prostatic stents, ureteral stents, vascular stents, or the like), biological fluid flow controlling implants, or the like. Further non-limiting examples of implant device include artificial hearts, artificial joints, artificial prosthetics, catheters, contact lens, mechanical heart valves, subcutaneous sensors, urinary catheters, vascular catheters, or the like.

In an embodiment, the at least one characteristic includes at least one parameter associated with a medical state (e.g., medical condition, disease state, disease attributes, etc.). Inflammation is a complex biological response to insults that can arise from, for example, chemical, traumatic, or infectious stimuli. It is a protective attempt by an organism to isolate and eradicate the injurious stimuli as well as to initiate the process of tissue repair. The events in the inflammatory response are initiated by a complex series of interactions involving inflammatory mediators, including those released by immune cells and other cells of the body. Histamines and eicosanoids, such as prostaglandins and leukotrienes, act on blood vessels at the site of infection to localize blood flow, concentrate plasma proteins, and increase capillary permeability.

Chemotactic factors, including certain eicosanoids, complement, and especially cytokines known as chemokines, attract particular leukocytes to the site of infection. Other inflammatory mediators, including some released by the summoned leukocytes, function locally and systemically to promote the inflammatory response. Platelet activating factors and related mediators function in clotting, which aids in localization and can trap pathogens. Certain cytokines, interleukins and TNF, induce further trafficking and extravasation of immune cells, hematopoiesis, fever, and production of acute phase proteins. Once signaled, some cells and/or their products directly affect the offending pathogens, for example by inducing phagocytosis of bacteria or, as with interferon, providing antiviral effects by shutting down protein synthesis in the host cells.

Oxygen radicals, cytotoxic factors, and growth factors can also be released to fight pathogen infection or to facilitate tissue healing. This cascade of biochemical events propagates and matures the inflammatory response, involving the local vascular system, the immune system, and various cells within the injured tissue. Under normal circumstances, through a complex process of mediator-regulated pro-inflammatory and anti-inflammatory signals, the inflammatory response eventually resolves itself and subsides. For example, the transient and localized swelling associated with a cut is an example of an acute inflammatory response. However, in certain cases resolution does not occur as expected. Prolonged inflammation, known as chronic inflammation, leads to a progressive shift in the type of cells present at the site of inflammation and is characterized by simultaneous destruction and healing of the tissue from the inflammatory process, as directed by certain mediators. Rheumatoid arthritis is an example of a disease associated with persistent and chronic inflammation.

Non-limiting suitable techniques for optically measuring a diseased state may be found in, for example, U.S. Pat. No. 7,167,734 (issued Jan. 23, 2007), which is incorporated herein by reference. In an embodiment, the at least one characteristic includes at least one of an electromagnetic energy absorption parameter, an electromagnetic energy emission parameter, an electromagnetic energy scattering parameter, an electromagnetic energy reflectance parameter, or an electromagnetic energy depolarization parameter. In an embodiment, the at least one characteristic includes at least one of an absorption coefficient, an extinction coefficient, or a scattering coefficient.

In an embodiment, the at least one characteristic includes at least one parameter associated with an infection marker (e.g., an infectious agent marker), an inflammation marker, an infective stress marker, a systemic inflammatory response syndrome marker, or a sepsis marker. Non-limiting examples of infection makers, inflammation markers, or the like may be found in, for example, Imam et al., *Radiotracers for imaging of infection and inflammation—A Review*, World J. Nucl. Med. 40-55 (2006), which is incorporated herein by reference. Non-limiting characteristics associated with an infection marker, an inflammation marker, an infective stress marker, a systemic inflammatory response syndrome marker, or a sepsis marker include at least one of an inflammation indication parameter, an infection indication parameter, a diseased state indication parameter, or a diseased tissue indication parameter.

In an embodiment, the response includes generating a visual, an audio, a haptic, or a tactile representation of at least one spectral parameter associated with a detected infection marker. In an embodiment, the response includes generating a visual, an audio, a haptic, or a tactile representation of at least one physical parameter indicative of at least one dimension of infected tissue region.

In an embodiment, the at least one characteristic includes at least one of a tissue water content, an oxy-hemoglobin concentration, a deoxyhemoglobin concentration, an oxygenated hemoglobin absorption parameter, a deoxygenated hemoglobin absorption parameter, a tissue light scattering parameter, a tissue light absorption parameter, a hematological parameter, or a pH level.

In an embodiment, the at least one characteristic includes at least one hematological parameter. Non-limiting examples of hematological parameters include an albumin level, a blood urea level, a blood glucose level, a globulin level, a hemoglobin level, erythrocyte count, a leukocyte count, or the like. In an embodiment, the infection marker includes at least one parameter associated with a red blood cell count, a lymphocyte level, a leukocyte count, a myeloid cell count, an erythrocyte sedimentation rate, or a C-reactive protein level. In an embodiment, the at least one characteristic includes at least one parameter associated with a cytokine plasma level or an acute phase protein plasma level. In an embodiment, the at least one characteristic includes at least one parameter associated with a leukocyte level.

In an embodiment, the at least one characteristic includes a spectral parameter associated with a biofilm-specific tag. In an embodiment, the at least one characteristic includes an optical density. In an embodiment, the at least one characteristic includes an opacity. In an embodiment, the at least one characteristic includes a refractivity. In an embodiment, the at least one characteristic includes an absorbance, reflectance, or a transmittance. In an embodiment, the at least one characteristic includes at least one of an inflammation indication parameter, an infection indication parameter, a diseased state indication parameter, or a diseased tissue indication parameter. In an embodiment, the at least one characteristic includes at least one of an electromagnetic energy absorption parameter, an electromagnetic energy emission parameter, an electromagnetic energy scattering parameter, an electromagnetic energy reflectance parameter, or an electromagnetic energy depolarization parameter. In an embodiment, the at least one characteristic includes at least one an absorption coefficient, an extinction coefficient, a scattering coefficient, or a fluorescence coefficient. In an embodiment, the at least one characteristic includes at least at least one of parameter associated with a biomarker, an infection marker, an inflammation marker, an infective stress marker, or a sepsis marker.

In an embodiment, the at least one characteristic includes at least one of an electromagnetic energy phase shift parameter, an electromagnetic energy dephasing parameter, or an electromagnetic energy depolarization parameter. In an embodiment, the at least one characteristic associated includes at least one of an absorbance, a reflectivity, or a transmittance. In an embodiment, the at least one characteristic associated includes at least one of a refraction or a scattering.

In an embodiment, the sensor component 502 is configured to determine at least one characteristic associated with one or more biological markers or biological components (e.g., cerebrospinal fluid components, blood components, or the like). In an embodiment, the sensor component 502 is configured to determine at least one characteristic associated with a tissue proximate the catheter device 102. In an embodiment, the sensor component 502 is configured to determine a spatial dependence associated with the least one characteristic. In an embodiment, the sensor component 502 is configured to determine a temporal dependence associated with the least one characteristic. In an embodiment, the sensor component 502 is configured to concurrently or sequentially determine at least one spatial dependence associated with the least one characteristic and at least one temporal dependence associated with the least one characteristic.

In an embodiment, the sensor component 502 is configured to determine at least one spectral parameter associated with one or more imaging probes (e.g., chromophores, fluorescent agents, fluorescent marker, fluorophores, molecular imaging probes, quantum dots, or radio-frequency identification transponders (RFIDs), x-ray contrast agents, or the like). In an embodiment, the sensor component 502 is configured to determine at least one characteristic associated with one or more imaging probes attached, targeted to, conjugated, bound, or associated with at least one inflammation markers. See, e.g., the following documents: Jaffer et al., Arterioscler. Thromb. Vasc. Biol. 2002; 22; 1929-1935 (2002); Kalchenko et al., J. of Biomed. Opt. 11 (5):50507 (2006); each of which is incorporated herein by reference.

In an embodiment, the one or more imaging probes include at least one carbocyanine dye label. In an embodiment, the sensor component 502 is configured to determine at least one characteristic associated with one or more imaging probes attached, targeted to, conjugated, bound, or associated with at least one biomarker or biological sample component.

In an embodiment, the one or more imaging probes include at least one fluorescent agent. In an embodiment, the one or more imaging probes include at least one quantum dot. In an embodiment, the one or more imaging probes include at least one radio-frequency identification transponder. In an embodiment, the one or more imaging probes include at least one x-ray contrast agent. In an embodiment, the one or more imaging probes include at least one molecular imaging probe.

Further non-limiting examples of imaging probes include fluorescein (FITC), indocyanine green (ICG), and rhodamine B. Non-limiting examples of other fluorescent dyes for use in fluorescence imaging include a number of red and near infrared emitting fluorophores (600-1200 nm) including cyanine dyes such as Cy5, Cy5.5, and Cy7 (Amersham Biosciences, Piscataway, N.J., USA) or a variety of Alexa Fluor dyes such as Alexa Fluor 633, Alexa Fluor 635, Alexa Fluor 647, Alexa Fluor 660, Alexa Fluor 680, Alexa Fluor 700, Alexa Fluor 750 (Molecular Probes-Invitrogen, Carlsbad, Calif., USA; see, also, U.S. Patent Pub. No. 2005/0171434 (published Aug. 4, 2005) (each of which is incorporated herein by reference), or the like.

Further non-limiting examples of imaging probes include IRDye800, IRDye700, and IRDye680 (LI-COR, Lincoln, Nebr., USA), NIR-1 and 1C5-OSu (Dejindo, Kumamotot, Japan), LaJolla Blue (Diatron, Miami, Fla., USA), FAR-Blue, FAR-Green One, and FAR-Green Two (Innosense, Giacosa, Italy), ADS 790-NS, ADS 821-NS (American Dye Source, Montreal, CA), NIAD-4 (ICx Technologies, Arlington, Va.), or the like. Further non-limiting examples of fluorophores include BODIPY-FL, europium, green, yellow and red fluorescent proteins, luciferase, or the like. Quantum dots of various emission/excitation properties can be used as imaging probes. See, e.g., Jaiswal, et al. Nature Biotech. 21:47-51 (2003) (which is incorporated herein by reference). Further non-limiting examples of imaging probes include those including antibodies specific for leukocytes, anti-fibrin antibodies, monoclonal anti-diethylene triamine pentaacetic acid (DTPA), DTPA labeled with Technetium-99m ($^{99m}TC$), or the like.

Further non-limiting examples of biomarkers include high-sensitivity C-reactive protein (hs-CRP), cardiac troponin T (cTnT), cardiac troponin I (cTnI), N-terminal-pro B-type natriuretic peptide (NT-proBNP), D-dimer, P-selectin, E-selectin, thrombin, interleukin-10, fibrin monomers, phospholipid microparticles, creatine kinase, interleukin-6, tumor necrosis factor-alpha, myeloperoxidase, intracellular adhesion molecule-1 (ICAM1), vascular adhesion molecule (VCAM), matrix metalloproteinase-9 (MMP9), ischemia modified albumin (IMA), free fatty acids, choline, soluble CD40 ligand, insulin-like growth factor, (see, e.g., Giannitsis, et al. *Risk stratification in pulmonary embolism based on biomarkers and echocardiography*. Circ. 112:1520-1521 (2005), Barnes, et al., *Novel biomarkers associated with deep venous throbosis: A comprehensive review*. Biomarker Insights 2:93-100 (2007); Kamphuisen, *Can anticoagulant treatment be tailored with biomarkers in patients with venous thromboembolism?* J. Throm. Haemost. 4:1206-1207 (2006); Rosalki, et al., *Cardiac biomarkers for detection of myocardial infarction: Perspectives from past to present. Clin. Chem.* 50:2205-2212 (2004); Apple, et al., *Future biomarkers for detection of ischemia and risk stratification in acute coronary syndrome*, Clin. Chem. 51:810-824 (2005); each of which is incorporated herein by reference.

In an embodiment, the sensor component 502 is configured to detect a spectral response (e.g., an emitted energy, a remitted energy, an energy absorption profile, energy emission profile, or the like) associated with a biomarker. Among biomarker examples include, but are not limited to, one or more substances that are measurable indicators of a biological state and can be used as indicators of normal disease state, pathological disease state, and/or risk of progressing to a pathological disease state. In some instances, a biomarker can be a normal blood component that is increased or decreased in the pathological state. A biomarker can also be a substance that is not normally detected in biological sample, fluid, or tissue, but is released into circulation because of the pathological state. In some instances, a biomarker can be used to predict the risk of developing a pathological state. For example, plasma measurement of lipoprotein-associated phospholipase A2 (Lp-PLA2) is approved by the U.S. Food & Drug Administration (FDA) for predicting the risk of first time stroke.

In other instances, the biomarker can be used to diagnose an acute pathological state. For example, elevated plasma levels of S-100b, B-type neurotrophic growth factor (BNGF), von Willebrand factor (vWF), matrix metalloproteinase-9 (MMP-9), and monocyte chemoattractant protein-1 (MCP-1) are highly correlated with the diagnosis of stroke (see, e.g., Reynolds, et al., *Early biomarkers of stroke*. Clin. Chem. 49:1733-1739 (2003), which is incorporated herein by reference).

In an embodiment, the sensor component 502 is configured to detect at least one characteristic associated with one or more biological sample components. In an embodiment, the at least one characteristic includes at least one of absorption coefficient information, extinction coefficient information, or scattering coefficient information associated with the at least one molecular probe. In an embodiment, the at least one characteristic includes spectral information indicative of a rate of change, an accumulation rate, an aggregation rate, or a rate of change associated with at least one physical parameter associated with a biological sample component.

In an embodiment, the sensor component 502 is configured to detect spectral information associated with a real-time change in one or more parameters associated with a biological sample. For example, in an embodiment, the sensor component 502 is configured to detect at least one of an emitted energy or a remitted energy associated with a real-time change in one or more parameters associated with a biological sample within one or more regions in the immediate vicinity of a catheter device 102. In an embodiment, the sensor component 502 includes one or more transducers 223a configured to detect sound waves associated with changes in a biological sample present proximate at least one of the outer surface and the inner surface of the body structure.

In an embodiment, the sensor component 502 is configured to detect at least one of an emitted energy or a remitted energy. In an embodiment, the sensor component 502 is configured to detect at least one of an emitted energy or a remitted energy associated with a biological subject. In an embodiment, the sensor component 502 is configured to detect an optical energy absorption profile of a target sample, a portion of a tissue, or portion of a biological sample within the biological subject. In an embodiment, the sensor component 502 is configured to detect an excitation radiation and an emission radiation associated with a portion of a target sample, a portion of a tissue, or portion of a biological sample within the biological subject. In an embodiment, the sensor component 502 is configured to detect at least one of an energy absorption profile and an energy reflection profile of a region within a biological subject.

In an embodiment, the sensor component 502 is configured to detect a spectral response from tissue of a biological subject. Blood is a tissue composed of, among other components, formed elements (e.g., blood cells such as erythrocytes, leukocytes, thrombocytes, or the like) suspend in a matrix (plasma). The heart, blood vessels (e.g., arteries, arterioles, capillaries, veins, venules, or the like), and blood components, make up the cardiovascular system. The cardiovascular system, among other things, moves oxygen, gases, and wastes to and from cells and tissues, maintains homeostasis by stabilizing body temperature and pH, and helps fight diseases.

In an embodiment, the sensor component 502 is configured to detect at least one of an emitted energy or a remitted energy associated with a portion of a cardiovascular system. In an embodiment, the sensor component 502 is configured to detect at least one of an emitted energy and a remitted energy associated with one or more blood components within a biological subject. In an embodiment, the sensor component 502 is configured to detect at least one of an emitted energy or a remitted energy associated with one or more formed elements within a biological subject. In an embodiment, the sensor component 502 is configured to detect spectral information associated with one or more blood components. In an embodiment, the sensor component 502 is configured to detect at least one of an emitted energy or a remitted energy associated with a real-time change in one or more parameters associated with at least one blood component within a biological subject. In an embodiment, the sensor component 502 is configured to detect an energy absorption of one or more blood components.

Non-limiting examples of detectable blood components include erythrocytes, leukocytes (e.g., basophils, granulocytes, eosinophils, monocytes, macrophages, lymphocytes, neutrophils, or the like), thrombocytes, acetoacetate, acetone, acetylcholine, adenosine triphosphate, adrenocorticotrophic hormone, alanine, albumin, aldosterone, aluminum, amyloid proteins (non-immunoglobulin), antibodies, apolipoproteins, ascorbic acid, aspartic acid, bicarbonate, bile acids, bilirubin, biotin, blood urea Nitrogen, bradykinin, bromide, cadmium, calciferol, calcitonin (ct), calcium, carbon dioxide, carboxyhemoglobin (as HbcO), cell-related plasma proteins, cholecystokinin (pancreozymin), cholesterol, citric acid, citrulline, complement components, coagulation factors, coagulation proteins, complement components, c-peptide, c-reactive protein, creatine, creatinine, cyanide, 11-deoxycortisol, deoxyribonucleic acid, dihydrotestosterone, diphosphoglycerate (phosphate), or the like.

Further non-limiting examples of detectable blood components include dopamine, enzymes, epidermal growth factor, epinephrine, ergothioneine, erythrocytes, erythropoietin, folic acid, fructose, furosemide glucuronide, galactoglycoprotein, galactose (children), gamma-globulin, gastric inhibitory peptide, gastrin, globulin, α-1-globulin, α-2-globulin, α-globulins, β-globulins, glucagon, glucosamine, glucose, immunoglobulins (antibodies), lipase p, lipids, lipoprotein (sr 12-20), lithium, low-molecular weight proteins, lysine, lysozyme (muramidase), α-2-macroglobulin, γ-mobility (non-immunoglobulin), pancreatic polypeptide, pantothenic acid, para-aminobenzoic acid, parathyroid hormone, pentose, phosphorated, phenol, phenylalanine, phosphatase, acid, prostatic, phospholipid, phosphorus, prealbumin, thyroxine-binding, proinsulin, prolactin (female), prolactin (male), proline, prostaglandins, prostate specific antigen, protein, protoporphyrin, pseudoglobulin I, pseudoglobulin II, purine, pyridoxine, pyrimidine nucleotide, pyruvic acid, CCL5 (RANTES), relaxin, retinol, retinol-binding protein, riboflavin, ribonucleic acid, secretin, serine, serotonin (5-hydroxytryptamine), silicon, sodium, solids, somatotropin (growth hormone), sphingomyelin, succinic acid, sugar, sulfates, inorganic, sulfur, taurine, testosterone (female), testosterone (male), triglycerides, triiodothyronine, tryptophan, tyrosine, urea, uric acid, water, miscellaneous trace components, or the like.

Non-limiting examples of α-Globulins examples include α1-acid glycoprotein, α1-antichymotrypsin, α1-antitrypsin, α1B-glycoprotein, α1-fetoprotein, α1-microglobulin, α1T-glycoprotein, α2HS-glycoprotein, α2-macroglobulin, 3.1 S Leucine-rich α2-glycoprotein, 3.8 S histidine-rich α2-glycoprotein, 4 S α2, α1-glycoprotein, 8 S α3-glycoprotein, 9.5 S α1-glycoprotein (serum amyloid P protein), Corticosteroid-binding globulin, ceruloplasmin, GC globulin, haptoglobin (e.g., Type 1-1, Type 2-1, or Type 2-2), inter-α-trypsin inhibitor, pregnancy-associated α2-glycoprotein, serum cholinesterase, thyroxine-binding globulin, transcortin, vitamin D-binding protein, Zn-α2-glycoprotein, or the like. Among β-globulins, examples include, but are not limited to, hemopexin, transferrin, β2-microglobulin, β2-glycoprotein I, β2-glycoprotein II, (C3 proactivator), β2-glycoprotein III, C-reactive protein, fibronectin, pregnancy-specific β1-glycoprotein, ovotransferrin, or the like. Among immunoglobulins examples include, but are not limited to, immunoglobulin G (e.g., IgG, $IgG_1$, $IgG_2$, $IgG_3$, $IgG_4$), immunoglobulin A (e.g., IgA, $IgA_1$, $IgA_2$), immunoglobulin M, immunoglobulin D, immunoglobulin E, κ Bence Jones protein, γ Bence Jones protein, J Chain, or the like.

Among apolipoproteins examples include, but are not limited to, apolipoprotein A-I (HDL), apolipoprotein A-II (HDL), apolipoprotein C-I (VLDL), apolipoprotein C-II, apolipoprotein C-III (VLDL), apolipoprotein E, or the like. Among γ-mobility (non-immunoglobulin) examples include, but are not limited to, 0.6 S γ2-globulin, 2 S γ2-globulin, basic Protein B2, post-γ-globulin (γ-trace), or the like. Among low-molecular weight proteins examples include, but are not limited to, lysozyme, basic protein B1, basic protein B2, 0.6 S γ2-globulin, 2 S γ 2-globulin, post γ-globulin, or the like.

Among complement components examples include, but are not limited to, C1 esterase inhibitor, C1q component, C1r component, C1s component, C2 component, C3 component, C3a component, C3b-inactivator, C4 binding protein, C4 component, C4a component, C4-binding protein, C5 component, C5a component, C6 component, C7 component, C8 component, C9 component, factor B, factor B (C3 proactivator), factor D, factor D (C3 proactivator convertase), factor H, factor H ($β_1$H), properdin, or the like. Among coagulation proteins examples include, but are not limited to, antithrombin III, prothrombin, antihemophilic factor (factor VIII), plasminogen, fibrin-stabilizing factor (factor XIII), fibrinogen, thrombin, or the like.

Among cell-Related Plasma Proteins examples include, but are not limited to, fibronectin, β-thromboglobulin, platelet factor-4, serum Basic Protease Inhibitor, or the like. Among amyloid proteins (Non-Immunoglobulin) examples include, but are not limited to, amyloid-Related apoprotein (apoSAA1), AA (FMF) (ASF), AA (TH) (AS), serum amyloid P component (9.5 S 7α1-glycoprotein), or the like. Among miscellaneous trace components examples include, but are not limited to, varcinoembryonic antigen, angiotensinogen, or the like.

In an embodiment, the sensor component 502 is configured to detect a spectral response associated with a real-time change in one or more parameters associated with at least one biological sample component (e.g., a cerebrospinal fluid component). Non-limiting examples of detectable cerebrospinal fluid components include adenosine deaminase, albumin, calcium, chloride, C-reactive protein, creatine kinase, creatinine, cystatin C, cytokines, glucose, hydrogen-carbonate, immunoglobulin G, interleukins, lactate, lactate dehydrogenase, lipids, lymphocytes, monocytes, mono-nuclear cells, myelin basic protein, neuron-specific enolase, potassium, proteins, S-100 protein, small molecules, sodium, $β_2$-microglobulin, or the like.

In an embodiment, the sensor component 502 is in optical communication along an optical path with at least one of the one or more energy emitters 220. In an embodiment, one or more of the energy emitters 220 are configured to direct an in vivo generated pulsed energy stimulus along an optical path for a duration sufficient to interact with one or more regions within the biological subject and for a duration sufficient for a portion of the in vivo generated pulsed energy stimulus to reach a portion of the sensor component 502 that is in optical communication along the optical path. In an embodiment, one or more of the energy emitters 220 are configured to direct optical energy along an optical path for a duration sufficient to interact with one or more regions within the biological subject and with at least a portion of the optical energy sensor component 502. In an embodiment, one or more of the energy emitters 220 are configured to emit a pulsed optical energy stimulus along an optical path for a duration sufficient to interact with a sample received within the one or more fluid-flow passageways 110, such that a portion of the pulsed optical energy stimulus is directed to a portion of the sensor component 502 that is in optical communication along the optical path.

In an embodiment, the system 100 includes one or more sensors 504. In an embodiment, the catheter device 102 includes one or more of the sensors 504. In an embodiment, the sensor component 502 includes one or more sensors 504.

Non-limiting examples of sensors 504 include acoustic wave sensors, aptamer-based sensors, biosensors, blood volume pulse sensors, cantilevers, conductance sensors, electrochemical sensors, fluorescence sensors, force sensors, heat sensors (e.g., thermistors, thermocouples, or the like), high resolution temperature sensors, differential calorimeter sensors, optical sensors, goniometry sensors, potentiometer sensors, resistance sensors, respiration sensors, sound sensors (e.g., ultrasound), Surface Plasmon Band Gap sensor (SPRBG), physiological sensors, surface plasmon sensors, or the like. Further non-limiting examples of sensors 504 include affinity sensors, bioprobes, biostatistics sensors, enzymatic sensors, in-situ sensors (e.g., in-situ chemical sensor), ion sensors, light sensors (e.g., visible, infrared, or the like), microbiological sensors, microhotplate sensors, micron-scale moisture sensors, nanosensors, optical chemical sensors, single particle sensors, or the like.

Further non-limiting examples of sensors 504 include chemical sensors, cavitand-based supramolecular sensors, nucleic acid sensors, deoxyribonucleic acid sensors (e.g., electrochemical DNA sensors, or the like), supramolecular sensors, or the like. In an embodiment, at least one of the one or more sensors 504 is configured to detect or measure the presence or concentration of specific target chemicals (e.g., blood components, biological sample component, cerebral spinal fluid component, infectious agents, infection indication chemicals, inflammation indication chemicals, diseased tissue indication chemicals, biological agents, molecules, ions, or the like).

Further non-limiting examples of sensors 504 include chemical transducers, ion sensitive field effect transistors (ISFETs), ISFET pH sensors, membrane-ISFET devices (MEMFET), microelectronic ion-sensitive devices, potentiometric ion sensors, quadruple-function ChemFET (chemical-sensitive field-effect transistor) integrated-circuit sensors, sensors with ion-sensitivity and selectivity to different ionic species, or the like. Further non-limiting examples of the one or more sensors 504 can be found in the following documents (each of which is incorporated herein by reference): U.S. Pat. No. 7,396,676 (issued Jul. 8, 2008) and U.S. Pat. No. 6,831,748 (issued Dec. 14, 2004); each of which is incorporated herein by reference.

In an embodiment, the one or more sensors 504 include one or more acoustic transducers, electrochemical transducers, photochemical transducer, optical transducers, piezoelectrical transducers, or thermal transducers. For example, in an embodiment, the one or more sensors 504 include one or more acoustic transducers. In an embodiment, the one or more sensors 504 include one or more thermal detectors, photovoltaic detectors, or photomultiplier detectors. In an embodiment, the one or more sensors 504 include one or more charge coupled devices, complementary metal-oxide-semiconductor devices, photodiode image sensor devices, whispering gallery mode micro cavity devices, or scintillation detector devices. In an embodiment, the one or more sensors 504 include one or more complementary metal-oxide-semiconductor image sensors.

In an embodiment, the one or more sensors 504 include one or more conductivity sensor. In an embodiment, the one or more sensors 504 include one or more spectrometers. In an embodiment, the one or more sensors include one or more Bayer sensors. In an embodiment, the one or more sensors include one or more Foveon sensors. In an embodiment, the one or more sensors 504 include one or more density sensors. In an embodiment, the one or more density sensors include one or more optical density sensors. In an embodiment, the one or more density sensors include one or more refractive index sensors. In an embodiment, the one or more refractive index sensors include one or more fiber optic refractive index sensors.

In an embodiment, the one or more sensors 504 include one or more surface plasmon resonance sensors. In an embodiment, the one or more sensors 504 are configured to detect target molecules. For example, surface-plasmon-resonance-based-sensors detect target molecules suspended in a fluid, for example, by reflecting light off thin metal films in contact with the fluid. Adsorbing molecules cause changes in the local index of refraction, resulting in detectable changes in the resonance conditions of the surface plasmon waves.

In an embodiment, the one or more sensors 504 include one or more localized surface plasmon resonance sensors. In an embodiment, detection of target molecules includes monitoring shifts in the resonance conditions of the surface plasmon waves due to changes in the local index of refraction associates with adsorption of target molecules. In an embodiment, the one or more sensors 504 include one or more functionalized cantilevers. In an embodiment, the one or more sensors 504 include a light transmissive support and a reflective metal layer. In an embodiment, the one or more sensors 504 include a biological molecule capture layer. In an embodiment, the biological molecule capture layer includes an array of different binding molecules that specifically bind one or more target molecules. In an embodiment, the one or more sensors 504 include a surface plasmon resonance microarray sensor having an array of micro-regions configured to capture target molecules.

In an embodiment, the one or more sensors 504 include one or more acoustic biosensors, amperometric biosensors, calorimetric biosensors, optical biosensors, or potentiometric biosensors. In an embodiment, the one or more sensors 504 include one or more fluid flow sensors. In an embodiment, the one or more sensors 504 include one or more differential electrodes. In an embodiment, the one or more sensors 504 include one or more biomass sensors. In an embodiment, the one or more sensors 504 include one or more immunosensors.

In an embodiment, one or more of the sensors 504 are configured to detect at least one characteristic associated with a biological subject. In an embodiment, one or more of the sensors 504 are configured to detect at least one characteristic associated with a biological sample (e.g., tissue, biological fluid, target sample, or the like). For example, in an embodiment, at least one of the one or more sensors 504 is configured to detect at least one characteristic associated with a biological sample proximate a surface (e.g., outer surface 108 or inner surface 110, or the like) of the catheter device 102. In an embodiment, one or more of the sensors 504 are configured to detect at least one of a characteristic of a biological sample proximate the catheter device 102, a characteristic of a tissue proximate the catheter device 102, and a physiological characteristic of the biological subject. In an embodiment, one or more of the sensors 504 are configured to determine one or more tissue spectroscopic properties, such as, for example, a transport scattering coefficient, an extinction coefficient, an absorption coefficient, a remittance, a transmittance, or the like.

In an embodiment, the at least one characteristic includes a physiological characteristic of the biological subject. Physiological characteristics such as, for example pH can be used to assess blood flow, a cell metabolic state (e.g., anaerobic metabolism, or the like), the presence of an infectious agent, a disease state, or the like. Among physiological characteristics examples include, but are not limited to, at least one of a temperature, a regional or local temperature, a pH, an impedance, a density, a sodium ion level, a calcium ion level, a potassium ion level, a glucose level, a lipoprotein level, a cholesterol level, a triglyceride level, a hormone level, a blood oxygen level, a pulse rate, a blood pressure, an intracranial pressure, a respiratory rate, a vital statistic, or the like.

In an embodiment, the at least one characteristic includes at least one of a temperature, a pH, an impedance, a density, a sodium ion level, a calcium ion level, a potassium ion level, a glucose level, a lipoprotein level, a cholesterol level, a triglyceride level, a hormone level, a blood oxygen level, a pulse rate, a blood pressure, an intracranial pressure, or a respiratory rate. In an embodiment, the at least one characteristic includes at least one hematological parameter. In an embodiment, the hematological parameter is associated with a hematological abnormality.

In an embodiment, the at least one characteristic includes one or more parameters associated with at least one of leukopenia, leukophilia, lymphocytopenia, lymphocytophilia, neutropenia, neutrophilia, thrombocytopenia, disseminated intravascular coagulation, bacteremia, and viremia. In an embodiment, the at least one characteristic includes at least one of an infection marker, an inflammation marker, an infective stress marker, a systemic inflammatory response syndrome marker, or a sepsis marker. In an embodiment, the infection marker includes at least one of a red blood cell count, a lymphocyte level, a leukocyte count, a myeloid count, an erythrocyte sedimentation rate, or a C-reactive protein level. In an embodiment, the at least one characteristic includes at least one of a cytokine plasma concentration or an acute phase protein plasma concentration.

In an embodiment, the at least one characteristic includes a characteristic associated with tissue proximate the catheter device 102. In an embodiment, the at least one characteristic includes a characteristic associated with a biological sample. In an embodiment, the at least one characteristic includes a characteristic of a specimen of the biological subject. In an embodiment, the at least one characteristic includes one or more spectroscopic properties (e.g., tissue spectroscopic properties, biological fluid spectroscopic properties, infectious agent spectroscopic properties, biomarker spectroscopic properties, or the like). In an embodiment, the at least one characteristic includes at least one characteristic (e.g., a spectral characteristic, a spectral signature, a physical quantity, a relative quantity, an environmental attribute, a physiologic characteristic, or the like) associated with a region within the biological subject. In an embodiment, the at least one characteristic includes a characteristic associated with a fluid-flow passageway 110 obstruction, a hematological abnormality, or a body fluid flow abnormality (e.g., a cerebrospinal fluid abnormality).

In an embodiment, the at least one characteristic includes a characteristic associated with a biological fluid flow vessel. In an embodiment, the at least one characteristic includes a characteristic associated with one or more biological sample components. In an embodiment, the at least one characteristic includes a characteristic associated with one or more imaging probes attached, targeted to, conjugated, bound, or associated with at least one inflammation markers. In an embodiment, the at least one characteristic includes a characteristic associated with one or more imaging probes attached, targeted to, conjugated, bound, or associated with at least one blood components. In an embodiment, the at least one characteristic includes a characteristic associated with one or more blood components.

In an embodiment, the at least one characteristic includes at least one parameter associated with an amount of energy-activatable disinfecting agent present in at least a portion of the tissue proximate a surface of the catheter device 102. In an embodiment, the at least one characteristic includes at least one of a sodium ion content, a chloride content, a superoxide anion content, or a hydrogen peroxide content. In an embodiment, the at least one characteristic includes at least one parameter associated with a tissue water content, an oxyhemoglobin concentration, a deoxyhemoglobin concentration, an oxygenated hemoglobin absorption parameter, a deoxygenated hemoglobin absorption parameter, a tissue light scattering parameter, a tissue light absorption parameter, a hematological parameter, or a pH level. In an embodiment, the at least one characteristic includes at least one parameter associated with a cytokine plasma concentration or an acute phase protein plasma concentration. In an embodiment, the at least one characteristic includes at least one parameter associated with a leukocyte level.

In an embodiment, the at least one characteristic includes at least one of a transmittance, an energy stimulus frequency change, energy stimulus frequency shift, an energy stimulus phase change, and energy stimulus phase shift. In an embodiment; the at least one characteristic includes at least one of a fluorescence, an intrinsic fluorescence, a tissue fluorescence, or a naturally occurring fluorophore fluorescence. In an embodiment, the at least one characteristic includes at least one of an electrical conductivity, electrical polarizability, or an electrical permittivity. In an embodiment, the at least one characteristic includes at least one of a thermal conductivity, a thermal diffusivity, a tissue temperature, or a regional temperature.

In an embodiment, the at least one characteristic includes a spectral parameter associated with a biofilm-specific tag. In an embodiment, the at least one characteristic includes an optical density. In an embodiment, the at least one characteristic includes an opacity. In an embodiment, the at least one characteristic includes a refractivity. In an embodiment, the at least one characteristic includes an absorbance, reflectance, or a transmittance.

In an embodiment, the at least one characteristic includes at least one of an inflammation indication parameter (e.g., an absence, a presence, or a severity indication parameter), an infection indication parameter, a diseased state indication parameter, or a diseased tissue indication parameter. In an embodiment, the at least one characteristic includes at least one of an electromagnetic energy absorption parameter, an electromagnetic energy emission parameter, an electromagnetic energy scattering parameter, an electromagnetic energy reflectance parameter, or an electromagnetic energy depolarization parameter. In an embodiment, the at least one characteristic includes at least one an absorption coefficient, an extinction coefficient, a scattering coefficient, or a fluorescence coefficient. In an embodiment, the at least one characteristic includes at least at least one of parameter associated with a biomarker, an infection marker, an inflammation marker, an infective stress marker, or a sepsis marker.

In an embodiment, the at least one characteristic includes at least one of a psychotic disorder indication parameter, a psychotic state indication parameter, a psychotic trait indication parameter, a psychosis indication parameter, or a predisposition for a psychosis indication parameter. In an embodiment, the at least one characteristic includes at least one of a psychotic disorder indication, psychotic state indication, a psychotic trait indication, a psychosis indication, or a predisposition for a psychosis indication.

In an embodiment, one or more of the sensors 504 are configured to detect a microbial presence proximate the body structure 104 of the catheter device 102. For example, in an embodiment, one or more of the sensors 504 are configured to detect absorbance, reflectance, or a transmittance spectra of one or more components indicative of a microbial presence in one or more regions proximate at least one of the outer surface 106, the inner surface 108, or within at least one of the one or more fluid-flow passageways 110 of the body structure 104.

In an embodiment, one or more of the sensors 504 are configured to detect spectral information associated with a biological sample in the vicinity of the catheter device 102. For example, in an embodiment, one or more of the sensors 504 are configured to detect at least one of an absorption coefficient, an extinction coefficient, or a scattering coefficient associated with the biological sample.

In an embodiment, one or more of the sensors 504 are configured to detect spectral information associated with a microbial presence. For example, in an embodiment, at least one of the one or more sensors 504 is configured to detect at least one of an emitted optical energy, a remitted optical energy, or an acoustic energy from a one or more regions proximate at least one of the outer surface 106, the inner surface 108, and within at least one of the one or more fluid-flow passageways 110 of the body structure 104, and to generate a first response based on a detected at least one of an emitted optical energy, a remitted optical energy, or an acoustic energy. In an embodiment, at least one of the one or more sensors 504 is configured to detect a fluorescence associated with an autofluorescent material of biological sample proximate the body structure 104.

In an embodiment, one or more of the sensors 504 are configured to detect a change in at least one of a phase, a polarization, or a refraction associated with a microbial presence. In an embodiment, one or more of the sensors 504 are configured to detect a microbial presence within the one or more fluid-flow passageways 110 based on one or more flow characteristics. In an embodiment, one or more of the sensors 504 are configured to detect a location associated with a microbial presence. In an embodiment, one or more of the sensors 504 are configured to detect spectral information associated with at least one of temporal metabolite information or spatial metabolite information associated with a microbial presence.

In an embodiment, the system 100 includes one or more computing devices 230 operably coupled to one or more sensors 504. In an embodiment, at least one computing device 230 is configured to process an output associated with one or more sensors 504. In an embodiment, the system 100 includes one or more computing devices 230 configured to concurrently or sequentially operate multiple sensors 504. In an embodiment, the system 100 is configured to compare an input associated with at least one characteristic associated with a tissue proximate a catheter device 102 to a data structure 260 including reference values, and to generate a response based in part on the comparison. In an embodiment, the system 100 is configured to compare an input associated with at least one physiological characteristic associated with a biological subject to a data structure 260 including reference values, and to generate a response based in part on the comparison. In an embodiment, the system 100 is configured to compare an input associated with at least one characteristic associated with a tissue proximate a catheter device 102 to a data structure 260 including reference values, and to generate a response based in part on the comparison.

In an embodiment, at least one computing device 230 is configured to perform a comparison of at least one detected characteristic to stored reference data, and to generate a response based at least in part on the comparison. For example, in an embodiment, at least one computing device 230 is configured to perform a comparison of at least one characteristic associated with the biological sample to stored reference data, and to initiate a treatment protocol based at least in part on the comparison. In an embodiment, at least one computing device 230 is configured to perform a comparison of a detected at least one of the emitted optical energy or the remitted optical energy from the region proximate the body structure 104 to reference spectral information, and to cause an emission of an energy stimulus from one or more energy emitters 220 to at least one of the outer surface 106 or the inner surface 108 of the body structure 104. In an embodiment, one or more computing devices 230 are communicatively coupled to one or more sensors 504 and configured to actuate a determination of the at least one characteristic associated with a biological specimen proximate a surface of the catheter device 102.

In an embodiment, a computing device 230 is configured to compare a measurand associated with the biological subject to a threshold value associated with a tissue spectral model and to generate a response based on the comparison. In an embodiment, a computing device 230 is configured to generate the response based on the comparison of a measurand that modulates with a detected heart beat of the biological subject to a target value associated with a tissue spectral model. In an embodiment, a computing device 230 is configured to concurrently or sequentially operate multiple energy emitters 220. In an embodiment, a computing device 230 is configured to compare an input associated with at least one characteristic associated with, for example, a tissue proximate a catheter device 102 to a database 258 of stored reference values, and to generate a response based in part on the comparison.

In an embodiment, the response includes, among other things, at least one of a response signal, an absorption parameter, an extinction parameter, a scattering parameter, a comparison code, a comparison plot, a diagnostic code, a treatment code, an alarm response, or a test code based on the comparison of a detected optical energy absorption profile to characteristic spectral signature information. In an embodiment, the response includes at least one of a display, a visual representation (e.g., a visual depiction representative of the detected (e.g., assessed, calculated, evaluated, determined, gauged, measured, monitored, quantified, resolved, sensed, or the like) information) component, a visual display of at least one spectral parameter, or the like. In an embodiment, the response includes a visual representation indicative of a parameter associated with an infection present in a region of a tissue proximate one or more sensors 504. In an embodiment, the response includes generating a representation (e.g., depiction, rendering, modeling, or the like) of at least one physical parameter associated with a biological specimen.

In an embodiment, the response includes generating at least one of a visual, an audio, a haptic, or a tactile representation of at least one of spectral component associated with a biofilm marker. In an embodiment, the response includes at least one of activating an authorization protocol, activating an authentication protocol, activating a software update protocol, activating a data transfer protocol, or activating a biofilm sterilization diagnostic protocol.

In an embodiment, the response includes one or more of a response signal, a control signal, a change to an energy stimulus parameter, a change in an excitation intensity, a change in an excitation frequency, a change in an excitation pulse frequency, a change in an excitation pulse ratio, a change in an excitation pulse intensity, a change in an excitation pulse duration time, a change in an excitation pulse repetition rate, or a change in an energy stimulus delivery regimen parameter. In an embodiment, the response includes one or more of sending information associated with at least one of an authentication protocol, an authorization protocol, an energy stimulus delivery protocol, an activation protocol, an encryption protocol, or a decryption protocol.

In an embodiment, at least one computing device 230 is configured to perform a comparison of the at least one characteristic associated with the biological sample to stored reference data, and to cause at least one of an emission of an energy stimulus from one or more of the energy emitters 220 to a biological sample received within at least one of the one or more fluid-flow passageways 110, and a delivery of an active agent from at least one disinfecting agent reservoir to an interior of at least one of the one or more fluid-flow passageways 110.

In an embodiment, the computing device 230 is configured to perform a comparison of a real-time measurand associated with a region proximate the catheter device 102 to infection marker information configured as a physical data structure 260 and to generate a response based at least in part on the comparison. In an embodiment, one or more computing devices 230 are operably coupled to at least one of the plurality of selectively actuatable energy waveguides 202*a*, and configured to actuate at least one of the plurality of selectively actuatable energy waveguides 202*a* in response to detected information from the one or more sensors 504.

In an embodiment, the system 100 includes, among other things, means for detecting at least one characteristic associated with a biological subject including at least one sensor component 502 having one or more sensors 504 and at least one computing device 230 operably coupled to the at least one sensor component 502. In an embodiment, the system 100 includes, among other things, means for detecting at least one of an emitted energy or a remitted energy including an interrogation energy emitter and one or more sensor components 502 having one or more sensors 504. In an embodiment, the means for detecting at least one of an emitted energy or a remitted energy includes at least one of a time-integrating optical component 506, a linear time-integrating component 508, a nonlinear optical component 510, or a temporal autocorrelating component 512. In an embodiment, means for detecting at least one of an emitted energy or a remitted energy includes one or more one-, two-, or three-dimensional photodiode arrays.

In an embodiment, the system 100 includes, among other things, circuitry 550 configured to determine a microorganism colonization event in one or more regions in the vicinity of the catheter device 102, for example, proximate at least one of the outer surface or the inner surface of the body structure 104. In an embodiment, circuitry includes one or more components operably coupled (e.g., communicatively coupled, electromagnetically, magnetically, acoustically, optically, inductively, electrically, capacitively coupleable, or the like) to each other. In an embodiment, circuitry includes one or more remotely located components. In an embodiment, remotely located components are operably coupled via wireless communication. In an embodiment, remotely located components are operably coupled via one or more receivers, transmitters, transceivers, or the like.

In an embodiment, the circuitry 550 configured to determine the microorganism colonization event includes at least one sensor component 502 having one or more sensors 504. In an embodiment, the circuitry 550 configured to determine the microorganism colonization event includes at least one sensor component 502 having a component identification code and configured to implement instructions addressed to the sensor component 502 according to the component identification code. In an embodiment, the circuitry 550 configured to determine the microorganism colonization event includes at least one sensor component 502 operably coupled to a microorganism colonization biomarker array.

In an embodiment, the circuitry 550 configured to determine the microorganism colonization event includes a computing device 230 operably coupled to one or more sensors 304, and configured to process sensor measurand information, and configured to cause the storing of the measurand information in a data storage medium. In an embodiment, the circuitry 550 configured to determine the microorganism colonization event includes at least one surface plasmon resonance microarray sensor. In an embodiment, the at least one surface plasmon resonance microarray sensor includes an array of micro-regions configured to capture target molecules.

In an embodiment, the circuitry 550 configured to determine the microorganism colonization event includes at least one of a charge-coupled device, a complementary metal-oxide-semiconductor device, a photodiode image sensor device, a Whispering Gallery Mode (WGM) micro cavity device, or a scintillation detector device. In an embodiment, the circuitry 550 configured to determine the microorganism colonization event includes at least one photoelectric device. In an embodiment, the circuitry 550 configured to determine the microorganism colonization event includes an imaging spectrometer. In an embodiment, the circuitry 550 configured to determine the microorganism colonization event includes at least one of a photo-acoustic imaging spectrometer, a thermo-acoustic imaging spectrometer, or a photo-acoustic/thermo-acoustic tomographic imaging spectrometer.

In an embodiment, the circuitry 550 configured to determine the microorganism colonization event includes a wavelength-tunable surface plasmon resonance sensor. In an embodiment, the circuitry 550 configured to determine the microorganism colonization event includes a surface plasmon resonance microarray sensor having a wavelength-tunable metal-coated grating. In an embodiment, the circuitry 550 configured to determine the microorganism colonization event includes one or more acoustic transducers, electro-chemical transducers, optical transducers, piezoelectric transducers, or thermal transducers. In an embodiment, the circuitry 550 configured to determine the microorganism colonization event includes one or more thermal detectors, photovoltaic detectors, or photomultiplier detectors. In an embodiment, the circuitry 550 configured to determine the microorganism colonization event includes one or more charge-coupled devices, complementary metal-oxide-semiconductor devices, photodiode image sensor devices, whispering gallery mode micro cavity devices, or scintillation detector devices. In an embodiment, the circuitry 550 configured to determine the microorganism colonization event includes one or more acoustic transducers. In an embodiment, the circuitry 550 configured to determine the microorganism colonization event includes one or more density sensors. In an embodiment, the circuitry 550 configured to determine the microorganism colonization event includes one or more optical density sensors. In an embodiment, the circuitry 550 configured to determine the microorganism colonization event includes one or more photoacoustic spectrometers.

In an embodiment, the circuitry 550 configured to determine the microorganism colonization event includes one or more refractive index sensors. In an embodiment, the circuitry 550 configured to determine the microorganism colonization event includes one or more fiber optic refractive index sensors. In an embodiment, the circuitry 550 configured to determine the microorganism colonization event includes one or more surface plasmon resonance sensors. In an embodiment, the circuitry 550 configured to determine the microorganism colonization event includes one or more localized surface plasmon resonance sensors.

In an embodiment, the circuitry 550 configured to determine the microorganism colonization event includes a light transmissive support and a reflective metal layer. In an embodiment, the circuitry 550 configured to determine the microorganism colonization event includes one or more acoustic biosensors, amperometric biosensors, calorimetric biosensors, optical biosensors, or potentiometric biosensors. In an embodiment, the circuitry 550 configured to determine the microorganism colonization event includes one or more fluid flow sensors. In an embodiment, the circuitry 550 configured to determine the microorganism colonization event includes one or more differential electrodes.

In an embodiment, the circuitry 550 configured to determine the microorganism colonization event includes one or more biomass sensors. In an embodiment, the circuitry 550 configured to determine the microorganism colonization event includes one or more immunosensors. In an embodiment, the circuitry 550 configured to determine the microorganism colonization event includes one or more functionalized cantilevers. In an embodiment, the circuitry 550 configured to determine the microorganism colonization event includes a biological molecule capture layer. In an embodiment, the biological molecule capture layer includes an array of different binding molecules that specifically bind one or more target molecules.

In an embodiment, the circuitry 550 configured to determine the microorganism colonization event includes biofilm marker information configured as a physical data structure. In an embodiment, the physical data structure includes a characteristic information section having characteristic microbial colonization spectral information representative of the presence of a microbial colonization proximate the catheter device 102.

In an embodiment, the system 100 includes, among other things, circuitry 560 configured to obtain information. In an embodiment, the circuitry 560 configured to obtain information includes circuitry 560 configured to obtain information associated with a delivery of the optical energy. In an embodiment, the circuitry 560 configured to obtain information includes circuitry configured to obtain at least one of a command stream, a software stream, or a data stream.

In an embodiment, the system 100 includes, among other things, circuitry 570 configured to store information. In an embodiment, the circuitry 570 configured to store information includes one or more data structures.

In an embodiment, the system 100 includes, among other things, circuitry 580 configured to provide information. In an embodiment, the circuitry 580 configured to provide information includes circuitry 580 configured to provide having infection marker information. In an embodiment, the circuitry 580 configured to provide information includes circuitry 580 configured to provide status information. In an embodiment, the circuitry 580 configured to provide information includes circuitry 580 configured to provide information regarding the detection at least one of the emitted optical energy or the remitted optical energy.

In an embodiment, the system 100 includes, among other things, circuitry 590 configured to perform a comparison of the determined at least one characteristic associated with the tissue or a biological fluid proximate the catheter device 102 to stored reference data following the delivery of the energy stimulus. In an embodiment, the catheter device 102 includes, among other things, circuitry configured to generate a response based at least in part on the comparison. In an embodiment, the circuitry 590 configured to perform a comparison includes, among other things, one or computing devices 230 configured to perform a comparison of the at least one characteristic associated with the tissue or a biological fluid proximate the catheter device 102 stored reference data following delivery of the sterilizing stimulus, and to generate a response based at least in part on the comparison.

In an embodiment, the system 100 is configured to initiate one or more treatment protocols. In an embodiment, the system 100 is configured to initiate at least one treatment regimen based on a detected spectral event. In an embodiment, the system 100 is configured to initiate at least one treatment regimen based on a detected biomarker event. In an embodiment, the system 100 is configured to initiate at least one treatment regimen based on a detected infection. In an embodiment, the system 100 is configured to initiate at least one treatment regimen based on a detected fluid vessel abnormality (e.g., an obstruction), a detected biological fluid abnormality (e.g., cerebrospinal fluid abnormalities, hematological abnormalities, components concentration or level abnormalities, flow abnormalities, or the like), a detected biological parameter, or the like.

Many of the disclosed embodiments can be electrical, electromechanical, software-implemented, firmware-implemented, or other otherwise implemented, or combinations thereof. Many of the disclosed embodiments can be software or otherwise in memory, such as one or more executable instruction sequences or supplemental information as described herein. For example, in an embodiment, in an embodiment, the catheter device 102 includes, among other things, one or more computing devices 230 configured to perform a comparison of the at least one characteristic associated with the biological subject to stored reference data, and to generate a response based at least in part on the comparison. In an embodiment, one or more computing devices 230 are configured to automatically control one or more of a frequency, a duration, a pulse rate, a duty cycle, or the like associated with an acoustic energy generated by the one or more transducers 223a based on a sensed parameter. In an embodiment, one or more computing devices 230 are configured to automatically control one or more of a frequency, a duration, a pulse rate, a duty cycle, or the like associated with the acoustic energy generated by the one or more transducers 223a based on a sensed parameter associated with a region within the biological subject.

Referring to FIG. 5, in an embodiment, the system 100 includes, among other things, a plurality of actuatable regions 592 that are independently actuatable between at least a first transmissive state and a second transmissive state. For example, in an embodiment, a catheter device 102 includes a plurality of actuatable regions 592 that are independently actuatable between at least a first transmissive state and a second transmissive state. In an embodiment, the plurality of actuatable regions 592 are configured to actuate between the at least first transmissive state and the second transmissive state in response to an applied voltage, electric current, electric potential, electromagnetic field, or the like. For example, in an embodiment, one or more of the plurality of actuatable regions 592 include a region comprising a ferromagnetic fluid whose transmittance changes as the rheology of the ferromagnetic fluid changes in response to an applied potential. In an embodiment, one or more of the plurality of actuatable regions 592 include a region comprising one or more light valves (e.g., suspended particle devices, or the like) including a film or a liquid suspension of conductive material and one or more conductive coatings that permit the passage of light in the presence of an applied voltage, and blocks the passage of light in the absences of an applied voltage.

In an embodiment, the plurality of actuatable regions 592 are configured to actuate electrochemically between the at least first transmissive state and the second transmissive state. For example, in an embodiment, the plurality of actuatable regions 592 includes one or more of tungsten oxide laminates having optical properties that are electrochemically controllable. In an embodiment, the plurality of actuatable regions 592 includes one or more of materials that change color in response to an applied voltage change.

In an embodiment, the plurality of actuatable regions 592 is energetically actuatable between the at least first transmissive state and the second transmissive state. In an embodiment, the plurality of actuatable regions 592 is UV-actuatable between the at least first transmissive state and the second transmissive state. In an embodiment, the plurality of actuatable regions 592 is photochemically actuatable between the at least first transmissive state and the second transmissive state. In an embodiment, the plurality of actuatable regions 592 is electrically actuatable between the at least first transmissive state and the second transmissive state. In an embodiment, the plurality of actuatable regions 592 is acoustically actuatable between the at least first transmissive state and the second transmissive state.

In an embodiment, the plurality of actuatable regions 592 is configured to actuate electro-optically between the at least first transmissive state and the second transmissive state.

In an embodiment, the plurality of actuatable regions 592 is actively controllable, via one or more computing device 230, between the at least first transmissive state and the second transmissive state. For example, in an embodiment, one or more computing devices 230 are used to actuate the plurality of actuatable regions 592 between an optically transparent state and an optically reflective state. In an embodiment, the plurality of actuatable regions 592 is controllably actuatable between a transmissive state and a reflective state.

The system 100 can include, among other things, one or more actively controllable reflective or transmissive components configured to outwardly transmit or internally reflect an energy stimulus propagated therethrough. In an embodiment, a catheter device 102 includes one or more actively controllable reflective or transmissive components configured to outwardly transmit or internally reflect an energy stimulus propagated therethrough.

In an embodiment, one or more of plurality of actuatable regions 592 are independently actuatable between at least a first transmissive state and a second transmissive state via at least one acoustically active material. In an embodiment, one or more of plurality of actuatable regions 592 are independently actuatable between at least a first transmissive state and a second transmissive state via at least one electro-mechanical switch. In an embodiment, one or more of plurality of actuatable regions 592 are independently actuatable between at least a first transmissive state and a second transmissive state via at least one electro-optic switch. In an embodiment, one or more of plurality of actuatable regions 592 are independently actuatable between at least a first transmissive state and a second transmissive state via at least one acousto-optic switch. In an embodiment, one or more of plurality of actuatable regions 592 are independently actuatable between at least a first transmissive state and a second transmissive state via at least one optical switch.

In an embodiment, the system 100 includes, among other things, a computing device 230 operably coupled to one or more of the plurality of actuatable regions 592. In an embodiment, the controller is configured to cause a change between transmissive states based on detected information from the one or more sensors 504.

In an embodiment, the catheter device 102 includes one or more computing devices 230 operably coupled to one or more of the plurality of actuatable regions 592. In an embodiment, at least one of the one or more computing devices 230 is configured to cause a change between the at least first transmissive state and the second transmissive state based on detected information from the one or more sensors 504. In an embodiment, at least one of the one or more computing devices 230 is configured to actuate one or more of the plurality of actuatable regions 592 between the at least first transmissive state and the second transmissive state based on a comparison of a detected characteristic associated with the biological sample proximate at least one of the outer surface or the inner surface of the body structure 104.

Figure 6:
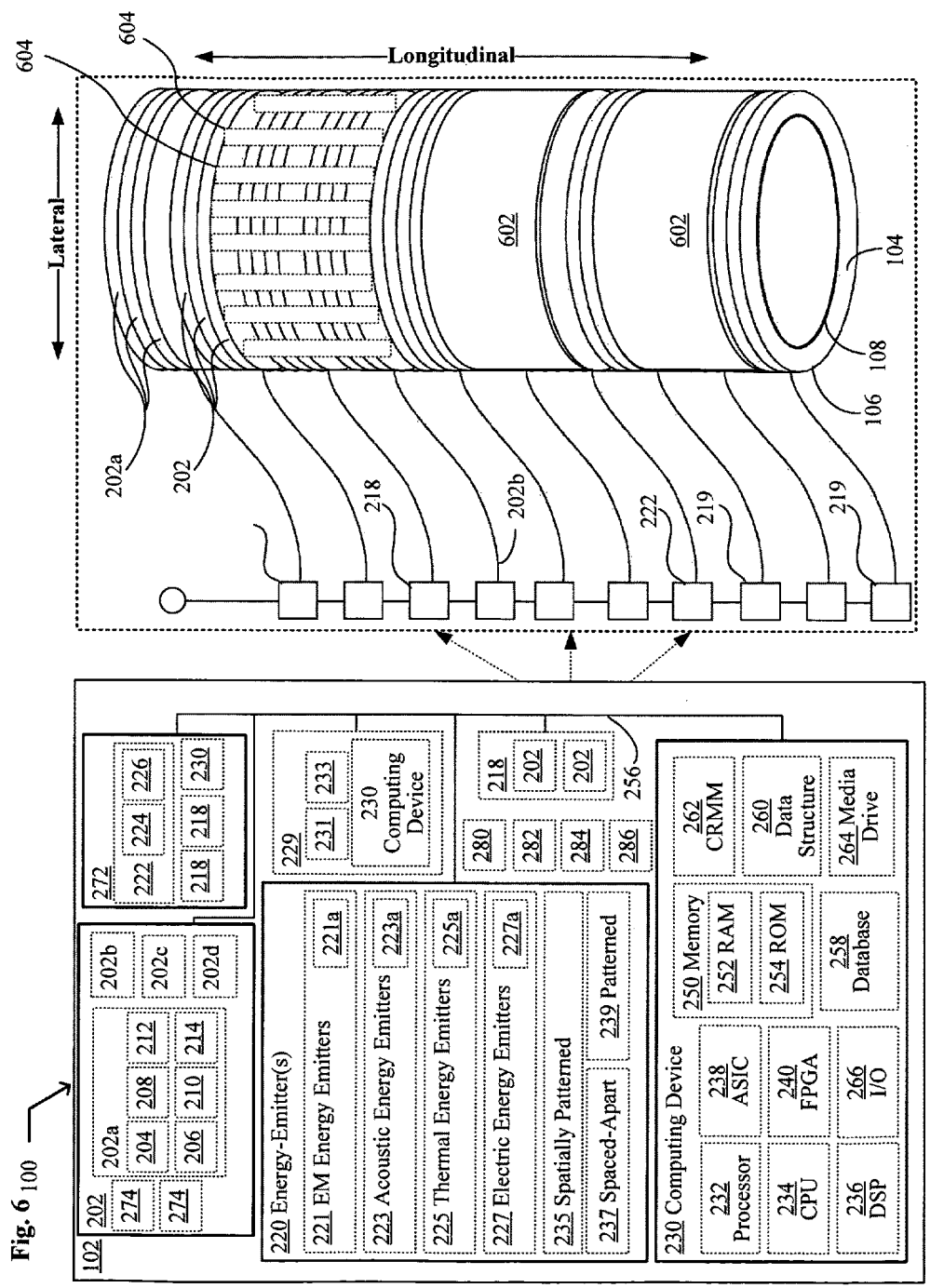
FIG. 6 is a schematic diagram of a system including a catheter device according to one embodiment.

Referring to FIG. 6, in an embodiment, the system 100 includes, among other things, one or more surface regions 602 that can be actuated (e.g., controllably actuated, energetically actuated, selectively actuated, or the like) between wettability states (e.g., between at least a first wettability state and a second wettability state). In an embodiment, a catheter device 102 includes one or more surface regions 602 that are can be actuated between at least a first wettability state and a second wettability state. For example, in an embodiment, the catheter device 102 includes, among other things, one or more controllable-wettability-components 604 that are energetically actuatable among a plurality of wettability states.

It may be possible to affect adhesion of, for example, bacteria and biofilm formation by changing at least one of a functional, structural, or chemical character of a surface on a catheter device 102. For example, it may be possible to affect adhesion of, for example, bacteria and biofilm formation by changing surface morphology. It may also be possible to modulate the adhesion and biofilm formation by modulating at least one of the functional, structural, or chemical characters of a surface on a catheter device 102. By modulating at least one of a functional, structural, or chemical character of a surface on a catheter device 102, it may also be possible to affect the transport properties of a fluid exposed to the surface on a catheter device 102.

In an embodiment, at least one of the one or more fluid-flow passageways 110 includes one or more surface regions 602 that are energetically actuatable between a substantially hydrophobic state and a substantially hydrophilic state. In an embodiment, at least one of the one or more fluid-flow passageways 110 includes a surface region 602 that is energetically actuatable between at least a first hydrophilic state and a second hydrophilic state. In an embodiment, at least one of the one or more fluid-flow passageways 110 includes a surface region 602 that is energetically actuatable between a hydrophobic state and a hydrophilic state. In an embodiment, at least one of the one or more fluid-flow passageways 110 includes a surface region 602 having a material that is switchable between a zwitterionic state and a non-zwitterionic state.

In an embodiment, at least one of the one or more fluid-flow passageways 110 includes at least one of an antimicrobial coating and a non-fouling coating. In an embodiment, at least one of the one or more fluid-flow passageways 110 includes an antimicrobial and a non-fouling coating. In an embodiment, at least one of the one or more fluid-flow passageways 110 includes a surface region 602 that is energetically actuatable between an antimicrobial state and a non-fouling state.

In an embodiment, the body structure 104 includes one or more protruding elements (e.g., nanostructures, microstructures, pillars, ridges, or the like) on its surface that recede in the presence of an applied current. The wettability of the surface can be controlled by altering the density of the protruding elements. See e.g., Spori et al., *Cassie-State Wetting Investigated by Means of a Hole-to-Pillar Density Gradient*, Langmuir, 2010, 26 (12), pp 9465-9473; which is incorporated herein by reference.

In an embodiment, the one or more surface regions are configured to photochemically actuate between the first wettability state and the second wettability state in the presence of an ultraviolet energy. In an embodiment, the one or more surface regions 602 are configured to actuate between the first wettability state and the second wettability state in the presence of an applied potential. In an embodiment, the one or more surface regions 602 are UV-manipulatable between the first wettability and the second wettability.

In an embodiment, the one or more surface regions 602 are configured to photochemically actuate between a substantially hydrophobic state and a substantially hydrophilic state. In an embodiment, the one or more surface regions 602 are configured to electrically actuate between a substantially hydrophobic state and a substantially hydrophilic state. In an embodiment, the one or more surface regions 602 include at least one ZnO nano-rod film, coating, or material that is UV-manipulatable between a superhydrophobic state and superhydrophilic state.

In an embodiment, the one or more surface regions 602 are energetically controllably actuatable between a substantially hydrophobic state and a substantially hydrophilic state. In an embodiment, the one or more surface regions 602 are energetically controllably actuatable between at least a first hydrophilic state and a second hydrophilic state. In an embodiment, the one or more surface regions 602 are energetically controllably actuatable between a hydrophobic state and a hydrophilic state. In an embodiment, the one or more surface regions 602 include a material that is switchable between a zwitterionic state and a non-zwitterionic state.

Controllable-wettability-components 604 can be made using a variety of methodologies and technologies including, for example, spray pyrolysis, electro-deposition, electro-deposition onto laser-drilled polymer molds, laser cutting and electro-polishing, laser micromachining, photolithography, surface micro-machining, soft lithography, x-ray lithography, LIGA techniques (e.g., X-ray lithography, electroplating, and molding), conductive paint silk screen techniques, conventional patterning techniques, injection molding, conventional silicon-based fabrication methods (e.g., inductively coupled plasma etching, wet etching, isotropic and anisotropic etching, isotropic silicon etching, anisotropic silicon etching, anisotropic GaAs etching, deep reactive ion etching, silicon isotropic etching, silicon bulk micromachining, or the like), complementary-symmetry/metal-oxide semiconductor (CMOS) technology, deep x-ray exposure techniques, or the like.

Further examples of methodologies and technologies for making controllable wettability components can be found, for example, in the following documents: Feng et al., *Reversible Super-hydrophobicity to Super-hydrophilicity Transition of Aligned ZnO Nanorod Films*, J. Am. Chem. Soc., 126, 62-63 (2004), Lin et al., Electrically Tunable Wettability of Liquid Crystal/Polymer Composite Films, Optics Express 16 (22): 17591-598 (2008), Spori et al., *Cassie-State Wetting Investigated by Means of a Hole-to-Pillar Density Gradient*, Langmuir, 2010, 26 (12), pp 9465-9473; Wang et al., *Photo-responsive Surfaces with Controllable Wettability*, Journal of Photochemistry and Photobiology C: Photochemistry Reviews, 8 (1): 18-29 (2007), U.S. Pat. No. 6,914,279 (issued Jul. 5, 2005), and U.S. Patent Publication No. 2008/0223717 (published Sep. 18, 2008); each of which is incorporated herein by reference.

The wettability of a substrate can be determined using various technologies and methodologies including contact angle methods, the Goniometer method, the Whilemy method, the Sessile drop technique, or the like. Wetting is a process by which a liquid interacts with a solid. Wettability (the degree of wetting) is determined by a force balance between adhesive and cohesive force and is often characterized by a contact angle. The contact angle is the angle made by the intersection of the liquid/solid interface and the liquid/air interface. Alternatively, it is the angle between a solid sample's surface and the tangent of a droplet's ovate shape at the edge of the droplet. Contact angle measurements provide a measure of interfacial energies and convey direct information regarding the degree of hydrophilicity or hydrophobicity of a surface. For example, superhydrophilic surfaces have contact angles less than about 5°, hydrophilic surfaces have contact angles less than about 90°, hydrophobic surfaces have contact angles greater than about 90°, and superhydrophobic surfaces have contact angles greater than about 150°.

In an embodiment, the catheter device 102 includes a body structure 104 including one or more controllable-wettability-components 604 having switchable wetting properties. In an embodiment, the catheter device 102 includes a body structure 104 including one or more controllable-wettability-components 604 that are energetically actuatable between at least a first wettability and a second wettability. In an embodiment, the one or more controllable-wettability-components 604 are acoustically, chemically, electro-chemically, electrically, optically, thermally, or photo-chemically actuatable between at least a first wettability and a second wettability.

In an embodiment, the one or more controllable-wettability-components 604 include at least one acousto-responsive material.

In an embodiment, the one or more controllable-wettability-components 604 include at least one photo-responsive material. Non-limiting examples of photo-responsive materials include SnO, $SnO_2$, $TiO_2$, $W_2O_3$, ZnO, or the like. In an embodiment, the one or more controllable-wettability-components 604 include at least one film, coating, or material including SnO, $SnO_2$, $TiO_2$, $W_2O_3$, ZnO, or the like. In an embodiment, the one or more controllable-wettability-components 604 are UV-manipulatable between at least a first wettability and a second wettability. In an embodiment, the one or more controllable-wettability-components 604 include one or more ZnO nano-rod films, coatings, or materials that are UV-manipulatable between a superhydrophobic state and superhydrophilic state. In an embodiment, the one or more controllable-wettability-components 604 include at least one electrochemically active material. Non-limiting examples of electrochemically active materials include electrochemically active polymers (e.g., polyaniline, polyethylenethioxythiophene, conjugated polymer poly(3-hexylthiophene), or the like), or the like.

In an embodiment, the one or more controllable-wettability-components 604 include one or more superhydrophobic conducting polypyrrole films, coatings, or components that are electrically switchable between an oxidized state and a neutral state, resulting in reversibly switchable superhydrophobic and superhydrophilic properties. (See, e.g., Lahann et al., *A Reversibly Switching Surface,* 299 (5605): 371-374 (2003) 21:47-51 (2003), which is incorporated herein by reference). In an embodiment, the one or more controllable-wettability-components 604 include one or more electrically isolatable fluid-support structures. See, e.g., U.S. Pat. No. 7,535,692 (issued May 19, 2009), which is incorporated herein by reference).

In an embodiment, the one or more controllable-wettability-components 604 include a plurality of volume-tunable nanostructures. See, e.g., U.S. Patent Publication No. 2008/0095977 (published Apr. 24, 2008), which is incorporated herein by reference). In an embodiment, the one or more controllable-wettability-components 604 include one or more tunable (electrically tunable) superhydrophobic conducting polypyrrole films, coatings, or components. See, e.g., Krupenki et al, *Electrically Tunable Superhydrophobic Nanostructured Surfaces*, Bell Labs Technical Journal 10 (3): 161-170 (2009), which is incorporated herein by reference). In an embodiment, the one or more controllable-wettability-components 604 include one or more electrically tunable crystal/polymer composites. In an embodiment, the one or more controllable-wettability-components 604 include a switchable surface. See e.g., Gras et al., *Intelligent Control of Surface Hydrophobicity*, ChemPhysChem 8 (14): 2036-2050 (2007); each of which is incorporated herein by reference.

Figure 7:
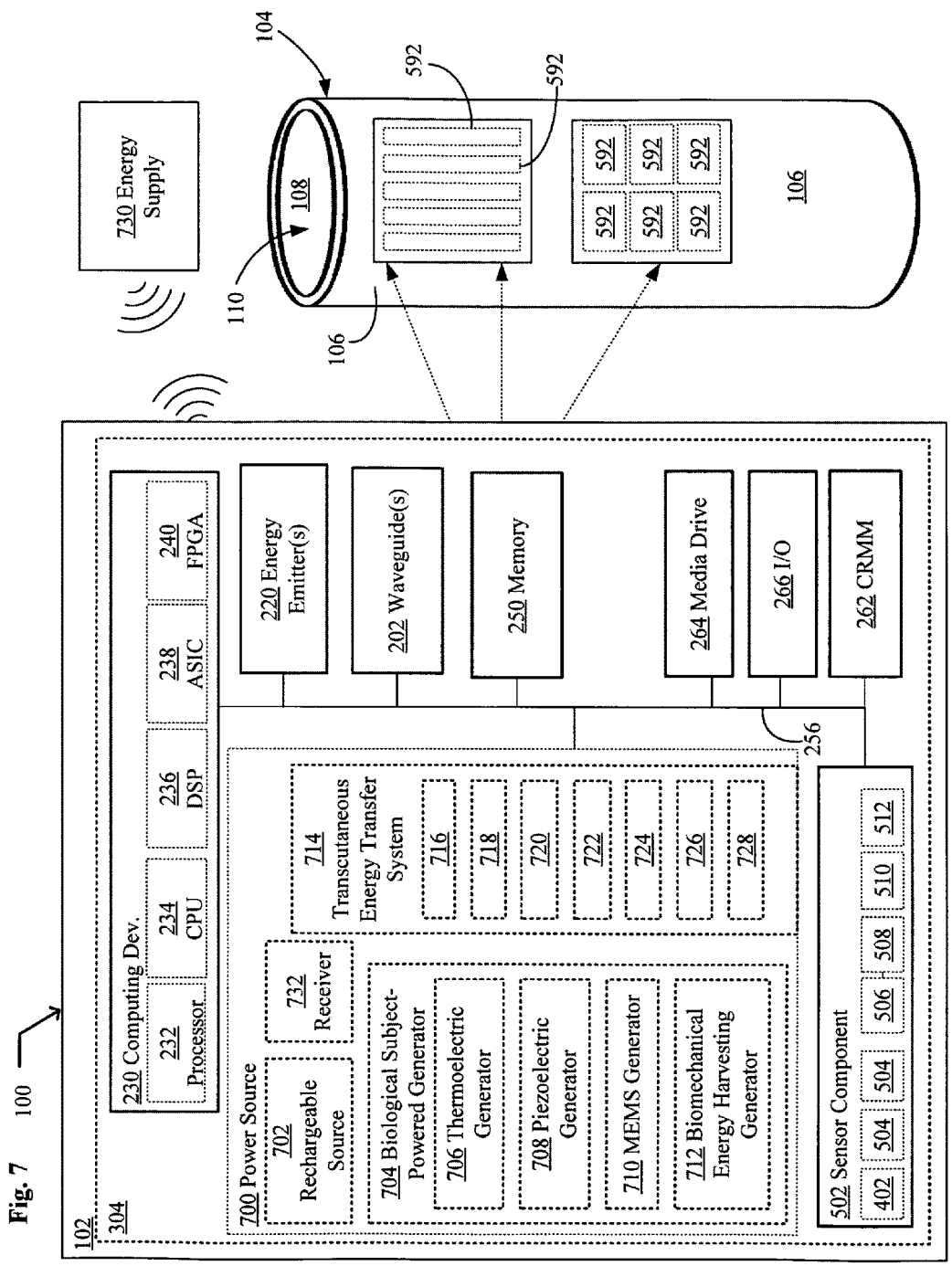
FIG. 7 is a schematic diagram of a system including a catheter device according to one embodiment.

Referring to FIG. 7, in an embodiment the system 100 includes, among other things, one or more power sources 700. In an embodiment, the catheter device 102 includes one or more power sources 700. In an embodiment, the power source 700 is electromagnetically, magnetically, acoustically, optically, inductively, electrically, or capacitively coupled to at least one of the energy waveguides 202 (e.g., selectively actuatable energy waveguides 202a), the energy emitters 220, the computing device 230, and the sensor component 502. Non-limiting examples of power sources 700 examples include one or more button cells, chemical battery cells, a fuel cell, secondary cells, lithium ion cells, micro-electric patches, nickel metal hydride cells, silver-zinc cells, capacitors, super-capacitors, thin film secondary cells, ultra-capacitors, zinc-air cells, or the like. Further non-limiting examples of power sources 700 include one or more generators (e.g., electrical generators, thermo energy-to-electrical energy generators, mechanical-energy-to-electrical energy generators, micro-generators, nano-generators, or the like) such as, for example, thermoelectric generators, piezoelectric generators, electromechanical generators, biomechanical-energy harvesting generators, or the like. In an embodiment, the power source 700 includes at least one rechargeable power source. In an embodiment, the power source 700 is carried by the catheter device 102. In an embodiment, the catheter device 102 can include, among other things, at least one of a battery, a capacitor, or a mechanical energy store (e.g., a spring, a flywheel, or the like).

In an embodiment, the power source 700 is configured to manage a duty cycle associated with emitting an effective dose of the energy stimulus from to at least one of the energy waveguides 202 (e.g., selectively actuatable energy waveguides 202a), or the energy emitters 220. In an embodiment, the catheter device 102 is configured to provide a voltage, via a power source 700 operably coupled to at least one of the energy waveguides 202 or the energy emitters 220, across at least a portion of the tissue proximate the catheter device 102.

In an embodiment, the power source 700 is configured to wirelessly receive power from a remote power supply 730. In an embodiment, the catheter device 102 includes one or more power receivers 732 configured to receive power from an in vivo or ex vivo power source. In an embodiment, the power source 700 is configured to wirelessly receive power via at least one of an electrical conductor or an electromagnetic waveguide. In an embodiment, the power source 700 includes one or more power receivers 732 configured to receive power from an in vivo or ex vivo power source. In an embodiment, the in vivo power source includes at least one of a thermoelectric generator, a piezoelectric generator, a microelectromechanical systems generator, or a biomechanical-energy harvesting generator.

In an embodiment, the catheter device 102 includes one or more generators configured to harvest mechanical energy from for example, acoustic waves, mechanical vibration, blood flow, or the like. For example, in an embodiment, the power source 700 includes at least one of a biological-subject (e.g., human)-powered generator 704, a thermoelectric generator 706, piezoelectric generator 708, electromechanical generator 710 (e.g., a microelectromechanical systems (MEMS) generator, or the like), biomechanical-energy harvesting generator 712, or the like.

In an embodiment, the biological-subject-powered generator 704 is configured to harvest thermal energy generated by the biological subject. In an embodiment, the biological-subject-powered generator 704 is configured to harvest energy generated by the biological subject using at least one of a thermoelectric generator 706, piezoelectric generator 708, electromechanical generator 710 (e.g., a microelectromechanical systems (MEMS) generator, or the like), biomechanical-energy harvesting generator 712, or the like. For example, in an embodiment, the biological-subject-powered generator 704 includes one or more thermoelectric generators 706 configured to convert heat dissipated by the biological subject into electricity. In an embodiment, the biological-subject-powered generator 704 is configured to harvest energy generated by any physical motion or movement (e.g., walking,) by biological subject. For example, in an embodiment, the biological-subject-powered generator 704 is configured to harvest energy generated by the movement of a joint within the biological subject. In an embodiment, the biological-subject-powered generator 704 is configured to harvest energy generated by the movement of a fluid (e.g., biological fluid) within the biological subject.

In an embodiment, the system 100, includes, among other things, a transcutaneous energy transfer system 714. In an embodiment, the catheter device 102 includes a transcutaneous energy transfer system 714. For example, in an embodiment, the catheter device 102 includes one or more power receivers 732 configured to receive power from at least one of an in vivo or an ex vivo power source. In an embodiment, the transcutaneous energy transfer system 714 is electromagnetically, magnetically, acoustically, optically, inductively, electrically, or capacitively coupled to at least one of the energy waveguides 202 (e.g., selectively actuatable energy waveguides 202a), the energy emitters 220, the computing device 230, or the sensor component 502.

In an embodiment, the transcutaneous energy transfer system 714 is configured to transfer power from at least one of an in vivo or an ex vivo power source to the catheter device 102. In an embodiment, the transcutaneous energy transfer system 714 is configured to transfer power to the catheter device 102 and to recharge a power source 700 within the catheter device 102.

In an embodiment, the transcutaneous energy transfer system 714 is electromagnetically, magnetically, acoustically, optically, inductively, electrically, or capacitively coupleable to an in vivo power supply. In an embodiment, the transcutaneous energy transfer system 714 includes at least one electromagnetically coupleable power supply 716, magnetically coupleable power supply 718, acoustically coupleable power supply 720, optically coupleable power supply 722, inductively coupleable power supply 724, electrically coupleable power supply 726, or capacitively coupleable power supply 728. In an embodiment, the energy transcutaneous transfer system 714 is configured to wirelessly receive power from a remote power supply 730.

The transcutaneous energy transfer system 714 can include, among other things, an inductive power supply. In an embodiment, the inductive power supply includes a primary winding operable to produce a varying magnetic field. The catheter device 102 can include, among other things, a secondary winding electrically coupled to one or more energy emitters 220 for providing a voltage to tissue proximate the catheter device 102 in response to the varying magnetic field of the inductive power supply. In an embodiment, the transcutaneous energy transfer system 714 includes a secondary coil configured to provide an output voltage ranging from about 10 volts to about 25 volts. In an embodiment, the transcutaneous energy transfer system 714 is configured to manage a duty cycle associated with emitting an effective amount of the sterilizing energy stimulus from one or more energy emitters 220. In an embodiment, the transcutaneous energy transfer system 714 is configured to transfer power to the catheter device 102 and to recharge a power source 700 within the catheter device 102.

In an embodiment, the catheter device 102 includes one or more coatings (e.g., optically active coatings, reflective coating, opaque coatings, transmissive coatings, etc.). In an embodiment, at least a portion of the body structure 104 includes a surface having a coating, coatings configured to treat or reduce the concentration of an infectious agent in the immediate vicinity of the implantable device 102

Non-limiting examples of coatings include anti-biofilm activity coatings, coatings having self-cleaning properties, coatings having self-cleaning, and antibacterial activity, or the like.

Further non-limiting examples of coatings include polymeric compositions that resist bacterial adhesion, antimicrobial coating, coatings that controllably release antimicrobial agents, quaternary ammonium silane coatings, chitosan coatings, or the like. Further non-limiting examples of coatings may be found in, for example, the following documents: U.S.

Pat. No. 7,348,021 (issued Mar. 25, 2008), U.S. Pat. No. 7,217,425 (issued May 15, 2007), U.S. Pat. No. 7,151,139 (issued Dec. 19, 2006), and U.S. Pat. No. 7,143,709 (issued Dec. 5, 2006); each of which is incorporated herein by reference. In an embodiment, at least a portion of an inner or an outer surface of the implantable device 102 includes one or more self-cleaning coating materials. Non limiting examples of self-cleaning coating (e.g., Lotus Effect) materials include superhydrophobic materials, carbon nanotubes with nanoscopic paraffin coating, or the like. Further non-limiting examples of self-cleaning (e.g., non fouling) coating materials include antimicrobial, and nonfouling zwitterionic polymers, zwitterionic surface forming materials, zwitterionic polymers, poly(carboxybetaine methacrylate) (pCBMA), poly(carboxybetaine acrylic amide) (pCBAA), poly(oligo (ethylene glycol) methyl ether methacrylate) (pOEGMA), poly(N,N-dimethyl-N-(ethoxycarbonylmethyl)-N-[2'- (methacryloyloxy)ethyl]-ammonium bromide), cationic pC8NMA, switchable pCBMA-1 C2, pCBMA-2, or the like. See, e.g., WO 2008/083390 (published Jul. 10, 2008) (which is incorporated herein by reference).

Further non-limiting examples of coatings include superhydrophobic conducting polypyrrole coatings that are electrically switchable between an oxidized state and a neutral state, resulting in reversibly switchable superhydrophobic and superhydrophilic properties (see, e.g., Lahann et al., *A Reversibly Switching Surface,* 299 (5605): 371-374 (2003) 21:47-51 (2003), which is incorporated herein by reference); coatings including electrically isolatable fluid-support structures (see, e.g., U.S. Pat. No. 7,535,692 (issued May 19, 2009), which is incorporated herein by reference); coatings including a plurality of volume-tunable nanostructures (see, e.g., U.S. Patent Publication No. 2008/0095977 (published Apr. 24, 2008), which is incorporated herein by reference); coatings including re-entrant surface structures (see, e.g., Tuteja et al., *Robust Omniphobic Surfaces,* Epub 2008 Nov. 10, 105 (47):18200-5 (2008), which is incorporated herein by reference); coatings including superhydrophobic conducting polypyrrole materials, coatings including zwitterionic polymers (see, e.g., Cheng et al., *A Switchable Biocompatible Polymer Surface with Self-Sterilizing and Nonfouling Capabilities,* Agnew. Chem. Int. Ed. 8831-8834 (2008), which is incorporated herein by reference); or the like.

Further non-limiting examples of coating include reflective coatings, beam-splitter coatings, broadband multilayer coatings, composite coatings, dielectric coatings, dielectric reflective coatings (e.g., dielectric high reflective coatings), grating waveguide coatings (e.g., high reflectivity grating waveguide coatings), IR reflective coatings, metallic reflective coatings (e.g., metallic high reflective coatings), multilayer coatings, narrow or broad band coatings, optical coatings, partial reflective coatings, polymeric coatings, single layer coatings, UV reflective coatings, UV-IR reflective coatings, or the like, and combinations thereof. For example, in an embodiment, the catheter device 102 includes at least one of an outer internally reflective or an inner internally reflective coating on the body structure 104. For example, in an embodiment, at least a portion of an inner surface 108 or an outer surface 106 of the catheter device 102 includes a coating configured to internally reflect at least a portion of an emitted energy stimulus within an interior of at least one of the one or more fluid-flow passageways 110. In an embodiment, at least a portion of the body structure 104 includes at least one of an outer internally reflective coating or an inner internally reflective coating.

The system 100 can include, among other things, one or more reflective materials. In an embodiment, the catheter device 102 includes a reflective material. For example, in an embodiment, at least a portion of the body structure 104 includes a reflective material. Non limiting examples of reflective materials include aluminum, aluminum oxide, barium sulfate, chromium, copper, fluorine, germanium, gold, hafnium dioxide, high refractive index materials, low refractive index materials, magnesium fluoride, nickel, nickel-chromium, platinum, quartz, rhodium, sapphire, silicon dioxide, silver, tantalum pentoxide, thorium fluorides, titanium, titanium dioxide, titanium oxide, tungsten, yttrium oxide, zinc oxide, zinc sulfide, zirconium, zirconium oxide, or the like, as well as compounds, composites, and mixtures thereof.

For example, in an embodiment, at least a portion of the catheter device 102 includes one or more coatings including at least one reflective material. In an embodiment, the reflective material includes at least one of aluminum, barium sulfate, gold, silver, titanium dioxide, or zinc oxide. In an embodiment, the reflective material includes an ultraviolet energy reflective material. In an embodiment, the ultraviolet energy reflective material comprises a metallic film. In an embodiment, the ultraviolet energy reflective material comprises enhanced aluminum. In an embodiment, the ultraviolet energy reflective material comprises enhanced aluminum overcoated with at least one of magnesium fluoride, silicon dioxide, or silicon monoxide. In an embodiment, the ultraviolet energy reflective material comprises enhanced aluminum overcoated with high phosphorous nickel. In an embodiment, the ultraviolet energy reflective material comprises barium sulfate.

In an embodiment, at least a portion of the body structure 104 includes an optical material that permits the transmission of at least a portion of an emitted energy stimulus from an interior of at least one of the one or more fluid-flow passageways 110 to an exterior of at least one of the one or more fluid-flow passageways 110. In an embodiment, at least a portion of the body structure 104 includes an optical material that internally reflects at least a portion of an emitted energy stimulus present within an interior of at least one of the one or more fluid-flow passageways 110. In an embodiment, at least a portion of the body structure 104 includes an optical material that internally reflects at least a portion of an emitted energy stimulus within an interior of at least one of the one or more fluid-flow passageways 110, without substantially permitting the transmission of the emitted energy stimulus through an exterior of the body structure 104. In an embodiment, at least a portion of the body structure 104 includes an optical material that internally directs at least a portion of an emitted energy stimulus along a substantially longitudinal direction of at least one of the one or more fluid-flow passageways 110. In an embodiment, wherein at least a portion of the body structure 104 includes an optical material that internally directs at least a portion of an emitted energy stimulus along a substantially lateral direction of at least one of the one or more fluid-flow passageways 110.

In an embodiment, the catheter device 102 includes at least one outer internally reflective coating on a body structure 104 defining the one or more fluid-flow passageways 110. In an embodiment, the catheter device 102 includes at least one inner internally reflective coating on a body structure 104 defining the one or more fluid-flow passageways 110.

The system 100 can include, among other things, one or more reflective surfaces (e.g., one or more surfaces reflective to an energy stimulus, etc.). In an embodiment, the catheter device 102 includes one or more reflective surfaces. For example, in an embodiment, at least a portion of the catheter device 102 includes a reflective surface. In an embodiment, the reflective surface forms at least a portion of the body structure 104. In an embodiment, at least one of the one or more fluid-flow passageways 110 includes a surface configured to laterally internally reflect or longitudinally internally reflect electromagnetic radiation transmitted therethrough. For example, in an embodiment, at least a portion of a body structure defining the one or more fluid-flow passageways 110 includes a reflective surface capable of reflecting at least about 50 percent of an energy stimulus emitted by one or more of the energy emitters 220 that impinges on the reflective surface. In an embodiment, at least a portion of a body structure defining the one or more fluid-flow passageways 110 includes a reflective surface that is reflective at a first wavelength and transmissive at a second wavelength different from the first wavelength. In an embodiment, at least one of the one or more fluid-flow passageways 110 includes one or more internally reflective components configured to manage a delivery of light to a biological sample received within the one or more fluid-flow passageways 110, and to manage a collection of reflected light from the biological sample.

In an embodiment, the reflective surface is reflective at a first polarization and transmissive at a second polarization. In an embodiment, the reflective surface is reflective at a first power level and transmissive at a second power level. For example, in an embodiment, the reflective surface is opaque at a first power level and transmissive at a second power level. In an embodiment, the reflective surface is reflective to a first wavelength at a first power level and reflective to a second wavelength at a second power level. In an embodiment, at least a portion of the body structure 104 includes a surface that is reflective to at least one of electromagnetic energy, acoustic energy, or thermal energy.

In an embodiment, at least a portion of the body structure 104 includes an inner surface that is internally reflective to electromagnetic radiation. In an embodiment, at least a portion of the body structure 104 includes a surface that is internally reflective to ultraviolet radiation. In an embodiment, at least a portion of the body structure 104 includes a surface that is internally reflective to infrared radiation. In an embodiment, at least a portion of the body structure 104 includes a surface configured to laterally internally reflect or longitudinally internally reflect electromagnetic radiation transmitted within the one or more fluid-flow passageways 110. In an embodiment, at least a portion of the body structure 104 includes a reflective surface capable of reflecting at least about 50 percent of an energy stimulus emitted by one or more of the energy emitters 220 that impinges on the reflective surface.

In an embodiment, the system 100 includes, among other things, means for reflecting at least a portion of an emitted energy stimulus within an interior of at least one of the one or more fluid-flow passageways 110. In an embodiment, the catheter device 102 includes means for reflecting at least a portion of an emitted energy stimulus within an interior of at least one of the one or more fluid-flow passageways 110. In an embodiment, the means for reflecting at least a portion of an emitted energy stimulus includes at least one waveguide 202, one or more energy emitters 220, and one or more computing devices 230. In an embodiment, the means for reflecting at least a portion of an emitted energy stimulus includes one or more energy emitters 220 and one or more coatings including optically active materials. In an embodiment, the catheter device 102 includes means for laterally reflecting or longitudinally reflecting electromagnetic radiation transmitted within an interior of at least one of the one or more fluid-flow passageways 110. In an embodiment, means for laterally reflecting or longitudinally reflecting electromagnetic radiation includes at least one waveguide 202, one or more energy emitters 220, or one or more computing devices 230.

In an embodiment, at least a portion of a body structure 104 includes one or more actively controllable reflective or transmissive components configured to outwardly transmit or internally reflect an energy stimulus propagated through at least one of the one or more fluid-flow passageways 110. In an embodiment, a computing device 230 is operably coupled to at least one of the one or more actively controllable reflective and transmissive components. In an embodiment, a computing device 230 is configured to cause an outward-transmission or internal-reflection of an energy stimulus propagated through at least one of the one or more fluid-flow passageways 110 based on, for example, detected information from a sensor component 502.

In an embodiment, the catheter device 102 includes one or more internally reflective components. In an embodiment, the one or more internally reflective components form at least a portion of the body structure 104. In an embodiment, the one or more internally reflective components are configured to manage a delivery of interrogation energy to a sample proximate a surface of the catheter device 102, and configured to manage a collection of emitted interrogation energy or remitted interrogation energy from the sample. In an embodiment, the one or more internally reflective components are configured to manage a delivery of interrogation energy to a sample within at least one of the one or more fluid-flow passageways 110, and to manage a collection of emitted interrogation energy or remitted interrogation energy from the sample. In an embodiment, the at least a portion of the body structure 104 includes a reflective surface capable of reflecting at least about 50 percent of an energy stimulus that impinges on the reflective surface.

In an embodiment, the catheter device 102 includes one or more optical materials forming part of at least a portion of the body structure 104. For example in an embodiment, the catheter device 102 includes one or more optical materials that are configured to reflect at least a portion of an energy stimulus propagating within the body structure 104. In an embodiment, the one or more optical materials permit the transmission of at least a portion of an emitted energy stimulus from an interior of at least one of the one or more fluid-flow passageways 110 to an exterior of at least one of the one or more fluid-flow passageways 110. In an embodiment, the one or more optical materials are configured to internally reflect at least a portion of an emitted energy stimulus present within an interior of at least one of the one or more fluid-flow passageways 110.

In an embodiment, at least a portion of a body structure 104 includes an optical material that internally reflects at least a portion of an emitted energy stimulus within an interior of at least one of the one or more fluid-flow passageways 110, without substantially permitting the transmission of the emitted energy stimulus through an exterior of the body structure. For example, in an embodiment, at least a portion of a body structure 104 includes an optical material that actuates between one or more transmissive states and one or more opaque state in the presences of an applied current or voltage.

In an embodiment, the one or more optical materials are configured to limit an amount of the energy stimulus that can traverse within the one or more fluid-flow passageways 110 and through the outer surface 106 of the body structure 104. In an embodiment, the one or more optical materials are configured to internally reflect at least a portion of an emitted energy stimulus from one or more of the energy emitters 220 into an interior of at least one of the one or more fluid-flow passageways 110.

In an embodiment, at least a portion of the one or more fluid-flow passageways 110 includes an optical material that directs at least a portion of an emitted energy stimulus along a substantially longitudinal direction of at least one of the one or more fluid-flow passageways 110. In an embodiment, at least a portion of the one or more fluid-flow passageways 110 includes an optical material that directs at least a portion of an emitted energy stimulus along a substantially lateral direction of at least one of the one or more fluid-flow passageways 110.

Figure 8:
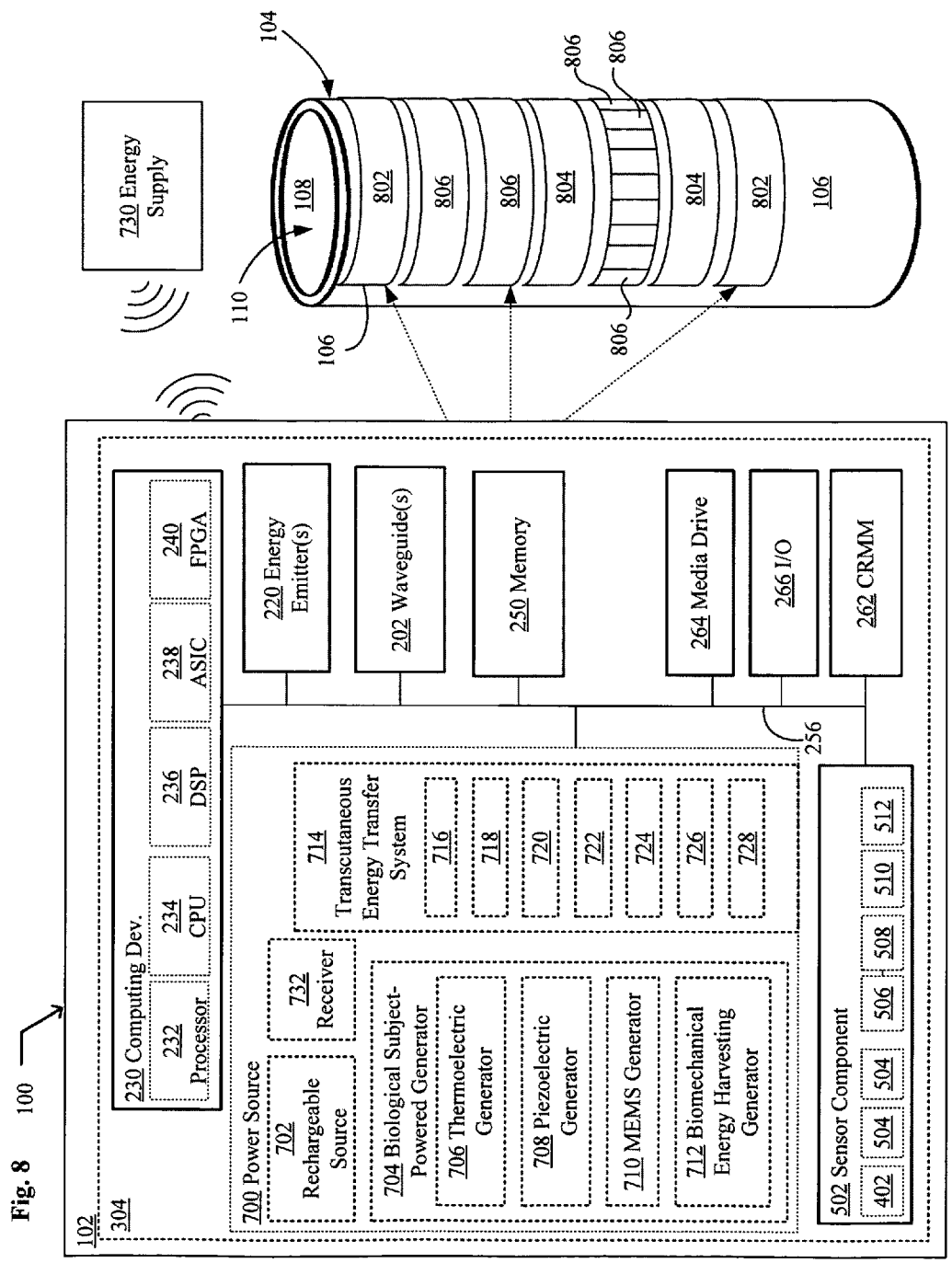
FIG. 8 is a schematic diagram of a system including a catheter device according to one embodiment.

Referring to FIG. 8, in an embodiment the system 100 includes, among other things, a plurality of independently activatable ultraviolet energy delivering substrates 802. In an embodiment, the catheter device 102 includes a plurality of independently activatable ultraviolet energy delivering substrates 802 configured to deliver a sterilizing energy stimulus to one or more regions proximate the catheter device 102. For example, in an embodiment, the plurality of independently activatable ultraviolet energy delivering substrates 802 define at least a portion of one or more surfaces of the body structure 104 and configured to deliver a sterilizing energy stimulus to one or more regions proximate the body structure 104.

In an embodiment, the plurality of independently activatable ultraviolet energy delivering substrates 802 include a radiation emitting coating. In an embodiment, the plurality of independently activatable ultraviolet energy delivering substrates 802 include one or more ultraviolet energy nanoparticles. In an embodiment, the plurality of independently activatable ultraviolet energy delivering substrates 802 include a light-emitting material. Non-limiting examples of light-emitting materials include electroluminescent materials, UV-electroluminescent materials, Near UV-electroluminescent, photoluminescent materials, or the like. Further non-limiting examples of light-emitting materials include titanium oxide phthalocyanine, p-doped zinc oxide, poly(p-phenylene vinylene)) conjugated polymers, or the like. In an embodiment, the plurality of independently activatable ultraviolet energy delivering substrates 802 include a light-emitting material configured to emit ultraviolet light energy in the presence of an energy stimulus.

In an embodiment, the plurality of independently activatable ultraviolet energy delivering substrates 802 include a light-emitting material configured to emit at least one of ultraviolet light B and ultraviolet light C energy in the presence of an energy stimulus. In an embodiment, the plurality of independently activatable ultraviolet energy delivering substrates 802 include a light-emitting material having one or more photo-absorption bands in the visible region of the electromagnetic spectrum. In an embodiment, the plurality of independently activatable ultraviolet energy delivering substrates 802 include a light-emitting material configured to emit germicidal light. In an embodiment, the plurality of independently activatable ultraviolet energy delivering substrates 802 include a light-emitting material configured to emit ultraviolet light energy in the presence of an electrical potential. In an embodiment, the plurality of independently activatable ultraviolet energy delivering substrates 802 includes one or more ultraviolet energy emitting phosphors. In an embodiment, the plurality of independently activatable ultraviolet energy delivering substrates 802 includes a trivalent phosphate configured to emit ultraviolet light C energy in the presence of an energy stimulus.

In an embodiment, the system 100 includes, among other things, a computing device 230 operably coupled to the plurality of independently activatable ultraviolet energy delivering substrates 802. In an embodiment, the computing device 230 is configured to activate one or more of the plurality of independently activatable ultraviolet energy delivering substrates 802 in response to detected microbial presence information from the sensor component 502.

In an embodiment, the system 100 includes, among other things, one or more self-cleaning surface regions 804. In an embodiment, the catheter device 102 includes one or more self-cleaning surface regions. For example, in an embodiment, the catheter device 102 includes one or more self-cleaning surface regions 804 including a self-cleaning coating composition.

In an embodiment, the one or more self-cleaning surface regions 804 include an energy-activatable self-cleaning material. In an embodiment, the one or more self-cleaning surface regions 804 include a chemically activatable self-cleaning material. In an embodiment, the one or more self-cleaning surface regions 804 include one or more of titanium dioxide, superhydrophobic materials, or carbon nanotubes with nanoscopic paraffin coatings. In an embodiment, the one or more self-cleaning surface regions 804 include one or more antimicrobial agents.

In an embodiment, the one or more self-cleaning surface regions 804 include one or more of non-fouling zwitterionic polymers, zwitterionic surface forming materials, zwitterionic polymers, poly(carboxybetaine methacrylate) (pCBMA), poly(carboxybetaine acrylic amide) (pCBAA), poly(oligo(ethylene glycol) methyl ether methacrylate) (pOEGMA), poly(N,N-dimethyl-N-(ethoxycarbonylmethyl)-N-[2'-(methacryloyloxy)ethyl]-ammonium bromide), cationic pC8NMA, switchable pCBMA-1 C2, or switchable pCBMA-2.

In an embodiment, the one or more self-cleaning surface regions 804 are configured to generate reactive-oxygen-species or a reactive-nitrogen-species when exposed to an energy stimulus. In an embodiment, the one or more self-cleaning surface regions 804 are configured to generate reactive-oxygen-species or a reactive-nitrogen-species in the presence of an applied voltage.

In an embodiment, the one or more self-cleaning surface regions 804 include a self-cleaning agent configured to hydrolyze when exposed to an energy stimulus. In an embodiment, the one or more self-cleaning surface regions 804 include a self-cleaning coating configured to degrade when exposed to an energy stimulus. In an embodiment, the one or more self-cleaning surface regions 804 include a blood-soluble material configured to degrade when exposed to blood in vivo. In an embodiment, the one or more self-cleaning surface regions 804 include one or more reflective materials or one or more self-cleaning materials. In an embodiment, the one or more self-cleaning surface regions 804 include one or more reflective coatings or one or more self-cleaning coatings. In an embodiment, the one or more self-cleaning surface regions 804 include at least one of an antimicrobial coating or a non-fouling coating. In an embodiment, the one or more self-cleaning surface regions 804 include an antimicrobial or a non-fouling coating. In an embodiment, the one or more self-cleaning surface regions 804 include a surface region that is energetically actuatable between an antimicrobial state and a non-fouling state.

In an embodiment, the system 100 includes, among other things, one or more selectively removable protective coatings 806. In an embodiment, the catheter device 102 includes one or more selectively removable protective coatings 806. For example, in an embodiment, the body structure includes a plurality of regions having one or more in vivo selectively removable protective coatings 806 defining at least a portion of one or more surfaces of the body structure 104. In an embodiment, the plurality of regions having the one or more in vivo selectively removable protective coatings 806 define a spaced-apart pattern of at least one repeating region comprising at least a first selectively removable protective coating material.

In an embodiment, the one or more in vivo selectively removable protective coatings 806 include a cell-rejecting compound. In an embodiment, the one or more in vivo selectively removable protective coatings 806 includes at least one of copper or silver. In an embodiment, the one or more in vivo selectively removable protective coatings 806 include a cell-rejecting polymer. In an embodiment, the one or more in vivo selectively removable protective coatings 806 includes at least one of poly(ethylene oxide), poly(ethylene glycol), or poly(styrene-isobutylene styrene). In an embodiment, the one or more in vivo selectively removable protective coatings 806 includes a photo-degradable material. In an embodiment, the one or more in vivo selectively removable protective coatings 806 includes a bioerodible material. In an embodiment, the one or more in vivo selectively removable protective coatings 806 includes body fluid soluble material. In an embodiment, the one or more in vivo selectively removable protective coatings 806 includes blood erodible material.

In an embodiment, the catheter device 102 includes circuitry 550 configured to determine the microorganism colonization event in one or more of the plurality of regions having the one or more in vivo selectively removable protective coatings 806. In an embodiment, the circuitry 550 configured to determine the microorganism colonization event includes biofilm marker information configured as a physical data structure. In an embodiment, the circuitry 550 configured to determine the microorganism colonization event includes one or more computing devices 230 operably coupled to one or more sensors 504 and configured to cause a removal of at least one of the one or more in vivo selectively removable protective coatings 806 one or more in vivo selectively removable protective coatings 806 based on detected information from the one or more sensors. In an embodiment, the body structure 104 is configured to transmit at least a portion of an emitted energy stimulus propagated within the body structure though one or more of the plurality of regions having had an in vivo selectively removable protective coating removed.

Referring to FIG. 9, the system 100 includes, among other things, one or more active agent assemblies 900. In an embodiment, the catheter device 102 includes at least one active agent assembly 900 including one or more reservoirs 902 (e.g., active agent reservoirs energy, sample reservoirs, biological sample reservoirs, tracer agent reservoirs, or the like, or combinations thereof).

In an embodiment, the active agent assembly 900 is configured to deliver one or more active agents from the at least one reservoir 902 to one or more regions proximate the body structure 104. For example, in an embodiment, the catheter device 102 includes one or more active agent assemblies 900 configured to deliver at least one active agent from the at least one reservoir 902 to at least one of a region 906 proximate an outer surface 106 and a region 908 proximate an inner surface 108 of the catheter device 102.

In an embodiment, the reservoir 902 includes at least one active agent composition having one or more active agents. Non-limiting examples of active agents include adjuvants, allergens, analgesics, anesthetics, antibacterial agents, antibiotics, antifungals, anti-inflammatory agents (e.g., nonsteroidal anti-inflammatory drugs), antimicrobials, antioxidants, antipyretics, anti-tumor agents, antivirals, bio-control agents, biologics or bio-therapeutics, chemotherapy agents, disinfecting agents, energy-activatable active agents, immunogens, immunological adjuvants, immunological agents, immuno-modulators, immuno-response agents, immuno-stimulators (e.g., specific immuno-stimulators, non-specific immuno-stimulators, or the like), immuno-suppressants, non-pharmaceuticals (e.g., cosmetic substances, or the like), pharmaceuticals, protease inhibitors or enzyme inhibitors, receptor agonists, receptor antagonists, therapeutic agents, tolerogens, toll-like receptor agonists, toll-like receptor antagonists, vaccines, or combinations thereof.

Further non-limiting examples of active agents include nonsteroidal anti-inflammatory drugs such as acemetacin, aclofenac, aloxiprin, amtolmetin, aproxen, aspirin, azapropazone, benorilate, benoxaprofen, benzydamine hydrochloride, benzydamine hydrochloride, bromfenal, bufexamac, butibufen, carprofen, celecoxib, choline salicylate, clonixin, desoxysulindac, diflunisal, dipyone, droxicam, etodolac, etofenamate, etoricoxib, felbinac, fenbufen, fenoprofen, fentiazac, fepradinol, floctafenine, flufenamic acid, indomethacin, indoprofen, isoxicam, ketoralac, licofelone, lomoxicam, loxoprofen, magnesium salicylate, meclofenamic acid, meclofenamic acid, mefenamic acid, meloxicam, morniflumate, niflumic acid, nimesulide, oxaprozen, phenylbutazone, piketoprofen, piroxicam, pirprofen, priazolac, propyphenazone, proquazone, rofecoxib, salalate, salicylamide, salicylic acid, sodium salicylate, sodium thiosalicylate, sulindac, suprofen, tenidap, tenoxicam, tiaprofenic acid, tolmetin, tramadol, trolamine salicylate, zomepirac, or the like.

Further non-limiting examples of active agents include energy-activatable active agents (e.g., chemical energy, electrical resistance, laser energy, terahertz energy, microwave energy, optical energy, radio frequency energy, acoustic energy, thermal energy, thermal resistance heating energy, or ultrasonic energy activatable active agents, or the like) or the like.

In an embodiment, the active agent includes at least one active agent that selectively targets bacteria. For example, in an embodiment, the active agent includes at least one bacteriophage that can, for example, selectively target bacteria. Bacteriophages generally comprise an outer protein hull enclosing genetic material. The genetic material can be, for example, ssRNA, dsRNA, ssDNA, or dsDNA. Bacteriophages are generally smaller than the bacteria they destroy generally ranging from about 20 nm to about 200 nm. Non-limiting examples of bacteriophages include T2, T4, T6, phiX-174, MS2, or the like). In an embodiment, the active agent includes at least one energy-activatable agent that selectively targets bacteria. For example, in an embodiment, the active agent includes at least one triplet excited-state photosensitizer that can, for example, selectively target bacteria.

Further non-limiting examples of active agents include triplet excited-state photosensitizers, reactive oxygen species, reactive nitrogen species, any other inorganic or organic ion or molecules that include oxygen ions, free radicals, peroxides, or the like. Further non-limiting examples of active agents include compounds, molecules, or treatments that elicit a biological response from any biological subject. Further non-limiting examples of disinfecting agents include therapeutic agents (e.g., antimicrobial therapeutic agents), pharmaceuticals (e.g., a drug, a therapeutic compound, pharmaceutical salts, or the like) non-pharmaceuticals (e.g., a cosmetic substance, or the like), neutraceuticals, antioxidants, phytochemicals, homeopathic agents, or the like. Further non-limiting examples of disinfecting agents include peroxidases (e.g., haloperoxidases such as chloroperoxidase, or the like), oxidoreductase (e.g., myeloperoxidase, eosinophil peroxidase, lactoperoxidase, or the like) oxidases, or the like.

Further non-limiting examples of active agents include one or more pore-forming toxins. Non limiting examples of pore-forming toxins include beta-pore-forming toxins, e.g., hemolysin, Panton-Valentine leukocidin S, aerolysin, Clostridial epsilon-toxin; binary toxins, e.g., anthrax, *C. perfringens* Iota toxin, *C. difficile* cytolethal toxins; cholesterol-dependent cytolysins; pneumolysin; small pore-forming toxins; and gramicidin A.

Further non-limiting examples of active agents include one or more pore-forming antimicrobial peptides. Antimicrobial peptides represent an abundant and diverse group of molecules that are naturally produced by many tissues and cell types in a variety of invertebrate, plant and animal species. The amino acid composition, amphipathicity, cationic charge and size of antimicrobial peptides allow them to attach to and insert into microbial membrane bilayers to form pores leading to cellular disruption and death. More than 800 different antimicrobial peptides have been identified or predicted from nucleic acid sequences, a subset of which are available in a public database (see, e.g., Wang & Wang, *Nucleic Acids Res.* 32:D590-D592, 2004); http://aps.unmc.edu/AP/main.php, which is incorporated herein by reference).

More specific examples of antimicrobial peptides include, among others, anionic peptides, e.g., maximin H5 from amphibians, small anionic peptides rich in glutamic and aspartic acids from sheep, cattle and humans, and dermcidin from humans; linear cationic alpha-helical peptides, e.g., cecropins (A), andropin, moricin, ceratotoxin, and melittin from insects, cecropin P1 from *Ascaris* nematodes, magainin 2, dermaseptin, bombinin, brevinin-1, esculentins and buforin II from amphibians, pleurocidin from skin mucous secretions of the winter flounder, seminalplasmin, BMAP, SMAP (SMAP29, ovispirin), PMAP from cattle, sheep and pigs, CAP18 from rabbits and LL37 from humans; cationic peptides enriched for specific amino acids, e.g., praline-containing peptides including abaecin from honeybees, praline- and arginine-containing peptides including apidaecins from honeybees, drosocin from *Drosophila*, pyrrhocoricin from European sap-sucking bug, bactenicins from cattle (Bac7), sheep and goats and PR-39 from pigs, praline- and phenylalanine-containing peptides including prophenin from pigs, glycine-containing peptides including hymenoptaecin from honeybees, glycine- and praline-containing peptides including coleoptericin and holotricin from beetles, tryptophan-containing peptides including indolicidin from cattle, and small histidine-rich salivary polypeptides, including histatins from humans and higher primates; anionic and cationic peptides that contain cysteine and from disulfide bonds, e.g., peptides with one disulphide bond including brevinins, peptides with two disulfide bonds including alpha-defensins from humans (HNP-1, HNP-2, cryptidins), rabbits (NP-1) and rats, beta-defensins from humans (HBD1, DEFB118), cattle, mice, rats, pigs, goats and poultry, and rhesus theta-defensin (RTD-1) from rhesus monkey, insect defensins (defensin A); and anionic and cationic peptide fragments of larger proteins, e.g., lactoferricin from lactoferrin, casocidin 1 from human casein, and antimicrobial domains from bovine alpha-lactalbumin, human hemoglobin, lysozyme, and ovalbumin (see, e.g., Brogden, *Nat. Rev. Microbiol.* 3:238-250, 2005, which is incorporated herein by reference).

Further non-limiting examples of active agents include antibacterial drugs. Non-limiting examples of antibacterial drugs include beta-lactam compounds such as penicillin, methicillin, nafcillin, oxacillin, cloxacillin, dicloxacillin, ampicillin, ticarcillin, amoxicillin, carbenicillin, and piperacillin; cephalosporins and cephamycins such as cefadroxil, cefazolin, cephalexin, cephalothin, cephapirin, cephradine, cefaclor, cefamandole, cefonicid, cefuroxime, cefprozil, loracarbef, ceforanide, cefoxitin, cefmetazole, cefotetan, cefoperazone, cefotaxime, ceftazidine, ceftizoxine, ceftriaxone, cefixime, cefpodoxime, proxetil, cefdinir, cefditoren, pivoxil, ceftibuten, moxalactam, and cefepime; other beta-lactam drugs such as aztreonam, clavulanic acid, sulbactam, tazobactam, ertapenem, imipenem, and meropenem; other cell wall membrane active agents such as vancomycin, teicoplanin, daptomycin, fosfomycin, bacitracin, and cycloserine; tetracyclines such as tetracycline, chlortetracycline, oxytetracycline, demeclocycline, methacycline, doxycycline, minocycline, and tigecycline; macrolides such as erythromycin, clarithromycin, azithromycin, and telithromycin; aminoglycosides such as streptomycin, neomycin, kanamycin, amikacin, gentamicin, tobramycin, sisomicin, and netilmicin; sulfonamides such as sulfacytine, sulfisoxazole, silfamethizole, sulfadiazine, sulfamethoxazole, sulfapyridine, and sulfadoxine; fluoroquinolones such as ciprofloxacin, gatifloxacin, gemifloxacin, levofloxacin, lomefloxacin, moxifloxacin, norfloxacin, and ofloxacin; antimycobacteria drugs such as isoniazid, rifampin, rifabutin, rifapentine, pyrazinamide, ethambutol, ethionamide, capreomycin, clofazimine, and dapsone; and miscellaneous antimicrobials such as colistimethate sodium, methenamine hippurate, methenamine mandelate, metronidazole, mupirocin, nitrofurantoin, polymyxin B, clindamycin, choramphenicol, quinupristin-dalfopristin, linezolid, spectrinomycin, trimethoprim, pyrimethamine, and trimethoprim-sulfamethoxazole.

Further non-limiting examples of active agents include antifungal agents. Non-limiting examples of antifungal agents include anidulafungin, amphotericin B, butaconazole, butenafine, caspofungin, clotrimazole, econazole, fluconazole, flucytosine griseofulvin, itraconazole, ketoconazole, miconazole, micafungin, naftifine, natamycin, nystatin, oxiconazole, sulconazole, terbinafine, terconazole, tioconazole, tolnaftate, and/or voriconazole.

Further non-limiting examples of active agents include anti-parasite agents. Non-limiting examples of anti-parasite agents include antimalaria drugs such as chloroquine, amodiaquine, quinine, quinidine, mefloquine, primaquine, sulfadoxine-pyrimethamine, atovaquone-proguanil, chlorproguanil-dapsone, proguanil, doxycycline, halofantrine, lumefantrine, and artemisinins; treatments for amebiasis such as metronidazole, iodoquinol, paromomycin, diloxanide furoate, pentamidine, sodium stibogluconate, emetine, and dehydroemetine; and other anti-parasite agents such as pentamidine, nitazoxanide, suramin, melarsoprol, eflornithine, nifurtimox, clindamycin, albendazole, and tinidazole. Further non-limiting examples of active agents include ionic silver, (SilvaSorb®, Medline Industries, Inc), anti-microbial silver compositions (Arglaes®, Medline Industries, Inc), or the like. Further non-limiting examples of active agents include superoxide-forming compositions. Further non-limiting examples of active agents include oxazolidinones, gram-positive antibacterial agents, or the like. See, e.g., U.S. Pat. No. 7,322,965 (issued Jan. 29, 2008), which is incorporated herein by reference.

In an embodiment, the active agent includes one or more antimicrobial agents. In an embodiment, the antimicrobial agent is an antimicrobial peptide. Amino acid sequence information for a subset of these can be found as part of a public database (see, e.g., Wang & Wang, *Nucleic Acids Res.* 32:D590-D592, 2004); http://aps.unmc.edu/AP/main.php, which is incorporated herein by reference). Alternatively, a phage library of random peptides can be used to screen for peptides with antimicrobial properties against live bacteria, fungi and/or parasites. The DNA sequence corresponding to an antimicrobial peptide can be generated ex vivo using standard recombinant DNA and protein purification techniques.

In an embodiment, one or more of the active agent include chemicals suitable to disrupt or destroy cell membranes. For example, some oxidizing chemicals can withdraw electrons from a cell membrane causing it to, for example, become destabilized. Destroying the integrity of cell membranes of, for example, a pathogen can lead to cell death.

In an embodiment, the catheter device 102 includes one or more active agent assemblies 900 configured to deliver at least one active agent from the at least one reservoir 902 to at least one of a region proximate an outer and an inner surface of the catheter device 102. In an embodiment, at least one of the one or more active agent assemblies 900 is configured to deliver one or more active agents in a spatially patterned distribution. In an embodiment, at least one of the one or more active agent assemblies 900 is configured to deliver one or more active agents in a temporally patterned distribution. In an embodiment, the catheter device 102 includes a plurality of spaced-apart-release-ports 910 adapted to deliver one or more active agents in a spatially patterned distribution. In an embodiment, the catheter device 102 includes a plurality of spaced apart controllable-release ports 910 adapted to deliver one or more active agents in a spatially patterned distribution.

In an embodiment, the catheter device 102 includes at least one computing device 230 operably coupled to one or more of the plurality of spaced-apart-release-ports 910 and configured to actuate one or more of the plurality of spaced-apart-release-ports between an active agent discharge state and an active agent retention state. In an embodiment, a computing device 230 is operable to actuate one or more of the plurality of spaced-apart-release-ports 910 between an active agent discharge state and an active agent retention state based on a comparison of a detected characteristic to stored reference data.

In an embodiment, the computing device 230 is operably coupled to the active agent assembly and configured to actively control one or more of the plurality of spaced-apart-release-ports 910. In an embodiment, at least one computing device 230 is operably coupled to one or more of the spaced-apart controllable-release ports 910 and configured to control at least one of a port release rate, a port release amount, and a port release pattern associated with a delivery of the one or more active agents. In an embodiment, at least one processor 232 is operably coupled to the active agent assembly 900 and configured to control at least one of a port release rate, a port release amount, or a port release pattern associated with the delivery of the one or more active agents from the at least one reservoir 902 to an interior of at least one of the one or more fluid-flow passageways 110.

In an embodiment, a computing device 230 is operably coupled to the active agent assembly 900 and configured to control at least one of an active agent delivery rate, an active agent delivery amount, an active agent delivery composition, a port release rate, a port release amount, or a port release pattern.

In an embodiment, at least one computing device 230 is operably coupled to one or more of the plurality of spaced-apart-release-ports 910 and configured to actuate one or more of the plurality of spaced-apart-release-ports 910 between an active agent discharge state and an active agent retention state. In an embodiment, the catheter device 102 includes one or more active agent assemblies 900 including one or more reservoirs 902 configured to deliver at least one active agent from the at least one reservoir 902 to at least one of a region 904 proximate an outer surface 108 or a region 906 proximate an inner surface 110 of the catheter device 102.

In an embodiment, the catheter device 102 includes one or more active agent assemblies 900 configured to deliver one or more disinfecting agents. In an embodiment, the catheter device 102 includes one or more active agent assemblies 900 configured to deliver at least one energy-activatable agent from at least one reservoir 902 to, for example, an interior of one or more fluid-flow passageways 110. Non-limiting examples of energy-activatable active agents include radiation absorbers, light energy absorbers, X-ray absorbers, photoactive agents, or the like. Non-limiting examples of photoactive agents include, but are not limited to photoactive antimicrobial agents (e.g., eudistomin, photoactive porphyrins, photoactive $TiO_2$, antibiotics, silver ions, antibodies, nitric oxide, or the like), photoactive antibacterial agents, photoactive antifungal agents, or the like. Further non-limiting examples of energy-activatable agent includes energy-activatable disinfecting agents, photoactive agents, or a metabolic precursor thereof. In an embodiment, the at least one energy-activatable agent includes at least one X-ray absorber. In an embodiment, the at least one energy-activatable agent includes at least one radiation absorber.

In an embodiment, the active agent assembly 900 is configured to deliver at least one energy-activatable disinfecting agent from at least one reservoir 902 to a biological sample proximate the catheter device 102. In an embodiment, the catheter device 102 includes one or more active agent assemblies 900 configured to deliver at least one energy-activatable disinfecting agent from the at least one reservoir 902 to tissue proximate at least one surface of the catheter device 102. In an embodiment, at least one of the one or more active agent assemblies 900 is configured to deliver at least one energy-activatable disinfecting agent in a spatially patterned distribution. In an embodiment, the active agent assembly 900 is configured to deliver at least one energy-activatable steroid to tissue proximate the at least one outer surface 108 of the catheter device 102.

In an embodiment, the at least one reservoir 902 includes, among other things, an acceptable carrier. In an embodiment, at least one active agent is carried by, encapsulated in, or forms part of, an energy-sensitive (e.g., energy-activatable), carrier, vehicle, vesicle, pharmaceutical vehicle, pharmaceutical carrier, pharmaceutically acceptable vehicle, pharmaceutically acceptable carrier, or the like.

Non-limiting examples of carriers include any matrix that allows for transport of, for example, a disinfecting agent across any tissue, cell membranes, or the like of a biological subject, or that is suitable for use in contacting a biological subject, or that allows for controlled release formulations of the compositions disclosed herein. Further non-limiting examples of carriers include at least one of creams, liquids, lotions, emulsions, diluents, fluid ointment bases, gels, organic and inorganic solvents, degradable or non-degradable polymers, pastes, salves, vesicle, or the like. Further non-limiting examples of carriers include cyclic oligosaccharides, ethasomes, hydrogels, liposomes, micelle, microspheres, liposhperes, niosomes, non-ionic surfactant vesicles, organogels, phospholipid surfactant vesicles, transfersomes, and virosomes. Further non-limiting examples of energy-sensitive carriers or the like include electrical energy-sensitive, light sensitive, pH-sensitive, ion-sensitive, acoustic energy sensitive, and ultrasonic energy sensitive carriers. Further non-limiting examples of carriers can be found in, for example, Timko et al., *Remotely Triggerable Drug Delivery Systems*. Advanced Materials, n/a. doi: 10.1002/adma.201002072 (2010); Tsutsui et al., *The Use of Microbubbles to Target Drug Delivery*, Cardiovascular Ultrasound, 2:23 doi: 10.1186/1476-7120-2-23 (2004); each of which is incorporated herein by reference.

In an embodiment, one or more active agents are carried by energy-sensitive vesicles (e.g., energy-sensitive cyclic oligosaccharides, ethasomes, hydrogels, liposomes, micelles, microspheres, niosomes, lipospheres, non-ionic surfactant vesicles, organogels, phospholipid surfactant vesicles, transfersomes, virosomes, or the like). In an embodiment, at least one of the one or more energy emitters 220 is configured to provide energy of a dose sufficient to liberate at least a portion of an active agent carried by the energy-sensitive vesicles.

In an embodiment, one or more active agents are conjugated to or encapsulated in one or more remotely triggerable delivery systems configured for release from the catheter device 102. In an embodiment, the triggerable delivery system is designed for single release or for repeated release of one or more active agents. In an embodiment, the triggered delivery system releases one or more active agents in response to temperature, electromagnetic radiation (e.g., UV, visible or near infrared radiation, radiofrequency, microwave, or the like), a magnetic field, ultrasound, or the like. For example, in an embodiment, application of electromagnetic radiation, a magnetic field, ultrasound, or the like can induce a thermal change sufficient for release of one or more active agents from a temperature-sensitive triggerable delivery system.

In an embodiment, the triggerable delivery system includes, among other things, liposomes, polymer vesicles, polymeric liposomes, polyelectrolyte microcontainers, multilayered capsules, micelles, dendrimers, microbubbles, or the like. In an embodiment, polymers are cross-linked with photolabile groups, allowing active agents to be released in response to light. An example of a photocleavable molecule includes among other things 2-nitrobenzyl ester. In an embodiment, one or more active agents are released from the delivery system by the reversible isomerization of molecules upon irradiation with near-UV or visible light. UV irradiation, for example, can induce phase transitions of natural and synthetic polymers, accompanied by reversible volume changes, allowing active agents to be released as the polymers shrink or swell. For example, azobenzenes which contain two phenyl groups and undergo conformational changes in response to UV light can be used as part of a molecular valve to control release of one or more active agents through a channel protein incorporated into liposomes.

In an embodiment, polymers are combined with magnetic oxide nanoparticles to form ferrogel materials which deform in response to a magnetic field, allowing for triggerable release of one or more active agents. In an embodiment, ferrogel materials include, among other things, ferrite particles cross-linked to or embedded in poly(vinyl alcohol), polyNIPAm, or gelatin. In the case of microbubbles, in an embodiment, ultrasound is used to trigger release of a gas from a stabilizing shell of lipid or polymer or, under conditions of low frequency, ultrasound can induce cavitation of microbubbles and disruption of nearby cell membranes sufficient to allow passage into the cells of co-administered active agents.

In an embodiment, the triggerable delivery system includes, among other things, metallic nanostructures, and particularly gold nanostructures. In an embodiment, under optical irradiation, electrons associated with metallic nanostructures oscillate in phase, a phenomenon referred to as surface plasmon resonance. In their excited state, the electrons subsequently decay through either radiative (fluorescence), nonradiative (lattice rearrangement), or photothermal (local heating) pathways. The specific decay pathway is dependent on the geometry of the nanoparticles and the nature of the excitation pulse. In an embodiment, lattice rearrangement and local heating induced in this manner can be used to trigger delivery of active agents. As a non-limiting example, gold nanorods can be melted into nanospheres using ultrafast laser pulses, effectively triggering release of surface-bound active agent as the gold lattice atoms rearrange. Heterogeneous mixtures of rods or rodlike structures with distinct geometries and resonant frequencies enable selective release of multiple ligands. For example, gold nanocapsules and gold nanorods exhibit SPR longitudinal modes at 800 nm and 1100 nm, respectively. Pulsed laser irradiation centered at either of these two resonant frequencies yields selective melting of the corresponding nanoparticles and selective release of associated active agents. Weakly bound ligands can also be released by localized heating below the nanoparticle melting threshold. Gold nanoparticles can also be configured into nanoshells (i.e., hollow or enclosed solid cores) or nanocages (i.e., hollow interior and porous walls).

In an embodiment, the triggerable delivery system includes a combination of liposomes or polymers and gold nanoparticles. In an embodiment, gold nanoparticle are combined with temperature-sensitive polymers for triggered release with near infrared radiation. In an embodiment, one or more active agents can be incorporated into gold cages covered with monolayers of heat labile polymer chains, formed by polymerizing polymers, e.g., n-isopropylacrylamine (NIPAm) and acrylamide (Am) precursors, with a disulfide initiator, the poly(NIPAm-co-Am) chains attached to the surface of the gold cages by Au—S linkages, forming a hydrophobic layer with lower critical solution temperatures tunable between about 32° C. to about 50° C. In another non-limiting example, one or more active agents can be co-encapsulated in liposomes in the presence of gold nanoparticles, the latter of which, in the presence of near infrared radiation, generate heat sufficient to disrupt the liposomes.

In an embodiment, triggerable membranes can be used as walls of reservoirs, allowing a large quantity of active agent to be contained and repeatedly released over time. For example, nanocomposite membranes consisting of a thermosensitive material, e.g., polyNIPAm-based nanogels and magnetic particles embedded in an ethylcellulose matrix, can be designed to achieve on-demand drug delivery upon application of an AC magnetic field. Alternatively, one or more active agents can be released from magnetically actuated microchips configured with an array of wells and a biodegradable covering such as, for example, poly-(D,L-lactic acid). In an embodiment, an active agent can be electrodeposited onto a thin film in the presence of magnetic oxide, e.g., $Fe_3O_4/SiO_2$, and released in response to a magnetic field. For further examples of triggerable delivery systems, see e.g., Timko et al., *Remotely Triggerable Drug Delivery Systems*. Advanced Materials, n/a. doi: 10.1002/adma.201002072 (2010); Tsutsui et al., *The Use of Microbubbles to Target Drug Delivery*, Cardiovascular Ultrasound, 2:23doi:10.1186/1476-7120-2-23 (2004); each of which is incorporated herein by reference.

In an embodiment, the catheter device 102 includes one or more biological sample reservoirs. In an embodiment, the catheter device 102 includes one or more biological specimen reservoirs. In an embodiment, the catheter device 102 includes one or more biological sample reservoirs. In an embodiment, the catheter device 102 includes one or more active agent assemblies 900 configured to receive one or more biological samples. In an embodiment, the biological sample reservoir is placed under the scalp of a user. In an embodiment, the biological sample reservoir is configured to allow for the removal of biological sample with a syringe. In an embodiment, the reservoir 902 includes a sensor component 502 configured to detect, for example, bacteria, cancer cells, blood, or proteins of a fluid sample received within. In an embodiment, the reservoir 902 is configured to allow the injection or introduction of antibiotics for cerebrospinal fluid infection or chemotherapy medication. In an embodiment, the reservoir 902 includes circuitry configured to detect at least one physical quantity, environmental attribute, or physiologic characteristic associated with, for example, a shunting process.

In an embodiment, the catheter device 102 includes one or more active agent assemblies 900 configured to deliver at least one tracer agent from at least one reservoir 902. In an embodiment, the catheter device 102 includes one or more active agent assemblies 900 including one or more tracer agent reservoirs configured to deliver at least one tracer agent. In an embodiment, the one or more active agent assemblies 900 are configured to deliver one or more tracer agents. Non-limiting examples of tracer agents include one or more in vivo clearance agents, magnetic resonance imaging agents, contrast agents, dye-peptide compositions, fluorescent dyes, or tissue specific imaging agents. In an embodiment, the one or more tracer agents include at least one fluorescent dye. In an embodiment, the one or more tracer agents include indocyanine green.

In an embodiment, active agent assembly 900 is further configured to concurrently or sequentially deliver one or more tracer agents and one or more energy-activatable disinfecting agents. In an embodiment, the active agent assembly 900 is further configured to deliver one or more tracer agents for indicating the presence or concentration of one or more energy-activatable disinfecting agents in at least a region proximate the catheter device 102. In an embodiment, the active agent assembly 900 is further configured to deliver one or more tracer agents for indicating the response of the one or more energy-activatable disinfecting agents to energy emitted from the one or more energy-emitting emitters 220.

In an embodiment, at least one of the one or more fluid-flow passageways 110 includes a photoactive agent. In an embodiment, at least one of the one or more fluid-flow passageways 110 includes a photoactive coating material. In an embodiment, at least one of the one or more fluid-flow passageways 110 includes a light-emitting material configured to emit ultraviolet light energy in the presence of an energy stimulus. In an embodiment, at least one of the one or more fluid-flow passageways 110 includes a light-emitting material configured to emit ultraviolet light energy in the presence of an electrical potential. In an embodiment, at least one of the one or more fluid-flow passageways 110 includes a photoactive agent having one or more photoabsorption bands in the visible region of the electromagnetic spectrum.

In an embodiment, the catheter device 102 includes one or more active agent assemblies 900 configured to deliver one or more ultraviolet energy absorbing agents from at least one reservoir 902 to one or more regions proximate the surface of the catheter device 102. In an embodiment, the catheter device 102 includes one or more energy waveguides 202 configured to guide an emitted ultraviolet energy stimulus to one or more regions proximate the surface of the catheter device 102.

In an embodiment, the reservoir 902 includes at least one ultraviolet energy absorbing agent having an absorption spectra in a germicidal light range. In an embodiment, the reservoir 902 includes at least one ultraviolet energy absorbing agent having an absorption spectra of about 100 nanometers to about 400 nanometers. In an embodiment, the one reservoir 902 includes at least one ultraviolet energy absorbing agent having an absorption spectra of about 100 nanometers to about 290 nanometers. In an embodiment, the reservoir 902 includes at least one ultraviolet energy absorbing agent having an absorption spectra of about 200 nanometers to about 290 nanometers. In an embodiment, the reservoir 902 includes at least one ultraviolet energy absorbing agent having an absorption spectra of about 280 nanometers to about 320 nanometers.

In an embodiment, the reservoir 902 includes at least one ultraviolet absorbing compound. In an embodiment, the reservoir 902 includes at least one of a nucleotide composition, a nucleoside composition, and a peptide nucleic acid composition. In an embodiment, the reservoir 902 includes a synthetic nucleic acid composition. In an embodiment, the one reservoir 902 includes a composition including at least one of an ultraviolet-A absorbing agent, an ultraviolet-B absorbing agent, and an ultraviolet-C absorbing agent. In an embodiment, the reservoir 902 includes a composition including at least one of sulisobenzone or thioctic acid. In an embodiment, the reservoir 902 includes a composition including at least one of 2-phenylbenzimidazole-5-sulfonic acid, cinnamic acid, ferrulic acid, salicylic acid, or methoxycinnamic acid.

Figure 10B:
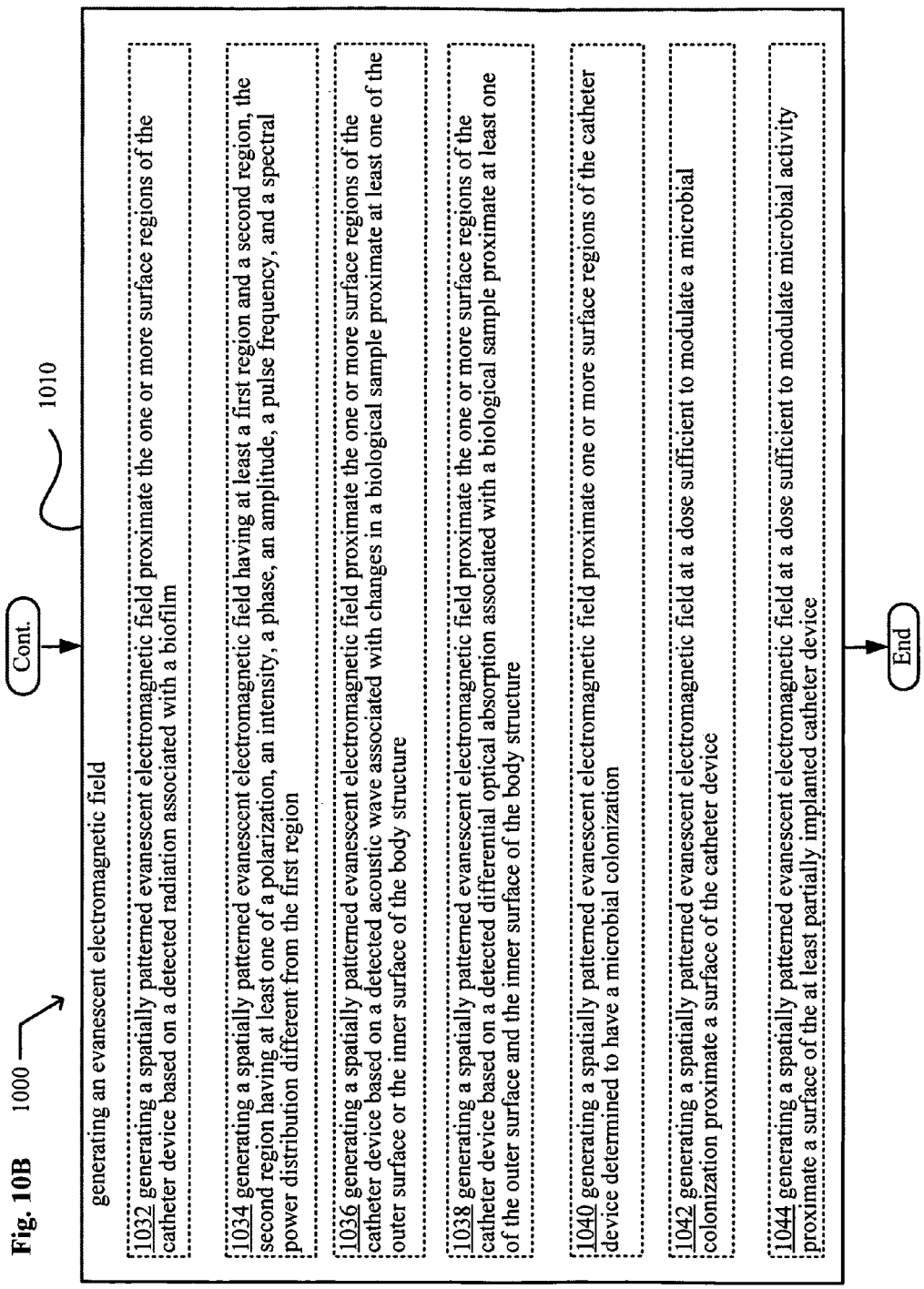
FIG. 10B is a flow diagram of a method according to one embodiment.

FIGS. 10A and 10B show an example of a method 1000 of inhibiting a microbial colonization of an implanted or at least partially implanted catheter device 102. At 1010, the method 1000 includes generating an evanescent electromagnetic field proximate one or more regions of at least one of an outer surface 106 or an inner surface 108 of a body structure 104 defining at least one fluid-flow passageway of the at least partially implanted catheter device 102 based on an automatically detected spectral parameter associated with a region proximate the at least one of the outer surface 106 or the inner surface 108 of the body structure 104 defining the at least one fluid-flow passageway 110.

At 1012, generating the evanescent electromagnetic field includes generating a spatially patterned evanescent electromagnetic field. At 1014, generating the evanescent electromagnetic field includes generating a spatially patterned evanescent electromagnetic field having at least a first region and a second region, the second region having at least one of a polarization, an intensity, a phase, an amplitude, a pulse frequency, or a spectral power distribution different from the first region. At 1016, generating the evanescent electromagnetic field includes generating a temporally patterned evanescent electromagnetic field. At 1018, generating the evanescent electromagnetic field includes generating a temporally patterned evanescent electromagnetic field having at least a first-in-time pattern and a second-in-time pattern, the second-in-time pattern having at least one of a polarization, an intensity, an amplitude, a phase, a wave vector (k), a pulse frequency, or a spectral power distribution different from the first-in-time pattern.

At 1020, generating the evanescent electromagnetic field includes generating a spatially patterned evanescent electromagnetic field proximate the one or more surface regions of the catheter device 102 based on a detected fluorescence. At 1022, generating the evanescent electromagnetic field includes generating an interference pattern via two or more evanescent electromagnetic fields proximate the one or more surface regions of the catheter device 102 based on a detected fluorescence. At 1024, generating the evanescent electromagnetic field includes generating a spatially patterned evanescent electromagnetic field proximate the one or more surface regions of the catheter device 102 based on a detected impedance. At 1026, generating the evanescent electromagnetic field includes generating a spatially patterned evanescent electromagnetic field proximate the one or more surface regions of the catheter device 102 based on a detected optical reflectance. At 1028, generating the evanescent electromagnetic field includes generating a spatially patterned evanescent electromagnetic field proximate the one or more surface regions of the catheter device 102 based on a detected heat transfer.

At 1030, generating the evanescent electromagnetic field includes generating a spatially patterned evanescent electromagnetic field proximate the one or more surface regions of the catheter device 102 based on a detected metabolic product associated with a biofilm. At 1032, generating the evanescent electromagnetic field includes generating a spatially patterned evanescent electromagnetic field proximate the one or more surface regions of the catheter device 102 based on a detected radiation associated with a biofilm. At 1034, generating the evanescent electromagnetic field includes generating a spatially patterned evanescent electromagnetic field proximate the one or more surface regions of the catheter device 102 in response to a change to a refractive index property of a plasmon supporting surface region. At 1036, generating the evanescent electromagnetic field includes generating a spatially patterned evanescent electromagnetic field proximate the one or more surface regions of the catheter device 102 based on a detected acoustic wave associated with changes in a biological sample proximate at least one of the outer surface 106 or the inner surface 108 of the body structure 104. At 1038, generating the evanescent electromagnetic field includes generating a spatially patterned evanescent electromagnetic field proximate the one or more surface regions of the catheter device 102 based on a detected differential optical absorption associated with a biological sample proximate at least one of the outer surface 106 or the inner surface 108 of the body structure 104.

At 1040, generating the evanescent electromagnetic field includes generating a spatially patterned evanescent electromagnetic field proximate one or more surface regions of the catheter device 102 determined to have a microbial colonization. At 1042, generating the evanescent electromagnetic field includes generating a spatially patterned evanescent electromagnetic field at a dose sufficient to modulate a microbial colonization proximate a surface of the catheter device 102. At 1044, generating the evanescent electromagnetic field includes generating a spatially patterned evanescent electromagnetic field at a dose sufficient to modulate microbial activity proximate a surface of the at least partially implanted catheter device 102.

Figure 11:
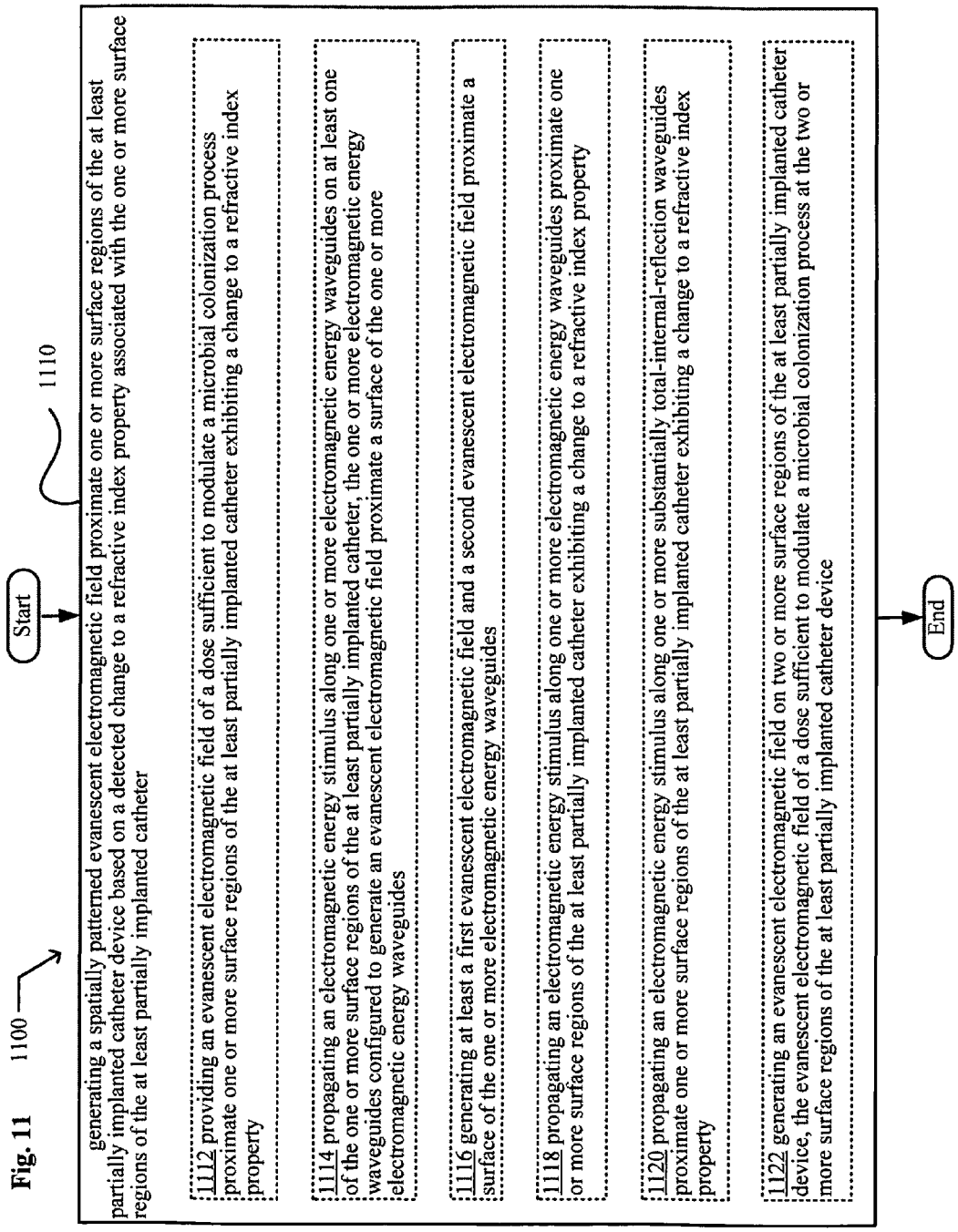
FIG. 11 is a flow diagram of a method according to one embodiment.

FIG. 11 shows an example of a method 1100 of modulating microbial activity proximate a surface of an at least partially implanted catheter device 102.

At 1110, the method 1100 includes generating a spatially patterned evanescent electromagnetic field proximate one or more surface regions of the at least partially implanted catheter device 102 based on a detected change to a refractive index property associated with the one or more surface regions of the at least partially implanted catheter. At 1112, generating the spatially patterned evanescent electromagnetic field includes providing an evanescent electromagnetic field of a dose sufficient to modulate a microbial colonization process proximate one or more surface regions of the at least partially implanted catheter exhibiting a change to a refractive index property. At 1114, generating the spatially patterned evanescent electromagnetic field includes propagating an electromagnetic energy stimulus along one or more electromagnetic energy waveguides 202 on at least one of the one or more surface regions of the at least partially implanted catheter, the one or more electromagnetic energy waveguides 202 configured to generate an evanescent electromagnetic field proximate a surface of the one or more electromagnetic energy waveguides 202.

At 1116, generating the spatially patterned evanescent electromagnetic field includes generating at least a first evanescent electromagnetic field and a second evanescent electromagnetic field proximate a surface of the one or more electromagnetic energy waveguides 202. In an embodiment, the second evanescent electromagnetic field includes at least one of a polarization, an intensity, an amplitude, a phase, a wave vector (k), a pulse frequency, or a spectral power distribution different from the first evanescent electromagnetic field.

At 1118, generating the spatially patterned evanescent electromagnetic field includes propagating an electromagnetic energy stimulus along one or more electromagnetic energy waveguides 202 proximate one or more surface regions of the at least partially implanted catheter exhibiting a change to a refractive index property. At 1120, generating the spatially patterned evanescent electromagnetic field includes propagating an electromagnetic energy stimulus along one or more substantially total-internal-reflection waveguides proximate one or more surface regions of the at least partially implanted catheter exhibiting a change to a refractive index property. At 1122, generating the spatially patterned evanescent electromagnetic field includes generating an evanescent electromagnetic field on two or more surface regions of the at least partially implanted catheter device 102, the evanescent electromagnetic field of a dose sufficient to modulate a microbial colonization process at the two or more surface regions of the at least partially implanted catheter device 102.

Figure 12B:
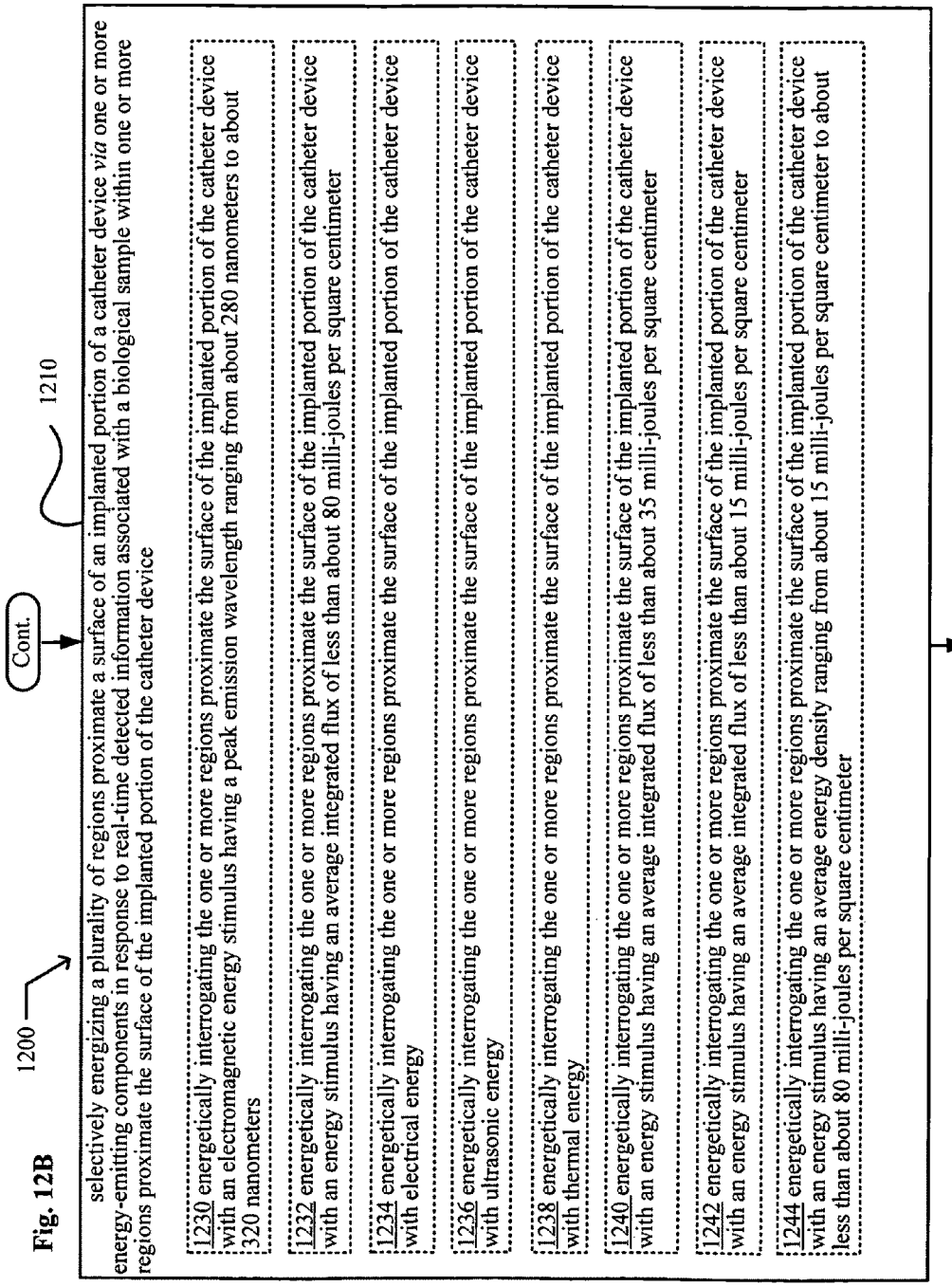
Figure 12C:
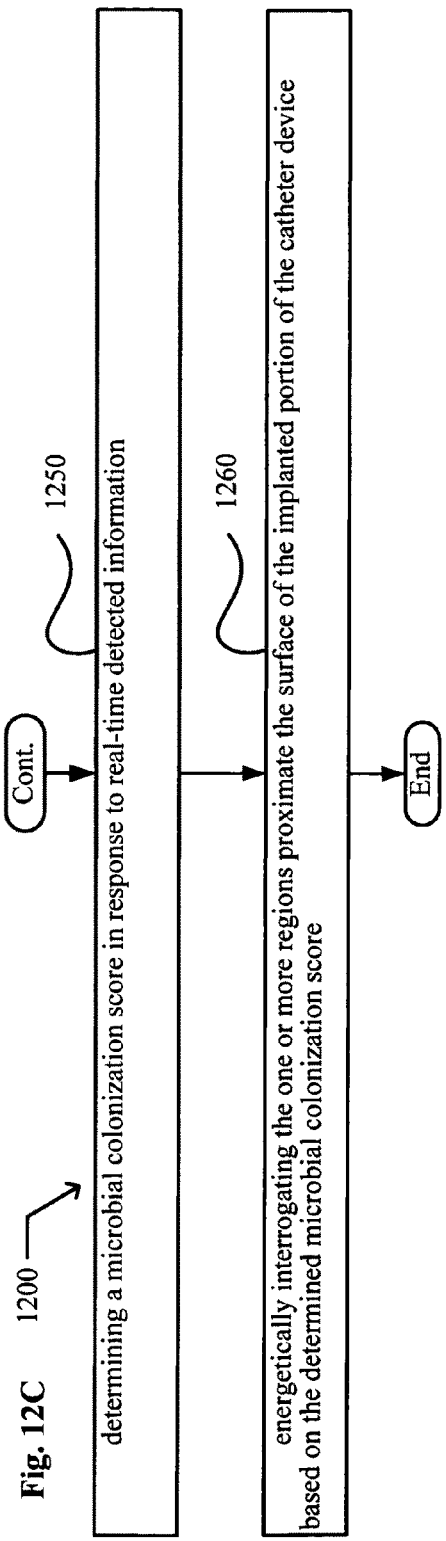

FIG. 12 shows an example of a method 1200. At 1210, the method 1200 includes selectively energizing a plurality of regions proximate a surface of an implanted portion of a catheter device 102 via one or more energy-emitting components including one or more energy emitters 220 and at least one computing device 230 in response to real-time detected information associated with a biological sample within one or more regions proximate the surface of the implanted portion of the catheter device 102. Non-limiting examples of energy-emitting components include electric circuits, electrical conductors, electrodes (e.g., nano- and micro-electrodes, patterned-electrodes, electrode arrays (e.g., multi-electrode arrays, micro-fabricated multi-electrode arrays, patterned-electrode arrays, or the like), electrocautery electrodes, or the like), cavity resonators, conducting traces, ceramic patterned electrodes, electro-mechanical components, lasers, quantum dots, laser diodes, light-emitting diodes (e.g., organic light-emitting diodes, polymer light-emitting diodes, polymer phosphorescent light-emitting diodes, microcavity light-emitting diodes, high-efficiency UV light-emitting diodes, or the like), arc flashlamps, incandescent emitters, transducers, heat sources, continuous wave bulbs, a quantum dot, ultrasound emitting elements, ultrasonic transducers, thermal energy emitting elements, or the like.

At 1212, selectively energizing the plurality of regions includes energetically interrogating those regions determined to have a microbial colonization based on the real-time detected information. At 1214, selectively energizing the plurality of regions includes energetically interrogating those regions determined to have a microbial colonization with a temporally patterned sterilizing-energy stimulus. At 1216, selectively energizing the plurality of regions includes energetically interrogating those regions determined to have a microbial colonization with a spatially patterned sterilizing-energy stimulus.

At 1218, selectively energizing the plurality of regions includes energetically interrogating those regions determined to have a microbial colonization based on the real-time detected change to a refractive index property. At 1220, selectively energizing the plurality of regions includes energetically interrogating one or more regions proximate at least one of an inner surface or an outer surface of the implanted portion of a catheter determined to have a microbial colonization based on the real-time detected information. At 1222, selectively energizing the plurality of regions includes directing an emitted energy stimulus via one or more selectively actuatable energy waveguides 202a to one or more regions determined to have a microbial colonization. At 1224, selectively energizing the plurality of regions includes controllably bending one or more portions of an optical waveguide to controllably emit light from one or more portions of a surface of the optical waveguide.

At 1226, selectively energizing the plurality of regions includes energetically interrogating the one or more regions proximate the surface of the implanted portion of the catheter device 102 with an electromagnetic energy stimulus having a peak emission wavelength ranging from about 100 nanometers to about 400 nanometers. At 1228, selectively energizing the plurality of regions includes energetically interrogating the one or more regions proximate the surface of the implanted portion of the catheter device 102 with an electromagnetic energy stimulus having a peak emission wavelength ranging from about 100 nanometers to about 320 nanometers.

At 1230, selectively energizing the plurality of regions includes energetically interrogating the one or more regions proximate the surface of the implanted portion of the catheter device 102 with an electromagnetic energy stimulus having a peak emission wavelength ranging from about 280 nanometers to about 320 nanometers. At 1232, selectively energizing the plurality of regions includes energetically interrogating the one or more regions proximate the surface of the implanted portion of the catheter device 102 with an energy stimulus having an average integrated flux of less than about 80 milli-joules per square centimeter.

At 1234, selectively energizing the plurality of regions includes energetically interrogating the one or more regions proximate the surface of the implanted portion of the catheter device 102 with electrical energy. At 1236, selectively energizing the plurality of regions includes energetically interrogating the one or more regions proximate the surface of the implanted portion of the catheter device 102 with ultrasonic energy. At 1238, selectively energizing the plurality of regions includes energetically interrogating the one or more regions proximate the surface of the implanted portion of the catheter device 102 with thermal energy.

At 1240, selectively energizing the plurality of regions includes energetically interrogating the one or more regions proximate the surface of the implanted portion of the catheter device 102 with an energy stimulus having an average integrated flux of less than about 35 milli-joules per square centimeter. At 1242, selectively energizing the plurality of regions includes energetically interrogating the one or more regions proximate the surface of the implanted portion of the catheter device 102 with an energy stimulus having an average integrated flux of less than about 15 milli joules per square centimeter. At 1244, selectively energizing the plurality of regions includes energetically interrogating the one or more regions proximate the surface of the implanted portion of the catheter device 102 with an energy stimulus having an average energy density ranging from about 15 milli-joules per square centimeter to about less than about 80 milli-joules per square centimeter.

At 1250, the method 1200 includes determining a microbial colonization score in response to real-time detected information. At 1260, the method 1200 includes energetically interrogating the one or more regions proximate the surface of the implanted portion of the catheter device 102 based on the determined microbial colonization score.

FIG. 13 shows an example of a method 1300 of a method of inhibiting biofilm formation in a catheter device 102.

At 1310, the method 1300 includes actuating one or more selectively actuatable energy waveguides 202a of a catheter device 102 in response to an in vivo detected change in a refractive index parameter associated with a biological sample proximate an outer surface or an inner surface of the catheter device 102.

At 1312, actuating the one or more selectively actuatable energy waveguides 202a includes energizing one or more computing devices 230 to provide a control signal to actuate at least one of the one or more selectively actuatable energy waveguides 202a between an optically transmissive state and an optically non-transmissive state.

At 1314, actuating the one or more selectively actuatable energy waveguides 202a includes causing at least one of the one or more selectively actuatable energy waveguides 202a to emit a sterilizing energy stimulus based on a target change in the refractive index parameter.

At 1316, actuating the one or more selectively actuatable energy waveguides 202a includes propagating electromagnetic energy in at least one of the one or more selectively actuatable energy waveguides 202a having a portion proximate the outer surface 106 or the inner surface 108 of the catheter device 102 having a threshold level change to an a refractive index parameter.

At 1320, the method 1300 includes providing a spatially patterned energy stimulus to one or more regions proximate the outer surface or the inner surface of the catheter device 102.

At 1322, providing the spatially patterned energy stimulus includes providing a spatially patterned energy stimulus having at least a first region and a second region different from the first region. In an embodiment, the first regions comprises one of a spatially patterned electromagnetic energy stimulus, a spatially patterned electrical energy stimulus, a spatially patterned ultrasonic energy stimulus, or a spatially patterned thermal energy stimulus, or the second region comprises a different one of a spatially patterned electromagnetic energy stimulus, a spatially patterned electrical energy stimulus, a spatially patterned ultrasonic energy stimulus, or a spatially patterned thermal energy stimulus.

At 1324, providing the spatially patterned energy stimulus includes providing an illumination pattern comprising at least a first region and a second region. In an embodiment, the second region having at least one of an emission intensity, an emission phase, an emission polarization, or an emission wavelength different from the first region. At 1326, providing the spatially patterned energy stimulus includes applying a voltage to two or more regions proximate at least one of the outer surface or the inner surface of the catheter device 102, the voltage of a dose sufficient to exceed a nominal dielectric strength of a cell plasma membrane. At 1328, providing the spatially patterned energy stimulus includes concurrently or sequentially providing at least a first energy stimulus and a second energy stimulus the second energy stimulus different from the first energy stimulus. In an embodiment, the first energy stimulus comprises one of an electromagnetic energy stimulus, an electrical energy stimulus, an ultrasonic energy stimulus, or a thermal energy stimulus, and the second energy stimulus comprises a different one of an electromagnetic energy stimulus, an electrical energy stimulus, an ultrasonic energy stimulus, or a thermal energy stimulus.

Figure 14:
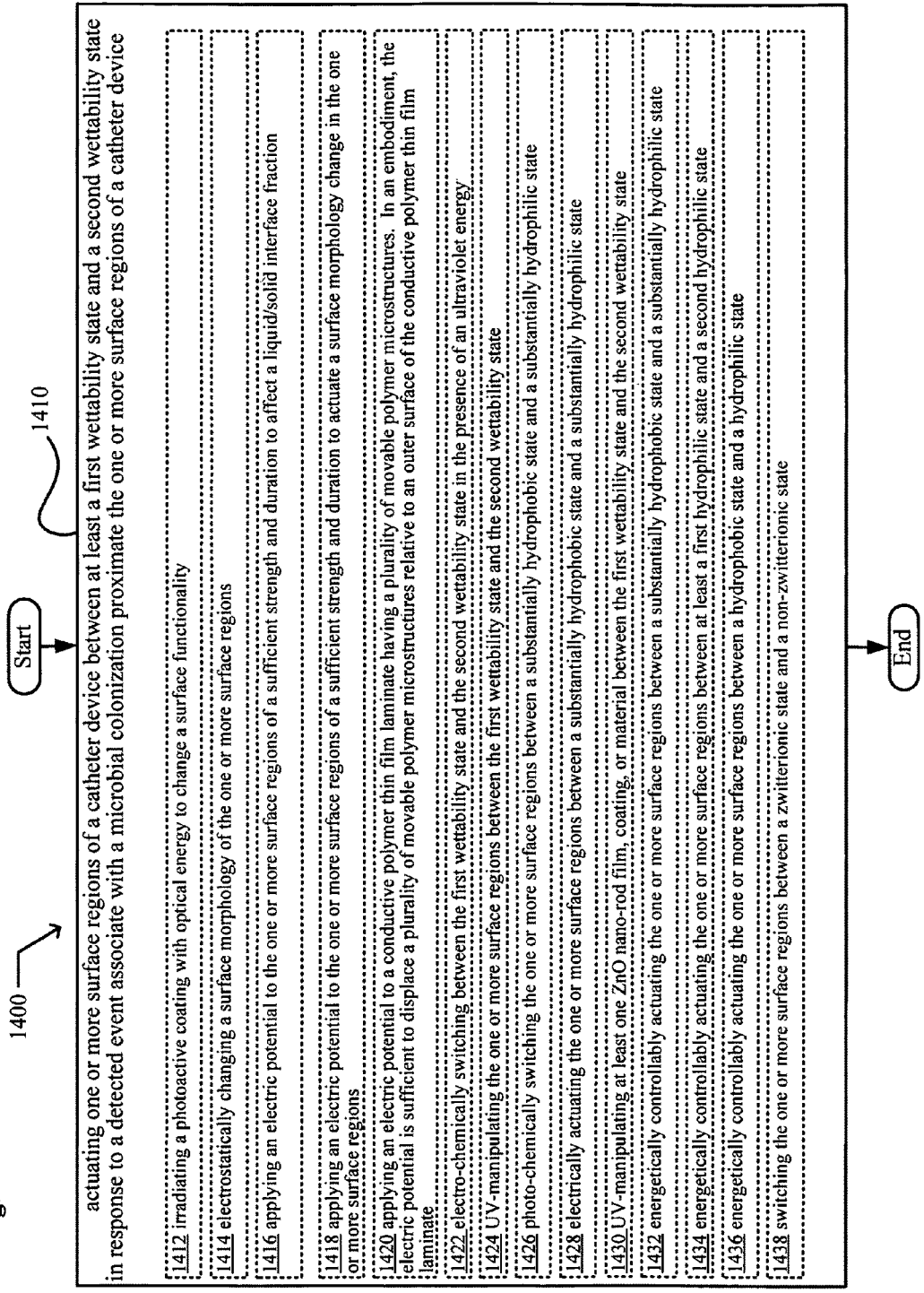
FIG. 14 is a flow diagram of a method according to one embodiment.

FIG. 14 shows an example of a method 1400 of method of inhibiting biofilm formation. At 1410, the method 1400 includes actuating one or more surface regions of a catheter device 102 between at least a first wettability state and a second wettability state in response to a detected event associate with a microbial colonization proximate the one or more surface regions of a catheter device 102. At 1412, actuating the one or more surface regions of the catheter device 102 includes irradiating a photoactive coating with optical energy to change a surface functionality. At 1414, actuating the one or more surface regions of the catheter device 102 includes electrostatically changing a surface morphology of the one or more surface regions. At 1416, actuating the one or more surface regions of the catheter device 102 includes applying an electric potential to the one or more surface regions of a sufficient strength and duration to affect a liquid/solid interface fraction. At 1418, actuating the one or more surface regions of the catheter device 102 includes applying an electric potential to the one or more surface regions of a sufficient strength and duration to actuate a surface morphology change in the one or more surface regions.

At 1420, actuating the one or more surface regions of the catheter device 102 includes applying an electric potential to a conductive polymer thin film laminate having a plurality of movable polymer microstructures. In an embodiment, the electric potential is sufficient to displace a plurality of movable polymer microstructures relative to an outer surface of the conductive polymer thin film laminate. At 1422, actuating the one or more surface regions of the catheter device 102 includes electro-chemically switching between the first wettability state and the second wettability state in the presence of an ultraviolet energy. At 1424, actuating the one or more surface regions of the catheter device 102 includes UV-manipulating the one or more surface regions between the first wettability state and the second wettability state. At 1426, actuating the one or more surface regions of the catheter device 102 includes photo-chemically switching the one or more surface regions between a substantially hydrophobic state and a substantially hydrophilic state. At 1428, actuating the one or more surface regions of the catheter device 102 includes electrically actuating the one or more surface regions between a substantially hydrophobic state and a substantially hydrophilic state At 1430, actuating the one or more surface regions of the catheter device 102 includes UV-manipulating at least one ZnO nano-rod film, coating, or material between the first wettability state and the second wettability state. At 1432, actuating the one or more surface regions of the catheter device 102 includes energetically controllably actuating the one or more surface regions between a substantially hydrophobic state and a substantially hydrophilic state. At 1434, actuating the one or more surface regions of the catheter device 102 includes energetically controllably actuating the one or more surface regions between at least a first hydrophilic state and a second hydrophilic state. At 1436, actuating the one or more surface regions of the catheter device 102 includes energetically controllably actuating the one or more surface regions between a hydrophobic state and a hydrophilic state. At 1438, actuating the one or more surface regions of the catheter device 102 includes switching the one or more surface regions between a zwitterionic state and a non-zwitterionic state.

Figure 15A:
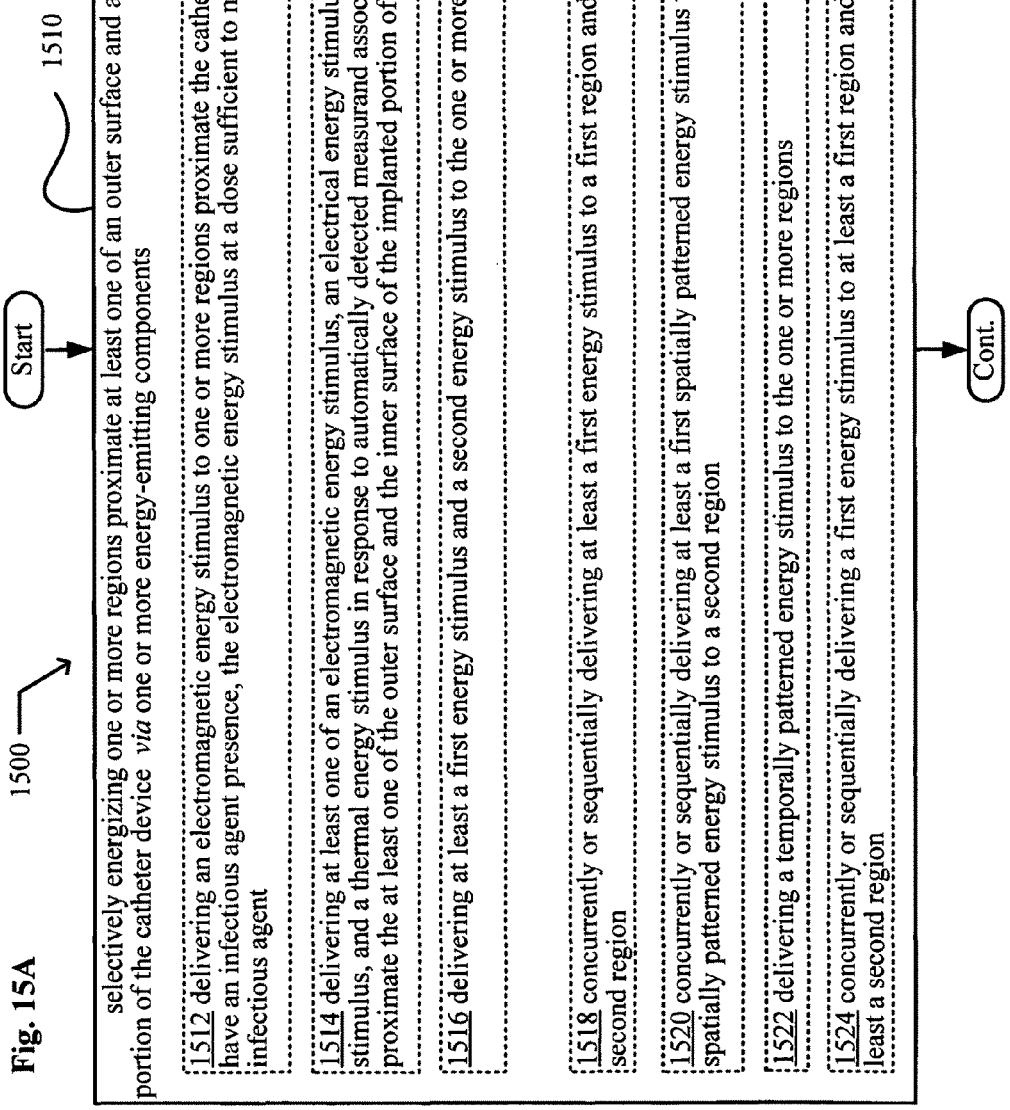
FIGS. 15A and 15B are flow diagrams of a method according to one embodiment.
Figure 15B:
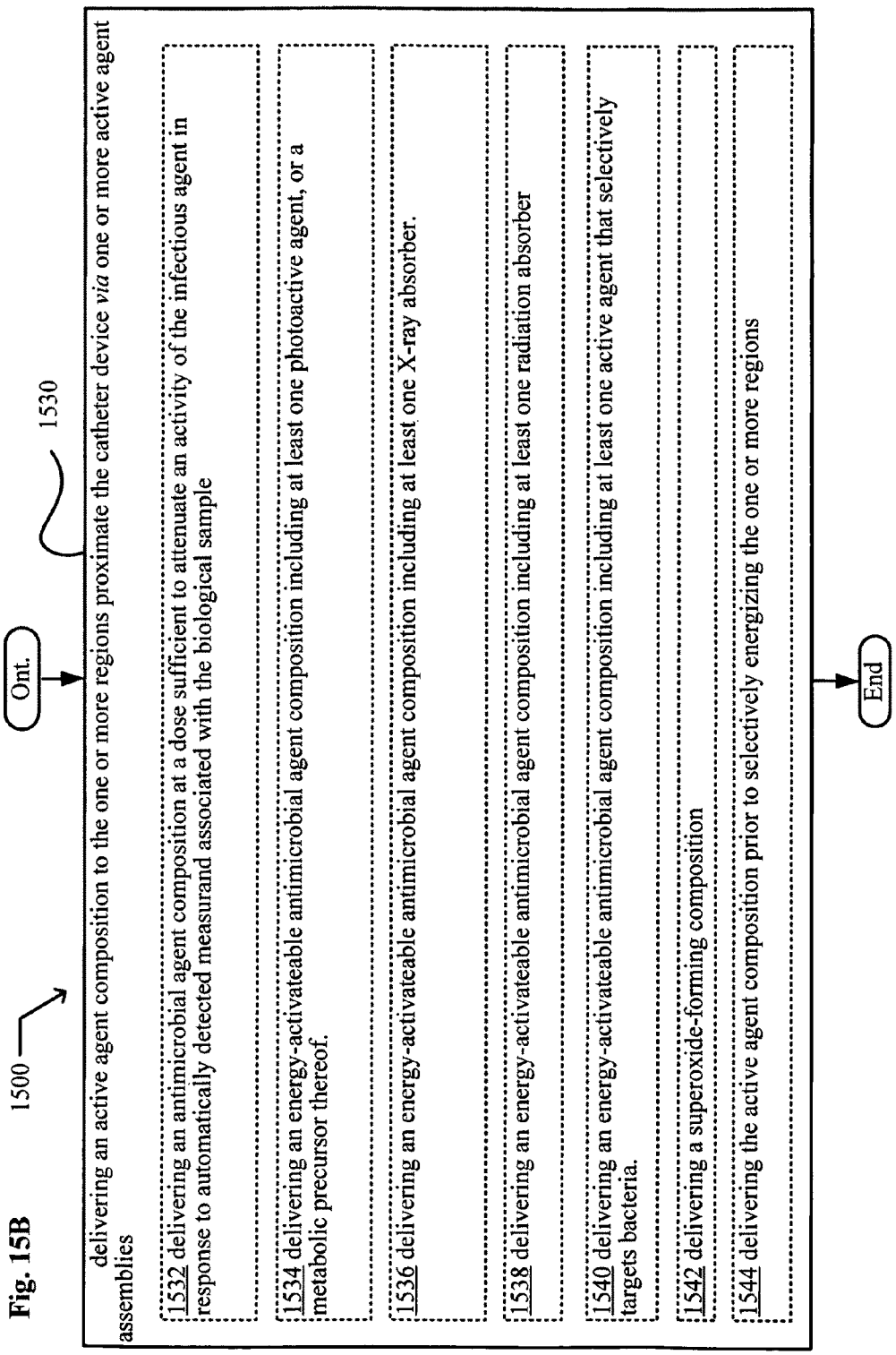

FIG. 15 shows an example of a method 1500 of inhibiting a microbial colonization of a surface of a catheter device 102.

At 1510, the method 1500 includes selectively energizing one or more regions proximate at least one of an outer surface 106 or an inner surface 108 of the implanted portion of the catheter device 102 via one or more energy-emitting components. In an embodiment, the method includes selectively energizing one or more regions proximate at least one of an outer surface 106 or an inner surface 108 of an implanted portion of the catheter device 102 via one or more energy-emitting components in response to an automatically detected measurand associated with biological sample proximate at least one of the outer surface or the inner surface of the implanted portion of the catheter device 102. At 1512, selectively energizing the one or more regions includes delivering an electromagnetic energy stimulus to one or more regions proximate the catheter device 102 determined to have an infectious agent presence, the electromagnetic energy stimulus at a dose sufficient to modulate an activity of the infectious agent. At 1514, selectively energizing the one or more regions includes delivering at least one of an electromagnetic energy stimulus, an electrical energy stimulus, an ultrasonic energy stimulus, or a thermal energy stimulus in response to automatically detected measurand associated with biological sample proximate the at least one of the outer surface or the inner surface of the implanted portion of the catheter device 102.

At 1516, selectively energizing the one or more regions includes delivering at least a first energy stimulus and a second energy stimulus to the one or more regions. In an embodiment, the second energy stimulus having at least one of an emission intensity, an emission phase, an emission polarization, or an emission wavelength different from the first energy stimulus. At 1518, selectively energizing the one or more regions includes concurrently or sequentially delivering at least a first energy stimulus to a first region and a second energy stimulus to a second region. At 1520, selectively energizing the one or more regions includes concurrently or sequentially delivering at least a first spatially patterned energy stimulus to a first region and a second spatially patterned energy stimulus to a second region. At 1522, selectively energizing the one or more regions includes delivering a temporally patterned energy stimulus to the one or more regions. At 1524, selectively energizing the one or more regions includes concurrently or sequentially delivering a first energy stimulus to at least a first region and a second energy stimulus to at least a second region. In an embodiment, the first energy stimulus comprises one of an electromagnetic energy stimulus, an electrical energy stimulus, an ultrasonic energy stimulus, or a thermal energy stimulus, and the second energy stimulus comprises a different one of an electromagnetic energy stimulus, an electrical energy stimulus, an ultrasonic energy stimulus, or a thermal energy stimulus.

At 1530, the method 1500 includes delivering an active agent composition to the one or more regions proximate the catheter device 102 via one or more active agent assemblies 900. In an embodiment, the method includes delivering an active agent composition to the one or more regions proximate the catheter device 102 via one or more active agent assemblies 900 in response to an automatically detected measurand associated with biological sample proximate the catheter device 102. At 1532, delivering the active agent composition includes delivering an antimicrobial agent composition at a dose sufficient to attenuate an activity of the infectious agent in response to automatically detected measurand associated with the biological sample. At 1534, delivering the active agent composition includes delivering an energy-activatable antimicrobial agent composition including at least one photoactive agent, or a metabolic precursor thereof. At 1536, delivering the active agent composition includes delivering an energy-activatable antimicrobial agent composition including at least one X-ray absorber. At 1538, delivering the active agent composition includes delivering an energy-activatable antimicrobial agent composition including at least one radiation absorber. At 1540, delivering the active agent composition includes delivering an energy-activatable antimicrobial agent composition including at least one active agent that selectively targets bacteria. At 1542, delivering the active agent composition includes delivering a superoxide-forming composition.

At 1544, delivering the active agent composition includes delivering the active agent composition prior to selectively energizing the one or more regions. In an embodiment, the method includes selectively energizing one or more regions proximate at least one of an outer surface 106 or an inner surface 108 of the implanted portion of the catheter device 102 via one or more energy-emitting components, and delivering an active agent composition to the one or more regions proximate at least one of an outer surface 106 or an inner surface 108 of the implanted portion of the catheter device 102 via one or more active agent assemblies, in response to an automatically detected measurand associated with biological sample proximate at least one of the outer surface or the inner surface of the implanted portion of the catheter device 102.

FIG. 16 shows an example of a method 1600. At 1610, the method 1600 includes concurrently or sequentially delivering to one or more regions proximate a surface of a catheter device 102 a spatially patterned sterilizing energy stimulus via a plurality of independently activatable ultraviolet energy delivering substrates 802. In an embodiment, the independently activatable ultraviolet energy delivering substrates 802 are configured to independently activate in response to a real-time detected measurand associated with a biological sample within the one or more regions proximate the surface of the catheter device 102. At 1612, concurrently or sequentially delivering to one or more regions proximate the surface of the catheter device 102 the spatially patterned sterilizing energy stimulus includes delivering a temporally patterned evanescent electromagnetic field stimulus having at least a first-in-time pattern and a second-in-time pattern. In an embodiment, the second-in-time pattern includes at least one of a polarization, an intensity, an amplitude, a phase, a wave vector (k), a pulse frequency, or a spectral power distribution different from the first-in-time pattern.

FIG. 17 shows an example of a method 1700. At 1710, the method 1700 includes concurrently or sequentially delivering to one or more regions proximate a surface of a catheter device 102 a temporally patterned sterilizing energy stimulus via a plurality of independently activatable ultraviolet energy delivering substrates 802 configured to independently activate in response to a real-time detected measurand associated with at least one of temporal metabolite information or spatial metabolite information associated with a biological sample within the one or more regions proximate the surface of the catheter device 102.

Figure 18A:
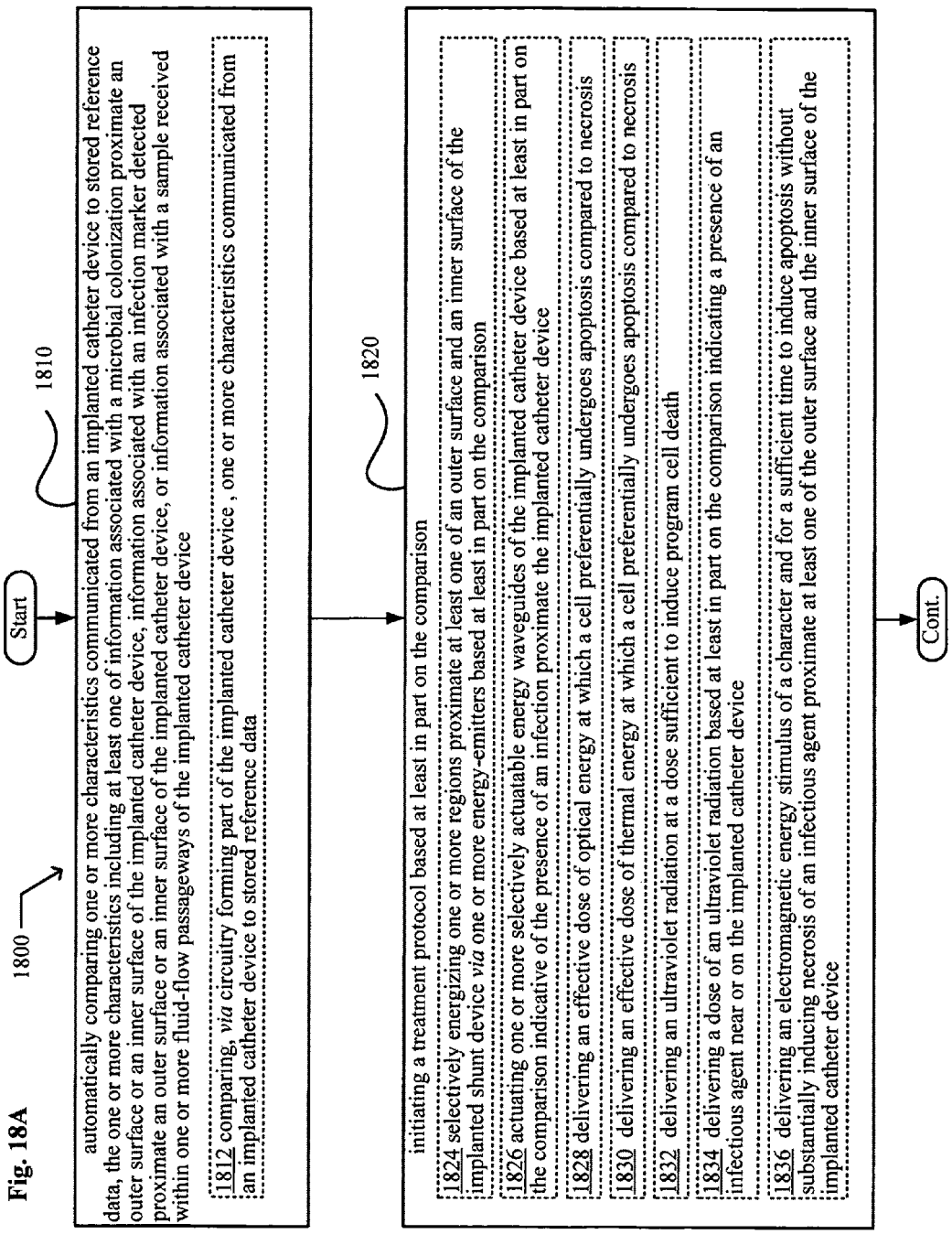
FIGS. 18A and 18B are flow diagrams of a method according to one embodiment.
Figure 18B:
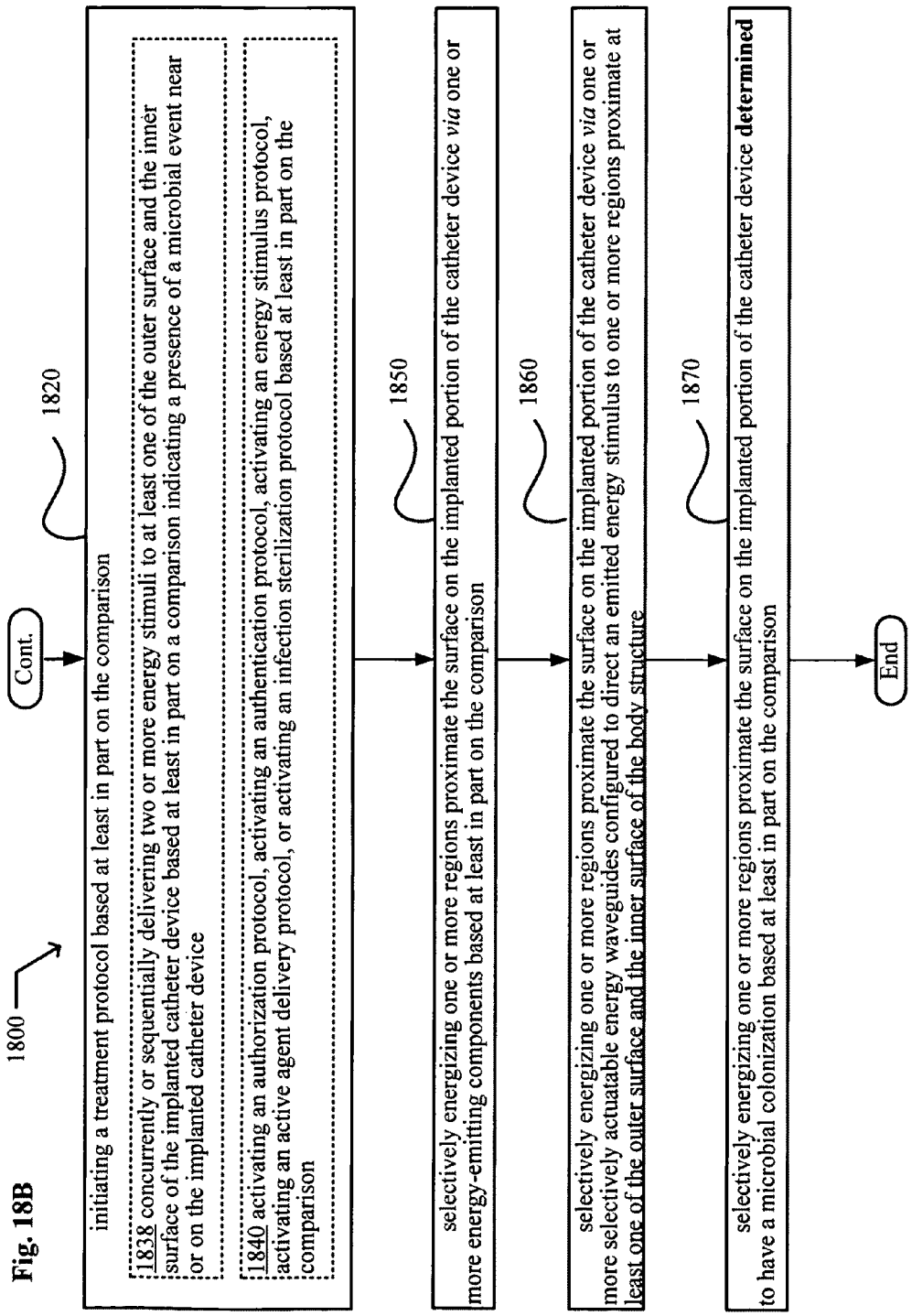

FIG. 18 shows an example of a method 1800. At 1810, the method 1800 includes automatically comparing one or more characteristics communicated from an implanted catheter device 102 to stored reference data, the one or more characteristics including at least one of information associated with a microbial colonization proximate an outer surface or an inner surface of the implanted catheter device 102, information associated with an infection marker detected proximate an outer surface or an inner surface of the implanted catheter device 102, or information associated with a sample (e.g., a fluid, a biological sample, or the like) received within one or more fluid-flow passageways of the implanted catheter device 102. At 1812, automatically comparing the one or more characteristics communicated from an implanted catheter device 102 to stored reference data includes comparing, via circuitry forming part of the implanted catheter device 102, one or more characteristics communicated from an implanted catheter device 102 to stored reference data.

At 1820, the method 1800 includes initiating a treatment protocol based at least in part on the comparison. At 1822, initiating the treatment protocol includes generating a spatially patterned evanescent electromagnetic field proximate the at least one of the outer surface and the inner surface of implanted catheter device 102 based at least in part on the comparison. At 1824, initiating the treatment protocol includes selectively energizing one or more regions proximate at least one of an outer surface 106 or an inner surface 108 of the implanted shunt device via one or more energy-emitters based at least in part on the comparison. At 1826, initiating the treatment protocol includes actuating one or more selectively actuatable energy waveguides 202a of the implanted catheter device 102 based at least in part on the comparison indicative of the presence of an infection proximate the implanted catheter device 102. At 1828, initiating the treatment protocol includes delivering an effective dose of optical energy at which a cell preferentially undergoes apoptosis compared to necrosis.

At 1830, initiating the treatment protocol includes delivering an effective dose of thermal energy at which a cell preferentially undergoes apoptosis compared to necrosis. At 1832, initiating the treatment protocol includes delivering an ultraviolet radiation at a dose sufficient to induce program cell death. At 1834, initiating the treatment protocol includes delivering a dose of an ultraviolet radiation based at least in part on the comparison indicating a presence of an infectious agent near or on the implanted catheter device 102. At 1836, initiating the treatment protocol includes delivering an electromagnetic energy stimulus of a character and for a sufficient time to induce apoptosis without substantially inducing necrosis of an infectious agent proximate at least one of the outer surface or the inner surface of the implanted catheter device 102. At 1838, initiating the treatment protocol includes concurrently or sequentially delivering two or more energy stimuli to at least one of the outer surface or the inner surface of the implanted catheter device 102 based at least in part on a comparison indicating a presence of a microbial event near or on the implanted catheter device 102. At 1840, initiating the treatment protocol includes activating an authorization protocol, activating an authentication protocol, activating an energy stimulus protocol, activating an active agent delivery protocol, or activating an infection sterilization protocol based at least in part on the comparison.

At 1850, the method 1800 includes selectively energizing one or more regions proximate the surface on the implanted portion of the catheter device 102 via one or more energy-emitting components based at least in part on the comparison. At 1860, the method 1800 includes selectively energizing one or more regions proximate the surface on the implanted portion of the catheter device 102 via one or more selectively actuatable energy waveguides configured to direct an emitted energy stimulus to one or more regions proximate at least one of the outer surface 106 or the inner surface 108 of the body structure 104. At 1870, the method 1800 includes selectively energizing one or more regions proximate the surface on the implanted portion of the catheter device 102 determined to have a microbial colonization based at least in part on the comparison.

FIG. 19 shows an example of a method 1900. At 1910, the method 1900 includes electronically comparing one or more characteristics communicated from an implanted catheter device 102 to stored reference data, the one or more characteristics including at least one of an in vivo detected microbial colonization presence proximate a surface of the catheter device 102, an in vivo real-time detected infection marker presence proximate a surface of the catheter device 102, in vivo detected measurand associated with a biofilm-specific tag, and a real-time obtained measurand associated with a microbial colonization presence proximate the catheter device 102. At 1920, the method 1900 includes initiating a treatment protocol based at least in part on the comparison.

FIG. 20 shows an example of a method 2000 of inhibiting biofilm formation in catheter device 102. At 2010, the method 2000 includes acoustically modulating one or more internally reflecting optical waveguides so as to partially emit an electromagnetic energy propagating within the one or more internally reflecting optical waveguides through at least one of an outer surface 106 or an inner surface 108 of the catheter device 102. At 2012, acoustically modulating the one or more internally reflecting optical waveguides includes applying an acoustic energy stimulus to the one or more internally reflecting optical waveguides of a character and for a sufficient duration to affect at least one of an index of refraction and a physical dimension of the one or more internally reflecting optical waveguides. At 2014, acoustically modulating the one or more internally reflecting optical waveguides includes acoustically modifying an index of refraction of at least one of the one or more internally reflecting optical waveguides so as to modulate an electromagnetic energy propagating within the one or more total-internal-reflection waveguides. At 2016, acoustically modulating the one or more internally reflecting optical waveguides includes deforming at least one of the one or more internally reflecting optical waveguides in response to an acoustic stimulus. In an embodiment, the acoustic stimulus is of a character and for a duration sufficient to cause the at least one of the one or more internally reflecting optical waveguides to emit a portion of the electromagnetic energy internally reflected within.

At 2020, the method 2000 includes selectively actuating one or more optical waveguides so as to partially emit an electromagnetic energy propagating within the one or more optical waveguides through at least one of an outer surface 106 or an inner surface 108 of the catheter device 102 in response to real-time detected information associated with a microbial colonization in one or more regions proximate at least one of an outer surface or an inner surface of the catheter device 102.

FIG. 21 shows an example of a method 2100. At 2110, the method 2100 includes detecting a measurand associated with a microbial presence proximate at a surface of a catheter device 102 using an interrogation energy having a first peak emission wavelength. At 2120, the method 1900 includes delivering a sterilizing stimulus having a second peak emission wavelength different from the first peak emission wavelength to one or more regions proximate the surface on the catheter device 102 in response to the detecting a measurand.

FIG. 22 shows an example of a method 2200. At 2210, the method 2200 includes real-time monitoring of a plurality of portions of a catheter device 102 for a microbial colonization by detecting spectral information associated with an interrogating stimulus having a first peak emission wavelength. At 2220, the method 2200 includes delivering a sterilizing stimulus having a second peak emission wavelength different from the first peak emission wavelength to select ones of the plurality of portions of the catheter device 102 based on a determined microbial colonization score.

FIG. 23 shows an example of a method 2300. At 2310, the method 2300 includes real-time monitoring at least one of an outer surface 106 or an inner surface 108 of an indwelling portion of a catheter device 102 for a microbial colonization by detecting spectral information associated with an interrogating stimulus having a first peak emission wavelength, the interrogating stimulus delivered to one or more region proximate the at least one of the outer surface or the inner surface of an indwelling portion of a catheter device 102.

At 2320, the method 2300 includes determining a microbial colonization score for the one or more region proximate the at least one of the outer surface or the inner surface of an indwelling portion of a catheter device 102 in response to detecting spectral information. At 2330, the method 2300 includes selective-delivering a sterilizing stimulus having a second peak emission wavelength different from the first peak emission wavelength to at least one of the one or more region proximate the at least one of the outer surface or the inner surface of an indwelling portion of a catheter device 102 based on a determined microbial colonization score.

FIG. 24 shows an example of a method 2400. At 2410, the method 2400 includes delivering an ultraviolet energy absorbing composition to one or more regions proximate a surface of a catheter device 102 prior to delivering a patterned energy stimulus to the one or more regions based on a detected measurand associated with biological sample proximate the one or more regions. At 2420, the method 2400 includes delivering a sterilizing ultraviolet energy stimulus to select ones of the one or more regions based on the detected measurand.

FIG. 25 shows an example of a method 2500. At 2510, the method 2500 includes delivering an ultraviolet energy absorbing composition to one or more regions proximate at least one of an outer surface 106 or an inner surface 108 of an implanted portion of a catheter device 102 prior to selectively energizing the one or more regions in response to a real-time detected spectral information associated with a microbial presence within the one or more regions.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for detecting position and/or velocity, control motors for moving and/or adjusting components and/or quantities). A data processing system can be implemented utilizing suitable commercially available components, such as those typically found in data computing/communication and/or network computing/communication systems.

The herein described subject matter sometimes illustrates different components contained within, or connected with, different other components. It is to be understood that such depicted architectures are merely examples, and that in fact, many other architectures can be implemented that achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably coupleable," to each other to achieve the desired functionality. Specific examples of operably coupleable include, but are not limited to, physically mateable and/or physically interacting components, and/or wirelessly interactable, and/or wirelessly interacting components, and/or logically interacting, and/or logically interactable components.

In an embodiment, one or more components may be referred to herein as "configured to," "configurable to," "operable/operative to," "adapted/adaptable," "able to," "conformable/conformed to," etc. Such terms (e.g., "configured to") can generally encompass active-state components and/or inactive-state components and/or standby-state components, unless context requires otherwise.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by the reader that each function and/or operation within such block diagrams, flowcharts, or examples can be implemented, individually and/or collectively, by a wide range of hardware, software, firmware, or virtually any combination thereof. Further, the use of "Start," "End," or "Stop" blocks in the block diagrams is not intended to indicate a limitation on the beginning or end of any functions in the diagram. Such flowcharts or diagrams may be incorporated into other flowcharts or diagrams where additional functions are performed before or after the functions shown in the diagrams of this application. In an embodiment, several portions of the subject matter described herein is implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal-bearing medium used to actually carry out the distribution. Non-limiting examples of a signal-bearing medium include the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

While particular aspects of the present subject matter described herein have been shown and described, it will be apparent to the reader that, based upon the teachings herein, changes and modifications can be made without departing from the subject matter described herein and its broader aspects and, therefore, the appended claims are to encompass within their scope all such changes and modifications as are within the true spirit and scope of the subject matter described herein. In general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). Further, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense of the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, the operations recited therein generally may be performed in any order. Also, although various operational flows are presented in a sequence(s), it should be understood that the various operations may be performed in orders other than those that are illustrated, or may be performed concurrently. Examples of such alternate orderings includes overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A method of inhibiting a microbial colonization of a surface on an implanted portion of a catheter device, comprising:
   selectively energizing one or more regions proximate at least one of an outer surface or an inner surface of the implanted portion of the catheter device via one or more energy-emitting components; and
   delivering an active agent composition to the one or more regions proximate at least one of the outer surface or the inner surface of the implanted portion of the catheter device via one or more active agent assemblies,
   in response to an automatically detected measurand associated with a biological sample proximate at least one of the outer surface or the inner surface of the implanted portion of the catheter device;
   wherein the selectively energizing the one or more regions includes delivering an electromagnetic energy stimulus to the one or more regions proximate at least one of the outer surface or the inner surface of the implanted portion determined to have an infectious agent presence, the electromagnetic energy stimulus at a dose sufficient to modulate an activity of the infectious agent.

2. A method of inhibiting a microbial colonization of a surface on an implanted portion of a catheter device, comprising:
   selectively energizing one or more regions proximate at least one of an outer surface or an inner surface of the implanted portion of the catheter device via one or more energy-emitting components; and
   delivering an active agent composition to the one or more regions proximate at least one of the outer surface or the inner surface of the implanted portion of the catheter device via one or more active agent assemblies,
   in response to an automatically detected measurand associated with a biological sample proximate at least one of the outer surface or the inner surface of the implanted portion of the catheter device;
   wherein the selectively energizing the one or more regions includes delivering at least a first energy stimulus and a second energy stimulus to the one or more regions, the second energy stimulus having at least one of an emission intensity, an emission phase, an emission polarization, or an emission wavelength different from the first energy stimulus.

3. A method of inhibiting a microbial colonization of a surface on an implanted portion of a catheter device, comprising:
   selectively energizing one or more regions proximate at least one of an outer surface or an inner surface of the implanted portion of the catheter device via one or more energy-emitting components; and
   delivering an active agent composition to the one or more regions proximate at least one of the outer surface or the inner surface of the implanted portion of the catheter device via one or more active agent assemblies,
   in response to an automatically detected measurand associated with a biological sample proximate at least one of the outer surface or the inner surface of the implanted portion of the catheter device;
   wherein the selectively energizing the one or more regions includes concurrently or sequentially delivering at least a first energy stimulus to a first region and a second energy stimulus to a second region.

4. A method of inhibiting a microbial colonization of a surface on an implanted portion of a catheter device, comprising:
   selectively energizing one or more regions proximate at least one of an outer surface or an inner surface of the implanted portion of the catheter device via one or more energy-emitting components; and
   delivering an active agent composition to the one or more regions proximate at least one of the outer surface or the inner surface of the implanted portion of the catheter device via one or more active agent assemblies,
   in response to an automatically detected measurand associated with a biological sample proximate at least one of the outer surface or the inner surface of the implanted portion of the catheter device;
   wherein the selectively energizing the one or more regions includes concurrently or sequentially delivering at least a first spatially patterned energy stimulus to a first region and a second spatially patterned energy stimulus to a second region.

5. A method of inhibiting a microbial colonization of a surface on an implanted portion of a catheter device, comprising:
   selectively energizing one or more regions proximate at least one of an outer surface or an inner surface of the implanted portion of the catheter device via one or more energy-emitting components; and
   delivering an active agent composition to the one or more regions proximate at least one of the outer surface or the inner surface of the implanted portion of the catheter device via one or more active agent assemblies,
   in response to an automatically detected measurand associated with a biological sample proximate at least one of the outer surface or the inner surface of the implanted portion of the catheter device;
   wherein the selectively energizing the one or more regions includes delivering a temporally patterned energy stimulus to the one or more regions.

6. A method of inhibiting a microbial colonization of a surface on an implanted portion of a catheter device, comprising:
   selectively energizing one or more regions proximate at least one of an outer surface or an inner surface of the implanted portion of the catheter device via one or more energy-emitting components; and
   delivering an active agent composition to the one or more regions proximate at least one of the outer surface or the inner surface of the implanted portion of the catheter device via one or more active agent assemblies,
   in response to an automatically detected measurand associated with a biological sample proximate at least one of the outer surface or the inner surface of the implanted portion of the catheter device;
   wherein the selectively energizing the one or more regions includes concurrently or sequentially delivering a first energy stimulus to at least a first region and a second energy stimulus to at least a second region, the first energy stimulus comprising one of an electromagnetic energy stimulus, an electrical energy stimulus, an acoustic energy stimulus, or a thermal energy stimulus, and the second energy stimulus comprising a different one of an electromagnetic energy stimulus, an electrical energy stimulus, an acoustic energy stimulus, or a thermal energy stimulus.

7. A method of inhibiting a microbial colonization of a surface on an implanted portion of a catheter device, comprising:
selectively energizing one or more regions proximate at least one of an outer surface or an inner surface of the implanted portion of the catheter device via one or more energy-emitting components; and
delivering an active agent composition to the one or more regions proximate at least one of the outer surface or the inner surface of the implanted portion of the catheter device via one or more active agent assemblies,
in response to an automatically detected measurand associated with a biological sample proximate at least one of the outer surface or the inner surface of the implanted portion of the catheter device;
wherein the delivering the active agent composition includes delivering an antimicrobial agent composition at a dose sufficient to attenuate an activity of an infectious agent in response to the automatically detected measurand associated with the biological sample.

8. A method of inhibiting a microbial colonization of a surface on an implanted portion of a catheter device, comprising:
selectively energizing one or more regions proximate at least one of an outer surface or an inner surface of the implanted portion of the catheter device via one or more energy-emitting components; and
delivering an active agent composition to the one or more regions proximate at least one of the outer surface or the inner surface of the implanted portion of the catheter device via one or more active agent assemblies,
in response to an automatically detected measurand associated with a biological sample proximate at least one of the outer surface or the inner surface of the implanted portion of the catheter device;
wherein the delivering the active agent composition includes delivering an energy-activatable antimicrobial agent composition including at least one photoactive agent, or a metabolic precursor thereof.

9. A method of inhibiting a microbial colonization of a surface on an implanted portion of a catheter device, comprising:
selectively energizing one or more regions proximate at least one of an outer surface or an inner surface of the implanted portion of the catheter device via one or more energy-emitting components; and
delivering an active agent composition to the one or more regions proximate at least one of the outer surface or the inner surface of the implanted portion of the catheter device via one or more active agent assemblies,
in response to an automatically detected measurand associated with a biological sample proximate at least one of the outer surface or the inner surface of the implanted portion of the catheter device;
wherein the delivering the active agent composition includes delivering an energy-activatable antimicrobial agent composition including at least one X-ray absorber.

10. A method of inhibiting a microbial colonization of a surface on an implanted portion of a catheter device, comprising:
selectively energizing one or more regions proximate at least one of an outer surface or an inner surface of the implanted portion of the catheter device via one or more energy-emitting components; and
delivering an active agent composition to the one or more regions proximate at least one of the outer surface or the inner surface of the implanted portion of the catheter device via one or more active agent assemblies,
in response to an automatically detected measurand associated with a biological sample proximate at least one of the outer surface or the inner surface of the implanted portion of the catheter device;
wherein the delivering the active agent composition includes delivering an energy-activatable antimicrobial agent composition including at least one active agent that selectively targets bacteria.

11. A method of inhibiting a microbial colonization of a surface on an implanted portion of a catheter device, comprising:
selectively energizing one or more regions proximate at least one of an outer surface or an inner surface of the implanted portion of the catheter device via one or more energy-emitting components; and
delivering an active agent composition to the one or more regions proximate at least one of the outer surface or the inner surface of the implanted portion of the catheter device via one or more active agent assemblies,
in response to an automatically detected measurand associated with a biological sample proximate at least one of the outer surface or the inner surface of the implanted portion of the catheter device;
wherein the delivering the active agent composition includes delivering a superoxide-forming composition.

* * * * *